United States Patent
Kanekiyo et al.

(10) Patent No.: US 12,084,489 B2
(45) Date of Patent: Sep. 10, 2024

(54) ANTIBODIES AND METHODS FOR THE DIAGNOSIS, PREVENTION, AND TREATMENT OF EPSTEIN BARR VIRUS INFECTION

(71) Applicants: The U.S.A., as represented by the Secretary, Department of Health and Human Services, Bethesda, MD (US); The Henry M. Jackson Foundation for the Advancement of Military Medicine, Inc., Bethesda, MD (US)

(72) Inventors: Masaru Kanekiyo, North Bethesda, MD (US); Michael Gordon Joyce, Washington, DC (US); Wei Bu, Potomac, MD (US); Jeffrey I. Cohen, Silver Spring, MD (US); Yaroslav Tsybovsky, Brunswick, MD (US)

(73) Assignees: The United States of America, as represented by the Secretary, Department of Health and Human Services, Bethesda, MD (US); The Henry M. Jackson Foundation for the Advancement of Military Medicine, Inc., Bethesda, MD (US)

(*) Notice: Subject to any disclaimer, the term of this patent is extended or adjusted under 35 U.S.C. 154(b) by 888 days.

(21) Appl. No.: 17/052,470

(22) PCT Filed: May 2, 2019

(86) PCT No.: PCT/US2019/030431
§ 371 (c)(1),
(2) Date: Nov. 2, 2020

(87) PCT Pub. No.: WO2019/213416
PCT Pub. Date: Nov. 7, 2019

(65) Prior Publication Data
US 2021/0171610 A1    Jun. 10, 2021

Related U.S. Application Data

(60) Provisional application No. 62/665,977, filed on May 2, 2018.

(51) Int. Cl.
C07K 16/08 (2006.01)
A61K 47/68 (2017.01)
C12Q 1/70 (2006.01)
G01N 33/569 (2006.01)

(52) U.S. Cl.
CPC ........ *C07K 16/085* (2013.01); *A61K 47/6803* (2017.08); *A61K 47/6839* (2017.08); *C12Q 1/705* (2013.01); *G01N 33/56994* (2013.01); *C07K 2317/24* (2013.01); *C07K 2317/31* (2013.01); *C07K 2317/55* (2013.01); *C07K 2317/73* (2013.01); *C07K 2317/76* (2013.01); *C07K 2317/92* (2013.01); *C12Q 2600/158* (2013.01); *G01N 2333/05* (2013.01); *G01N 2800/26* (2013.01)

(58) Field of Classification Search
None
See application file for complete search history.

(56) References Cited

U.S. PATENT DOCUMENTS

2006/0182740 A1* 8/2006 Yang .................. A61P 37/06
424/133.1

OTHER PUBLICATIONS

Bu et al., "Immunization with Components of the Viral Fusion Apparatus Elicits Antibodies That Neutralize Epstein-Barr Virus in B Cells and Epithelial Cells," *Immunity* 50: 1305-1316, 2019.
International Search Report and Written Opinion for PCT/US2019/030431, dated Aug. 13, 2019, 25 pages.
Sathiyamoorthy et al., "Inhibition of EBV-Mediated Membrane Fusion by Anti-gHg1 Antibodies," *Proc. Natl. Acad. Sci.*, vol. USA, vol. 114:E8703-E8710, 2017.
Snijder et al., "An Antibody Targeting the Fusion Machinery Neutralizes Dual-Tropic Infection and Defines a Site of Vulnerability on Epstein-Barr Virus," *Immunity*, vol. 48:799-811, 2018.
Sathiyamoorthy et al., "Structural basis for Epstein-Barr virus host cell tropism mediated by gp42 and gHgL entry glycoproteins", *Nature Communications*, vol. 7, No. 1, Dec. 8, 2016(14 pages).

* cited by examiner

*Primary Examiner* — Stacy B Chen
(74) *Attorney, Agent, or Firm* — Klarquist Sparkman, LLP

(57) ABSTRACT

Anti-EBV gH antibodies, anti-EBV gL antibodies, anti-EBV gH/gL antibodies, and compositions of matter useful for the detection, diagnosis, prevention, and treatment of Epstein Barr Virus infection in humans, and methods of using those compositions of matter for the same.

32 Claims, 18 Drawing Sheets

Specification includes a Sequence Listing.

US 12,084,489 B2

ANTIBODIES AND METHODS FOR THE DIAGNOSIS, PREVENTION, AND TREATMENT OF EPSTEIN BARR VIRUS INFECTION

CROSS REFERENCE TO RELATED APPLICATIONS

This application is the U.S. National Stage of International Application No. PCT/US2019/030431, filed May 2, 2019, which was published in English under PCT Article 21(2), which claims the benefit of U.S. Provisional Patent Application Ser. No. 62/665,977, filed May 2, 2018, which is incorporated herein by reference.

FIELD OF THE INVENTION

The present invention is directed to compositions of matter useful for the diagnosis, prevention, and treatment of Epstein Barr Virus infections in humans and to methods of using those compositions of matter for the same.

BACKGROUND

Epstein-Barr-Virus (EBV) is a human herpesvirus that infects over 90% of the population world-wide with a life-long persistence in its host. In most cases, primary infection occurs during early childhood and is usually subclinically symptomatic. In contrast, if infection is retarded and happens during adolescence or adulthood, it is regularly symptomatic, causing a benign, normally self-limiting, lymphoproliferative syndrome termed infectious mononucleosis (IM) in up to 50% of cases. Although the disease is normally self-limiting, prolonged forms of chronic active EBV infection (CAEBV) with fatal outcome have been reported. EBV infection also significantly increases the risk of developing Hodgkin disease and other types of lymphoma later in life. EBV infection is also an independent risk factor for multiple sclerosis later in life. In addition, EBV is causally associated with a heterogeneous group of malignant diseases like nasopharyngeal carcinoma, gastric carcinoma, and various types of lymphoma, and the WHO classifies EBV as a class I carcinogen.

Besides the above described medical conditions caused by EBV, patients with primary or secondary immune defects, like transplant recipients, are at elevated risk for EBV-associated diseases because of the detrimental effect of immunosuppressive agents on the immune-control of EBV-infected B cells. EBV-associated posttransplant lymphoproliferative disorder (PTLD) is an important form of posttransplant complications, occurring in up to 20% of organ recipients. Importantly, immunocompromised transplant recipients who are immunologically naive for EBV at the onset of immunosuppression are at a particular high risk of developing life-threatening PTLD due to a primary EBV infection, e.g. often caused after transplantation via transmission of the virus through a donor organ due to the high prevalence of EBV. Due to impaired T-cell immunity that results from exposure to immunosuppressive drugs, these patients are unable to effectively prime EBV-specific T-cells that play a critical role in controlling proliferation of EBV-infected B cells. In contrast, patients who are EBV-seropositive at transplant have a much lower risk for developing PTLD, demonstrating the essential role of EBV-specific T-cells in eliminating virally infected cells. In general, patients who are EBV-seronegative before transplantation are at a much higher risk to develop EBV-associated diseases, since transmission of donor EBV in transplanted organs or natural infection with the virus causes lymphoproliferative disease in EBV-seronegative recipients after transplantation. As with many virus-associated diseases a promising approach for diagnosing and/or treating virus infection and its consequences in the host is the use of antibodies that specifically recognize the virus. This is also true in the case of reducing the high risk of PTLD in seronegative patients by identifying them and treating them prior to the transplantation.

Primary infection by EBV usually occurs by contact of saliva from infected individuals with epithelial cells in the oropharynx, where virus is amplified through lytic replication and subsequently infects B cells (Longnecker et al., 2013). Alternatively, EBV may directly infect resting B cells in the tonsillar crypts. Infected B cells traffic to lymphoid tissues where most of these B cells are latently infected with limited or no expression of viral genes. Latently infected B cells can traffic back to the oropharynx, where EBV is amplified by lytic replication in epithelial cells, and shed into saliva to spread to new hosts. Therefore, infection of both B cells and epithelial cells is important for the EBV life cycle.

EBV uses different combinations of glycoproteins to infect B cells and epithelial cells. Entry into B cells is initiated by attachment of EBV gp350 to its cellular receptor CR2 (Fingeroth et al., 1984). gH/gL and gp42 form a complex in which gp42 binds to HLA class II molecules (Spriggs et al., 1996); gB is subsequently activated to fuse virions with the B cell membrane (McShane and Longnecker, 2004). Infection of epithelial cells is initiated by attachment of EBV BMFR2 to integrins (Tugizov et al., 2003), followed by binding of gH/gL to integrins and ephrin receptor 2A (Chen et al., 2018; Zhang et al., 2018), and then activation of gB to trigger virion membrane fusion to epithelial cells. EBV gp350 and gp42 are unique in EBV and nonhuman lymphocryptoviruses, while gH/gL and gB, the core fusion machinery, are conserved among all herpesviruses.

Sera from EBV-infected persons are able to neutralize infection of B cells and epithelial cells (Sashihara et al., 2009; Thorley-Lawson and Poodry, 1982; Tugizov et al., 2003). Since antibody to gp350 is the major contributor to neutralizing antibody in human sera for B cell infection (North et al., 1982; Pearson et al., 1970; Thorley-Lawson and Poodry, 1982), nearly all clinical trials of EBV prophylactic vaccines have used gp350 as the sole immunogen (Cohen, 2015). The contribution of antibodies to other EBV glycoproteins, such as gH/gL and gp42, to neutralize B cell and epithelial cell infection has not been investigated. Although epithelial cell infection is an important part of the EBV life cycle and epithelial cell malignancies are more common than B cell cancers, vaccines targeting epithelial cell infection have not been reported.

Membrane fusion is critical for herpesvirus infections. In addition to fusion of the virion envelope with the plasma membrane of cells to initiate infection, many viruses spread in tissues by cell-to-cell fusion (Sattentau, 2008; Zhong et al., 2013). This may allow the virus to avoid neutralizing antibody and other antiviral activities present in plasma. Cell-to-cell contact is important for efficient infection of epithelial cells by EBV (Imai et al., 1998). Thus, induction of antibodies that block fusion may have a critical role in preventing initiation of infection as well as virus spread.

These EBV-associated diseases highlight the need for a better understanding of herpesviruses and their role in mammalian diseases. As part of this understanding, there is a great need for additional diagnostic and therapeutic agents capable of detecting the presence of EBV in an individual and effectively inhibiting EBV infection and replication. Accordingly, it is an objective of the present invention to specifically identify EBV-associated polypeptides and to use that identification specificity to produce compositions of matter useful in the prevention, therapeutic treatment and diagnostic detection of EBV in individuals.

SUMMARY

The invention is in part based on antibodies that recognize Epstein Barr virus (EBV) glycoprotein H (gH), glycoprotein L (gL), or a gH/gL complex, and the use of such antibodies in the detection and diagnosis during active EBV infection. The inventors isolated monoclonal antibodies (mAbs) from humans naturally infected with EBV. Characterization of these antibodies using multiple methods with gH protein, gL protein, gH/gL complex, and/or cells in culture, revealed that the mAbs of this disclosure (including those monoclonal antibodies named the 770F9, 770F5, 770E4, 769C5, 770F12, 770F3, 770G10, 769C3, 769B2, 769A7, 769C4, 769B10, 770E9, 769C2, 770F8, 770E8, 770E6, 770F10, 770G2, and 770F7 clones) were EBV-specific, had greater EBV neutralizing activity on B cells, and had at least comparable neutralizing activity on epithelial cells, relative to previously known murine antibodies, such as E1D1, CL40 and CL59. Thus, the mAbs of this disclosure are high value mAbs with potential uses in immunoassay development, and as immunodiagnostic reagents for clinical sample and tissue confirmation of EBV, and treatment or prevention of EBV infection and EBV-associated diseases and disorders.

This disclosure provides an antibody that binds, preferably specifically, to an EBV gH protein, gL protein, or gH/gL complex. Optionally, the antibody is a monoclonal antibody, antibody fragment, chimeric antibody, humanized antibody, single-chain antibody or antibody that competitively inhibits the binding of an anti-EBV gH antibody, an anti-EBV gL antibody, or anti-EBV gH/gL antibody to its respective antigenic epitope. The antibodies of this disclosure may optionally be produced in CHO cells or other mammalian cells, such as 293F cells, insect cells, bacterial cells, or yeast cells, and preferably inhibit the growth or proliferation of or induce the death of a cell to which they bind. For diagnostic purposes, the antibodies of this disclosure may be detectably labeled, attached to a solid support, or the like, such as a lateral flow assay device which provides for point-of-care detection and/or diagnosis of EBV infection.

This disclosure also provides vectors comprising DNA encoding any of the herein described antibodies. Host cells comprising any such vector are also provided. By way of example, the host cells may be CHO cells, other mammalian cells, insect cells, bacterial cells, or yeast cells. A process for producing any of the herein described antibodies is further provided and comprises culturing host cells under conditions suitable for expression of the desired antibody and recovering the desired antibody from the cell culture.

The disclosure also provides a composition of matter comprising an anti-EBV gH antibody, an anti-EBV gL antibody, or an anti-EBV gH/gL antibody as described herein, in combination with a carrier. Optionally, the carrier is a pharmaceutically acceptable carrier.

This disclosure also provides an article of manufacture comprising a container and a composition of matter contained within the container, wherein the composition of matter may comprise an anti-EBV gH antibody, an anti-EBV gL antibody, or an anti-EBV gH/gL antibody as described herein. The article may optionally comprise a label affixed to the container, or a package insert included with the container, that refers to the use of the composition of matter for the prevention, therapeutic treatment or diagnostic detection of an EBV infection.

This disclosure also provides the use of an anti-EBV gH antibody, an anti-EBV gL antibody, or anti-EBV gH/gL antibody as described herein, for the preparation of a medicament useful in the prevention or treatment of a condition which is responsive to the anti-EBV gH antibody, anti-EBV gL antibody, or anti-EBV gH/gL antibody.

This disclosure also provides any isolated antibody comprising one or more of the complementary determining regions (CDRs), including a CDR-L1, CDR-L2, CDR-L3, CDR-H1, CDR-H2, or CDR-H3 sequence disclosed herein, or any antibody that binds to the same epitope as such antibody.

This disclosure also provides a method for inhibiting the growth of a cell that expresses an EBV gH or gL protein, or a gH/gL complex, including contacting the cell with an antibody that binds to the EBV gH or gL protein, or gH/gL complex, wherein the binding of the antibody to the EBV gH or gL protein, or gH/gL complex, causes inhibition of the growth of the cell expressing the EBV gH or gL protein, or gH/gL complex. In these methods, the cell may be one or more of a B lymphocyte and an epithelial cell. Binding of the antibody to the EBV gH or gL protein, or gH/gL complex, causes death of the cell expressing the EBV gH or gL protein, or gH/gL complex. Optionally, the antibody is a monoclonal antibody, antibody fragment, chimeric antibody, humanized antibody, or single-chain antibody. Antibodies employed in the methods of this disclosure may optionally be conjugated to a growth inhibitory agent or cytotoxic agent such as a toxin. The antibodies employed in the methods of this disclosure may optionally be produced in CHO cells or other mammalian cells, insect cells, bacterial cells, or yeast cells.

This disclosure also provides a method of preventing an EBV infection in an individual by administering to the individual a therapeutically effective amount of an antibody that binds to an EBV gH protein, EBV gL protein, or a gH/gL complex, thereby resulting in the effective prevention of the infection in the individual. In certain aspects, the individual is EBV-naïve, and such treatments prevents primary infection with EBV. This disclosure also provides a method of therapeutically treating an individual having an EBV infection, by administering to the individual a therapeutically effective amount of an antibody that binds to an EBV gH protein, EBV gL protein, or a gH/gL complex, thereby resulting in the effective therapeutic treatment of the infection in the individual. In these therapeutic methods, the antibody may be a monoclonal antibody, antibody fragment, chimeric antibody, humanized antibody, or single-chain antibody. Antibodies employed in these methods may optionally be conjugated to a growth inhibitory agent or cytotoxic agent such as a toxin. The antibodies employed in these methods of this disclosure may optionally be produced in CHO cells or other mammalian cells, insect cells, bacterial cells, or yeast cells.

This disclosure also provides is a method of determining the presence of an EBV gH or gL protein, or a gH/gL complex, in a sample suspected of containing such protein, or complex, by exposing the sample to an antibody that binds to an EBV gH or gL protein, or gH/gL complex, and determining binding of the antibody to the gH or gL protein, or gH/gL complex, in the sample, wherein the presence of such binding is indicative of the presence of an EBV gH or gL protein, or gH/gL complex, in the sample. Optionally, the sample may contain cells (which may be fibroblasts, keratinocytes, or dendritic cells) suspected of expressing an EBV gH or gL protein, or a gH/gL complex. The antibody employed in these methods may optionally be detectably labeled, attached to a solid support, or the like.

This disclosure also provides methods of diagnosing the presence of an EBV infection in an individual, by detecting the level of an EBV gH or gL protein, or a gH/gL complex, in a test sample of tissue cells obtained from the individual, wherein detection of an EBV gH or gL protein, or gH/gL complex, protein in the test sample is indicative of the presence of EBV infection in the individual from which the test sample was obtained.

This disclosure also provides methods of diagnosing the presence of an EBV infection in an individual, by contacting a test sample comprising tissue cells obtained from the individual with an antibody that binds to an EBV gH or gL protein, or a gH/gL complex, and detecting the formation of a complex between the antibody and an EBV gH or gL protein, or a gH/gL complex, in the test sample, wherein the formation of a complex is indicative of the presence of an EBV infection in the individual. Optionally, the antibody employed is detectably labeled, attached to a solid support, or the like. In these methods, the test sample of tissue cells may be obtained from an individual suspected of having a viral infection.

This disclosure also provides methods of treating or preventing an EBV infection-related disorder by administering to a subject in need of such treatment an effective amount of an antagonist of an EBV gH or gL protein, or a gH/gL protein complex. The EBV infection-related disorder may be infectious mononucleosis (glandular fever), hemophagocytic lymphohistiocytosis (HLH; also termed virus-associated hemophagocytic syndrome), non-malignant B-cell lymphoproliferative disorders, particular forms of cancer, such as B-cell lymphomas (including Hodgkin's lymphomas and non-Hodgkin's lymphomas such as Burkitt's lymphoma and diffuse large B-cell lymphoma (DLBCL)), gastric cancer, nasopharyngeal carcinoma, and conditions associated with human immunodeficiency virus (HIV), such as hairy leukoplakia and central nervous system lymphomas, autoimmune diseases, including dermatomyositis, systemic lupus erythematosus, rheumatoid arthritis, Sjögren's syndrome, multiple sclerosis, and posttransplant lymphoproliferative disorder (PTLD), as well as lymproliferative disorders observed in patients with organ transplantation under immunosuppressive treatment. The EBV infection-related disorder may also be any one of several inherited combined immunodeficiencies (CIDs) that result in increased susceptibility to EBV infection and development of EBV-driven diseases, including, for example, individuals with mutations in SH2D1A, ITK, MAGT1, CTPS1, CD27, CD70, CORO1A, and RASGRP1. In these genetically determined immunodeficiencies, the penetrance of the EBV susceptibility is high with more than 50% of patients presenting with at least one severe episode of EBV-driven LPD, including Hodgkin and non-Hodgkin lymphomas. The EBV infection-related disorder may also be seen in HIV-infected patients with acquired immunodeficiency syndrome (AIDS) who often experience lymphoproliferation disorders driven by EBV and represent one of the most frequent causes of death in patients with AIDS. In these methods, the antagonist of the EBV gH or gL protein, or a gH/gL complex, is an anti-EBV gH antibody, an anti-EBV gL antibody, or an anti-EBV gH/gL complex, antibody of this disclosure. Effective treatment or prevention of the disorder may be a result of direct killing or growth inhibition of cells that express an EBV gH or gL protein, or gH/gL complex, or by antagonizing the production of an EBV gH or gL protein, or a gH/gL complex.

This disclosure also provides methods of binding an antibody to a cell that expresses an EBV gH or gL protein, or a gH/gL complex, by contacting a cell that expresses such EBV protein, or complex, with an antibody of this disclosure under conditions which are suitable for binding of the antibody to the EBV gH or gL protein, or gH/gL complex to the cell, and allowing binding therebetween. The antibody may be labeled with a molecule or compound that is useful for qualitatively and/or quantitatively determining the location and/or amount of binding of the antibody to the cell.

This disclosure also provides for the use of an EBV anti-EBV gH antibody, anti-EBV gL antibody, or anti-EBV gH/gL complex, in the preparation of a medicament useful for (i) the therapeutic treatment or diagnostic detection of an EBV infection, (ii) the therapeutic treatment of an EBV infection-related disorder, or (iii) the prevention of a primary infection in an individual. In certain aspects of the invention, the individual is EBV-naïve.

This disclosure also provides a method for inhibiting the production of additional viral particles in an EBV-infected individual or cell, wherein the growth of the EBV infected cell is at least in part dependent upon the expression of an EBV gH or gL protein, or a gH/gL complex, (wherein the EBV gH or gL protein, or a gH/gL complex, may be expressed either within the infected cell itself or a cell that produces polypeptide(s) that have a growth potentiating effect on the infected cells), by contacting the EBV gH or gL protein, or a gH/gL complex, with an antibody that binds to the EBV gH or gL protein, or a gH/gL complex, thereby antagonizing the growth-potentiating activity of the EBV gH or gL protein, or a gH/gL complex, and, in turn, inhibiting the growth of the infected cell. Preferably the growth of the infected cell is completely inhibited. More preferably, binding of the antibody to the EBV gH or gL protein, or a gH/gL complex, induces the death of the infected cell. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells, human cells, or other mammalian cells, insect cells, bacterial cells, or yeast cells.

This disclosure also provides methods of treating a viral infection in an individual, wherein the infection is at least in part dependent upon the expression of an EBV gH or gL protein, or gH/gL complex, by administering to the individual a therapeutically effective amount of an antibody that binds to the EBV gH or gL protein, or gH/gL complex, thereby antagonizing the activity of the EBV gH or gL protein, or gH/gL complex, and resulting in the effective prevention or therapeutic treatment of the infection in the individual. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells, human cells, or other mammalian cells, insect cells, bacterial cells, or yeast cells.

Further embodiments will be evident to the skilled artisan upon a reading of the present specification.

Sequence Listing

The Sequence Listing is submitted as an ASCII text file, created on Nov. 2, 2020, 177 KB, which is incorporated by reference herein. This disclosure provides the following sequences:

SEQUENCE LISTING
The Sequence Listing is submitted as an ASCII text file, created on November 2, 2020, 177 KB, which is incorporated by reference herein. This disclosure provides the following sequences:

| SEQ ID NO | Description | Sequence |
|---|---|---|
| 1 | 770F9 clone Heavy Chain variable region amino acid sequence | EVQLVEAGGGLVRPGGSLRLSCDASGFTFSD SYMSWIRQAPGRGLEWVALISGSGFRIFYGD SVKGRFTISRDNAKKSLYLQLSSLRADDTAI YYCARDTTHFDSWGQGTLVTVSS |
| 2 | 770F9 clone Heavy Chain variable region nucleotide sequence | GAGGTGCAGCTGGTGGAGGCAGGAGGAGGCCTGGTGCGGCC CGGAGGCTCTCTGAGACTGAGCTGTGACGCCTCCGGCTTCA CCTTTTCCGATTCTTACATGTCCTGGATCAGACAGGCACCT GGAAGAGGCCTGGAGTGGGTGGCCCTGATCAGCGGCAGCGG CTTCAGAATCTTCTACGGCGACTCTGTGAAGGGCAGGTTCA CCATCTCTCGCGATAACGCCAAGAAGAGCCTGTATCTGCAG CTGAGCTCCCTGAGGGCCGACGATACAGCCATCTACTATTG CGCCCGCGACACCACACACTTTGATAGCTGGGGCCAGGGCA CCCTGGTGACAGTGTCTAGC |
| 3 | 770F9 clone Heavy Chain CDR1 amino acid sequence (AA26-32) | GFTFSDS |
| 4 | 770F9 clone Heavy Chain CDR2 amino acid sequence (AA52-56) | SGSGFR |
| 5 | 770F9 clone Heavy Chain CDR3 amino acid sequence (AA95-102) | DTTHFDS |
| 6 | 770F9 clone Kappa Chain variable region amino acid sequence | DIQMTQSPSSLSASVGDRVTITCRASQGINNYLAWFQQKPG KAPKSLIYAASNLQSGVPSRFSGSGSGTDFTLTISSLQPED FATYYCQHYNNFPFTFGPGTTSGHQ |
| 7 | 770F9 clone Kappa Chain variable region nucleotide sequence | GACATCCAGATGACCCAGAGCCCAAGCTCCCTGTCCGCCTC TGTGGGCGATCGGGTGACCATCACATGTAGAGCCTCCCAGG GCATCAACAATTACCTGGCCTGGTTTCAGCAGAAGCCCGGC AAGGCCCCTAAGTCTCTGATCTATGCAGCCAGCAACCTGCA GTCCGGCGTGCCTTCTCGGTTTAGCGGCTCCGGCTCTGGCA CAGACTTCACCCTGACAATCTCTAGCCTGCAGCCAGAGGAT TTCGCCACCTACTATTGCCAGCACTACAACAATTTCCCCTT CACCTTCGGCCCCGGCACCACATCCGGCCACCAG |
| 8 | 770F9 clone Kappa Chain CDR1 amino acid sequence (AA24-34) | RASQG1NNYLA |
| 9 | 770F9 clone Kappa Chain CDR2 amino acid sequence (AA50-56) | AASNLQS |
| 10 | 770F9 clone Kappa Chain CDR3 amino acid sequence (AA89-97) | QHYNNFPFT |
| 11 | 770F5 clone Heavy Chain variable region amino acid sequence | EVQLVESGGGLVKPGGSLRLSCSASGFTFSSYSMNWVRQAPGK GLEFVSAITSRGTYIYYADSVKGRFTVSRDNAKNSLYLQMSNV RDEDTAVYYCAREMAGYSSTFDYWGQGALVTVSF |
| 12 | 770F5 clone Heavy Chain variable region nucleotide sequence | GAGGTGCAGCTGGTGGAGTCCGGCGGAGGCCTGGTGAAGCCA GGAGGCTCTCTGAGGCTGTCCTGTTCTGCCAGCGGCTTCACC TTTAGCTCCTACTCCATGAACTGGGTGCGGCAGGCACCTGG CAAGGGCCTGGAGTTCGTGTCCGCCATCACCTCTAGGGGCA CATACATCTACTATGCCGACTCTGTGAAGGGCCGGTTTACC GTGAGCAGAGATAACGCCAAGAATAGCCTGTATCTGCAGAT GTCCAATGTGAGGGACGAGGATACAGCCGTGTACTATTGCG CCCGCGAGATGGCCGGCTACTCTAGCACCTTCGACTATTGG GGCCAGGGCGCCCTGGTGACAGTGTCTTTT |

SEQUENCE LISTING

The Sequence Listing is submitted as an ASCII text file, created on November 2, 2020, 177 KB, which is incorporated by reference herein.
This disclosure provides the following sequences:

| SEQ ID NO | Description | Sequence |
|---|---|---|
| 13 | 770F5 clone Heavy Chain CDR1 amino acid sequence (AA26-32) | GFTFSSY |
| 14 | 770F5 clone Heavy Chain CDR2 amino acid sequence (AA52-56) | TSRGTY |
| 15 | 770F5 clone Heavy Chain CDR3 amino acid sequence (AA95-102) | EMAGYSSTFDY |
| 16 | 770F5 clone Kappa Chain variable region amino acid sequence | EIVLTQSPATLSVSPGEGATLSCRASQGINRYIAWYQHKPGQAPRLLIYDASNRANGIPARFSGRGSGTDFSLTISALEPEDSAVYCQQRSNWPPYTFGQGTKLEIK |
| 17 | 770F5 clone Kappa Chain variable region nucleotide sequence | GAGATCGTGCTGACCCAGTCTCCTGCCACACTGAGCGTGTCCCCAGGAGAGGGAGCCACCCTGTCTTGTAGGGCCAGCCAGGGCATCAACCGCTACATCGCCTGGTATCAGCACAAGCCAGGACAGGCACCAAGGCTGCTGATCTACGACGCCAGCAACAGGGCAAATGGCATCCCCGCACGGTTCTCCGGCAGAGGCTCTGGCACCGACTTTAGCCTGACAATCTCCGCCCTGGAGCCTGAGGATTCTGCCGTGTACTATTGCCAGCAGCGGAGCAATTGGCCCCCTTATACCTTCGGCCAGGGCACAAAGCTGGAGATCAAG |
| 18 | 770F5 clone Kappa Chain CDR1 amino acid sequence (AA24-34) | RASQGINRYIA |
| 19 | 770F5 clone Kappa Chain CDR2 amino acid sequence (AA50-56) | DASNRAN |
| 20 | 770F5 clone Kappa Chain CDR3 amino acid sequence (AA89-97) | QQRSNVVPPYT |
| 21 | 770E4 clone Heavy variable region Chain amino acid sequence | EVQLVESGGGLVRPGGSLRLSCSASGFTFSSYSMNWVRQAPGKGLEFVSAITSRGTYIYYADSVKGRFTVSRDNAKNSLYLQMTNVRDEDTAVYYCAREMAGYSSTFDYWGQGALVTVSS |
| 22 | 770E4 clone Heavy variable region Chain nucleotide sequence | GAGGTGCAGCTGGTGGAGTCCGGCGGAGGCCTGGTGAGGCCCGGAGGCTCTCTGCGCCTGAGCTGTTCCGCCTCTGGCTTCACCTTTAGCTCCTACAGCATGAACTGGGTGAGGCAGGCACCTGGCAAGGGCCTGGAGTTCGTGAGCGCCATCACCTCCAGAGGCACATACATCTACTATGCCGACTCCGTGAAGGGCCGGTTCACCGTGAGCCGGGATAACGCCAAGAATAGCCTGTATCTGCAGATGACCAATGTGCGGGACGAGGATACAGCCGTGTACTATTGCGCCAGAGAGATGGCCGGCTACTCTAGCACCTTCGACTATTGGGGACAGGGCGCCCTGGTGACAGTGTCCTCT |
| 23 | 770E4 clone Heavy Chain CDR1 amino acid sequence (AA26-32) | GFTFSSY |
| 24 | 770E4 clone Heavy Chain CDR2 amino acid sequence (AA52-56) | TSRGTY |
| 25 | 770E4 clone Heavy Chain CDR3 amino acid sequence (AA95-102) | EMAGYSSTFDY |
| 26 | 770E4 clone Kappa Chain variable region amino acid sequence | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPQVTFGGGTKVEIK |

SEQUENCE LISTING

The Sequence Listing is submitted as an ASCII text file, created on November 2, 2020, 177 KB, which is incorporated by reference herein.

This disclosure provides the following sequences:

| SEQ ID NO | Description | Sequence |
|---|---|---|
| 27 | 770E4 clone Kappa Chain variable region nucleotide sequence | GACATCCAGATGACCCAGTCCCCTAGCTCCCTGAGCGCCTCC GTGGGCGACCGGGTGACCATCACATGTAGAGCCTCTCAGGG CATCAGGAACGATCTGGGCTGGTACCAGCAGAAGCCCGGCA AGGCCCCTAAGCGCCTGATCTATGCAGCCTCTAGCCTGCAGT CTGGCGTGCCAAGCCGGTTCTCTGGCAGCGGCTCCGGCACC GAGTTTACCCTGACAATCTCCTCTCTGCAGCCAGAGGATTTC GCCACATACTATTGCCTGCAGCACAATAGCTACCCCCAGGT GACCTTTGGCGGCGGCACAAAGGTGGAGATCAAG |
| 28 | 770E4 clone Kappa Chain CDR1 amino acid sequence (AA24-34) | RASQGIRNDLG |
| 29 | 770E4 clone Kappa Chain CDR2 amino acid sequence (AA50-56) | AASSLQS |
| 30 | 770E4 clone Kappa Chain CDR3 amino acid sequence (AA89-97) | LQHNSYPQVT |
| 31 | 769C5 clone Heavy Chain variable region amino acid sequence | EVQLVESGGGWQPGRSLRLSCAASGFTFRRHAMHWVRQAPG QGLEWLSMIYSDGTNKIYADSVKGRFTISRDNSKNTLY LQMDSVGAEDTATYFCATEPQTGRGPLDYWGRGTLVIVSS |
| 32 | 769C5 clone Heavy Chain variable region nucleotide sequence | GAGGTGCAGCTGGTGGAGTCCGGCGGAGGAGTGGTGCAGCC AGGCCGGAGCCTGAGGCTGAGCTGTGCAGCCTCCGGCTTCA CCTTTCGGAGACACGCCATGCACTGGGTGCGGCAGGCACCA GGACAGGGCCTGGAGTGGCTGTCTATGATCTACAGCGACGG CACAAACAAGATCTATGCCGATTCTGTGAAGGGCCGGTTCA CCATCTCCAGAGACAACTCTAAGAATACACTGTACCTGCAG ATGGACAGCGTGGGAGCAGAGGATACCGCAACATATTTTG CGCAACCGAGCCACAGACAGGAAGGGGACCTCTGGATTACT GGGGAAGGGGCACCCTGGTCATCGTGAGCTCC |
| 33 | 769C5 clone Heavy Chain CDR1 amino acid sequence (AA26-32) | GFTFRRH |
| 34 | 769C5 clone Heavy Chain CDR2 amino acid sequence (AA52-56) | YSDGTN |
| 35 | 769C5 clone Heavy Chain CDR3 amino acid sequence (AA95-102) | EPQTGRGPLDY |
| 36 | 769C5 clone Kappa Chain variable region amino acid sequence | DIQMTQSPSSLSASVGDRVTITCRASQGIINYLAWYQQKPG KAPKLLIYAASTLLSGVPSRFSGSGTGTDFTLTISSLQPED VATYYCQKYHNAPRTFGQGTKVDIK |
| 37 | v clone Kappa Chain variable region nucleotide sequence | GACATCCAGATGACCCAGTCTCCTAGCTCCCTGTCCGCCTC TGTGGGCGATCGGGTGACCATCACATGTAGAGCCAGCCAGG GCATCATCAACTACCTGGCCTGGTATCAGCAGAAGCCCGGC AAGGCCCCTAAGCTGCTGATCTACGCAGCCTCTACCCTGCT GAGCGGCGTGCCATCCAGGTTCAGCGGCTCCGGCACCGGAA CAGACTTTACCCTGACAATCTCTAGCCTGCAGCCAGAGGAT GTGGCCACATACTATTGCCAGAAGTATCACAATGCACCACG GACCTTCGGCCAGGGAACAAAGGTGGACATCAAG |
| 38 | 769C5 clone Kappa Chain CDR1 amino acid sequence (AA24-34) | RASQGIINYLA |
| 39 | 769C5 clone Kappa Chain CDR2 amino acid sequence (AA50-56) | AASTLLS |

SEQUENCE LISTING

The Sequence Listing is submitted as an ASCII text file, created on November 2, 2020, 177 KB, which is incorporated by reference herein.

This disclosure provides the following sequences:

| SEQ ID NO | Description | Sequence |
|---|---|---|
| 40 | 769C5 clone Kappa Chain CDR3 amino acid sequence (AA89-97) | QKYHNAPRT |
| 41 | 770F12 clone Heavy Chain variable region amino acid sequence | EVQLLESGGGLVQPGGSLRLSCAASGFTFNSYAMNWVRQAPG KGLEWVSGISSSAAGRHYADSVKGRFTISRDNSKNTLYLQMS GLRAEDTAVYFCAKAGARNYYYGMDVVVGQGTTVTVSS |
| 42 | 770F12 clone Heavy Chain variable region nucleotide sequence | GAGGTGCAGCTGCTGGAGTCCGGCGGAGGCCTGGTGCAGCCA GGAGGCTCTCTGAGGCTGAGCTGTGCAGCCTCCGGCTTCAC CTTTAACTCTTATGCCATGAATTGGGTGAGGCAGGCACCTG GCAAGGGCCTGGAGTGGGTGTCCGGCATCAGCTCCTCTGCC GCAGGCCGGCACTACGCAGACTCTGTGAAGGGCCGGTTCAC CATCAGCCGGGATAACAGCAAGAATACACTGTATCTGCAGA TGTCCGGCCTGAGGGCAGAGGACACCGCCGTGTACTTTTGC GCCAAGGCCGGCGCCCGCAACTACTATTACGGAATGGACGT GTGGGGACAGGGAACCACAGTGACAGTGAGCTCC |
| 43 | 770F12 clone Heavy Chain CDR1 amino acid sequence (AA26-32) | GFTFNSY |
| 44 | 770F12 clone Heavy Chain CDR2 amino acid sequence (AA52-56) | SSSAAG |
| 45 | 770F12 clone Heavy Chain CDR3 amino acid sequence (AA95-102) | AGARNYYYGMDV |
| 46 | 770F12 clone Kappa Chain variable region amino acid sequence | EIVMTQSPATLSVSPGERATLSCRASQGVSSNLAWYQQKFGQA PRLLIFSASTRATGTPARFSGSGSGTEFTLTISSLQSEDFAVY YCQQYDNWPLSFGGGTKVEIK |
| 47 | 770F12 clone Kappa Chain variable region nucleotide sequence | GAGATCGTGATGACCCAGAGCCCAGCCACACTGTCCGTGTC TCCTGGAGAGAGGGCCACCCTGTCTTGTAGAGCCAGCCAGG GCGTGAGCTCCAACCTGGCATGGTACCAGCAGAAGTTCGGC CAGGCCCCACGGCTGCTGATCTTTAGCGCCTCCACCAGGGC AACCGGAACACCAGCCCGCTTCTCTGGCAGCGGCTCCGGCA CAGAGTTTACCCTGACAATCTCTAGCCTGCAGTCCGAGGAC TTCGCCGTGTACTATTGCCAGCAGTATGATAATTGGCCCCT GTCTTTTGGCGGCGGCACAAAGGTGGAGATCAAG |
| 48 | 770F12 clone Kappa Chain CDR1 amino acid sequence (AA24-34) | RASQGVSSNLA |
| 49 | 770F12 clone Kappa Chain CDR2 amino acid sequence (AA50-56) | SASTRAT |
| 50 | 770F12 clone Kappa Chain CDR3 amino acid sequence (AA89-97) | QQYDNWPLS |
| 51 | 770F3 clone Heavy Chain variable region amino acid sequence | QVHLQESGPGPVKPSETLSLTCTVSRGSMSGYYWTWIRLPPGK GLEWIGNIHDSGTTDYNPSLRNRVSISADASKSQFYLKLSSVT AADTAVYYCVRDGRYFGATALDPWGQGSLVTVSP |
| 52 | 770F3 clone Heavy Chain variable region nucleotide sequence | CAGGTGCACCTGCAGGAGTCTGGCCCAGGACCAGTGAAGCC ATCTGAGACACTGAGCCTGACCTGTACAGTGTCCGGGGCT CTATGAGCGGCTACTATTGGACATGGATCAGGCTGCCACCT GGCAAGGGCCTGGAGTGGATCGGCAACATCCACGACAGCGG CACCACAGATTACAACCCTTCCCTGCGGAATAGAGTGTCCAT CTCTGCCGACGCCAGCAAGTCCCAGTTCTATCTGAAGCTGAG CTCCGTGACCGCAGCAGACACAGCCGTGTACTATTGCGTGA |

SEQUENCE LISTING
The Sequence Listing is submitted as an ASCII text file, created on November 2, 2020, 177 KB, which is incorporated by reference herein.
This disclosure provides the following sequences:

| SEQ ID NO | Description | Sequence |
|---|---|---|
|  |  | GGGATGGCCGCTACTTTGGAGCAACCGCCCTGGACCCCTGG GGACAGGGCTCCCTGGTGACAGTGTCTCCA |
| 53 | 770F3 clone Heavy Chain CDR1 amino acid sequence (AA26-32) | RGSMSGY |
| 54 | 770F3 clone Heavy Chain CDR2 amino acid sequence (AA52-56) | HDSGT |
| 55 | 770F3 clone Heavy Chain CDR3 amino acid sequence (AA95-102) | DGRYFGATALDP |
| 56 | 770F3 clone Kappa Chain variable region amino acid sequence | EIVLTQSPATLSLSPGERATLSCRASQGLNRYLAWYQQKPGQA PRLLIYDASNRATGIPARFSGRGSGTDFSLTISALEPEDSAVY YCQQRSNVVPPYTFGQGTKLEIK |
| 57 | 770F3 clone Kappa Chain variable region nucleotide sequence | GAGATCGTGCTGACCCAGTCTCCTGCCACACTGAGCCTGTCC CCAGGAGAGAGGGCCACCCTGTCTTGTAGGGCCAGCCAGGG CCTGAACAGGTACCTGGCCTGGTATCAGCAGAAGCCAGGAC AGGCACCAAGGCTGCTGATCTACGACGCCAGCAATAGAGCA ACAGGCATCCCCGCACGGTTCTCCGGCAGAGGCTCTGGCAC CGACTTTAGCCTGACAATCTCCGCCCTGGAGCCTGAGGATTC TGCCGTGTACTATTGCCAGCAGAGAAGCAACTGGCCCCCTT ATACCTTCGGCCAGGGCACAAAGCTGGAGATCAAG |
| 58 | 770F3 clone Kappa Chain CDR1 amino acid sequence (AA24-34) | RASQGLNRYLA |
| 59 | 770F3 clone Kappa Chain CDR2 amino acid sequence (AA50-56) | DASNRAT |
| 60 | 770F3 clone Kappa Chain CDR3 amino acid sequence (AA89-97) | QQRSNWPPYT |
| 61 | 770G10 clone Heavy Chain variable region amino acid sequence | EVQLVESGGGVVQPGRSLKISCAVSGFDLSSFGMHWVRQAPG KGLEWLSVISHDGNRKFYADSVKGRFTISRDTSKNTLYLQMN SLRTEDTALYYCAREPYTSGWFFGWFDPWGQGTLVTVSS |
| 62 | 770G10 clone Heavy Chain variable region nucleotide sequence | GAGGTGCAGCTGGTGGAGTCTGGCGGAGGAGTGGTGCAGCCA GGCCGGAGCCTGAAGATCTCCTGTGCCGTGTCTGGCTTCGA CCTGAGCTCCTTTGGCATGCACTGGGTGCGGCAGGCACCAG GCAAGGGCCTGGAGTGGCTGTCCGTGATCTCTCACGACGGC AACAGGAAGTTCTACGCCGATTCCGTGAAGGGCCGGTTTAC CATCAGCAGAGACACCTCCAAGAACACACTGTATCTGCAGA TGAATTCTCTGAGGACCGAGGATACAGCCCTGTACTATTGC GCAAGGGAGCCATACACAAGCGGCTGGTTCTTTGGCTGGTT CGATCCTTGGGGCCAGGGCACCCTGGTGACAGTGTCTAGC |
| 63 | 770G10 clone Heavy Chain CDR1 amino acid sequence (AA26-32) | GFDLSSF |
| 64 | 770G10 clone Heavy Chain CDR2 amino acid sequence (AA52-56) | SHDGNR |
| 65 | 770G10 clone Heavy Chain CDR3 amino acid sequence (AA95-102) | EPYTSGWFFGWFDP |

SEQUENCE LISTING

The Sequence Listing is submitted as an ASCII text file, created on November 2, 2020, 177 KB, which is incorporated by reference herein.
This disclosure provides the following sequences:

| SEQ ID NO | Description | Sequence |
|---|---|---|
| 66 | 770G10 clone Lambda Chain variable region amino acid sequence | QSALTQPASVSGSPGQSITLSCTGTSRDVGDYNYVSWYQQHPG KAPKLIMYEVHKRPSGISNRFSGSKSGTTASLTISGLQADDEG DYYCSSYTSKNTYVFGSGTQVT |
| 67 | 770G10 clone Lambda Chain variable region nucleotide sequence | CAGTCCGCCCTGACCCAGCCAGCCTCTGTGAGCGGCTCCCCC GGCCAGTCCATCACACTGTCTTGTACCGGCACATCCCGGGAC GTGGGCGATTACAACTACGTGAGCTGGTACCAGCAGCACCC AGGCAAGGCACCTAAGCTGATCATGTATGAGGTGCACAAGC GGCCCTCTGGCATCAGCAATAGATTCTCTGGCAGCAAGTCC GGCACCACAGCCAGCCTGACCATCTCCGGCCTGCAGGCAGA CGATGAGGGCGACTACTATTGCAGCTCCTACACCTCTAAGA ACACATACGTGTTCGGCAGCGGCACCCAGGTGACA |
| 68 | 770G10 clone Lambda Chain CDR1 amino acid sequence (AA24-34) | TGTSRDVGDYNYVS |
| 69 | 770G10 clone Lambda Chain CDR2 amino acid sequence (AA50-56) | EVHKRPS |
| 70 | 770G10 clone Lambda Chain CDR3 amino acid sequence (AA89-97) | SSYTSKNTYV |
| 71 | 769C3 clone Heavy Chain variable region amino acid sequence | QVHLVQSGAEMKKPGASVKVSCKASGGSFSIYAISWVRQAPG QGPEWVGGIVPISDTTTYAQRFQGRVTVTADKSTDTAYMELR SLTSEDTAVYYCARDPGYYDISGYYHRAFDIWGQGTMVSVSS |
| 72 | 769C3 clone Heavy Chain variable region nucleotide sequence | CAGGTGCACCTGGTGCAGAGCGGCGCAGAGATGAAGAAGCC AGGCGCCAGCGTGAAGGTGTCCTGTAAGGCCTCTGGCGGCT CTTTCAGCATCTACGCCATCTCCTGGGTGCGGCAGGCACCA GGACAGGGCCCTGAGTGGGTGGGCGGCATCGTGCCCATCTC TGACACCACAACCTACGCCCAGCGGTTTCAGGGCAGAGTGA CAGTGACCGCCGACAAGTCCACAGATACCGCCTATATGGAG CTGAGGTCCCTGACATCTGAGGACACCGCCGTGTACTATTG CGCCAGGGACCCCGGCTACTATGATATCAGCGGCTACTATC ACCGCGCCTTCGATATCTGGGGCCAGGGCACAATGGTGTCC GTGAGCTCC |
| 73 | 769C3 clone Heavy Chain CDR1 amino acid sequence (AA26-32) | GGSFSIY |
| 74 | 769C3 clone Heavy Chain CDR2 amino acid sequence (AA52-56) | VPISDT |
| 75 | 769C3 clone Heavy Chain CDR3 amino acid sequence (AA103-113) | DPGYYDISGYYHRAFDI |
| 76 | 769C3 clone Lambda Chain variable region amino acid sequence | QSALTQPPSVSGAPGQRVTISCTGSSSNIGAGHDVHWYQQFP APQLLIFGNNNRPSGVPDRFSGSNAGTSASLTITGLQTADEA KTDYYCQSYDNSLSGTVFGGGTKLT |
| 77 | 769C3 clone Lambda Chain variable region nucleotide sequence | CAGAGCGCCCTGACCCAGCCACCTAGCGTGTCCGGCGCACC AGGCCAGCGGGTGACCATCTCCTGTACAGGCAGCTCCTCTA ATATCGGAGCAGGACACGACGTGCACTGGTACCAGCAGTTC CCAAAGACAGCCCCCCAGCTGCTGATCTTTGGCAACAATAA CCGGCCTTCCGGCGTGCCAGATAGATTCTCTGGCAGCAATG CCGGCACCTCCGCCTCTCTGACCATCACAGGCCTGCAGACA GCCGACGAGGCCGATTACTATTGCCAGTCTTATGACAACAG CCTGTCCGGCACCGTGTTTGGAGGAGGAACCAAGCTGACA |
| 78 | 769C3 clone Lambda Chain CDR1 amino acid sequence (AA24-34) | TGSSSNIGAGHDVH |

SEQUENCE LISTING
The Sequence Listing is submitted as an ASCII text file, created on
November 2, 2020, 177 KB, which is incorporated by reference herein.
This disclosure provides the following sequences:

| SEQ ID NO | Description | Sequence |
|---|---|---|
| 79 | 769C3 clone Lambda Chain CDR2 amino acid sequence (AA50-56) | GNNNRPS |
| 80 | 769C3 clone Lambda Chain CDR3 amino acid sequence (AA89-97) | QSYDNSLSGTV |
| 81 | 769B2 clone Heavy Chain variable region amino acid sequence | QVHLVQSGAEVKKSGSSVTVSCRAAGGSFSIYAITWVRQAPG HGLEWMGGIVPMSDTVTYAQEFQARVTISADKSTNTAYMELR SLKYADSAIYFCARDPGYYDKSGYYHRAFDIWGQGTLVTVSS |
| 82 | 769B2 clone Heavy Chain variable region nucleotide sequence | CAGGTGCACCTGGTGCAGTCCGGCGCAGAGGTGAAGAAGTC TGGCAGCTCCGTGACCGTGAGCTGTAGGGCAGCAGGAGGCT CCTTCTCTATCTACGCCATCACATGGGTGCGCCAGGCACCA GGACACGGCCTGGAGTGGATGGGAGGAATCGTGCCTATGTC CGACACCGTGACATACGCCCAGGAGTTTCAGGCCCGGGTGA CCATCAGCGCCGATAAGTCCACCAACACAGCCTATATGGAG CTGCGGAGCCTGAAGTACGCCGACAGCGCCATCTATTTCTG CGCCCGGGACCCCGGCTACTATGATAAGTCTGGCTACTATC AAGAGCCTTTGATATCTGGGGCCAGGGCACCCTGGTGACAG TGTCTAGC |
| 83 | 769B2 clone Heavy Chain CDR1 amino acid sequence (AA26-32) | GGSFSIY |
| 84 | 769B2 clone Heavy Chain CDR2 amino acid sequence (AA52-56) | VPMSDT |
| 85 | 769B2 clone Heavy Chain CDR3 amino acid sequence (AA95-102) | DPGYYDKSGYYHRAFDI |
| 86 | 769B2 clone Lambda Chain variable region amino acid sequence | QSVLTQPPSVSGAPGQRVTISCTGGGSNIGADHDVHWYQQYP GAAPKLLIFGDNNRPSGVPDRFSGSKSGTSASLAITGLQAED EADYYCQSYDNSLSRAVFGGGTKLT |
| 87 | 769B2 clone Lambda Chain variable region nucleotide sequence | CAGAGCGTGCTGACCCAGCCACCTAGCGTGTCCGGCGCACC AGGCCAGAGGGTGACCATCAGCTGTACAGGAGGAGGCTCCA ACATCGGAGCAGACCACGATGTGCACTGGTACCAGCAGTAT CCAGGAGCAGCACCAAAGCTGCTGATCTTCGGCGACAACAA TCGGCCTTCCGGCGTGCCAGATAGATTTTCTGGCAGCAAGT CCGGCACCTCTGCCAGCCTGGCCATCACAGGCCTGCAGGCA GAGGACGAGGCAGATTACTATTGCCAGTCTTACGACAATTC CCTGTCTCGGGCCGTGTTCGGAGGAGGAACCAAGCTGACA |
| 88 | 769B2 clone Lambda Chain CDR1 amino acid sequence (AA24-34) | TGGGSNIGADHDVH |
| 89 | 769B2 clone Lambda Chain CDR2 amino acid sequence (AA50-56) | GDNNRPS |
| 90 | 769B2 clone Lambda Chain CDR3 amino acid sequence (AA89-97) | QSYDNSLSRAV |
| 91 | 769A7 clone Heavy Chain variable region amino acid sequence | QVQLQESGPGLVRPSETLSLTCSVSGGSIIGYYWSWIRQPPG KGLEWIGYIFYSDNIRYSPSLKSRVAISADSSRNEVSLRLNS VTAADTAVYYCARDGNYYDSSGPTRLWFDPWGQGTLVTVSS |

SEQUENCE LISTING

The Sequence Listing is submitted as an ASCII text file, created on November 2, 2020, 177 KB, which is incorporated by reference herein.
This disclosure provides the following sequences:

| SEQ ID NO | Description | Sequence |
|---|---|---|
| 92 | 769A7 clone Heavy Chain variable region nucleotide sequence | CAGGTGCAGCTGCAGGAGTCCGGCCCAGGCCTGGTGAGGCC CTCCGAGACACTGTCTCTGACATGTAGCGTGTCCGGCGGCTC CATCATCGGCTACTATTGGTCTTGGATCAGACAGCCACCTGG CAAGGGCCTGGAGTGGATCGGCTACATCTTCTATAGCGACA ACATCAGGTACTCTCCCAGCCTGAAGAGCCGCGTGGCAATC TCCGCCGATAGCTCCCGGAACGAGGTGTCTCTGAGACTGAA TAGCGTGACCGCCGCCGACACAGCCGTGTACTATTGCGCCC GGGACGGCAATTACTATGATTCTAGCGGCCCTACCAGACTG TGGTTTGATCCATGGGGCCAGGGCACCCTGGTGACAGTGTC CTCT |
| 93 | 769A7 clone Heavy Chain CDR1 amino acid sequence (AA26-32) | GGSIIGY |
| 94 | 769A7 clone Heavy Chain CDR2 antino acid sequence (AA52-56) | FYSDN |
| 95 | 769A7 clone Heavy Chain CDR3 amino acid sequence (AA95-102) | DGNYYDSSGPTRLWFDP |
| 96 | 769A7 clone Lambda Chain variable region amino acid sequence | QSVLTQPPSVSGAPGQRVSISCTGSTSNIGADYDVHWYQHSP GTGPRLLIFGSTNRPSGVPDRFSGSKSGTSASLAITGLQADD EAEYYCQSYDRTLGGYVFGTGTQVT |
| 97 | 769A7 clone Lambda Chain variable region nucleotide sequence | CAGTCTGTGCTGACCCAGCCACCTAGCGTGTCCGGCGCACC AGGCCAGAGGGTGTCTATCAGCTGTACCGGCTCCACATCTA ACATCGGCGCCGACTACGATGTGCACTGGTATCAGCACTCC CCAGGAACCGGACCCAGACTGCTGATCTTCGGCTCTACAAA TAGGCCTAGCGGCGTGCCAGACCGGTTCAGCGGCAGCAAGT CTGGCACCAGCGCCTCCCTGGCCATCACAGGCCTGCAGGCA GACGATGAGGCCGAGTACTATTGCCAGAGCTACGATCGGAC CCTGGGCGGATACGTGTTCGGAACCGGCACACAGGTGACA |
| 98 | 769A7 clone Lambda Chain CDR1 amino acid sequence (AA24-34) | TGSTSNIGADYDVH |
| 99 | 769A7 clone Lambda Chain CDR2 amino acid sequence (AA50-56) | GSTNRPS |
| 100 | 769A7 clone Lambda Chain CDR3 amino acid sequence (AA89-97) | QSYDRTLGGYV |
| 101 | 769C4 clone Heavy Chain variable region amino acid sequence | QVQLMQSGAEVRKPGSSVRVSCTASGGTFTNFAFTWVRRAPG QGLEWMGGFLPFFGTSNYAQHLQGRVAITADKSTSTVYMELR SLRPEDTGVYYCARASGDTGGYYLSYYYGMDVWGQGTTVTV SS |
| 102 | 769C4 clone Heavy Chain variable region nucleolide sequence | CAGGTGCAGCTGATGCAGTCTGGCGCAGAGGTGCGGAAGCC AGGCAGCTCCGTGAGAGTGAGCTGTACCGCCTCCGGCGGCA CCTTCACAAACTTCGCCTTTACATGGGTGCGGAGAGCACCA GGACAGGGCCTGGAGTGGATGGGCGGCTTTCTGCCTTTCTTT GGCACCAGCAATTATGCACAGCACCTGCAGGGAAGGGTGGC AATCACAGCCGACAAGTCCACCTCTACAGTGTACATGGAGC TGAGGTCCCTGCGCCCCGAGGACACCGGCGTGTACTATTGC GCCAGAGCCTCTGGCGATACAGGCGGCTACTATCTGAGCTA CTATTACGGAATGGACGTGTGGGGACAGGGAACCACAGTGA CCGTGTCTAGC |
| 103 | 769C4 clone Heavy Chain CDR1 (AA26-32) | GGTFTNF |

SEQUENCE LISTING

The Sequence Listing is submitted as an ASCII text file, created on November 2, 2020, 177 KB, which is incorporated by reference herein.

This disclosure provides the following sequences:

| SEQ ID NO | Description | Sequence |
|---|---|---|
| 104 | 769C4 clone Heavy Chain CDR2 (AA52-57) | LPFFGT |
| 105 | 769C4 clone Heavy Chain CDR3 (AA99-116) | ASGDTGGYYLSYYYGMDV |
| 106 | 769C4 clone Kappa Chain variable region amino acid sequence | DIVMTQSPLSLPVTPGEPASISCRSSQSLLHTNGYNYLDWYL QKPGQSPQLLIYLGSNRASGVPDRFSGSGSGTDFTLKGGVEA EDVGVYYCVRALRGLSFGGGTEVEIE |
| 107 | 769C4 clone Kappa Chain variable region nucleotide sequence | GACATCGTGATGACCCAGTCCCCACTGTCTCTGCCCGTGACA CCTGGCGAGCCAGCCTCTATCAGCTGTCGGAGCTCCCAGTCT CTGCTGCACACCAACGGCTACAATTATCTGGATTGGTACCTG CAGAAGCCCGGCCAGAGCCCTCAGCTGCTGATCTATCTGGG CAGCAACAGGGCCTCCGGCGTGCCCGACCGCTTCTCCGGCT CTGGCAGCGGCACCGACTTCACCCTGAAGGGAGGAGTGGAG GCAGAGGACGTGGGCGTGTACTATTGCGTGCGGGCCCTGAG AGGCCTGTCTTTCGGCGGCGGCACAGAGGTGGAGATCGAG |
| 108 | 769C4 clone Kappa Chain CDR1 (AA24-39) | RSSQSLLHTNGYNYLD |
| 109 | 769C4 clone Kappa Chain CDR2 (AA55-61) | LGSNRAS |
| 110 | 769C4 clone Kappa Chain CDR3 (AA93-100) | VRALRGLS |
| 111 | 769B10 clone Heavy Chain variable region amino acid sequence | EVQLVESGGGIVQPGGSLRVSCAASGFSLSDHYMDVVVRQAP GRGLEWVGRSRNKENSFIIEFAASVRRRFTISRDDSNSLLHL QMNNLKSEDTAVYFCARVGYYDLVVSGYSGNWYIDVWGRGTL VTVSS |
| 112 | 769B10 clone Heavy Chain variable region nucleotide sequence | GAGGTGCAGCTGGTGGAGTCCGGCGGAGGAATCGTGCAGCC AGGAGGCTCTCTGCGGGTGAGCTGTGCAGCCTCCGGCTTCTC TCTGAGCGACCACTACATGGATTGGGTGAGACAGGCACCTG GAAGGGGCCTGGAGTGGGTGGGCCGCTCTCGGAACAAGGA GAATAGCTTCACCACAGAGTTTGCCGCCTCCGTGCGGAGAA GGTTCACCATCAGCCGGGACGATTCCAACTCTCTGCTGCAC CTGCAGATGAACAATCTGAAGTCTGAGGACACAGCCGTGTA TTTTTGCGCCCGCGTGGGCTACTATGACCTGTGGAGCGGCT ACTCCGGCAATTGGTATATCGACGTGTGGGGAAGGGGCACC CTGGTCATCGTGAGCTCC |
| 113 | 769B10 clone Heavy Chain CDR1 (AA26-32) | GFSLSDH |
| 114 | 769B10 clone Heavy Chain CDR2 (AA52-59) | RNKENSFT |
| 115 | 769B10 clone Heavy Chain CDR3 (AA101-118) | VGYYDLWSGYSGNWYIDV |
| 116 | 769B10 clone Kappa Chain variable region amino acid sequence | DIQMTQSPSSLSASLGDSVTITCRASQTMSNFLNVVYQQKP GKAPKFLIYAASRLQSGVPSRFSGSGSGTQFTLTISNLQPE DFATYYCQQSFIFPYTFGGGTKVEVE |
| 117 | 769B10 clone Kappa Chain variable region nucleotide sequence | GACATCCAGATGACCCAGAGCCCTAGCTCCCTGTCTGCCAG CCTGGGCGATTCCGTGACCATCACATGTCGGGCCTCCCAGA CAATGTCTAACTTCCTGAATTGGTACCAGCAGAAGCCCGGC AAGGCCCCTAAGTTTCTGATCTATGCAGCCAGCCGGCTGCA GTCCGGCGTGCCAAGCCGGTTCAGCGGCAGCGGCAGCGGCA CCCAGTTTACCCTGACAATCTCTAACCTGCAGCCAGAGGAC TTCGCCACATACTATTGCCAGCAGTCCTTCATCTTTCCCTA CACCTTTGGCGGCGGCACAAAGGTGGAGGTGGAG |

SEQUENCE LISTING
The Sequence Listing is submitted as an ASCII text file, created on
November 2, 2020, 177 KB, which is incorporated by reference herein.
This disclosure provides the following sequences:

| SEQ ID NO | Description | Sequence |
|---|---|---|
| 118 | 769B10 clone Kappa Chain CDR1 (AA24-34) | RASQTMSNFLN |
| 119 | 769B10 clone Kappa Chain CDR2 (AA50-56) | AASRLQS |
| 120 | 769B10 clone Kappa Chain CDR3 (AA89-97) | QQSFIFPYT |
| 121 | 770E9 clone Heavy Chain variable region amino acid sequence | QVQLVQSGAEVKKPGASVKVSCKTSGYTFSRYAISWVRQAP GQGLEWVGWINPYTGTANYAQILQGRVTVTTDTSTTTAYME LRSLTSDDTAMYYCARHLPGTAVASYFGQGSLVTVSF |
| 122 | 770E9 clone Heavy Chain variable region nucleotide sequence | CAGGTGCAGCTGGTGCAGTCCGGCGCAGAGGTGAAGAAGCC AGGAGCCTCTGTGAAGGTGAGCTGTAAGACATCCGGCTACA CCTTCTCTCGGTATGCAATCAGCTGGGTGAGACAGGCACCA GGACAGGGCCTGGAGTGGGTGGGCTGGATCAACCCTTACAC AGGCACCGCCAATTATGCCCAGATCCTGCAGGGCCGGGTGA CAGTGACCACAGACACCTCTACCACAACCGCCTACATGGAG CTGAGGAGCCTGACATCCGACGATACCGCCATGTACTATTG CGCAAGGCACCTGCCAGGAACAGCAGTGGCCAGCTATTTCG GCCAGGGCTCCCTGGTGACCGTGTCTTTT |
| 123 | 770E9 clone Heavy Chain CDR1 (AA26-32) | GYTFSRY |
| 124 | 770E9 clone Heavy Chain CDR2 (AA52-57) | NPYTGT |
| 125 | 770E9 clone Heavy Chain CDR3 (AA99-108) | HLPGTAVASY |
| 126 | 770E9 clone Kappa Chain variable region amino acid sequence | EIVMTQSPSSSVSPGERATLSCRASQGVSSNLAWYQQKFGQ APRLLIFSASTRATGTPARFSGSGSGTEFTLTISSLQSEDF AVYYCQQYDNWPLSFGGGTKVEIK |
| 127 | 770E9 clone Kappa Chain variable region nucleotide sequence | GAGATCGTGATGACCCAGTCTCCAAGCTCCTCTGTGAGCCCT GGAGAGAGGGCCACACTGAGCTGTAGAGCCTCCCAGGGCGT GAGCTCCAACCTGGCATGGTACCAGCAGAAGTTCGGCCAGG CCCCACGGCTGCTGATCTTTTCCGCCTCTACCAGGGCAACCG GAACACCAGCACGCTTCAGCGGCTCCGGCTCTGGCACAGAG TTTACCCTGACAATCTCTAGCCTGCAGTCCGAGGACTTCGCC GTGTACTATTGCCAGCAGTATGATAATTGGCCCCTGTCTTTT GGCGGCGGCACCAAGGTGGAGATCAAG |
| 128 | 770E9 clone Kappa Chain CDR1 (AA23-33) | RASQGVSSNLA |
| 129 | 770E9 clone Kappa Chain CDR2 (AA49-55) | SASTRAT |
| 130 | 770E9 clone Kappa Chain CDR3 (AA88-96) | QQYDNWPLS |
| 131 | 769C2 clone Heavy Chain variable region amino acid sequence | EVQLVESGGGLVKPGGSLRLSCAASGFTFSTYAMDWVRQAPG KGLEWVSLISSRSSNIYYSDSVKGRFTISRDNAKNSLFLQMN SLRAEDTAVYYCAREAGGFHSHFDMWGQGTLVTVSS |
| 132 | 769C2 clone Heavy Chain variable region nucleotide sequence | GAGGTGCAGCTGGTGGAGTCTGGCGGAGGCCTGGTGAAGCC AGGAGGCTCTCTGAGGCTGAGCTGTGCAGCCTCCGGCTTCA CCTTTTCTACATACGCAATGGACTGGGTGCGGCAGGCACCTG GCAAGGGCCTGGAGTGGGTGAGCCTGATCAGCTCCAGGTCT AGCAACATCTACTATAGCGACTCCGTGAAGGGCCGGTTCAC CATCAGCCGGGATAACGCCAAGAATAGCCTGTTTCTGCAGA |

SEQUENCE LISTING

The Sequence Listing is submitted as an ASCII text file, created on November 2, 2020, 177 KB, which is incorporated by reference herein.
This disclosure provides the following sequences:

| SEQ ID NO | Description | Sequence |
|---|---|---|
| | | TGAATTCCCTGAGGGCCGAGGACACAGCCGTGTACTATTGC GCAAGGGAGGCAGGAGGATTCCACAGCCACTTTGATATGTG GGGCCAGGGCACCCTGGTGACAGTGTCCTCT |
| 133 | 769C2 clone Heavy Chain CDR1 (AA26-32) | GFTFSTY |
| 134 | 769C2 clone Heavy Chain CDR2 (AA52-57) | SSRSSN |
| 135 | 769C2 clone Heavy Chain CDR3 (AA99-109) | EAGGFHSHFDM |
| 136 | 769C2 clone Lambda Chain variable region amino acid sequence | QSVLTQPASVSGSLGQSVTISCTGTSSDVGGYDYVSVVYQQH PGKAPKLMIFEVNNRPSGVSTRFSGSKSGNTASLTISGLQAE DEADYYCNSYSTTTTWVFGGGTSLT |
| 137 | 769C2 clone Lambda Chain variable region nucleotide sequence | CAGTCTGTGCTGACCCAGCCAGCCTCTGTGAGCGGCTCCCTG GGCCAGAGCGTGACAATCTCCTGTACCGGCACAAGCTCCGA CGTGGGAGGATACGATTATGTGAGCTGGTACCAGCAGCACC CAGGCAAGGCACCTAAGCTGATGATCTTCGAGGTGAACAAT CGGCCCTCCGGCGTGTCTACCAGATTTTCTGGCAGCAAGTCC GGCAACACCGCCTCTCTGACAATCAGCGGCCTGCAGGCAGA GGACGAGGCAGATTACTATTGCAATTCTTATAGCACCACAA CCACATGGGTGTTCGGAGGAGGCACCTCCCTGACA |
| 138 | 769C2 clone Lambda Chain CDR1 (AA23-36) | TGTSSDVGGYDYVS |
| 139 | 769C2 clone Lambda Chain CDR2 (AA52-58) | EVNNRPS |
| 140 | 769C2 clone Lambda Chain CDR3 (AA91-100) | NSYSTTTTWV |
| 141 | 770F8 clone Heavy Chain variable region amino acid sequence | EVQLVESGGGLVRPGGSLRLSCSASGFTFSSYSMNWVRQAP GKGLEFVSAITSRGTYIYYADSVKGRFTVSRDNAKNSLYLQ MTNVRDEDTAVYYCAREMAGYSSTFDYWGQGALVTVSS |
| 142 | 770F8 clone Heavy Chain variable region nucleotide sequence | GAGGTGCAGCTGGTGGAGTCCGGCGGAGGCCTGGTGAGGCC CGGAGGCTCTCTGCGCCTGAGCTGTTCCGCCTCTGGCTTCA CCTTTAGCTCCTACAGCATGAACTGGGTGAGGCAGGCACCT GGCAAGGGCCTGGAGTTCGTGAGCGCCATCACCTCCAGAGG CACATACATCTACTATGCCGACTCCGTGAAGGGCCGGTTCA CCGTGAGCCGGGATAACGCCAAGAATAGCCTGTATCTGCAG ATGACCAATGTGCGGGACGAGGATACAGCCGTGTACTATTG CGCCAGAGAGATGGCCGGCTACTCTAGCACCTTCGACTATT GGGGACAGGGCGCCCTGGTGACAGTGTCCTCT |
| 143 | 770F8 clone Heavy Chain CDR1 (AA26-32) | GFTFSSY |
| 144 | 770F8 clone Heavy Chain CDR2 (AA52-57) | TSRGTY |
| 145 | 770F8 clone Heavy Chain CDR3 (AA99-109) | EMAGYSSTFDY |
| 146 | 770F8 clone Lambda Chain variable region amino acid sequence | QSVLSQPASVSGSPGQSITISCTGTSSDIGGYDYVSWYQQY ASGKPKLMIYEVSNRPSGVSNRFSGSKSGNTASLTISGLQA EDEADYYCISYTTITTLWVFGGGTKLT |
| 147 | 770F8 clone Lambda Chain variable region nucleotide sequence | CAGTCTGTGCTGAGCCAGCCAGCCTCTGTGAGCGGCTCCCCT GGCCAGAGCATCACCATCTCCTGTACCGGCACAAGCTCCGA CATCGGCGGCTACGATTACGTGAGCTGGTACCAGCAGTATT CTGGCAAGGCCCCAAAGCTGATGATCTACGAGGTGAGCAAC AGGCCATCCGGCGTGTCTAATAGATTCTCTGGCAGCAAGTC CGGCAACACCGCCTCTCTGACAATCAGCGGCCTGCAGGCAG |

SEQUENCE LISTING

The Sequence Listing is submitted as an ASCII text file, created on November 2, 2020, 177 KB, which is incorporated by reference herein.

This disclosure provides the following sequences:

| SEQ ID NO | Description | Sequence |
|---|---|---|
| | | AGGACGAGGCAGATTACTATTGCATCTCCTATACCACAATC ACCACACTGTGGGTGTTTGGCGGCGGCACCAAGCTGACA |
| 148 | 770F8 clone Lambda Chain CDR1 (AA23-36) | TGTSSDIGGYDYVS |
| 149 | 770F8 clone Lambda Chain CDR2 (AA52-58) | EVSNRPS |
| 150 | 770F8 clone Lambda Chain CDR3 (AA91-101) | ISYTTITTLWV |
| 151 | 770E8 clone Heavy Chain variable region amino acid sequence | EVQLLESGGGLVQPGGSLRLSCAASGFTFDSYAINWVRQAPG KGLEWVSAISSSGGGRHYADSVRGRFTISRDNSKNTLYLHMS GLRAEDTAVYFCAKAGARNYYYGMDVWGQGTTVTVSS |
| 152 | 770E8 clone Heavy Chain variable region nucleotide sequence | GAGGTGCAGCTGCTGGAGTCCGGCGGAGGCCTGGTGCAGCCA GGAGGCTCTCTGAGGCTGAGCTGTGCCGCCTCCGGCTTCACC TTTGACTCTTATGCCATCAACTGGGTGAGACAGGCACCTGG CAAGGGCCTGGAGTGGGTGTCCGCCATCAGCTCCTCTGGCG GAGGCAGGCACTACGCAGACTCTGTGCGGGGCAGATTCACC ATCTCTCGCGATAACAGCAAGAATACACTGTATCTGCACAT GTCCGGCCTGAGGGCAGAGGACACCGCCGTGTACTTTTGCG CCAAGGCCGGCGCCAGAAATTACTATTACGGAATGGACGTG TGGGGACAGGGAACCACAGTGACAGTGAGCTCC |
| 153 | 770E8 clone Heavy Chain CDR1 (AA26-32) | GFTFDSY |
| 154 | 770E8 clone Heavy Chain CDR2 (AA52-57) | SSSGGG |
| 155 | 770E8 clone Heavy Chain CDR3 (AA99-110) | AGARNYYYGMDV |
| 156 | 770E8 clone Lambda Chain variable region amino acid sequence | QSVLSQPPSASGTPGQTVTISCSGGNSNIGKNFVYWYRQLPGTA PKLLIHSNDRRPSGVPDRFSGSKSGTSASLAISGLRSEDEADYY CAAWDDSLTGLFGTGTRVT |
| 157 | 770E8 clone Lambda Chain variable region nucleotide sequence | CAGAGCGTGCTGTCCCAGCCACCTAGCGCCTCCGGCACCCC AGGCCAGACCGTGACAATCTCTTGTAGCGGCGGCAACTCCA ATATCGGCAAGAACTTCGTGTACTGGTATAGGCAGCTGCCA GGAACCGCACCAAAGCTGCTGATCCACTCCAATGACAGACG GCCCTCTGGCGTGCCAGATAGGTTTTCCGGCTCTAAGAGCGG CACATCCGCCTCTCTGGCCATCTCTGGCCTGCGCAGCGAGGA CGAGGCAGATTACTATTGCGCAGCATGGGACGATTCTCTGA CCGGCCTGTTCGGCACCGGCACAAGGGTGACA |
| 158 | 770E8 clone Lambda Chain CDR1 (AA27-35) | SGGNSNIGKNFVY |
| 159 | 770E8 clone Lambda Chain CDR2 (AA51-57) | SNDRRPS |
| 160 | 770E8 clone Lambda Chain CDR3 (AA90-99) | AAWDDSLTGL |
| 161 | 770E6 clone Heavy Chain variable region amino acid sequence | EVQLVESGGGVVQPGRSLRLSCAASGFTFSTYGIHWVRQAPGK GLEWVAWSRDGGFKYYADSVKGRFTISRDNSENTMFLQMNS LRAEDTAVYYCAKEGYSGGYGAYFESWGQGTLVAVSS |
| 162 | 770E6 clone Heavy Chain variable region nucleotide sequence | GAGGTGCAGCTGGTGGAGAGCGGCGGAGGAGTGGTGCAGC CAGGCCGGAGCCTGAGACTGAGCTGTGCCGCCTCCGGCTTC ACCTTTTCCACATACGGCATCCACTGGGTGCGGCAGGCACCT GGCAAGGGCCTGGAGTGGGTGGCAGTGGTGAGCAGGGACG GAGGCTTCAAGTACTATGCCGATTCCGTGAAGGGCAGGTTT ACCATCTCTCGCGACAACAGCGAGAATACAATGTTCCTGCA |

SEQUENCE LISTING

The Sequence Listing is submitted as an ASCII text file, created on November 2, 2020, 177 KB, which is incorporated by reference herein. This disclosure provides the following sequences:

| SEQ ID NO | Description | Sequence |
|---|---|---|
| | | GATGAACTCTCTGCGGGCCGAGGATACCGCCGTGTACTATT GCGCCAAGGAGGGCTATTCCGGCGGCTACGGCGCCTATTTT GAGTCTTGGGGCCAGGGCACACTGGTGGCCGTGAGCTCC |
| 163 | 770E6 clone Heavy Chain CDR1 (AA26-32) | GFTFSTY |
| 164 | 770E6 clone Heavy Chain CDR2 (AA52-57) | SRDGGF |
| 165 | 770E6 clone Heavy Chain CDR3 (AA99-111) | EGYSSFFYGAYFES |
| 166 | 770E6 clone Kappa Chain variable region amino acid sequence | EIVMTQSPFSLSVSPGERATLSCRASQSISSHLAWYQQKPGQAP RLVMYGASTRATGIPARFSGSGSGTEFTLIISSLQSEDFAVYYC HQYDNWPVTIGQGTKVEIK |
| 167 | 770E6 clone Kappa Chain variable region nucleotide sequence | GAGATCGTGATGACCCAGAGCCCATTCTCCCTGTCTGTGAGC CCAGGAGAGAGGGCCACACTGTCCTGTAGAGCCTCCCAGTC TATCAGCTCCCACCTGGCATGGTACCAGCAGAAGCCAGGAC AGGCACCTAGGCTGGTCATGTATGGCGCCTCTACCAGGGCA ACAGGCATCCCTGCACGCTTCAGCGGCTCCGGCTCTGGCACC GAGTTTACACTGATCATCTCTAGCCTGCAGTCCGAGGACTTT GCCGTGTACTATTGCCACCAGTACGATAACTGGCCCGTGACC ATCGGCCAGGGCACAAAGGTGGAGATCAAG |
| 168 | 770E6 clone Kappa Chain CDR1 (AA24-34) | RASQSISSHLA |
| 169 | 770E6 clone Kappa Chain CDR2 (AA50-56) | GASTRAT |
| 170 | 770E6 clone Kappa Chain CDR3 (AA89-97) | HQYDNWPVT |
| 171 | 770F10 clone Heavy Chain variable region amino acid sequence | EVQLVESGGGFAQPGRSLRISCSASGFTFDDYAIHWVRQAP GKGLEWVSGIIWNSDLKDYADSVKGRFTISRDTAKNSLYLQ MNSLRADDTALYYCARVTGYNYGSALDAFGIWGTGTMVIVSS |
| 172 | 770F10 clone Heavy Chain variable region nucleotide sequence | GAGGTGCAGCTGGTGGAGTCCGGCGGAGGATTCGCACAGCC AGGCCGGAGCCTGCGGATCTCTTGTAGCGCCTCCGGCTTCA CCTTTGACGATTACGCAATCCACTGGGTGCGGCAGGCACCT GGCAAGGGCCTGGAGTGGGTGTCTGGCATCATCTGGAACAG CGACCTGAAGGATTACGCCGACAGCGTGAAGGGCAGGTTCA CCATCTCCCGCGATACAGCCAAGAACTCTCTGTATCTGCAG ATGAATAGCCTGCGGGCCGACGATACCGCCCTGTACTATTG CGCCAGGGTGACAGGCTACAATTATGGCTCCGCCCTGGACG CCTTTGGCATCTGGGGCACCGGCACAATGGTCATCGTGAGCT CC |
| 173 | 770F10 clone Heavy Chain CDR1 (AA26-32) | GFTFDDY |
| 174 | 770F10 clone Heavy Chain CDR2 (AA52-57) | IWNSDL |
| 175 | 770F10 clone Heavy Chain CDR3 (AA99-113) | VTGYNYGSALDAFGI |
| 176 | 770F10 clone Kappa Chain variable region amino acid sequence | DIQMTQSPSSLSASVGDRVTITGRASQSISRWLAWYQQKPG KAPKLLIFQASTLESGVSSRFSGSGSGTEFTLTISSLQPDD FATYYCQQYNSYYSFGQGTKLEIK |

SEQUENCE LISTING
The Sequence Listing is submitted as an ASCII text file, created on November 2, 2020, 177 KB, which is incorporated by reference herein. This disclosure provides the following sequences:

| SEQ ID NO | Description | Sequence |
|---|---|---|
| 177 | 770F10 clone Kappa Chain variable region nucleotide sequence | GACATCCAGATGACCCAGTCCCCAAGCTCCCTGAGCGCCTC CGTGGGCGATCGGGTGACCATCACAGGCAGAGCCTCTCAGA GCATCTCCAGGTGGCTGGCCTGGTACCAGCAGAAGCCCGGC AAGGCCCCTAAGCTGCTGATCTTCCAGGCCTCCACCCTGGA GTCTGGCGTGTCTAGCCGGTTCTCTGGCAGCGGCTCCGGCA CAGAGTTTACCCTGACAATCTCCTCTCTGCAGCCCGACGAT TTCGCCACCTACTATTGTCAGCAGTATAACTCTTACTATAG CTTTGGCCAGGGCACAAAGCTGGAGATCAAG |
| 178 | 770F10 clone Kappa Chain CDR1 (AA24-34) | RASQSISRWLA |
| 179 | 770F10 clone Kappa Chain CDR2 (AA50-56) | QASTLES |
| 180 | 770F10 clone Kappa Chain CDR3 (AA89-96) | QQYNSYYS |
| 181 | 770G2 clone Heavy Chain variable region amino acid sequence | HVQLVQSGGEVKKPGASVKVSCKASGYTFTDYGISWVRQAP GQGLEWMGWISTYKGDTHYAQKFQGRVTMTADTSTSTAYME LRSLRSDGTAVYYCARSYDYVWISYRYRTNFDYWGQGTLVT VSS |
| 182 | 770G2 clone Heavy Chain variable region nucleotide sequence | CACGTGCAGCTGGTGCAGTCTGGCGGAGAGGTGAAGAAGCC AGGAGCCAGCGTGAAGGTGTCCTGTAAGGCCTCTGGCTACA CCTTCACAGACTATGGAATCTCTTGGGTGCGGCAGGCACCT GGACAGGGCCTGGAGTGGATGGGCTGGATCAGCACATACAA GGGCGACACCCACTATGCCCAGAAGTTTCAGGGCAGGGTGA CCATGACAGCCGATACCTCTACAAGCACCGCCTACATGGAG CTGAGGTCCCTGCGCTCTGACGGCACAGCCGTGTACTATTG CGCCCGGAGCTACGATTACGTGTGGATCTCCTACCGGTATA GAACCAACTTCGATTATTGGGGCCAGGGCACACTGGTGACC GTGAGCTCC |
| 183 | 770G2 clone Heavy Chain CDR1 (AA26-32) | GYTFTDY |
| 184 | 770G2 clone Heavy Cliain CDR2 (AA52-57) | STYKGD |
| 185 | 770G2 clone Heavy Chain CDR3 (AA99-115) | SYDYVWISYRYRTNFDY |
| 186 | 770G2 clone Kappa Chain variable region amino acid sequence | AIQMTQSPFSLSASVGDRVTITCRASQGIGNDLGWYQQIPGR APKLLIYAASNLQSGVPSRFSGSGSGTDFTLTITSLQPEDFA TYYCLQDYTYPYSFGQGTKLEIK |
| 187 | 770G2 clone Kappa Chain variable region nucleotide sequence | GCCATCCAGATGACACAGAGCCCTTTCAGCCTGTCCGCCTCT GTGGGCGACCGGGTGACCATCACATGTAGAGCCTCCCAGGG CATCGGCAACGATCTGGGCTGGTATCAGCAGATCCCCGGCA GGGCCCCTAAGCTGCTGATCTACGCAGCCAGCAATCTGCAG TCCGGCGTGCCATCTCGGTTCAGCGGCTCCGGCTCTGGCACA GACTTTACCCTGACAATCACCTCTCTGCAGCCAGAGGACTTC GCCACATACTATTGCCTGCAGGATTACACCTATCCCTACAGC TTTGGCCAGGGCACCAAGCTGGAGATCAAG |
| 188 | 770G2 clone Kappa Chain CDR1 (AA24-34) | RASQGIGNDLG |
| 189 | 770G2 clone Kappa Chain CDR2 (AA50-56) | AASNLQS |
| 190 | 770G2 clone Kappa Chain CDR3 (AA89-97) | LQDYTYPYS |

SEQUENCE LISTING

The Sequence Listing is submitted as an ASCII text file, created on November 2, 2020, 177 KB, which is incorporated by reference herein. This disclosure provides the following sequences:

| SEQ ID NO | Description | Sequence |
|---|---|---|
| 191 | 770F7 clone Heavy Chain variable region amino acid sequence | QVQFQQWGAGLLKPSETLSLTCGVYGGSLSGYYWSVVIRQTP GKGLEWIGEINHTGTTNYNPSLKSRVTMSVDTSKNQFSLKMS SLTAADTALYYCAREGAPRWALKRPSNWFDPWGQGTLVTVSS |
| 192 | 770F7 clone Heavy Chain variable region nucleotide sequence | CAGGTGCAGTTCCAGCAGTGGGGAGCAGGCCTGCTGAAGCC TTCTGAGACACTGAGCCTGACATGTGGCGTGTACGGCGGCT CCCTGTCTGGCTACTATTGGTCCTGGATCAGACAGACCCCAG GCAAGGGCCTGGAGTGGATCGGAGAGATCAACCACACAGG CACCACAAACTATAATCCCAGCCTGAAGTCCCGGGTGACCA TGTCCGTGGACACATCTAAGAATCAGTTCAGCCTGAAGATG AGCTCCCTGACCGCCGCCGATACAGCCCTGTACTATTGCGCA AGGGAGGGAGCACCAAGATGGGCCCTGAAGAGGCCCTCCA ACTGGTTTGACCCTTGGGGCCAGGGCACCCTGGTGACAGTG TCTAGC |
| 193 | 770F7 clone Heavy Chain CDR1 (AA26-32) | GGSLSGY |
| 194 | 770F7 clone Heavy Chain CDR2 (AA52-56) | NHTGT |
| 195 | 770F7 clone Heavy Chain CDR3 (AA98-114) | EGAPRVVALKRPSNWFDP |
| 196 | 770F7 clone Kappa Chain variable region amino acid sequence | EIVLTQSPVSLSLSPGERATLSCRASQSISSTYLAWYQQIPG QAPRLLIYGASSRAAGIPDRFSGGGSGTDFTLTISRLEPEDF AVYYCQQYGSSPRSFGQGTKLEIK |
| 197 | 770F7 clone Kappa Chain variable region nucleotide sequence | GAGATCGTGCTGACCCAGTCCCCAGTGAGCCTGTCCCTGTCT CCAGGAGAGAGGGCCACCCTGTCTTGTAGAGCCAGCCAGTC CATCAGCTCCACATACCTGGCCTGGTATCAGCAGATCCCAG GACAGGCACCTAGGCTGCTGATCTACGGAGCCTCTAGCAGG GCAGCAGGCATCCCCGACCGCTTCTCTGGCGGAGGCAGCGG CACCGACTTCACCCTGACAATCAGCCGGCTGGAGCCTGAGG ACTTCGCCGTGTACTATTGCCAGCAGTATGGCTCCTCTCCA AGGTCCTTTGGCCAGGGCACAAAGCTGGAGATCAAG |
| 198 | 770F7 clone Kappa Chain CDR1 (AA24-35) | RASQSISSTYLA |
| 199 | 770F7 clone Kappa Chain CDR2 (AA51-57) | GASSRAA |
| 200 | 770F7 clone Kappa Chain CDR3 (AA90-98) | QQYGSSPRS |

BRIEF DESCRIPTION OF THE FIGURES

FIG. 1A shows neutralization of EBV infection of B cells and epithelial cells by mAb 769B10. FIG. 1B shows an inhibition of fusion of B cells and epithelial cells by 769B10 mAb. The percentage of fusion is defined as the (RLUSerum/RLUNegative Serum)×100%. The dotted lines represent the background of the assay. FIG. 1C shows the kinetics of binding of 769B10 Fab to gH/gL and gH/gL/gp42.

FIG. 5A shows the results for the 769B10 mAb clone; FIG. 5B shows the results for the 769C2 mAb clone.

FIG. 7A shows EBV gp350 antibody, gH/gL antibody, and gp42 antibody titers in human plasma measured by LIPS assay. Antibody titers are expressed as luciferase relative light units (RLU). Solid circles are samples from 34 EBV seropositive subjects (positive for viral capsid antigen [VCA] IgG antibody); open circles are the serum from EBV seronegative subjects (4 subjects). The horizontal blue line represents the median of antibody titers. The horizontal dotted lines are the cut off value defined as twice the value of the buffer control. FIGS. 7B and 7C show the neutralization of EBV infection of Raji B cells (FIG. 7B) and SVKCR2 epithelial cells (FIG. 7C) by mAb 72A1 (directed against gp350), F-2-1 (directed against gp42), or E1D1 (directed against gL). FIG. 7D shows neutralizing antibody titers in sera of EBV seropositive subjects measured using B cell neutralization (Raji cells) and epithelial cells neutralization (SVKCR2 cells and AGS cells) assays. The horizontal dark line is the median of the neutralizing antibody titers. The dotted line represents the detection limit of the assay. FIG. 7E shows neutralizing antibody titers in the two epithelial cell lines, SVKCR2 and AGS, demonstrating a significant correlation (p<0.0001). FIGS. 7F-7H show the correlation of gH/gL antibody titers measured by LIPS with neutralizing titers in SVKCR2 epithelial cells (FIG. 7F), AGS epithelial cells (FIG. 7G), and B cells (FIG. 7H). FIG. 7I shows antibody titers measured by LIPS assay. Human IVIG was incubated with VV-infected cells expressing EBV gp350, gH/gL, or gp42 four sequential times to remove antibodies to each EBV glycoprotein, and the antibody titers after each round of depletion were measured by LIPS assay. The percentage of remaining antibodies was calculated by (AbrVV/Abcontrol) %. The Abcontrol is the titer after incubation with control VV-infected cells that do not express any EBV gene, and the AbrVV is the titer after incubation with VV-infected cells that express EBV glycoproteins. The horizontal dotted lines indicate 10% of antibody remaining. FIG. 7J shows the reduction in EBV infection of B cells (Raji cells) and epithelial cells (SVKCR2 cells) by IVIG in which antibodies to individual EBV glycoproteins were depleted using VV-infected cells expressing EBV glycoproteins. The percentage of infectivity reduction was calculated by $(1-IC_{50\text{-}depleted}/IC_{50\text{-}control}) \times 100$ in which $IC_{50\text{-}depleted}$ is the neutralizing antibody titer of depleted IVIG, and $IC_{50\text{-}control}$ is the neutralizing antibody titer of IVIG incubated with control VV-infected cells. FIGS. 7K and 7L show the percent EBV infectivity of B cells (FIG. 7K) and epithelial cells (FIG. 7L) after incubation of virus with IVIG depleted of antibody to gp350 (left panel), gH/gL (middle panel), or gp42 (right panel) using cells expressing the corresponding glycoproteins.

DETAILED DESCRIPTION

I. Definitions

Figure 1A:
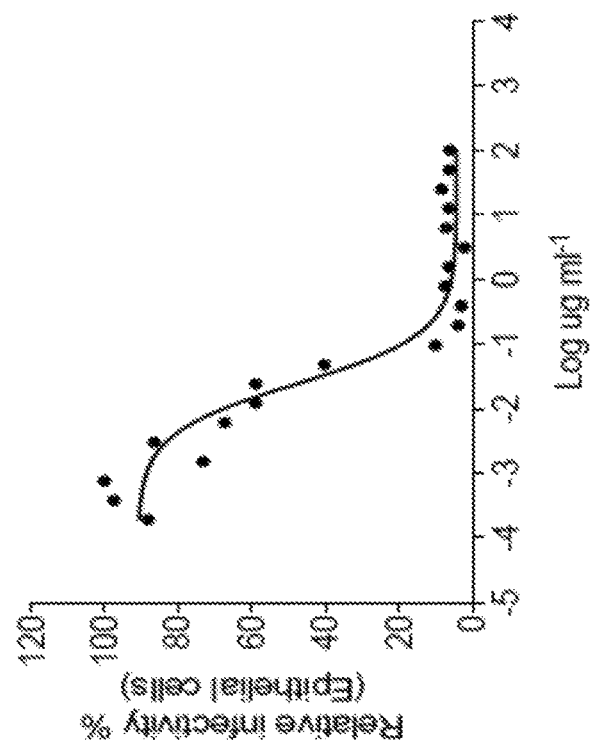
FIGS. 1A-1C show characterizations of mAb 769B10 of this disclosure.
Figure 1A:
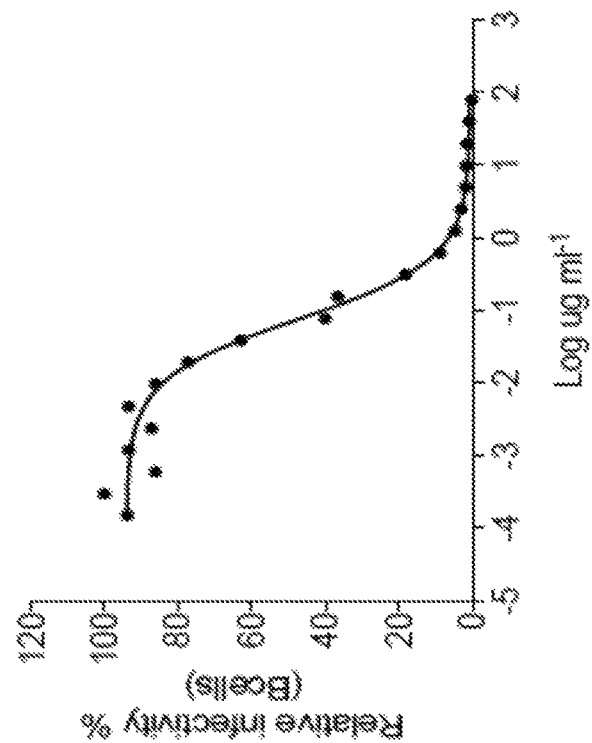

As used herein, "EBV gH protein" and "gH", can be used interchangeably, and refer to Epstein Barr Virus polypeptides. Likewise, the terms "EBV gL protein" and "gL", can be used interchangeably, and also refer to Epstein Barr Virus polypeptides. The term "gH/gL" refers to a complex comprising the EBV gH and gL proteins. The EBV proteins described herein may be isolated from a variety of sources, such as from human tissue types or from another source, or prepared by recombinant or synthetic methods. All disclosures in this specification which refer to the EBV gH protein, or the EBV gL protein, refer to each of the polypeptides individually as well as jointly. For example, descriptions of the preparation of, purification of, derivation of, formation of antibodies to or against, formation of gH binding oligopeptides to or against, administration of, compositions containing, treatment of a disease with, etc., pertain to each polypeptide of the disclosure individually. The term EBV gH protein, or EBV gL protein, also includes variants of the proteins disclosed herein.

A "native sequence EBV gH protein" comprises a polypeptide having the same amino acid sequence as the corresponding EBV gH protein derived from nature. Likewise, a "native sequence EBV gL protein" comprises a polypeptide having the same amino acid sequence as the corresponding EBV gL protein derived from nature. Such native sequence EBV proteins can be isolated from nature or can be produced by recombinant or synthetic means. The term "native sequence EBV gH protein" specifically encompasses naturally-occurring forms of the specific EBV gH protein, such as naturally-occurring variant forms (e.g., alternatively spliced forms) and naturally-occurring allelic variants of the polypeptide. The native sequence EBV gH proteins disclosed herein may be mature or full-length native sequence polypeptides comprising the full-length amino acids sequences. The term "native sequence EBV gL protein" specifically encompasses naturally-occurring forms of the specific EBV gL protein, such as naturally-occurring variant forms (e.g., alternatively spliced forms) and naturally-occurring allelic variants of the polypeptide. The native sequence EBV gL proteins disclosed herein may be mature or full-length native sequence polypeptides comprising the full-length amino acids sequences.

As used herein, "EBV gH protein variant" means an EBV gH protein, preferably an active EBV gH protein, as defined herein having at least about 80% amino acid sequence identity with a full-length native sequence EBV gH protein sequence as disclosed herein, or any other fragment of a full-length EBV gH protein sequence as disclosed herein (such as those encoded by a nucleic acid that represents only a portion of the complete coding sequence for a full-length EBV gH protein). Such EBV gH protein variants include, for example, EBV gH proteins wherein one or more amino acid residues are added or deleted, at the N- or C-terminus of the full-length native amino acid sequence. Ordinarily, an EBV gH protein variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence EBV gH protein sequence as disclosed herein, or any other specifically defined fragment of a full-length EBV gH protein sequence as disclosed herein. Optionally, gH variant polypeptides will have no more than one conservative amino acid substitution as compared to the native EBV gH protein sequence, alternatively no more than 2, 3, 4, 5, 6, 7, 8, 9, or 10 conservative amino acid substitutions as compared to the native EBV gH protein sequence.

As used herein, "EBV gL protein variant" means an EBV gL protein, preferably an active EBV gL protein, as defined herein having at least about 80% amino acid sequence identity with a full-length native sequence EBV gL protein sequence as disclosed herein, or any other fragment of a full-length EBV gL protein sequence as disclosed herein (such as those encoded by a nucleic acid that represents only a portion of the complete coding sequence for a full-length EBV gL protein). Such EBV gL protein variants include, for example, EBV gL proteins wherein one or more amino acid residues are added or deleted, at the N- or C-terminus of the full-length native amino acid sequence. Ordinarily, an EBV gL protein variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence EBV gL protein sequence as disclosed herein, or any other specifically defined fragment of a full-length EBV gL protein sequence as disclosed herein. Optionally, gL variant polypeptides will have no more than one conservative amino acid substitution as compared to the native EBV gL protein sequence, alternatively no more than 2, 3, 4, 5, 6, 7, 8, 9, or 10 conservative amino acid substitutions as compared to the native EBV gL protein sequence.

As used herein, "gH/gL complex" and "gH/gL" can be used interchangeably. A gH/gL complex refers to a multi-domain structure comprising one EBV gH protein and one EBV gL protein. EBV gH/gL complexes are usually formed through noncovalent interaction of the gH and gL proteins, although in certain situations, it may be useful to engineer the gH and/or gL proteins to from covalent interactions that might stabilize the complex or impart other useful properties thereto. Any gH and gL protein, including fragments and variant, disclosed herein, can be used to form a gH/gL complex.

"Percent (%) amino acid sequence identity" with respect to the EBV gH protein sequences identified herein is defined as the percentage of amino acid residues in a candidate sequence that are identical to the amino acid residues in the specific EBV gH protein sequence, after aligning the sequences and introducing gaps, if necessary, to achieve the maximum percent sequence identity, and not considering any conservative substitutions as part of the sequence identity. Likewise, "Percent (%) amino acid sequence identity" with respect to the EBV gL protein sequences identified herein is defined as the percentage of amino acid residues in a candidate sequence that are identical to the amino acid residues in the specific EBV gL protein sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, % amino acid sequence identity values may be generated using the sequence comparison computer program ALIGN-2, wherein the complete source code for the ALIGN-2 program is provided in U.S. Pat. No. 7,160,985, which is incorporated herein by reference. The ALIGN-2 sequence comparison computer program was authored by Genentech, Inc. and the source code thereof has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California or may be compiled from the source code. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as 100 times the fraction X/Y, where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A.

"gH variant polynucleotide" or "gH variant nucleic acid sequence" means a nucleic acid molecule which encodes an EBV gH protein, preferably an active EBV gH protein, as defined herein and which has at least about 80% nucleic acid sequence identity with a nucleic acid sequence encoding a full-length native sequence EBV gH protein sequence as disclosed herein, or any other fragment of a full-length EBV gH protein sequence as disclosed herein (such as those encoded by a nucleic acid that represents only a portion of the complete coding sequence for a full-length EBV gH protein). Ordinarily, a gH variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence EBV gH protein sequence, an extracellular domain of an EBV gH protein or any other fragment of a full-length EBV gH protein sequence. Variants do not encompass the native nucleotide sequence.

"gL variant polynucleotide" or "gL variant nucleic acid sequence" means a nucleic acid molecule which encodes an EBV gL protein, preferably an active EBV gL protein, as defined herein and which has at least about 80% nucleic acid sequence identity with a nucleic acid sequence encoding a full-length native sequence EBV gL protein sequence as disclosed herein, or any other fragment of a full-length EBV gL protein sequence as disclosed herein (such as those encoded by a nucleic acid that represents only a portion of the complete coding sequence for a full-length EBV gL protein). Ordinarily, a gL variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence EBV gL protein sequence, or any fragment of a full-length EBV gL protein sequence. Variants do not encompass the native nucleotide sequence.

Ordinarily, variant polynucleotides of the invention are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Isolated," when used to describe the various EBV proteins disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The polypeptide may be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or silver stain. Isolated polypeptide includes polypeptide in situ within recombinant cells, since at least one component of the EBV protein natural environment will not be present. Ordinarily, however, isolated polypeptide will be prepared by at least one purification step.

An "isolated" EBV gH or gL protein-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers (1995).

"Stringent conditions" or "high stringency conditions" as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" used herein refers to a chimeric polypeptide comprising an EBV gH protein, or gL protein, an anti-gH antibody, or an anti-gL antibody, fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of an EBV protein (for example, EBV gH or gL), or complexes of such proteins, which retain a biological and/or an immunological activity of a native or naturally-occurring EBV protein (such as gH, gL or a gH/gL complex), wherein "biological" activity refers to a biological function (either inhibitory or stimulatory) caused by a native or naturally-occurring EBV protein, other than the ability to induce the production of an antibody against an antigenic epitope possessed by native EBV protein, and an "immunological" activity refers to the ability to induce the production of an antibody against an antigenic epitope possessed by the EBV native or naturally-occurring protein.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an EBV infection if, after receiving a therapeutic amount of an anti-gH antibody, anti-gL antibody, or anti-gH/gL antibody, according to the methods of this disclosure, the patient shows observable and/or measurable reduction in or absence of one or more of the following: reduction in the number of infected cells or absence of the infected cells; reduction in the number of infected cells; inhibition (i.e., slow to some extent and preferably stop) of EBV infection including the spread of infection into neurological tissues; inhibition (i.e., slow to some extent and preferably stop) of infection spread; inhibition, to some extent, and/or relief to some extent, of one or more of the symptoms associated with the viral infection; reduced morbidity and mortality, and improvement in quality of life issues. To the extent the anti-gH antibody, anti-gL antibody, or anti-gH/gL antibody may prevent growth or infection and/or kill existing infected cells, it may be cytostatic and/or cytotoxic. Reduction of these signs or symptoms may also be felt by the patient. The above parameters for assessing successful treatment and improvement in the EBV-associated diseases and disorders are readily measurable by routine procedures familiar to a medical provider.

"Chronic" administration refers to administration of the agent(s) in a continuous mode as opposed to an acute mode, to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a viral infection refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody of this disclosure can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate or a lateral flow assay device; in others, it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an anti-EBV gH antibody, anti-EBV gL antibody, or an anti-EBV gH/gL antibody) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of gH antibody, anti-EBV gL antibody, or an anti-EBV gH/gL antibody, as disclosed herein, is an amount sufficient to carry out a specifically stated purpose. An "effective amount" may be determined empirically and in a routine manner, in relation to the stated purpose.

The term "therapeutically effective amount" refers to an amount of an antibody, to "treat" a disease or disorder in a subject or mammal. In the case of an EBV infection, the therapeutically effective amount of the drug may reduce the number of infected cells; inhibit (i.e., slow to some extent and preferably stop) spread of the infection into other cells, such as lymphatic or neurological cells organs; and/or relieve to some extent one or more of the symptoms associated with the infection. See the definition herein of "treating." To the extent the drug may prevent growth and/or kill existing infected cells, it may be cytostatic, cytotoxic, anti-inflammatory, immunomodulatory, and/or immunosuppressing.

A "growth inhibitory amount" of an anti-EBV gH antibody, anti-EBV gL antibody, or anti-EBV gH/gL antibody is an amount capable of inhibiting the growth of a cell, especially virus infected cell, either in vitro or in vivo. A "growth inhibitory amount" of an anti-EBV gH antibody, anti-EBV gL antibody, or anti-EBV gH/gL antibody, for purposes of inhibiting infected cell growth, may be determined empirically and in a routine manner.

A "cytotoxic amount" of an anti-gH antibody, gH-binding oligopeptide, anti-gL antibody, or gL-binding oligopeptide is an amount capable of causing the destruction of a cell, especially virus infected cell, either in vitro or in vivo. A "cytotoxic amount" of an anti-gH antibody, gH-binding oligopeptide, anti-gL antibody, or gL-binding oligopeptide for purposes of inhibiting cell growth may be determined empirically and in a routine manner.

The term "antibody" is used in the broadest sense and specifically covers, for example, single anti-gH, anti-gL, and anti-gH/gL, monoclonal antibodies (including agonist, antagonist, and neutralizing antibodies), anti-gH, anti-gL, and anti-gH/gL antibody compositions with polyepitopic specificity, polyclonal antibodies, single chain anti-gH, anti-gL, and anti-gH/gL antibodies, and fragments of anti-gH, anti-gL, and anti-gH/gL antibodies (see below), as long as they exhibit the desired biological or immunological activity or specificity. The term "immunoglobulin" (Ig) is used interchangeably with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells because at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes.

There are five classes of immunoglobulins: IgA, IgD, IgE, IgG, and IgM, having heavy chains designated α, δ, ε, γ, and μ, respectively. The γ and α classes are further divided into subclasses based on relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of an antibody for its antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 3-30, or more typically, 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, useful monoclonal antibodies of this disclosure may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape, etc.), and human constant region sequences.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide-linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) can recognize and bind antigen, although at a lower affinity than the entire binding site.

"Single-chain Fv" (also abbreviated as "sFv" or "scFv") are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all at least one, and typically two, variable domains, in which all or substantially all the hypervariable loops correspond to those of a non-human immunoglobulin and all or substantially all the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-25 (1986); Riechmann et al., Nature 332:323-329 (1988); and Presta, Curr. Op. Struct. Biol. 2:593-96 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "binds specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50-fold, or at least about 500-fold, or at least about 1,000-fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, MD (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by the values (e.g., Kd values). The difference between the two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of this disclosure. Illustrative embodiments are described in the following.

The "Kd" or "Kd value" according to this disclosure, is a measure of the solution binding affinity of a Fab for an antigen. The Kd can be measured using several known methods, including, but not limited to, biolayer interferometry (BLI), isothermal titration calorimetry (ITC), and composition gradient multi-angle static light scattering (CG-MALS). In one method, a radiolabeled antigen binding assay (RIA) is performed using the Fab version of an antibody of interest and its antigen. Such a method can be performed by equilibrating a Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 mcg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate, 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 microliter/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. The Kd or Kd value may also be measured by using surface plasmon resonance assays using a BIAcore™-2000 or a BIAcore™-3000 (BIAcore, Inc., Piscataway, NJ) at 25° C. with immobilized antigen CM5 chips at approx. 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds $10^6$ M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrometer (Aviv Instruments) or a 8000-series SLM-Aminco spectrophotometer (ThermoSpectronic) with a stir red cuvette.

An "on-rate" or "rate of association" or "association rate" or "kon" according to this disclosure can also be determined with the same surface plasmon resonance technique described above using a BIAcore™-2000 or a BIAcore™-3000 (BIAcore, Inc., Piscataway, NJ) at 25° C. with immobilized antigen CM5 chips at approx. 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of 1 M ethanolamine to block unreacted groups. For kinetics measurements, two-fold serial dilutions of Fab (0.78 nM to 500 nM) are injected in PBS with 0.05% Tween 20 (PB ST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) was calculated as the ratio koff/kon. See, e.g., Chen, Y., et al., (1999) J. Mol Biol 293:865-81. However, if the on-rate exceeds $10^6$ M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the disclosure and the other associated with a reference/comparator antibody) such that one of skill in the art would consider the difference between the two values to be of statistical significance within the context of the biological characteristic measured by the values (e.g., Kd values, HAMA response). The difference between the two values is preferably greater than about 10%, preferably greater than about 20%, preferably greater than about 30%, preferably greater than about 40%, preferably greater than about 50% as a function of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is an EBV gp350 polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H and 78H; for instance, the amino acid residues at those positions may be 71A, 73T and/or 78A. The VL acceptor human framework may be identical in sequence to the VL human immunoglobulin framework sequence or human consensus framework sequence.

Antibodies of this disclosure may be able to compete for binding to the same epitope as is bound by a second antibody. Monoclonal antibodies are considered to share the "same epitope" if each blocks binding of the other by 40% or greater at the same antibody concentration in a standard in vitro antibody competition binding analysis.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. For the VL, the subgroup may be subgroup kappa I as in Kabat et al. For the VH the subgroup is subgroup III in Kabat et al.

A "VH subgroup III consensus framework" comprises the consensus sequence obtained from the amino acid sequences in variable heavy subgroup III of Kabat et al.

A "VL subgroup I consensus framework" comprises the consensus sequence obtained from the amino acid sequences in variable light kappa subgroup I of Kabat et al.

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", "HV" or "CDR", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). Several hypervariable region delineations are in use and are encompassed herein. The Kabat Complementarity Determining Regions (CDRs) are based on sequence variability and are the most commonly used. The "contact" hypervariable regions are based on an analysis of the available complex crystal structures. The residues from each of these hypervariable regions are noted below. Unless otherwise denoted, Kabat numbering is employed. Hypervariable region locations are generally: amino acids 24-34 (HVR-L1), amino acids 49-56 (HVR-L2), amino acids 89-97 (HVR-L3), amino acids 26-35A (HVR-H1), amino acids 49-65 (HVR-H2), and amino acids 93-102 (HVR-H3). Hypervariable regions may also comprise "extended hypervariable regions" as follows: amino acids 24-36 (L1), and amino acids 46-56 (L2) in the VL, numbered according to Kabat et al., supra for each of these definitions.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity or binding specificity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-55 (1995); Yelton et al. J. Immunol. 155:1994-2004 (1995); Jackson et al., J. Immunol. 154(7):3310-19 (1995); and Hawkins et al, J. Mol. Biol. 226:889-96 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

An antibody "which binds" an antigen of interest, e.g. an EBV polypeptide antigen target, is one that binds the antigen with sufficient affinity such that the antibody is useful as a diagnostic and/or therapeutic agent in targeting a viral particle, or a cell or a tissue expressing the antigen, and does not significantly cross-react with other proteins, such as other herpes virus proteins. The extent of binding of the antibody to a "non-target" protein will often be less than about 10% of the binding of the antibody to its target protein as determined by fluorescence activated cell sorting (FACS) analysis or radioimmunoprecipitation (RIA). Regarding the binding of an antibody to a target molecule, the terms "specific binding" or "specifically binds to" or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or "is specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" may refer to binding where a molecule binds to a particular polypeptide or epitope on a particular polypeptide without substantially binding to any other polypeptide or polypeptide epitope.

An antibody that "inhibits the growth of infected cells expressing an EBV gH protein, gL protein, or gH/gL complex" or a "growth inhibitory" antibody is one which results in measurable growth inhibition of infected cells expressing or overexpressing the appropriate EBV protein. The EBV gH protein or gL protein, or gH/gL complex may be a transmembrane polypeptide, or complex, expressed on the surface of an infected cell or may be a polypeptide that is produced and secreted by an infected cell. Preferred growth inhibitory anti-gH, anti-gL, or anti-gH/gL, antibodies inhibit growth of EBV gH protein, gL protein, or gH/gL-expressing cells by greater than 20%, preferably from about 20% to about 50%, and even more preferably, by greater than 50% (e.g., from about 50% to about 100%) as compared to the appropriate control, the control typically being cells not treated with the antibody or oligopeptide being tested. Growth inhibition can be measured at an antibody concentration of about 0.1 to 30 mcg/ml or about 0.5 nM to 200 nM in cell culture, where the growth inhibition is determined 1-10 days after exposure of the cells to the antibody. Growth inhibition of cells in vivo can be determined in various ways such as is described in the Examples section below. The antibody is growth inhibitory in vivo if administration of the anti-gH antibody, anti-gL antibody, or anti-gH/gL antibody, at about 1 μg/kg to about 100 mg/kg body weight results in reduction in infected cells or inhibited EBV proliferation within about 1 day to 3 months from the first administration of the antibody, preferably within about 1 to 5 days.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRT, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (USA) 95:652-56 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRT, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

An antibody that "induces cell death" is one that causes a viable cell to become nonviable. The cell is one that expresses an EBV protein (e.g., a gH, a gL protein), or and EBV protein complex (e.g., a gH/gL complex), or that is infected with EBV. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody or oligopeptide can induce cell death, loss of membrane integrity as evaluated by uptake of propidium iodide (PI), trypan blue (see Moore et al. Cytotechnology 17:1-11 (1995)) or 7AAD can be assessed relative to untreated cells.

A "gH-expressing cell" is a cell which expresses an endogenous or transfected EBV gH protein, which may include expression either on the cell surface or in a secreted form. A "gL-expressing cell" is a cell which expresses an endogenous, or transfected, EBV gL protein, which may include expression either on the cell surface or in a secreted form. A "gH/gL complex-expressing cell" is a cell which expresses a gH/gL complex comprising endogenous, or transfected, EBV gH and gL proteins.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD, or IgM.

The word "label" when used herein refers to a detectable compound or composition which is conjugated directly or indirectly to an antibody or oligopeptide to generate a "labeled" antibody or oligopeptide. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents, enzymes and fragments thereof such as nucleolytic enzymes, antibiotics, immune suppressants, and toxins such as small molecule toxins or enzymatically active toxins of bacterial, fungal, plant or animal origin, including fragments and/or variants thereof. An antiviral agent causes destruction of virus-infected cells.

A "growth inhibitory agent" when used herein refers to a compound or composition which inhibits growth of a cell, especially an EBV-infected cell, either in vitro or in vivo. Thus, the growth inhibitory agent may be one which significantly reduces the percentage of EBV-infected cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

II. Compositions and Methods

A. Anti-gH, Anti-gL, and Anti-gH/gL Antibodies

This disclosure provides anti-gH antibodies, anti-gL antibodies, and anti-gH/gL antibodies, that may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous or intraperitoneal injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R1N=C=NR$, where R and R1 are different alkyl groups.

Animals are immunized against the antigen, immunogenic conjugates, or derivatives by combining, e.g., 100 mcg or 5 mcg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, California USA, and SP-2 and derivatives e.g., X63-Ag8-653 cells available from the American Type Culture Collection, Manassas, Virginia, USA. Human myeloma and mouse-human heteromyeloma cell lines also have been described for producing human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (MA) or enzyme-linked immunosorbent assay (ELISA). The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

Monoclonal antibodies or antibody fragments may be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-66 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

Anti-gH, anti-gL, and anti-gH/gL antibodies of this disclosure may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-25 (1986); Riechmann et al., Nature, 332:323-29 (1988); and Presta, Curr. Op. Struct. Biol., 2:593-96 (1992)).

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is important to reduce antigenicity and HAMA response (human anti-mouse antibody) when the antibody is intended for human therapeutic use. According to the "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a framework region derived from the consensus sequence of all human antibodies of a subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity or specificity for the target antigen(s), is achieved. In general, the hypervariable region residues are directly and most substantially involved in influencing antigen binding.

Various forms of humanized anti-gH, and anti-gL, antibodies are contemplated. For example, the humanized antibody may be an antibody fragment, such as a Fab, which is optionally conjugated with one or more cytotoxic agent(s) to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-58 (1993); Bruggemann et al., Year in Immuno. 7:33 (1993); U.S. Pat. Nos. 5,545,806, 5,569,825, 5,591,669 (all of GenPharm); 5,545,807; and WO 97/17852.

Alternatively, phage display technology (McCafferty et al., Nature 348:552-53 (1990)) can be used to produce human antibodies and antibody fragments in vitro, from immunoglobulin variable (V) domain gene repertoires from unimmunized donors. Using this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-71 (1993). Several sources of V-gene segments can be used for phage display. Clackson et al., Nature, 352:624-28 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-97 (1991), or Griffith et al., EMBO J. 12:725-34 (1993). See, also, U.S. Pat. Nos. 5,565,332 and 5,573,905.

As discussed above, human antibodies may also be generated in vitro in activated B cells (see, for example, U.S. Pat. Nos. 5,567,610 and 5,229,275).

4. Antibody Fragments

In certain circumstances, there are advantages to using antibody fragments, rather than whole antibodies. The smaller size of the fragments allows for rapid clearance, and may lead to improved access to EBV-infected cells or organs in a mammal.

Various techniques have been developed to produce antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-67 (1992)). Using another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques to produce antibody fragments will be apparent to the skilled practitioner. The antibody of choice may also be a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870. Such linear antibody fragments may be monospecific or bispecific.

5. Bispecific Antibodies

Bispecific antibodies have binding specificities for at least two different epitopes. Exemplary bispecific antibodies may bind to two different epitopes of a gH protein, a gL protein, or a gH/gL complex. Other such antibodies may combine a gH or gL binding site with a binding site for another protein, such as, for example, an EBV protein (e.g., gp350). Alternatively, an anti-gH, anti-gL, or anti-gH/gL, arm may be combined with an arm which binds to a triggering molecule on a leukocyte such as a T-cell receptor molecule (e.g. CD3) (see, e.g., Baeuerle, et al., Curr. Opin. Mol. Ther. 11(1):22-30 (2009)), or Fc receptors for IgG (FcγR), such as FcγRT (CD64), FcγRII (CD32) and FcγRIII (CD16), to focus and localize cellular defense mechanisms to the gH, gL, or gH/gL-expressing cell. Bispecific antibodies may also be used to localize cytotoxic agents to EBV-infected cells which express an EBV protein, such as gH or gL, or complexes thereof. These antibodies possess a gH or gL- binding arm and an arm which binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. Nos. 5,821,337 and 6,407,213 teach bispecific anti-ErbB2/anti-CD3 antibodies. Additional bispecific antibodies that bind an epitope on the CD3 antigen and a second epitope have been described in U.S. Pat. No. 5,078,998 (anti-CD3/tumor cell antigen); U.S. Pat. No. 5,601,819 (anti-CD3/IL-2R; anti-CD3/CD28; anti-CD3/CD45); U.S. Pat. No. 6,129,914 (anti-CD3/malignant B cell antigen); U.S. Pat. No. 7,112,324 (anti-CD3/CD19); U.S. Pat. No. 6,723,538 (anti-CD3/CCR5); U.S. Pat. No. 7,235,641 (anti-CD3/EpCAM); U.S. Pat. No. 7,262,276 (anti-CD3/ovarian tumor antigen); and U.S. Pat. No. 5,731,168 (anti-CD3/CD4IgG).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-39 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-59 (1991).

Using a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three-polypeptide fragment when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Preferably, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For details of generating bispecific antibodies see, for example, Suresh, Methods in Enzymology 121:210 (1986).

Using another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with several cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med. 175: 217-25 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed could bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-53 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized to produce antibody homodimers. The "diabody" technology described by Hollinger et al., Proc. Natl. Acad. Sci. USA 90:6444-48 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments using single-chain Fv (sFv) dimers has also been reported. See Gruber, J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of this disclosure. Heteroconjugate antibodies are composed of two covalently joined antibodies. Such antibodies have been proposed to target immune system cells to unwanted cells (see U.S. Pat. No. 4,676,980), and for treatment of HIV infection (see WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of this disclosure may be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody preferably further comprises at least two (and preferably four) light chain variable domain polypeptides. The multivalent antibody may comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the disclosure with respect to effector function, e.g., to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-95 (1992) and Shopes, B. J. Immunol. 148:2918-22 (1992). Homodimeric antibodies with enhanced anti-viral activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-30 (1989).

To increase the serum half-life of the antibody, a salvage receptor binding epitope may be incorporated into the antibody (especially an antibody fragment) as described in U.S. Pat. No. 5,739,277. The term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Immunoconjugates

The disclosure also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

This disclosure further contemplates an immunoconjugate formed between an antibody and a compound with nucleolytic activity (e.g., a ribonuclease or a DNA endonuclease such as a deoxyribonuclease; DNase).

For selective destruction of an EBV-infected cell, the antibody may comprise a radioactive atom. A variety of radioactive isotopes are available to produce radioconjugated anti-gH antibodies or anti-gL antibodies. Examples include At211, I131, I125, Y90, Re186, Re188, Sm153, Bi212, P32, Pb212 and radioactive isotopes of Lu. When the conjugate is used for diagnosis, it may comprise a radioactive atom for scintigraphic studies, for example tc99m or 1123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the disclosure expressly contemplate, but are not limited to, an ADC prepared with cross-linker reagents: BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available from Pierce Biotechnology, Inc., Rockford, IL).

Alternatively, a fusion protein comprising an anti-EBV gH antibody, anti-EBV gL antibody, or anti-gH/gL antibody and a cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibody may also be conjugated to a "receptor" (such streptavidin) for utilization in pre-targeting of viral infected cells, wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-gH, anti-gL, and anti-gH/gL antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485, 045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of this disclosure can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

C. Screening for Anti-EBV gH, Anti-gL, and Anti-gH/gL Antibodies with the Desired Properties Techniques for generating antibodies that bind to EBV gH protein, EBV gL protein, or EBV gH/gL complexes, have been described above. One may further select antibodies or oligopeptides with certain biological characteristics, as desired.

The growth inhibitory effects of an anti-gH antibody, anti-gL antibody, or anti-gH/gL antibody, of this disclosure may be assessed by methods known in the art, e.g., using cells which express an EBV gH protein, an EBV gL protein, or complexes thereof, either endogenously or following transfection with a nucleic acid molecule encoding an EBV gH, or gL, protein. For example, appropriate EBV infected cells may be treated with an anti-gH, an anti-gL, or an anti-gH/gL, monoclonal antibody of this disclosure at various concentrations for a few days (e.g., 2-7) and stained with crystal violet or MTT or analyzed by some other colorimetric assay. Another method of measuring proliferation would be by comparing 3H-thymidine uptake by the cells treated in the presence or absence an anti-gH, anti gL, antibody, or anti-gH/gL, e of the disclosure. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of infected cells in vivo can be determined in various ways known in the art. Preferably, the anti-gH, anti-gL, or anti-gH/gL antibody will inhibit cell proliferation of an EBV infected cell in vitro or in vivo by about 25-100% compared to the untreated infected cell, more preferably, by about 30-100%, and even more preferably by about 50-100% or 70-100%. Growth inhibition can be measured at an antibody concentration of about 0.5 to 30 µg/ml or about 0.5 nM to 200 nM in cell culture, where the growth inhibition is determined 1-10 days after exposure of the cells to the antibody. The antibody is growth inhibitory in vivo if administration of the anti-gH, anti-gL, or anti-gH/gL antibody at about 1 µg/kg to about 100 mg/kg body weight results in reduction in cell growth or proliferation within about 5 days to 3 months from the first administration of the antibody, preferably within about 5 to 30 days.

To select for an anti-gH, anti-gL, or anti-gH/gL antibody that induces cell death, loss of membrane integrity as indicated by, e.g., propidium iodide (PI), trypan blue or 7AAD uptake may be assessed relative to control. A PI uptake assay can be performed in the absence of complement and immune effector cells. Cells expressing EBV gH protein, and/or EBV gL protein, are incubated with medium alone or medium containing the appropriate anti-gH, anti-gL, or anti-gH/gL antibody (e.g., at about 10 µg/ml), anti-gL antibody-. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those antibodies that induce statistically significant levels of cell death as determined by PI uptake may be selected as cell death-inducing antibodies.

To screen for antibodies that bind to an epitope on an EBV gH protein. An EBV gL protein, or an EBV gH/gL complex, bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody or oligopeptide binds the same site or epitope as a known anti-gH, anti-gL, or anti-gH/gL antibody. Alternatively or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of an EBV gH or gL protein, or gH/gL complex, can be used in competition assays with the test antibodies or with a test antibody and an antibody with a characterized or known epitope.

D. Variants of Anti-gH, anti-gL, or Anti-gH/gL Antibodies

In addition to the anti-gH, anti-gL, and anti-gH/gL, antibodies described herein, it is contemplated that variants of anti-gH, anti-gL, and anti-gH/gL antibodies can be prepared. Anti-gH, anti-gL, and anti-gH/gL antibody variants can be prepared by introducing appropriate nucleotide changes into the encoding DNA, and/or by synthesis of the desired antibody or polypeptide. Those skilled in the art will appreciate that amino acid changes may alter post-translational processes of anti-gH, anti-gL, or anti-gH/gL antibodies, such as changing the number or position of glycosylation sites or altering the membrane anchoring characteristics.

Variations in the sequences of anti-gH, anti-gL, and anti-gH/gL antibodies described herein can be made, for example, using any of the techniques and guidelines for conservative and non-conservative mutations set forth, for instance, in U.S. Pat. No. 5,364,934. Variations may be a substitution, deletion, or insertion of one or more codons encoding the antibody or polypeptide that results in a change in the amino acid sequence as compared with the native sequence antibody or polypeptide. Optionally, the variation is by substitution of at least one amino acid with any other amino acid in one or more of the domains of the anti-gH, anti-gL, or anti-gH/gL antibody. Guidance in determining which amino acid residue may be inserted, substituted or deleted without adversely affecting the desired activity may be found by comparing the sequence of the -anti-gH, anti-gL, or anti-gH/gL antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions, or substitutions of amino acids in the sequence and testing the resulting variants for activity exhibited by the full-length or mature native sequence.

Fragments of anti-gH, anti-gL, and anti-gH/gL antibodies, are provided herein. Such fragments may be truncated at the N-terminus or C-terminus, or may lack internal residues, for example, when compared with a full length native antibody. Certain fragments lack amino acid residues that are not essential for a desired biological activity of the anti-gp350 antibody.

Fragments of anti-gH, anti-gL, and anti-gH/gL antibodies may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-gH antibody fragments share at least one biological and/or immunological activity with the native anti-gH antibodies disclosed herein. Likewise, anti-gL antibody fragments share at least one biological and/or immunological activity with the native anti-gL antibodies disclosed herein.

Conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of an anti-gH, anti-gL, or anti-gH/gL antibody is accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce an anti-gH, anti-gL, or anti-gH/gL antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-85 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Any cysteine residue not involved in maintaining the proper conformation of an anti-gH, anti-gL, or anti-gH/gL antibody also may be substituted, generally with serine, to improve the oxidative stability of the molecule and prevent aberrant crosslinking. Conversely, cysteine bond(s) may be added to an anti-gH, anti-gL, or anti-gH/gL antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. To identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the EBV protein (e.g., gH or gL), or complex thereof. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of an anti-gH, anti-gL, or anti-gH/gL antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-gH, anti-gL, or anti-gH/gL antibody.

E. Modifications of Anti-gH, Anti-gL, and Anti-gH/gL Antibodies

Covalent modifications of anti-gH, anti-gL, and anti-gH/gL antibodies are included within the scope of this disclosure. One type of covalent modification includes reacting targeted amino acid residues of an anti-gH, anti-gL, or anti-gH/gL antibody with an organic derivatizing agent that can react with selected side chains or the N- or C-terminal residues of the antibody. Derivatization with bifunctional agents is useful, for instance, for crosslinking an anti-gH, anti-gL, or anti-gH/gL antibody to a water-insoluble support matrix or surface for use in purifying antibodies, or detection of a gH, or gL protein, or a gH/gL protein complex, in biological samples, or EBV diagnostic assays. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of an anti-gH, anti-gL, or anti-gH/gL antibody included within the scope of this disclosure comprises altering the native glycosylation pattern of the antibody or polypeptide. "Altering the native glycosylation pattern" is intended for purposes herein to mean deleting one or more carbohydrate moieties found in a native sequence an anti-gH, anti-gL, or anti-gH/gL antibody (either by removing the underlying glycosylation site or by deleting the glycosylation by chemical and/or enzymatic means), and/or adding one or more glycosylation sites that are not present in the native sequence anti-gH, anti-gL, or anti-gH/gL antibody. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl galactosamine, galactose, or xylose to a hydroxyamino acid, most commonly serine or threonine, although 5-hydroxyproline or 5-hydroxylysine may also be used.

Addition of glycosylation sites to an anti-gH, anti-gL, or anti-gH/gL antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-gH, anti-gL, or anti-gH/gL antibody (for O-linked glycosylation sites). The sequence of an anti-gH, anti-gL, or anti-gH/gL antibody may optionally be altered through changes at the DNA level, particularly by mutating the DNA encoding the—antibody at preselected bases such that codons are generated that will translate into the desired amino acids.

Another means of increasing the number of carbohydrate moieties on an anti-gH, anti-gL, or anti-gH/gL antibody is by chemical or enzymatic coupling of glycosides to the polypeptide. Such methods are described in the art, e.g., in WO 87/05330 published 11 Sep. 1987, and in Aplin and Wriston, C R C Crit. Rev. Biochem., pp. 259-306 (1981).

Removal of carbohydrate moieties present on an anti-gH, anti-gL, or anti-gH/gL antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved using a variety of endo- and exo-glycosidases as described by Thotakura et al., Meth. Enzymol., 138:350 (1987).

Another type of covalent modification of an anti-gH, anti-gL, or anti-gH/gL antibody comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

The anti-gH, anti-gL, and anti-gH/gL antibodies of this disclosure may also be modified in a way to form chimeric molecules comprising an anti-gH, anti-gL, or anti-gH/gL antibody fused to another, heterologous polypeptide or amino acid sequence.

Such a chimeric molecule may comprise a fusion of an anti-gH, anti-gL, or anti-gH/gL antibody with a tag polypeptide, which provides an epitope to which an anti-tag antibody can selectively bind. The epitope tag is generally placed at the amino- or carboxyl-terminus of the anti-gH, anti-gL, or anti-gH/gL antibody. The presence of such epitope-tagged forms of an anti-gH, anti-gL, or anti-gH/gL antibody can be detected using an antibody against the tag polypeptide. Also, provision of the epitope tag enables the anti-gH, anti-gL, or anti-gH/gL antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-16 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-10 (1988)); the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

Alternatively, the chimeric molecule may comprise a fusion an anti-gH, anti-gL, or anti-gH/gL antibody with an immunoglobulin or a region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-gH, anti-gL, or anti-gH/gL antibody in place of at least one variable region within an Ig molecule. Preferably, the immunoglobulin fusion includes the hinge, CH2 and CH3, or the hinge, CH1, CH2 and CH3 regions of an IgG1 molecule. For the production of immunoglobulin fusions, see also U.S. Pat. No. 5,428,130.

F. Preparation of Anti-gH, Anti-gL, and Anti-gH/Antibodies

The description below relates primarily to production of an anti-gH, anti-gL, or anti-gH/gL antibody, by culturing cells transformed or transfected with a vector containing an anti-gH antibody, an anti-gL antibody, or an anti-gH/gL antibody, -encoding nucleic acid molecule. It is, of course, contemplated that alternative methods, which are well known in the art, may be employed to prepare anti-gH, anti-gL, and anti-gH/gL, antibodies. For instance, the appropriate amino acid sequence, or portions thereof, may be produced by direct peptide synthesis using solid-phase techniques (e.g., Stewart et al., Solid-Phase Peptide Synthesis, W.H. Freeman Co., San Francisco, CA (1969); Merrifield, J. Am. Chem. Soc., 85:2149-54 (1963)). In vitro protein synthesis may be performed using manual techniques or by automation. Automated synthesis may be accomplished, for instance, using an Applied Biosystems Peptide Synthesizer (Foster City, CA) using manufacturer's instructions. Various portions of an anti-gH, anti-gL, or anti-gH/gL antibody may be chemically synthesized separately, and then combined using chemical or enzymatic methods to produce the desired, final anti-gH, anti-gL, or anti-gH/gL antibody.

1. Isolation of DNA Encoding an Anti-gH, Anti-gL, or Anti-gH/gL Antibody

DNA encoding an anti-gH, anti-gL, or anti-gH/gL antibody may be obtained from a cDNA library prepared from tissue believed to possess an anti-gH, anti-gL, or anti-gH/gL antibody mRNA, and to express it at a detectable level. Accordingly, human anti-gH, anti-gL, or anti-gH/gL antibody DNA can be conveniently obtained from a cDNA library prepared from human tissue. The anti-gH, anti-gL, or anti-gH/gL antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding an anti-gH, anti-gL, or anti-gH/gL antibody is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acids having protein coding sequences may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-gH, anti-gL, or anti-gH/gL antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, CaCl2, CaPO4, liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown, Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including E. coli W3110 strain 1A2, which has the complete genotype tonA; E. coli W3110 strain 9E4, which has the complete genotype tonA ptr3; E. coli W3110 strain 27C7 (ATCC 55,244), which has the complete genotype tonA ptr3 phoA EIS (argF-lac)169 degP ompT kanr; E. coli W3110 strain 37D6, which has the complete genotype tonA ptr3 phoA E15 (argF-lac)169 degP ompT rbs7 ilvG kanr; E. coli W3110 strain 40B4, which is strain 37D6 with a non-kanamycin resistant degP deletion mutation; and an E. coli strain having mutant periplasmic protease disclosed in U.S. Pat. No. 4,946,783. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in EBV or EBV-infected cell destruction. Full length antibodies have greater half-life in circulation. Production in E. coli is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the E. coli cell paste in a soluble fraction and can be purified through, e.g., a protein A or G column depending on the isotype. Final purification can be carried out similar to the process for purifying antibody expressed, e.g., in CHO cells.

In addition to prokaryotes, eukaryotic microbes such as filamentous fungi or yeast are suitable cloning or expression hosts for an anti-gH, anti-gL, or anti-gH/gL antibody-encoding vectors. Saccharomyces cerevisiae is a commonly used lower eukaryotic host microorganism. Others include Schizosaccharomyces pombe (Beach and Nurse, Nature, 290: 140 [1981]; EP 139,383 published 2 May 1985); Kluyveromyces hosts (U.S. Pat. No. 4,943,529; Fleer et al., Bio/Technology, 9:968-975 (1991)) such as, e.g., K. lactis (MW98-8C, CBS683, CBS4574; Louvencourt et al., J. Bacteriol., 154(2):737-742 [1983]), K. fragilis (ATCC 12,424), K. bulgaricus (ATCC 16,045), K. wickeramii (ATCC 24,178), K. waltii (ATCC 56,500), K. drosophilarum (ATCC 36,906; Van den Berg et al., Bio/Technology, 8:135 (1990)), K. thermotolerans, and K. marxianus; yarrowia (EP 402,226); Pichia pastoris (EP 183,070; Sreekrishna et al., J. Basic Microbiol., 28:265-278 [1988]); Candida; Trichoderma reesia (EP 244,234); Neurospora crassa (Case et al., Proc. Natl. Acad. Sci. USA, 76:5259-5263 [1979]); Schwanniomyces such as Schwanniomyces occidentalis (EP 394,538 published 31 Oct. 1990); and filamentous fungi such as, e.g., Neurospora, Penicillium, Tolypocladium (WO 91/00357 published 10 Jan. 1991), and Aspergillus hosts such as A. nidulans (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and A. niger (Kelly and Hynes, EMBO J., 4:475-479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, The Biochemistry of Methylotrophs, 269 (1982).

Suitable host cells for the expression of glycosylated anti-gH, anti-gL, and anti-gH/gL, antibodies are derived from multicellular organisms. Examples of invertebrate cells include insect cells such as Drosophila S2 and Spodoptera Sf9, as well as plant cells, such as cell cultures of cotton, corn, potato, soybean, Petunia, tomato, and tobacco. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to this disclosure, particularly for transfection of Spodoptera frugiperda cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production, and cultured in conventional nutrient media modified as appropriate for inducing promoters, selecting transformants, or amplifying the genes encoding the desired sequences.

3. Selection and Use of a Replicable Vector

The nucleic acid molecule (e.g., cDNA or genomic DNA) encoding an anti-gH, anti-gL, or anti-gH/gL antibody may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Anti-gH, anti-gL, or anti-gH/gL monoclonal antibodies may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-gH, anti-gL, or anti-gH/gL antibody-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion, the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up an anti-gH, anti-gL, or anti-gH/gL antibody-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the anti-gH, anti-g, or anti-gH/gL antibody-encoding nucleic acid sequence to direct mRNA synthesis. Promoters recognized by a variety of potential host cells are well known. Promoters suitable for use with prokaryotic hosts include the β-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980)), and hybrid promoters such as the tac promoter (deBoer et al., Proc. Natl. Acad. Sci. USA, 80:21-25 (1983)). Promoters for use in bacterial systems also will contain a Shine-Dalgarno sequence operably linked to the DNA encoding an anti-gH, anti-gL, or anti-gH/gL antibody.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription of a nucleic acid encoding an anti-gH, anti-gL, or anti-gH/gL antibody in mammalian host cells is controlled, for example, by promoters obtained from the genomes of viruses such as polyoma virus, fowlpox virus (UK 2,211,504), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding an anti-gH, anti-gL, or anti-gH/gL antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-gp350 antibody coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody.

Still other methods, vectors, and host cells suitable for adaptation to the synthesis of an anti-gH, anti-gL, or anti-gH/gL antibody in recombinant vertebrate cell culture are described in Gething et al., Nature, 293:620-25 (1981); Mantei et al., Nature, 281:40-46 (1979); EP 117,060; and EP 117,058.

4. Culturing the Host Cells

The host cells used to produce an anti-gH, anti-gL, or anti-gH/gL antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657, 866; 4,927,762; 4,560,655; or 5,122,469; WO 90/03430;

WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence EBV gH or gL protein, or gH/gL complex, or against a synthetic peptide based on the DNA sequences provided herein or against exogenous sequence fused to gH or gL DNA, and encoding a specific antibody epitope.

6. Purification of Anti-gH, Anti-gL, and Anti-gH/gL Antibodies

Forms of an anti-gH, anti-gL, or anti-gH/gL antibody may be recovered from culture medium or from host cell lysates. If membrane-bound, it can be released from the membrane using a suitable detergent solution (e.g. Triton-X 100) or by enzymatic cleavage. Cells employed in expression of an anti-gH, anti-gL, or anti-gH/gL antibody can be disrupted by various physical or chemical means, such as freeze-thaw cycling, sonication, mechanical disruption, or cell lysing agents.

It may be desired to purify anti-gH, anti-gL, or anti-gH/gL antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-gH, anti-gL, or anti-gH/gL antibody, and EBV gH or gL protein. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used, and the anti-gH, anti-gL, or anti-gH/gL antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, NJ) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

G. Pharmaceutical Formulations

Therapeutic formulations of anti-gH, anti-gL, and anti-gH/gL, antibodies of this disclosure are prepared for storage by mixing the antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the indication being treated, preferably those with complementary activities that do not adversely affect each other. For example, in addition to anti-gH, anti-gL, or anti-gH/gL antibody, it may be desirable to include in the one formulation, an additional antibody, e.g., a second anti-gH, anti-gL, or anti-gH/gL antibody that binds a different epitope on the EBV gH or gL protein or gH/gL complex. Alternatively, or additionally, the composition may further comprise a cytokine, an anti-inflammatory agent, or an interferon. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

H. Diagnosis and Treatment Using Anti-gH, Anti-gL, or Anti-gH/gL Antibodies

EBV gH, gL, and gH/gL expression may be evaluated using an in vivo diagnostic assay, e.g., by administering a molecule (such as anti-gH, anti-gL, or anti-gH/gL, antibody) that binds the molecule to be detected, and is tagged with a detectable label (e.g., a radioactive isotope or a fluorescent label) and externally scanning the patient for localization of the label.

As described above, -anti-gH, anti-gL, and anti-gH/gL, antibodies of this disclosure have various non-therapeutic applications. The anti-gH, anti-gL, and anti-gH/gL, antibodies of this disclosure are useful for diagnosis and staging of EBV infections. The antibodies are also useful for purification or immunoprecipitation of EBV gH, or gL, protein, or complexes thereof, from cells, for detection and quantitation of EBV gH, or gL, protein, or complexes thereof, in vitro, e.g., in an ELISA or a Western blot, to kill and eliminate gH, gL, or gH/gL-expressing cells from a population of mixed cells as a step in the purification of other cells.

Currently, EBV infection prevention and treatment involves preventing transmission of the virus, vaccination, or administration of interferons. Anti-gH, anti-gL, or anti-gH/gL antibody therapy (such as by passive immunotherapy) may be especially desirable in elderly patients or immunocompromised patients or pregnant patients who may not tolerate the side effects of vaccination or vaccine components or interferons, or who cannot mount an immunological response.

A conjugate comprising anti-gH, anti-gL, or anti-gH/gL antibody conjugated with a cytotoxic agent may be administered to the patient. Preferably, the immunoconjugate bound to the anti-gH, anti-gL, or anti-gH/gL antibody is internalized by the cell, resulting in increased therapeutic efficacy of the immunoconjugate in killing the infected cell to which it binds. Preferably, the cytotoxic agent targets or interferes with the nucleic acid in the infected cell. The anti-gH, anti-gL, or anti-gH/gL, antibodies, or conjugates thereof, are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody or oligopeptide is preferred.

Other therapeutic regimens may be combined with the administration of an anti-gH, anti-gL, or anti-gH/gL antibody. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of an anti-gH, anti-gL, or anti-gH/gL antibody with administration of an antibody directed against another EBV antigen.

The therapeutic treatment methods of this disclosure may include the combined administration of an anti-gH, anti-gL, or anti-gH/gL antibody (or antibodies) and an interferon.

For the prevention or treatment of EBV infection or EBV-associated disease, the dosage and mode of administration of these antibodies and therapeutic proteins will be chosen by the medical provider according to known criteria. The appropriate dosage of antibody or oligopeptide will depend on the type of disease to be treated, as defined above, the severity and course of the disease, whether the antibody or oligopeptide is administered for preventive or therapeutic purposes, previous therapy, the patient's clinical history and response to the antibody or oligopeptide and the discretion of the medical provider. The antibody or oligopeptide is suitably administered to the patient at one time or over a series of treatments. Preferably, the antibody or oligopeptide is administered by intravenous infusion or by subcutaneous injections. Depending on the type and severity of the disease, about 1 mcg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of an anti-gH, anti-gL, or anti-gH/gL antibody. However, other dosage regimens may be useful. A typical daily dosage might range from about 1 mcg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to medical providers of skill in the art.

Aside from administration of an anti-gH, anti-gL, or anti-gH/gL antibody to a patient, this disclosure contemplates administration of the antibody by gene therapy. Such administration of nucleic acid encoding the antibody is encompassed by the expression "administering a therapeutically effective amount of an antibody." See, for example, WO96/07321 concerning the use of gene therapy to generate intracellular antibodies.

There are two major approaches to getting the nucleic acid (optionally contained in a vector) into the patient's cells; in vivo and ex vivo. For in vivo delivery, the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

Anti-gH, anti-gL, and anti-gH/gL, antibodies of the disclosure can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail above, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, to minimize side effects or therapeutic complications, certain other Fc regions may be used.

These antibodies may include an antibody that competes for binding or binds substantially to, the same epitope as the antibodies of the disclosure. Antibodies having the biological characteristics of the present anti-gH, anti-gL, and anti-gH/gL, antibodies of this disclosure are also contemplated, specifically including the in vivo targeting, and infection inhibiting or preventing, or cytotoxic characteristics.

The present anti-gH, anti-gL, and anti-gH/gL, antibodies are useful for treating an EBV infection or alleviating one or more symptoms of the infection in a mammal. The antibody can bind to at least a portion of an infected cell that express EBV gH, or EBV gL, protein or a complex thereof, in the mammal. Preferably, the antibody or oligopeptide is effective to destroy or kill EBV gH, or EBV gL-expressing cells, or inhibit the growth of such cells, in vitro or in vivo, upon binding to an EBV gH or gL protein, or a complex thereof, on the cell. Such an antibody includes a naked anti-gH, anti-gL, or anti-gH/gL antibody (not conjugated to any agent). Naked antibodies that have cytotoxic or cell growth inhibition properties can be further harnessed with a cytotoxic agent to render them even more potent in EBV or EBV-infected cell destruction. Cytotoxic properties can be conferred to an anti-gH, anti-gL, or anti-gH/gL antibody by, e.g., conjugating the antibody with a cytotoxic agent, to form an immunoconjugate as described herein. The cytotoxic agent or a growth inhibitory agent is preferably a small molecule.

This disclosure also provides a composition comprising an anti-gH, anti-gL, or anti-gH/gL antibody of the disclosure, and a carrier. For the purposes of treating EBV infection, compositions can be administered to the patient in need of such treatment, wherein the composition can comprise one or more anti-gH, anti-gL, or anti-gH/gL, antibodies present as an immunoconjugate or as the naked antibody. The compositions may comprise these antibodies or oligopeptides in combination with other therapeutic agents. The formulation may be a therapeutic formulation comprising a pharmaceutically acceptable carrier.

This disclosure also provides isolated nucleic acids encoding the anti-gH, anti-gL, or anti-gH/gL, antibodies. Nucleic acids encoding both the H and L chains and especially the hypervariable region residues, chains which encode the native sequence antibody as well as variants, modifications and humanized versions of the antibody, are encompassed.

The disclosure also provides methods useful for treating an EBV infection or alleviating one or more symptoms of the infection in a mammal, comprising administering a therapeutically effective amount of an anti-gH, anti-gL, or anti-gH/gL antibody of this disclosure to the mammal. The antibody therapeutic compositions can be administered short term (acutely) or chronically, or intermittently as directed by a medical professional. Also provided are methods of inhibiting the growth of, and killing an EBV gH, EBV gL, or EBV gH/gL-expressing cell.

This disclosure also provides methods useful for treating or preventing posttransplant lymphoproliferative disorder (PTLD) in a mammal. In these methods, the antibodies or fragments thereof, are particularly effective for PTLD in EBV-seronegative persons (i.e., not previously infected with EBV) and given within a few days of solid organ or bone marrow transplant. In these methods, multiple doses of the antibodies, or functional fragments thereof, may be given over time (for example, in persons undergoing solid organ transplants, these proteins may be given within 72 hours of transplant and additional doses may be given at 1, 4, 6, 8, 12, and 16 weeks after transplant). Virtually all transplant recipients are screened for EBV and CMV serology prior to transplant. The antibodies, or functional fragments thereof, may also be administered to EBV-seropositive persons, but the rate of PTLD is lower is EBV seropositive persons than seronegative persons. In these methods, the antibodies, or functional fragments thereof, and an EBV vaccine may be co-administered. In these co-administration methods, the antibodies, or functional fragments thereof, and the vaccine(s) may be administered on the same day at different sites, as is done for combined treatment with vaccine and immunoglobulin for rabies, hepatitis B, or tetanus exposure. In these methods, a single dose of the antibodies, or functional fragments thereof, would likely be given because the recipient would be expected to produce antibody in response to the vaccine.

This disclosure also provides methods useful for preventing EBV infection or reducing EBV disease in EBV seronegative patients with congenital or acquired immune deficiencies, such as XLP1 (X-linked lymphoproliferative disease) or XMEN (X-linked immunodeficiency with magnesium defect, Epstein-Barr virus infection, and neoplasia disease). These patients are at high risk for developing severe disease if they become infected with EBV.

I. Articles of Manufacture and Kits

This disclosure also provides assay devices, kits, and articles of manufacture comprising at least one anti-gH, anti-gL, or anti-gH/gL antibody of this disclosure, optionally linked to a label, such as a fluorescent or radiolabel. The articles of manufacture may contain materials useful for the detection, diagnosis, or treatment of EBV infection. A preferred device is a lateral flow assay device which provides for point-of-care detection and/or diagnosis of an EBV infection. The article of manufacture comprises a container and a label or package insert on or associated with the container. Suitable containers include, for example, bottles, vials, syringes, etc. The containers may be formed from a variety of materials such as glass or plastic. The container holds a composition which is effective for detecting or treating the EBV infection and may have a sterile access port (for example the container may be an intravenous solution bag or a vial having a stopper pierceable by a hypodermic injection needle). At least one active agent in the composition is an anti-gH, anti-gL, or anti-gH/gL of this disclosure. The label or package insert indicates that the composition is used for detecting or treating EBV infection. The label or package insert may further comprise instructions for using the antibody composition, e.g., in the testing or treating of the infected patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for EBV-infected cell killing assays, for purification, or immunoprecipitation of EBV protein (e.g., gH or gL), or complexes thereof, from cells. For isolation and purification of an EBV gH or gL protein, or a gH/gL complex, the kit can contain an anti-gH, anti-gL, or anti-gH/gL antibodies coupled to beads (e.g., sepharose beads). Kits can be provided which contain the antibodies for detection and quantitation of an EBV gH or gL protein, or complexes thereof, in vitro, e.g., in an ELISA or a Western blot. As with the article of manufacture, the kit comprises a container and a label or package insert on or associated with the container. The container holds a composition comprising at least one anti-gH, anti-gL, or anti-gH/gL antibody of the disclosure. Additional containers may be included that contain, e.g., diluents and buffers, control antibodies. The label or package insert may provide a description of the composition as well as instructions for the intended in vitro or diagnostic use.

The anti-gH, anti-gL, or anti-gH/gL antibody of this disclosure may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those described in U.S. Pat. Nos. 5,559,041, 5,714,389, 5,120,643, and 6,228,660 all of which are incorporated herein by reference in their entireties. The anti-gH, anti-gL, or anti-gH/gL antibody of this disclosure may also be used in a lateral flow assay device in conjunction with other antibodies to detect multiple EBV proteins or other herpesvirus proteins using a single biological sample from a subject or patient being tested on one portable, point-of-care device.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

All patent and literature references cited in the present specification are hereby incorporated by reference in their entirety.

EXAMPLES

Example 1

Isolation and Characterization of Monoclonal Antibodies to gH/gL

PBMCs cells from healthy blood bank donors with high neutralizing titers to EBV were incubated with a gH/gL Avi-His probe labeled using an in vitro biotinylation kit (Avidity) and followed by fluorochrome-conjugated streptavidin. Single B cells binding to gH/gL were sorted by flow cytometry into single wells of a 96-well plate. Immunoglobulin heavy and light chains were amplified by RT-PCR and the sequence of the variable region of both chains was determined. Expi293F cells (Thermo-Fisher Scientific) were transfected with plasmids expressing the reconstructed immunoglobulin heavy and light chains and antibodies in the supernatant were screened for binding to gH/gL and EBV neutralizing activity. mAb 769B10 (B10) was initially selected for further characterization based on its ability to bind gH/gL complex and neutralize EBV infection of B cells and epithelial cells.

87

Example 2

Testing Cross-Competition of Antibodies

Antibody cross-competition was performed as described previously (Ngwuta, J. O., et al., (2015) Sci. Transl. Med. 7) with modifications. Briefly, gHgL or gp42 protein was immobilized on HIS1K biosensors (ForteBio) through C-terminal (gHgL) or N-terminal (gp42) poly-histidine tag in assay buffer (PBS with 1% BSA), and the protein-loaded biosensors were equilibrated with assay buffer. The biosensors were dipped in competitor antibodies (30 µg/mL in assay buffer) for 300 sec followed by analyte antibodies (30 µg/mL in assay buffer) or immune sera (serial dilutions with assay buffer) for 300 sec with a short baseline step (60 sec) in between the two antibody steps. All assays were performed at 30° C. with agitation of 1,000 rpm in an Octet HTX instrument (ForteBio). Percent inhibition of antibody binding by competing mAbs was determined as:

inhibition (%)=100−[(analyte antibody binding in the presence competitor mAb)/(analyte antibody binding in the presence of isotype control mAb)]×100.

Figure 1B:
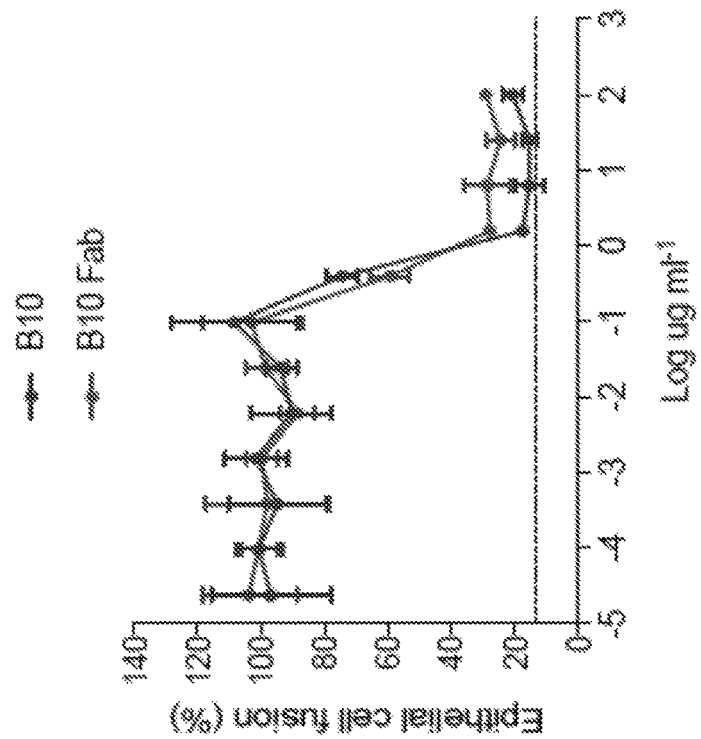
Figure 1B:
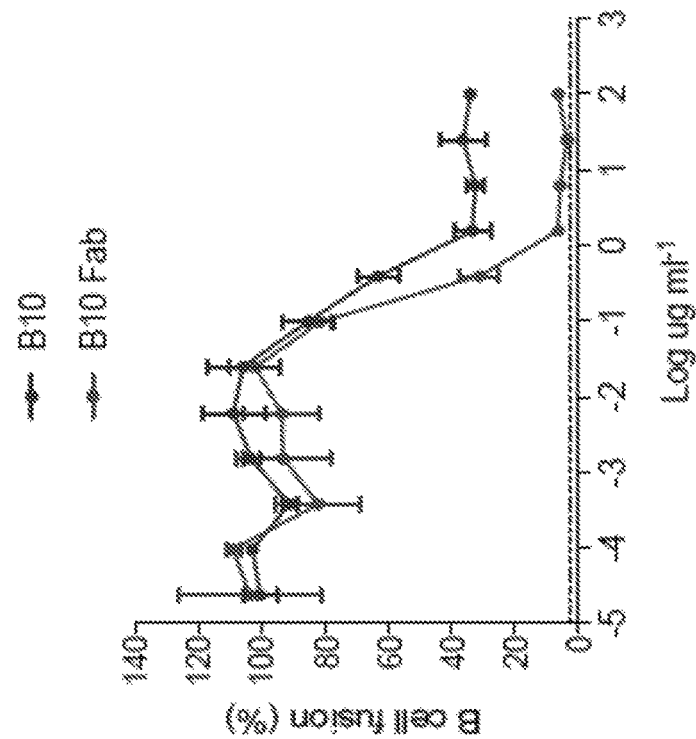
Figure 1C:
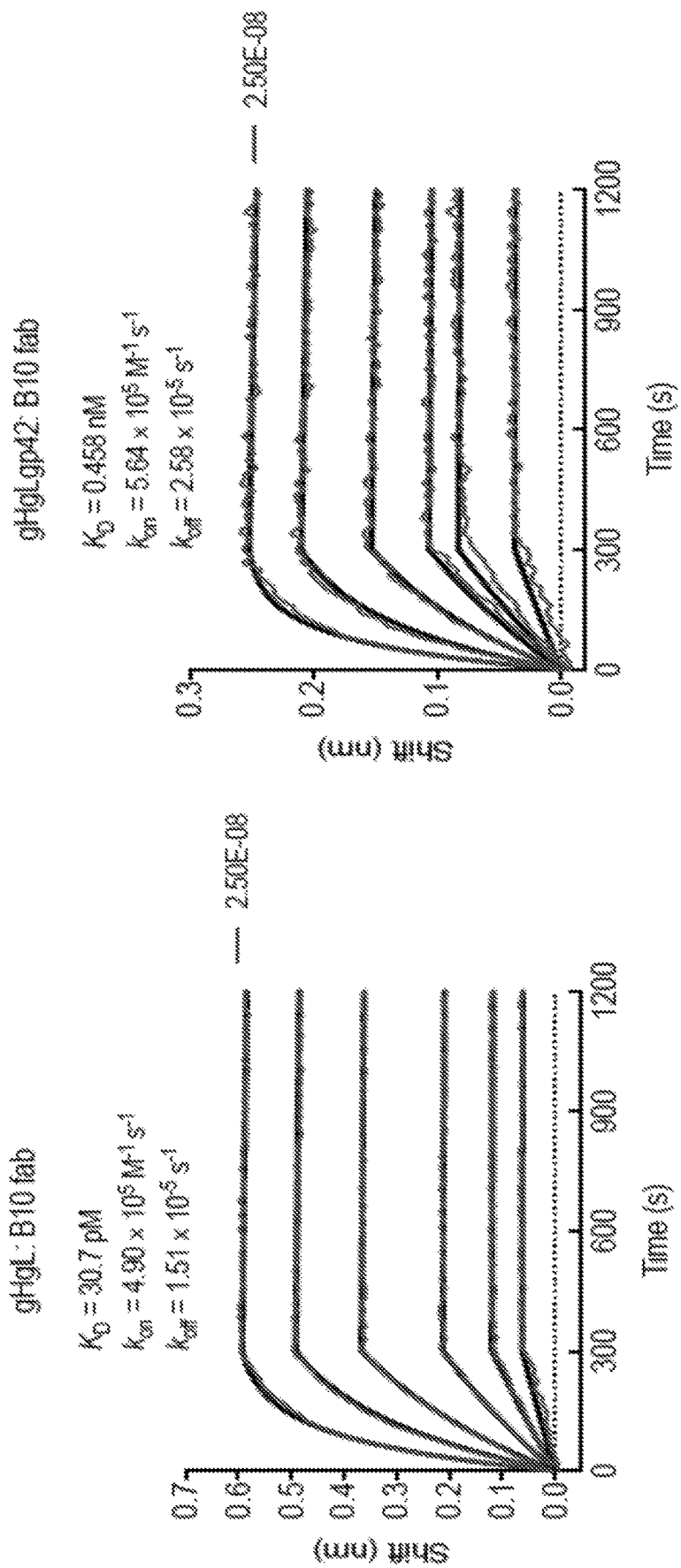

We first used mAb 769B10 (B10), and which neutralizes EBV infection of B cells and epithelial cells (FIG. 1A) and inhibits B cell and epithelial cell fusion (FIG. 1B). Kinetic assays indicated that the affinity of the Fab fragment of 769B10 for gH/gL ($K_D$=30.7 pM) appears >10 times stronger than for gH/gL/gp42 ($K_D$=458 pM) (FIG. 1C), presumably due to the presence of gp42 which competes with 769B10 binding to the gp42 binding site on gH/gL. In addition, mAb 769B10 competes with mAb CL40, which binds to the gp42 binding site on gH/gL (Sathiyamoorthy et al., (2017) Proc. Natl. Acad. Sci. 201704661), suggesting that 769B10 recognizes a similar epitope as CL40.

Example 3

Neutralization of EBV Infection in B Cells

Figure 2:
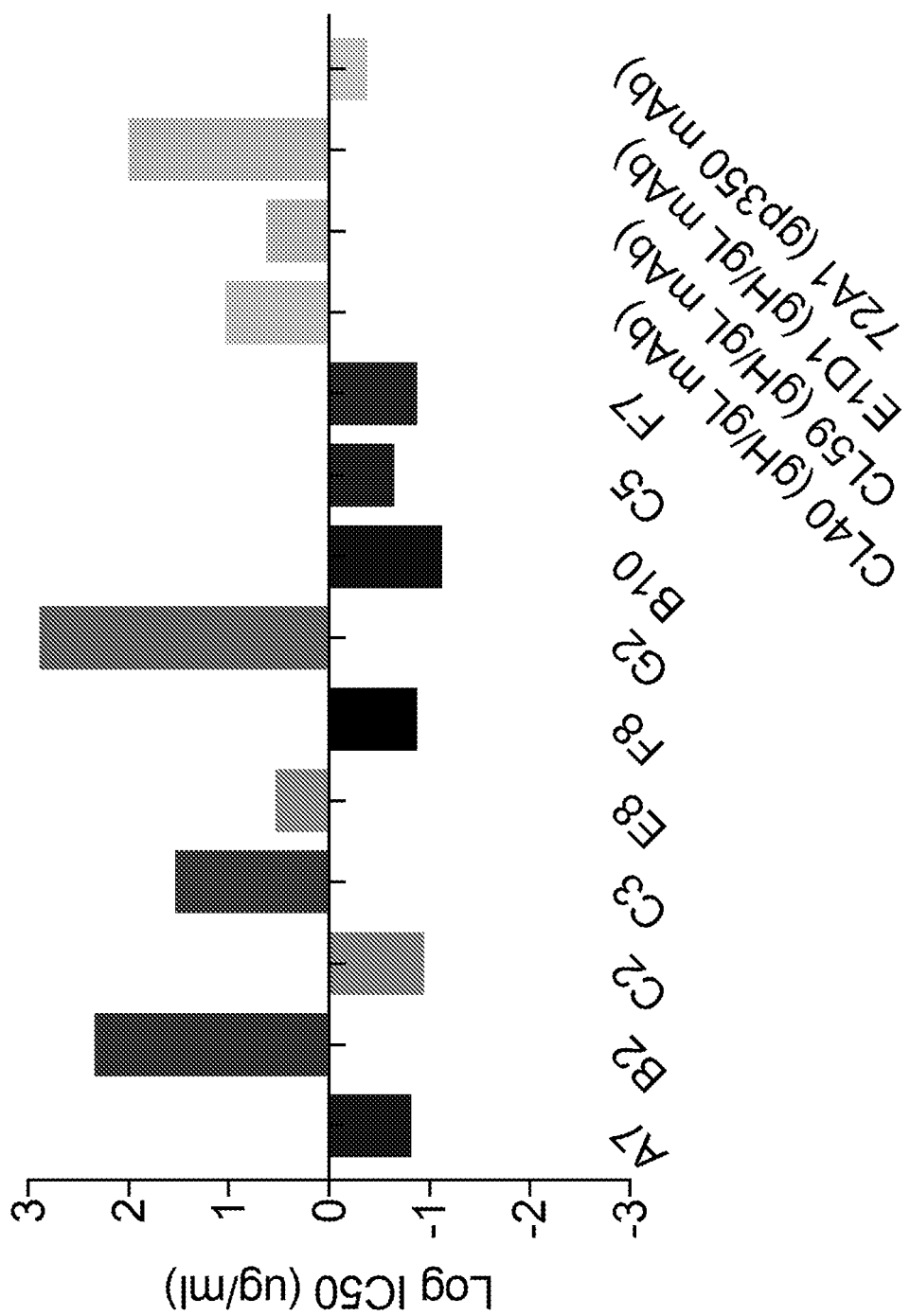
FIG. 2 shows neutralization of EBV infection in B cells, performed by serially diluting mAbs. The concentration of mAb, which inhibits infectivity by 50% ($IC_{50}$) based on reduction of the number of GFP-positive cells, was calculated by non-linear regression analysis.

The potency of the mAbs in neutralization of EBV infection in B cells was examined by serially diluting mAbs and 25 µl of the diluted sample was incubated with EBV that expresses GFP (EBV-GFP) for 2 hours. The mixture was added to Raji cells in 96-well plates and incubated for 3 days in a 37° C. incubator. Cells were washed with PBS and fixed in 2% paraformaldehyde in PBS. GFP-positive cells were quantified using a flow cytometer. The concentration of mAb that inhibits infectivity by 50% ($IC_{50}$) based on reduction of the number of GFP-positive cells was calculated by non-linear regression analysis. The most potent mAbs were 769A7 (A7), 769C2 (C2), 769C5 (C5), 770F8 (F8), 769B10 (B10), and 770F7 (F7) (FIG. 2; lower µg/ml indicates less antibody needed to neutralize infection).

Example 4

Neutralization of EBV Infection in Epithelial Cells

Figure 3:
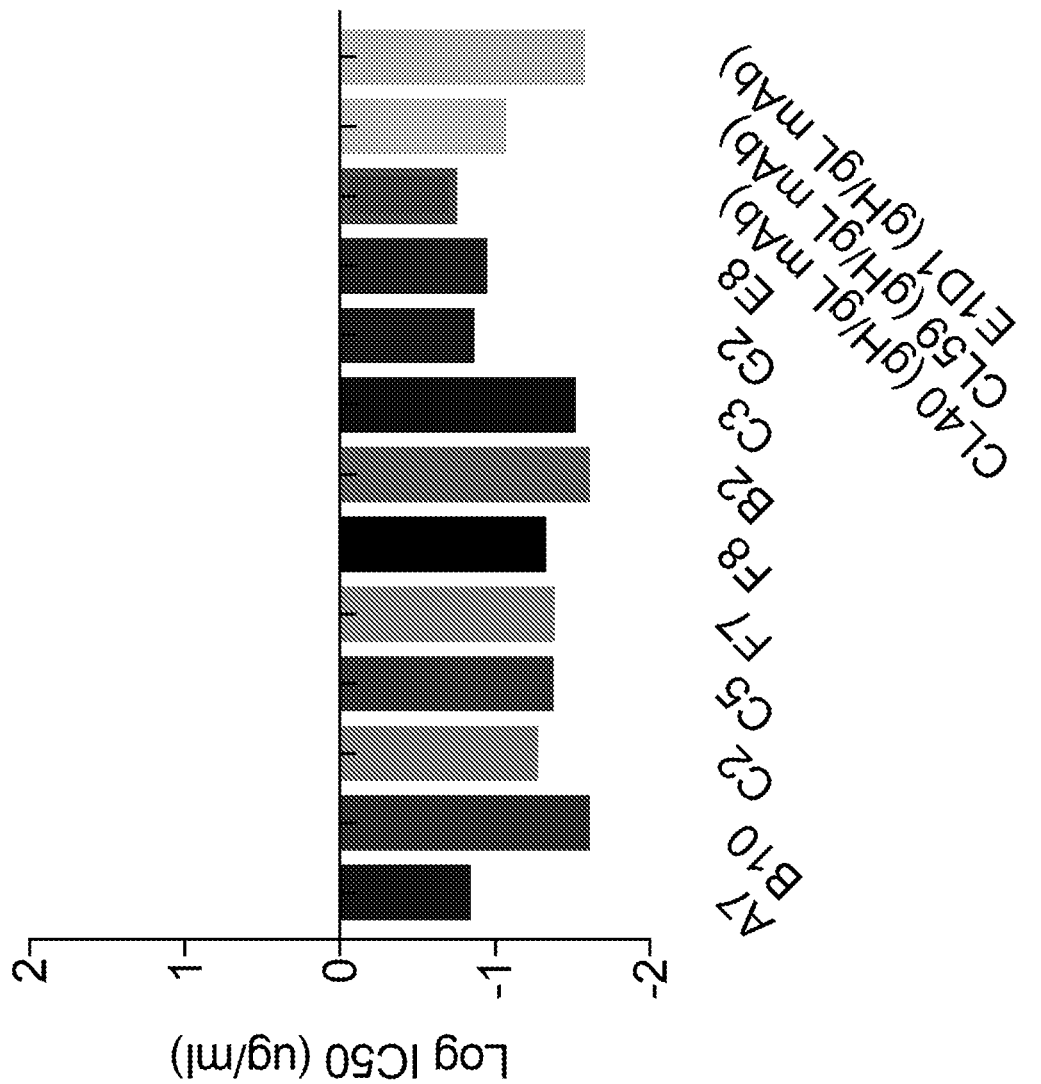
FIG. 3 shows neutralization of EBV infection in epithelial cells, performed by serially diluting mAbs. The concentration of mAb, which inhibits infectivity by 50% ($IC_{50}$) based on reduction of the number of GFP-positive cells, was calculated by non-linear regression analysis.

Neutralization of EBV infection in epithelial cells was examined by serially diluting mAbs and 25 µl of the diluted sample was incubated with EBV that expresses GFP (EBV-GFP) for 2 hours. The mixture was added to SVKCR2 cells in 96-well plates and incubated for 3 days in a 37° C. incubator. Cells were washed with PBS, treated with trypsin, and fixed in 2% paraformaldehyde in PBS. GFP-positive cells were quantified using a flow cytometer. The concentration of mAb, which inhibits infectivity by 50% ($IC_{50}$) based on reduction of the number of GFP-positive cells, was calculated by non-linear regression analysis. Each of the mAbs inhibited epithelial cell infection; the most potent mAbs were 769B10 (B10), 769B2 (B2), 769C3 (C3), and E1D1 (FIG. 3; lower µg/ml indicates less antibody needed to neutralize infection of cells).

Example 5 mAbs Block EBV Glycoprotein-Mediated Cell-to-Cell Fusion

Figure 4A:
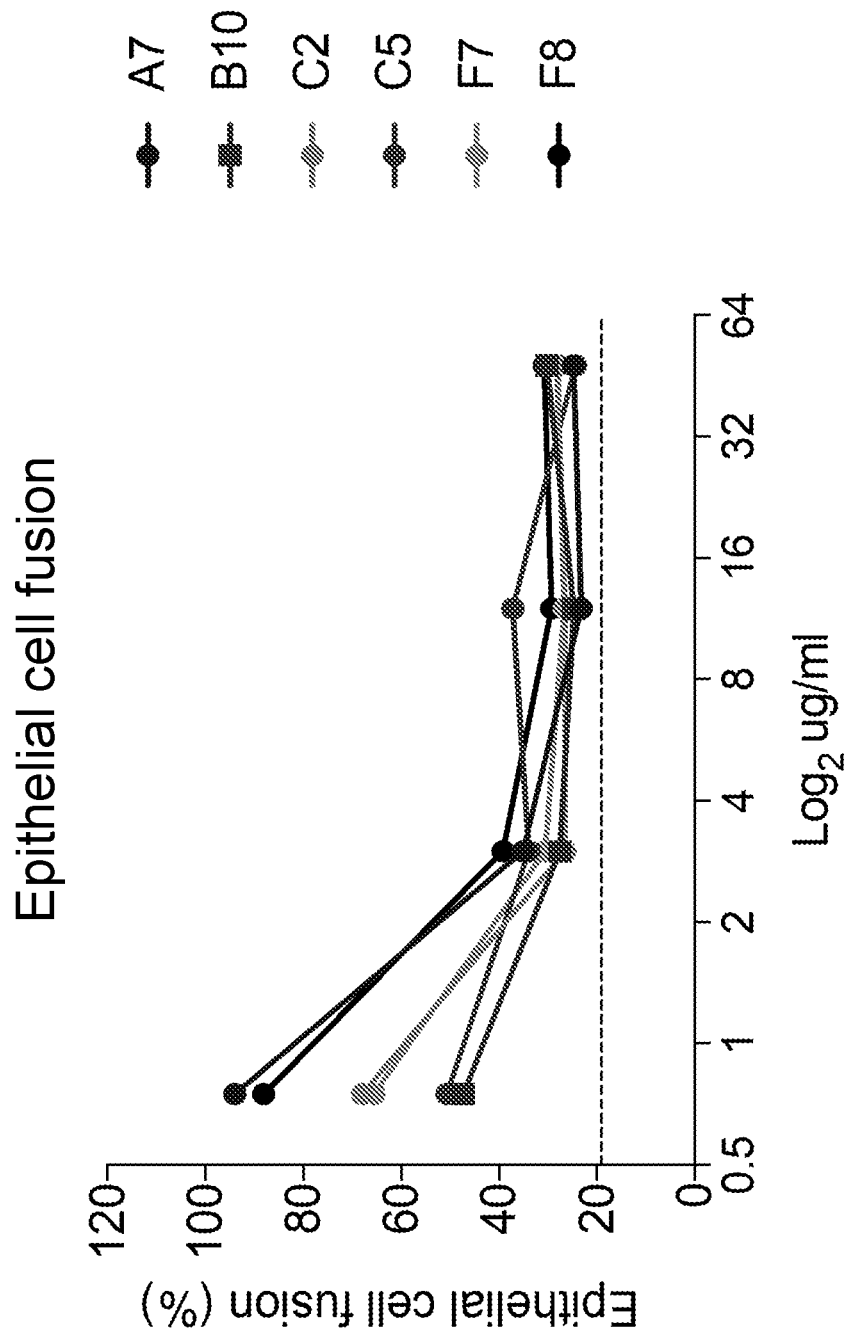
FIGS. 4A and 4B show the results of epithelial cell and B cell fusion assays used to determine if mAbs could block cell-to-cell fusion. The results show that several mAbs of this disclosure inhibit epithelial cell fusion (FIG. 4A), and several inhibit epithelial cell fusion (FIG. 4B).
Figure 4B:
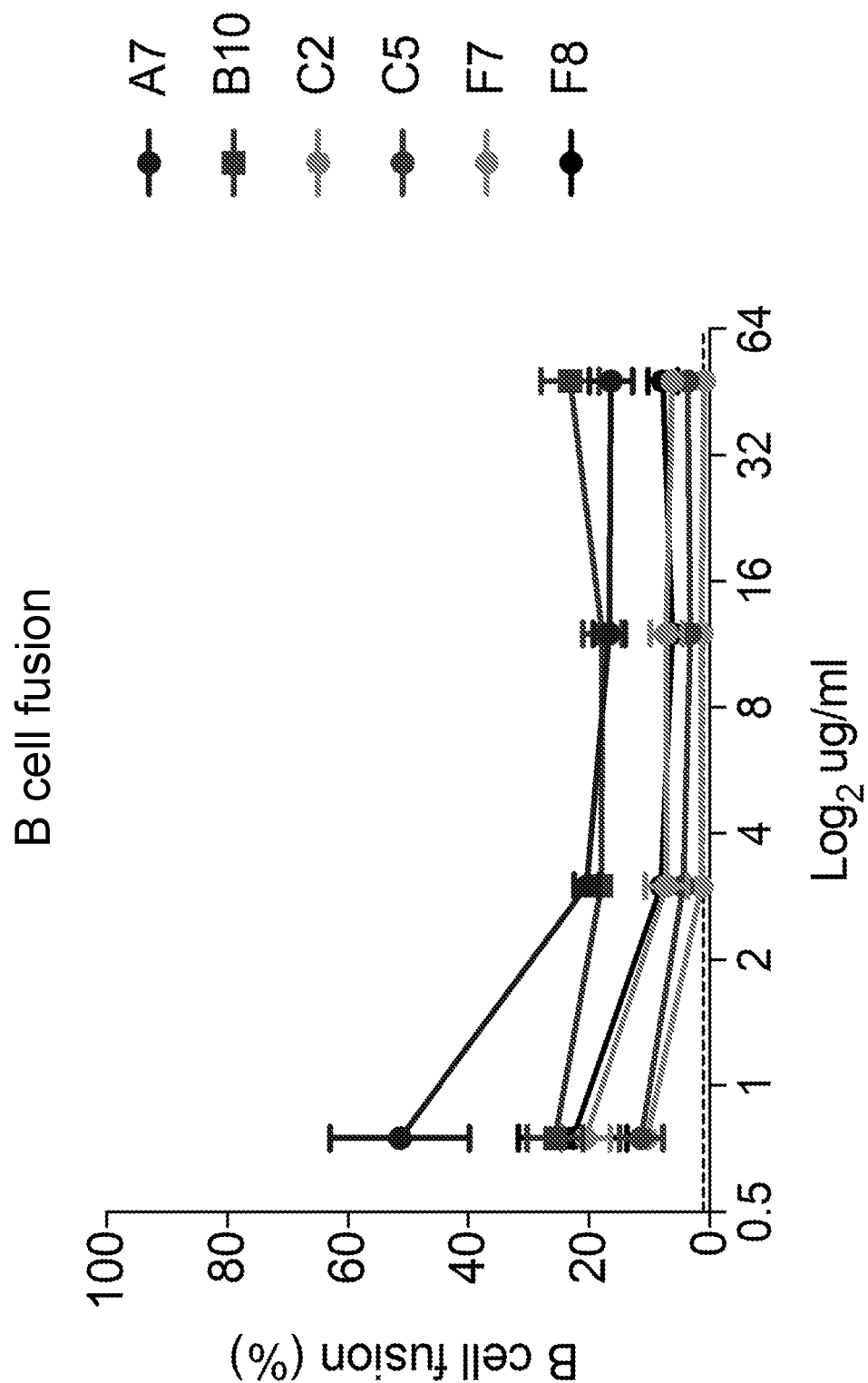
Figure 5A:
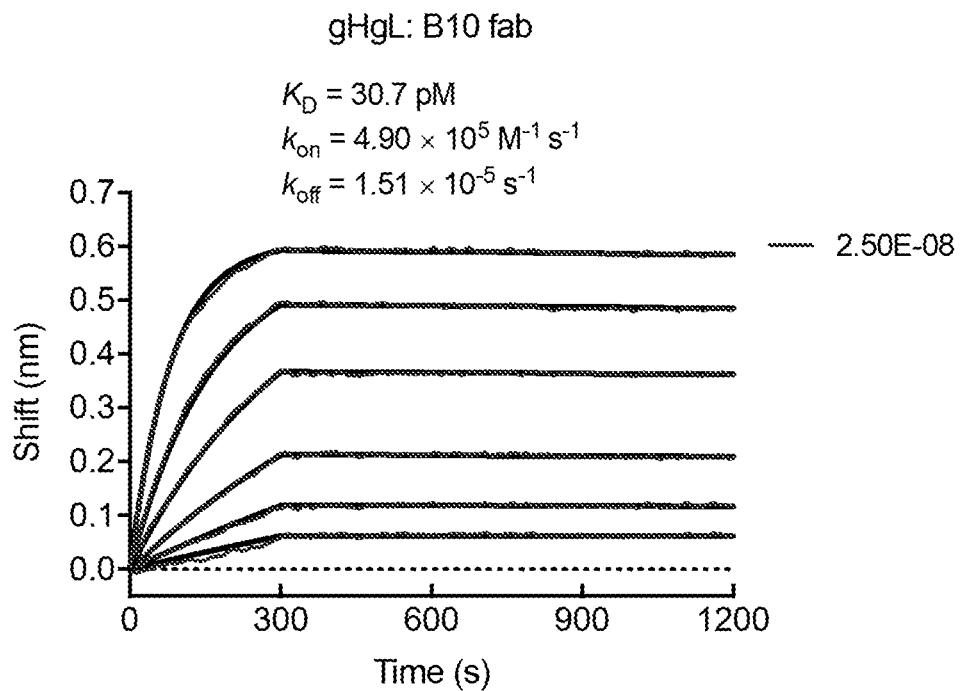
FIGS. 5A-5B show the results of biolayer interferometry assays to assess the kinetics of EBV gH/gL Fab fragments of mAbs.
Figure 5A:
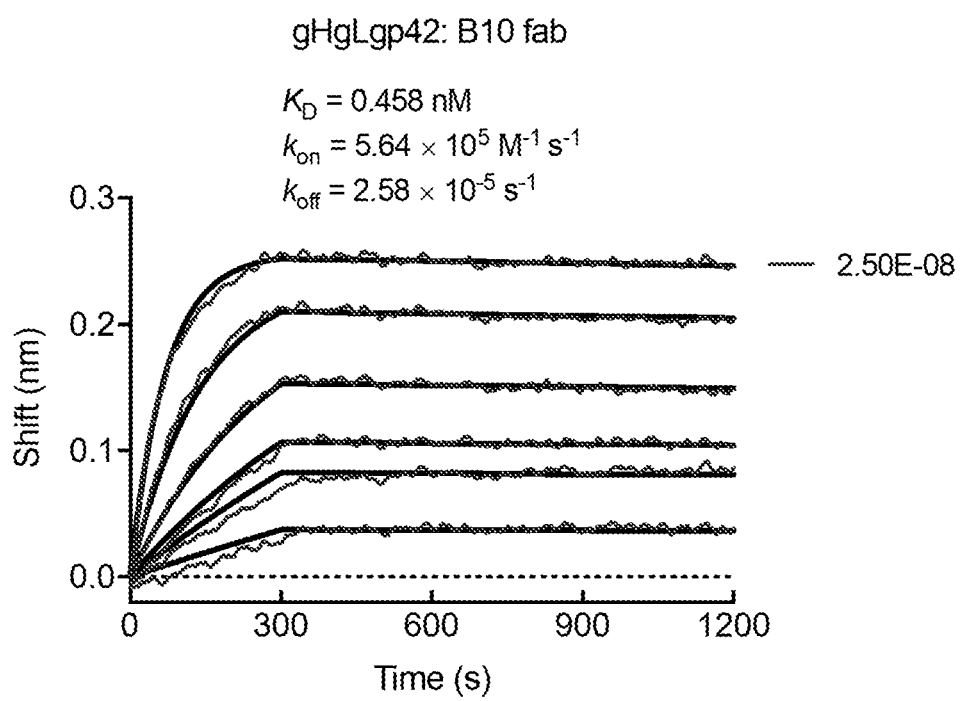
Figure 5B:
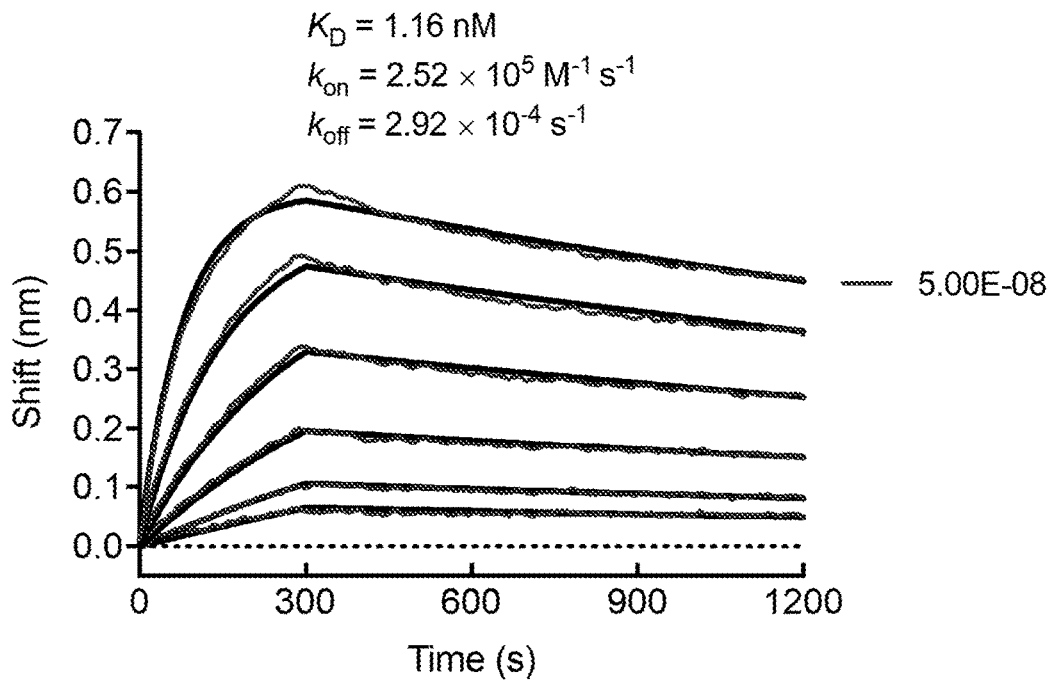
Figure 5B:
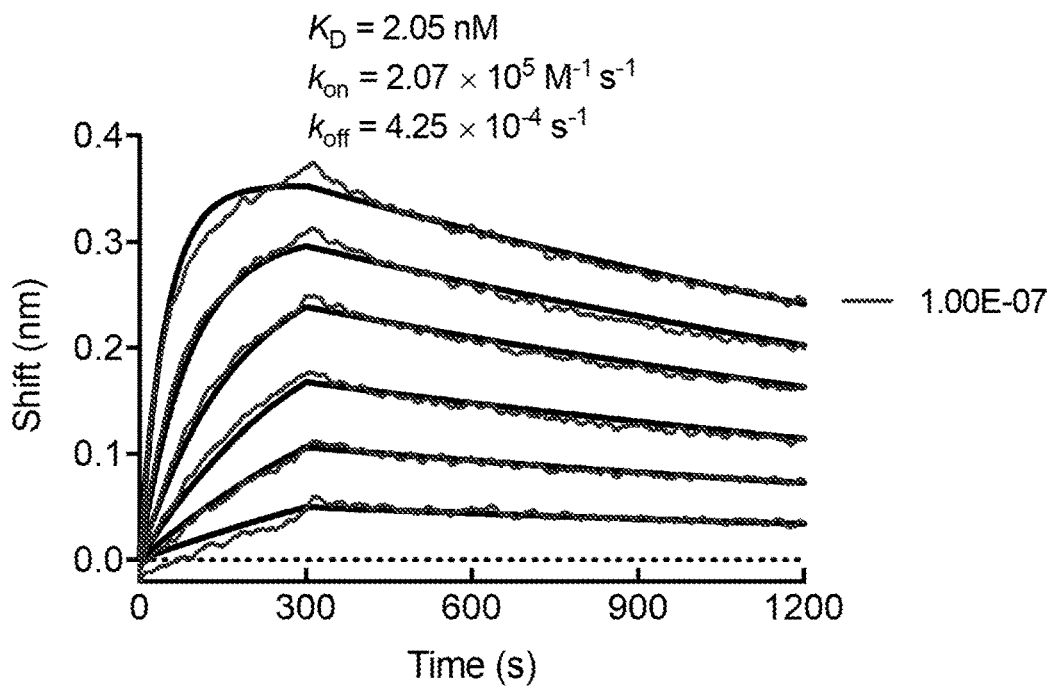
Figure 5C:
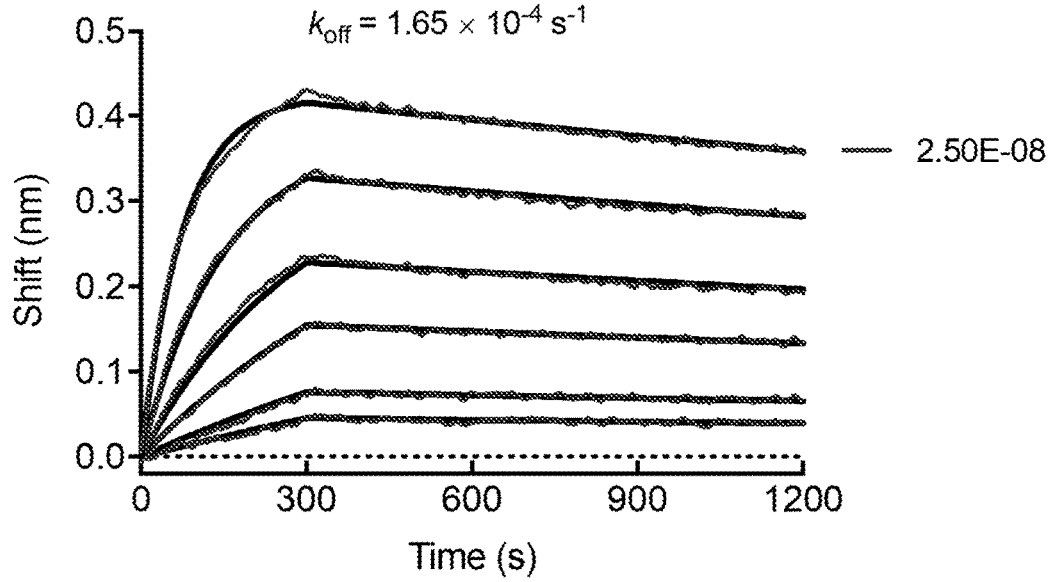
FIG. 5C shows the results for the 770F7 mAb clone.
Figure 5C:
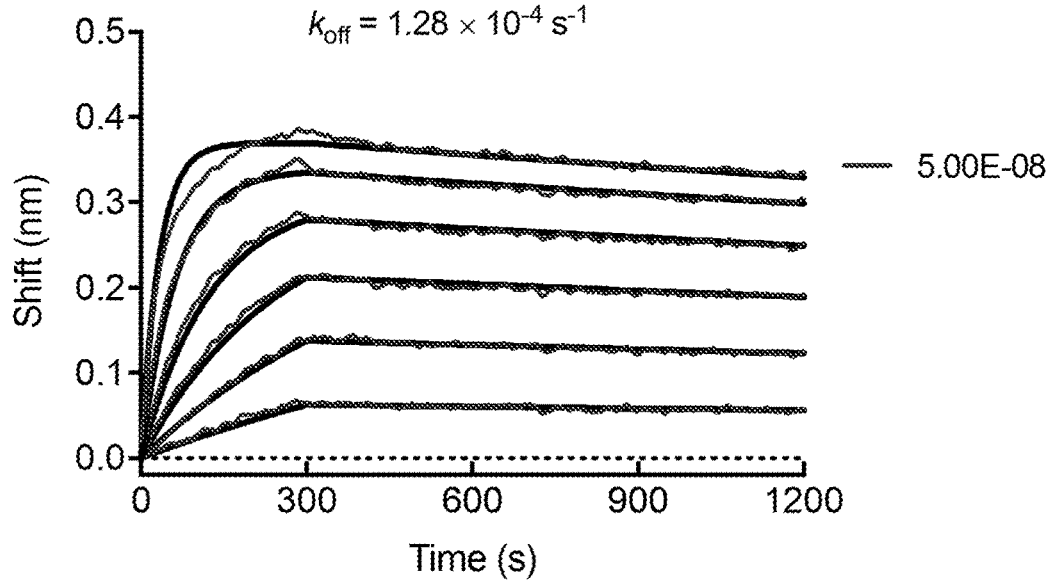

Epithelial cell and B cell fusion assays were used to determine if mAbs could block cell-to-cell fusion. For epithelial cell fusion assays, HEK 293-T14 cells that express T7 RNA polymerase were incubated with CHO-K1 cells that had been transfected with plasmids encoding gB, gH, gL under the control the CMV IE promoter, and a plasmid encoding luciferase under the control of the T7 polymerase promoter. B cell fusion assays were performed using Daudi-T7 B lymphocytes that stably express T7 RNA polymerase and were incubated with CHO-K1 cells that had been transfected with plasmids encoding EBV gB, gH, gL and gp42 under the control of a CMV IE promoter, and a plasmid encoding luciferase under the control of the T7 polymerase promoter. To quantify the ability of sera to inhibit fusion, HEK 293T14 cells and transfected CHO-K1 cells, or Daudi B cells and transfected CHO-K1 cells were incubated in the presence of sera from immunized monkeys overnight, the cells were then lysed, and luciferase activity was quantified using a luminometer. The results show that several mAbs inhibit epithelial cell fusion, especially 769B10 (B10) and 769C5 (C5) (FIG. 4A), and several inhibit epithelial cell fusion especially 770F7 (F7) and 769C5 (C5) (FIG. 4B).

Example 6

Binding Kinetics of Antigen-Binding Fragments (Fabs)

Binding kinetics of antigen-binding fragment (Fab) of antibody and gH/gL was measured by biolayer interferometry. Soluble gH/gL or gH/gL/gp42 was immobilized on a HIS1K biosensors (Fortebio) through HIS-tag on gH/gL or gH/gL/gp42 protein and the biosensors were then equilibrated with assay buffer (PBS with 1% BSA). The Fab binding was recorded by dipping the gH/gL- or gH/gL/gp42-immobilized biosensors into a dilution series of Fab (0.39-25 nM) for 300 sec, and the biosensors were dipped into buffer to record dissociation of Fab for 900 sec. The curve fit was performed by Octet Analysis Software (v9.0) with 1:1 binding model with global fit using entire association and dissociation steps. From these association ('on rate', $k_a$) and dissociation rates ('off rate', $k_d$), the equilibrium dissociation constant ('binding constant', $K_D$) was calculated $K_D=k_d/k_a$.

Example 7

Figure 6:
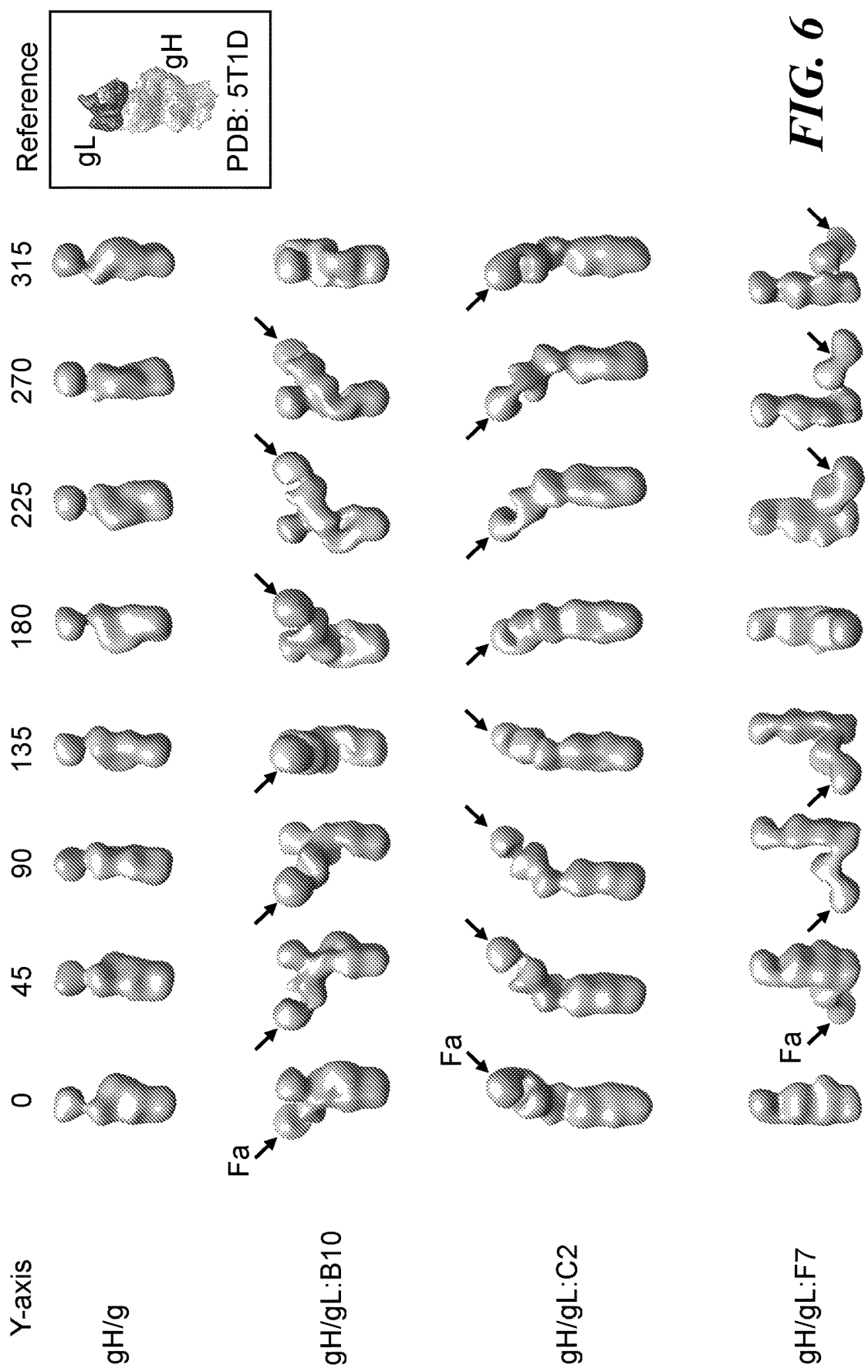
FIG. 6 shows reconstruction of gH/gL and gH/gL:Fab complex using negative-stain electron microscopy.

Negative-Stain Electron Microscopy Reconstruction of gH/gL and gH/gL:Fab Complex Protein samples containing gHgL alone or in a binary complex with the Fab fragment of antibody 769B10 (B10), 769C2 (C2), or 770F7 (F7) were diluted to approximately 0.01-0.02 mg/mL with buffer composed of 10 mM HEPES, pH 7, and 150 mM NaCl. A 4.8-4, drop was applied to a freshly glow-discharged carbon-film grid for 15 s. After several washes with the above buffer, the adsorbed proteins were stained with 0.75% uranyl formate. Images were collected semi-automatically with SerialEM (Mastronarde D N, J Struct Biol. 2005 October; 152(1):36-51) on an FEI Tecnai T20 electron microscope operating at 200 kV and equipped with a 2 k×2 k Eagle CCD camera at a pixel size of 0.22 nm/px (nominal magnification: 100,000). For each specimen, micrographs were recorded at 0°, 15°, 30°, and 45° tilt. For the purpose of CTF correction, tilted micrographs were divided into slices parallel to the vertical axis of the micrograph, which nearly coincides with the microscope tilt axis. Particles were picked automatically using in-house developed software (Y.T., unpublished) and inspected manually using e2boxer from the EMAN2 software package (Tang et al., J Struct Biol 2007: 157, 38-46). The original datasets for gHgL, gHgL/B10, gHgL/C2, and gHgL/F7 contained 35,555, 48,053, 31,981, and 39,642 particles, respectively. Each dataset was subjected to reference-free alignment followed by classification via correspondence analysis in SPIDER (Shaikh et al, Nat Protoc 2008: 3, 1941-1974) such that each class contained approximately 100 particles. Classes representing the target protein or complex as determined by visual examination were selected, and the corresponding particles were combined. This produced the final datasets containing 19,884, 18,973, 13,845, and 20,704 particles, respectively, for gHgL, gHgL/B10, gHgL/C2, and gHgL/F7. Initial 3D models were generated using EMAN2 from the selected 2D classes obtained with SPIDER or from selected 2D classes obtained separately with Relion 1.4 (Scheres S H, J Struct Biol. 2012 December; 180(3):519-30). The initial models were refined by following the protocol for three-dimensional reconstruction and refinement using reference projections in SPIDER (Frank et al, J. Struct. Biol. 1996; 116: 190-199). The refined models produced by SPIDER were low-pass filtered and used, along with the corresponding particle stack, as input to the 3D refinement procedure of FREALIGN (Grigorieff N, J Struct Biol. 2007; 157: 117-125) with separation into 3D classes (Lyumkis et al. J struct Biol. 2013; 183: 377-388). The final resolutions of the best classes were 26.1 Å, 28.1 Å, 25.5 Å, and 25.8 Å for gHgL, gHgL/B10, gHgL/C2, and gHgL/F, respectively, as determined with the Fourier Shell Correlation server of the Protein Data Bank in Europe (www.ebi.ac.uk/pdbe/emdb/validation/fsc/) using a correlation threshold of 0.5. Molecular model fitting was performed in UCSF Chimera (Pettersen et al, J. Comput. Chem. 2004: 25, 1605-12). For illustration purposes, the maps were low-pass filtered to resolution of 30 Å. The results of this analysis are shown in FIG. 6.

Example 8

Specificity of Neutralizing Antibodies in Both B Cells and Epithelial Cells

Figure 7A:
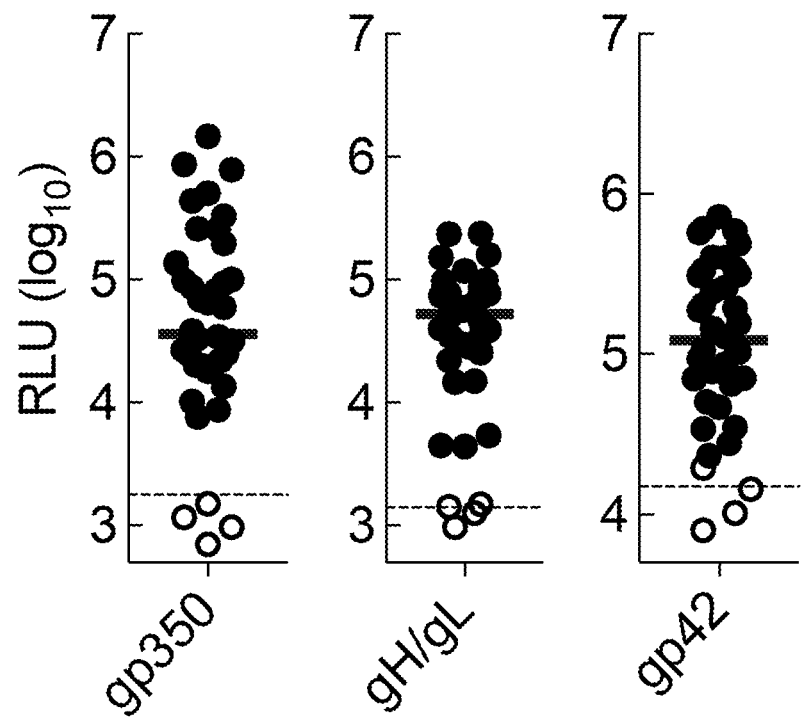
FIGS. 7A-7L show the results of analyses into the contribution of glycoprotein antibodies to B cell and epithelial cell neutralizing titers in human sera and plasma.

The contribution of neutralizing antibodies in human plasma to EBV viral glycoproteins was determined by assessing the specificity of neutralizing antibodies in both B cells and epithelial cells. Serum samples from either EBV seronegative or seropositive (viral capsid antigen seropositive) healthy donors were tested for antibodies to EBV gp350, gH/gL, and gp42 using a luciferase immunoprecipitation system (LIPS) assay (Sashihara et al., 2009 Virology 391:249-56). Of 38 samples, all 34 seropositive individuals had detectable antibodies to EBV gp350, gH/gL, and gp42 (FIG. 7A). No antibodies to gp350 and gH/gL were detected in seronegative subjects, while antibodies to gp42 were detected at a very low level in 2 of 4 seronegative individuals (FIG. 7A).

Figure 7B:
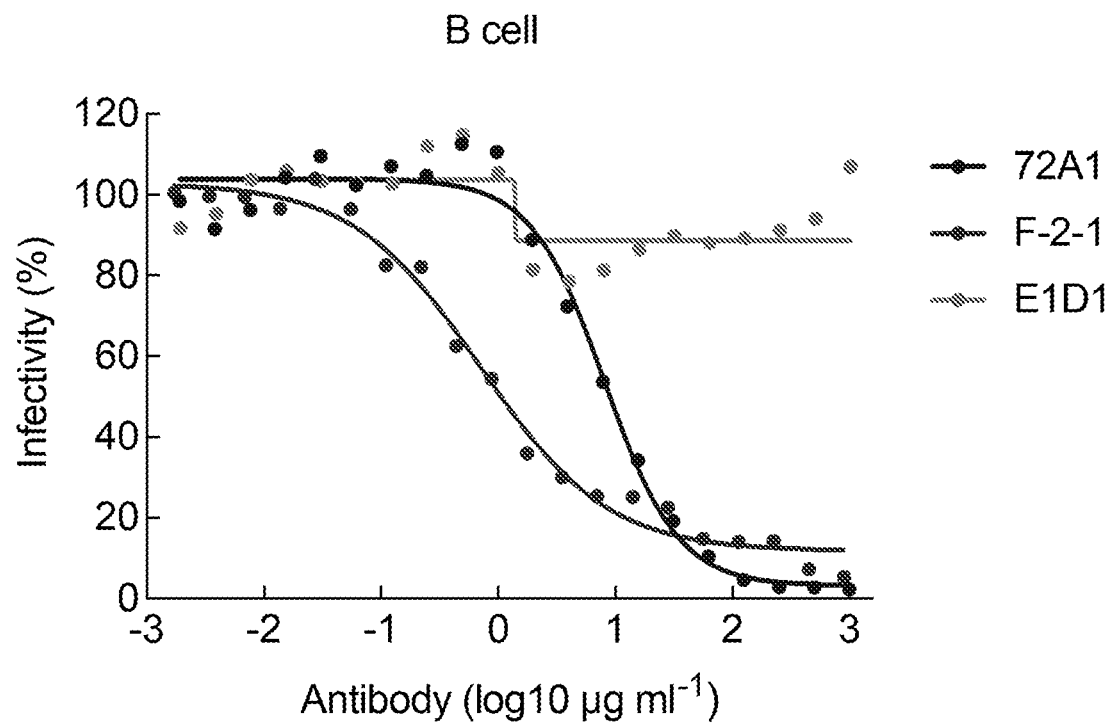
Figure 7C:
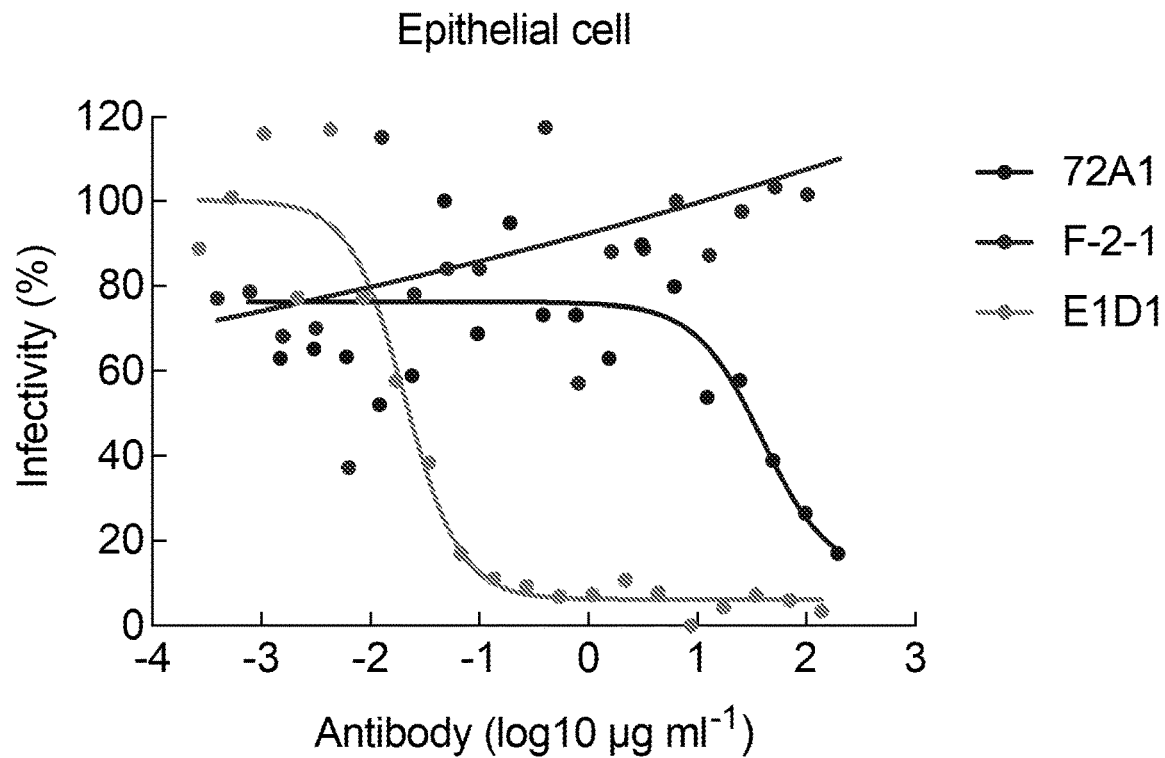
Figure 7D:
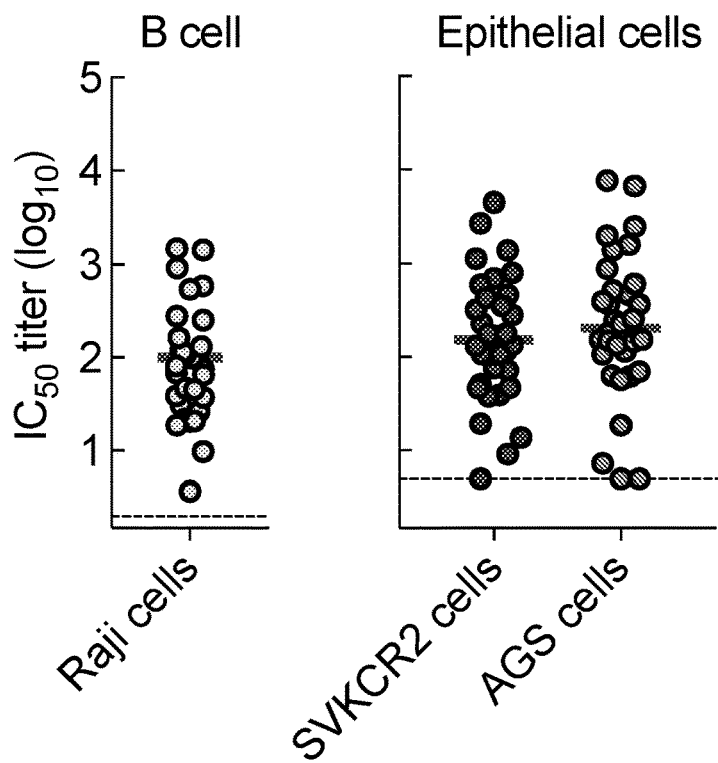
Figure 7E:
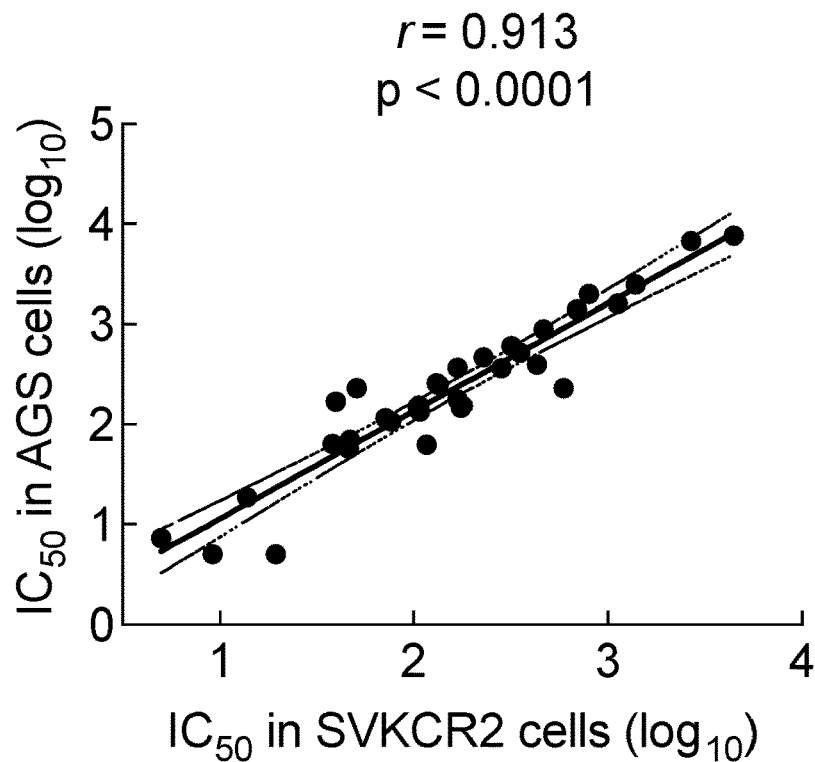
Figure 7F:
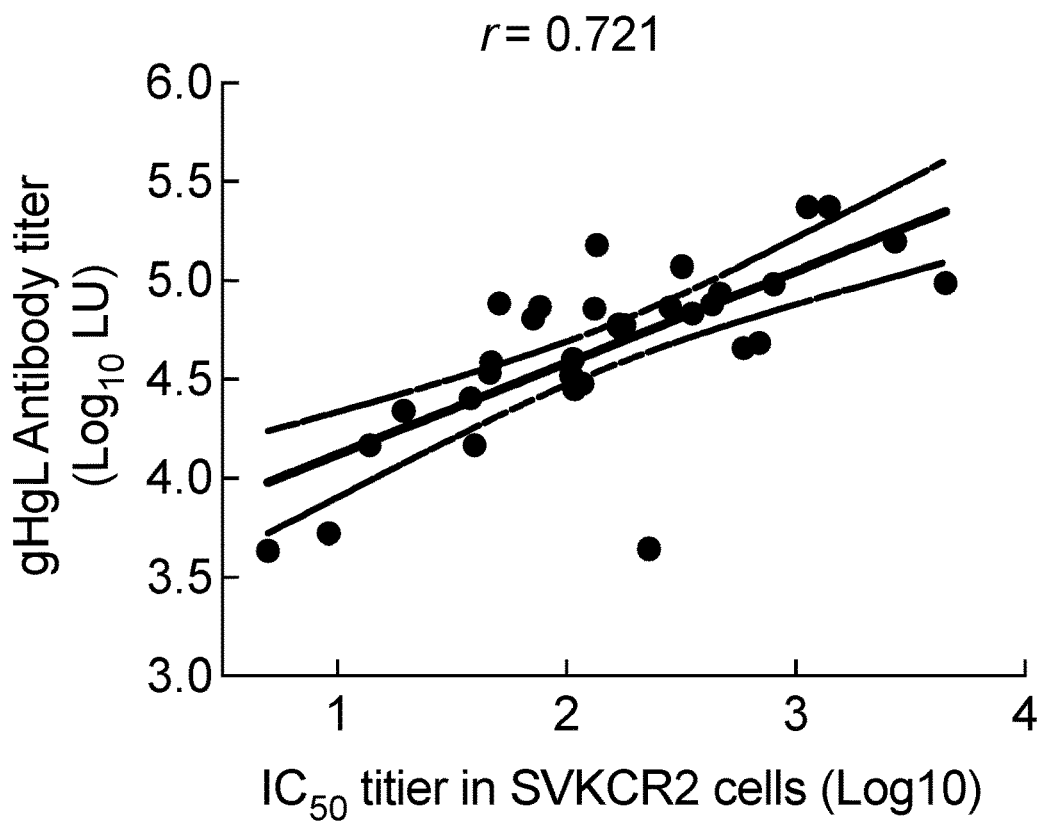
Figure 7G:
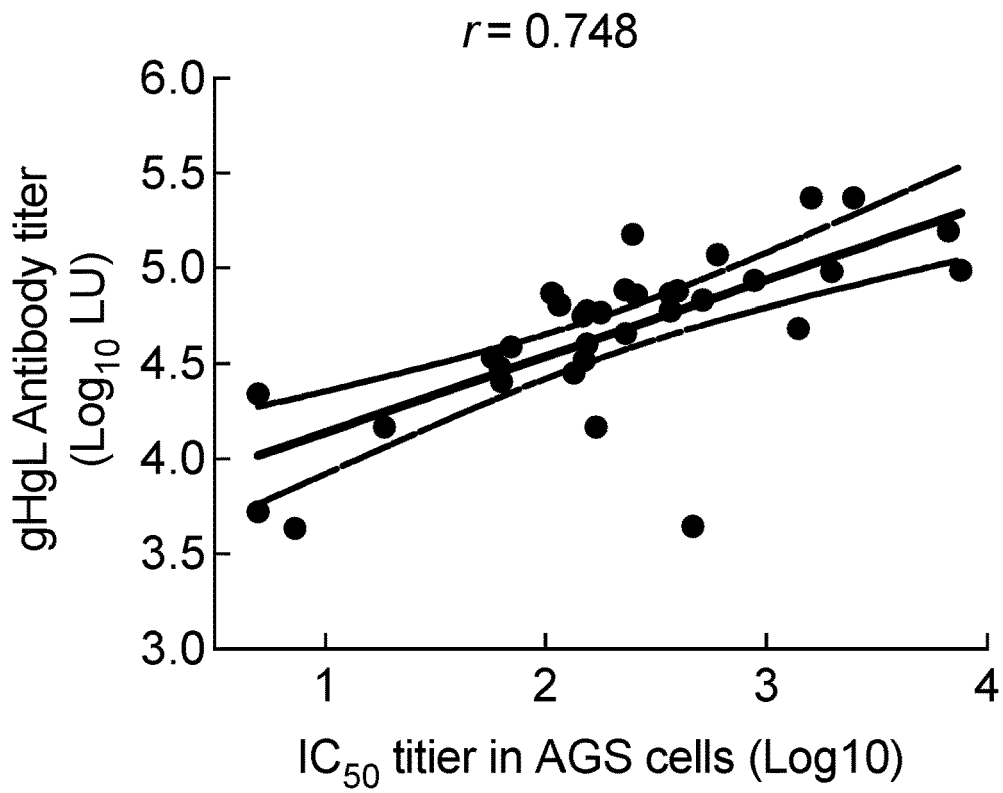
Figure 7H:
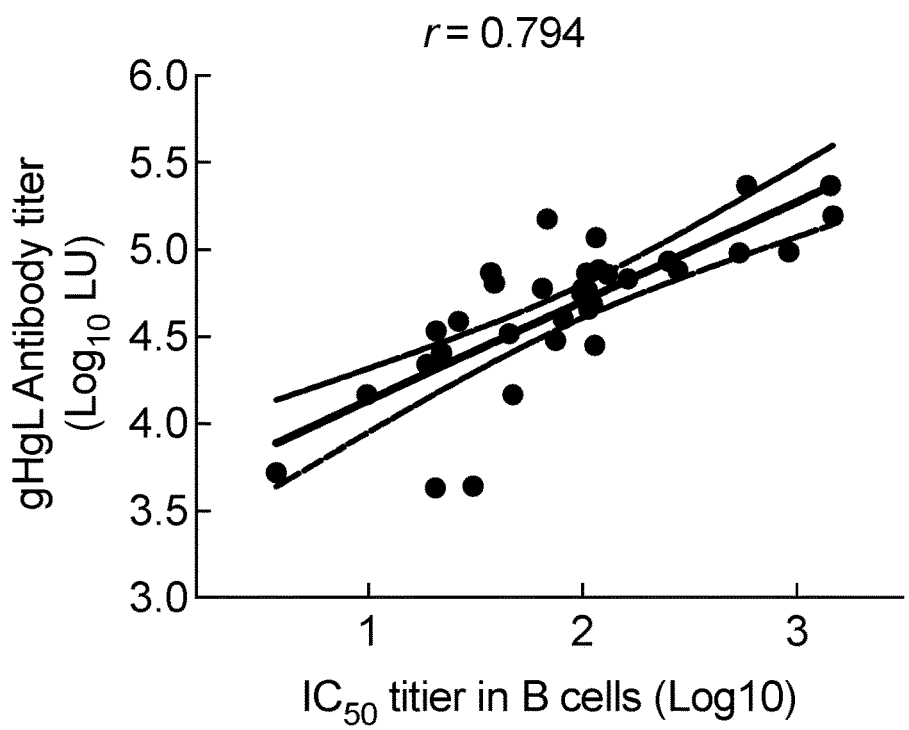

Neutralizing antibody titers were nex measured in an EBV-negative B cell line (Sashihara et al., supra) and two different epithelial cell lines (SVKCR2 and AGS cells) using a GFP-reporter neutralization assay. For the neutralization assays, a set of monoclonal antibodies (mAbs) were utilized as controls. These control antibodies, 72A1, E1D1, and F-2-1, are known to bind gp350 (Hoffman et al., 1980, Proc. Natl. Acad. Sci. 77:2979-83), gL (Sathiyamoorthy et al., 2016, Nat. Commun. 7) and gp42 (Li et al., 1995, J Virol 69:3987-94), respectively. mAbs 72A1 and F-2-1, but not E1D1, neutralized virus on B cells (FIG. 7B). In contrast, E1D1 neutralized virus on SVKCR2 epithelial cells, while 72A1 or F-2-1 had negligible neutralizing activity in epithelial cells ((FIG. 7C). The geometric mean titer of sera that neutralized virus infection by 50% ($IC_{50}$) in B cells for EBV seropositive individuals was 87.0 (95% CI, 54.4-139.2) (FIG. 7D). Serum samples from EBV seropositive persons neutralized virus infection of SVKCR2 epithelial cells with a geometric mean $IC_{50}$ of 153.8 (95% CI, 89.8-263.5) (FIG. 7D). We also measured neutralization using AGS gastric adenocarcinoma cells that do not express CR2 to rule out potential neutralization through inhibition of a gp350-CR2 interaction. The titer of neutralizing antibodies in AGS cells correlated with those in SVKCR2 cells (r=0.913), indicating that exogenous expression of CR2 did not affect the measurement of neutralizing activity in epithelial cells (FIG. 7E). Binding antibody titers to gH/gL correlated with neutralizing $IC_{50}$ titers in SVKCR2 (r=0.721) and AGS epithelial cells (r=0.748) (FIGS. 7F and 7G), and also correlated with neutralizing $IC_{50}$ titers in B cells (r=0.794) (FIG. 711).

Figure 7I:
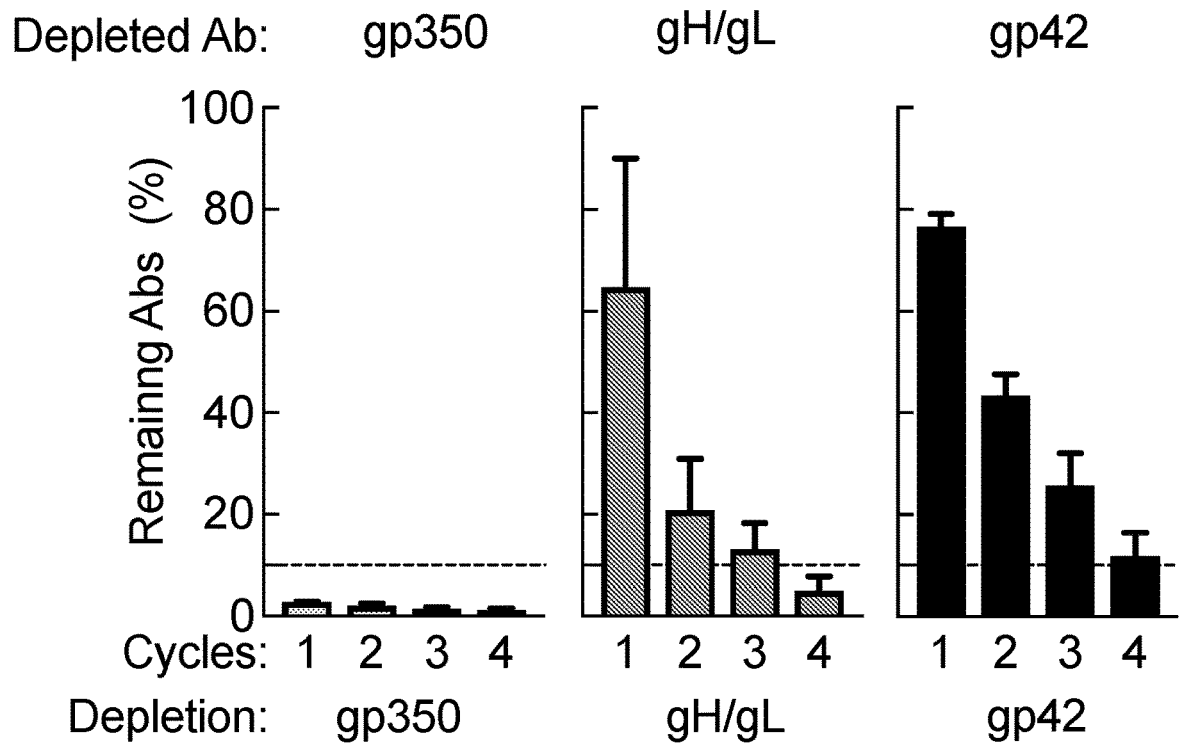

While antibodies to gp350 have been reported to be the major component in human sera that neutralizes B cell infection (Thorley-Lawson and Poodry, 1982, J Virol 43, 730-6), the relative contributions of antibodies to gH/gL and gp42 in human sera to neutralize EBV have not been studied. To address this, antibodies to EBV glycoproteins were depleted from human plasma and their relative contribution to neutralize virus infection of B cells and epithelial cells was quantified. HeLa cells infected with recombinant vaccinia viruses (VVs) expressing gp350, gH/gL, or gp42 were used to deplete antibodies from human plasma. gp350, gH/gL and gp42 expression was confirmed on the cell surface after infection with VVs by staining with mAbs 72A1, E1D1, and F-2-1, respectively. For antibody depletions, human intravenous immunoglobulin (IVIG) derived from plasma of >1,000 healthy donors was used; therefore, the results are more representative than using a small number of blood donors. To ensure that specific EBV glycoprotein antibodies were sufficiently depleted, four sequential rounds of depletion using HeLa cells expressing individual EBV glycoproteins were performed, and the remaining antibody to EBV glycoproteins in IVIG after each round of depletion were quantified by LIPS assay. Up to 4 rounds of depletion successfully depleted >95%, >90%, and approx. 90% of gp350-, gH/gL-, and gp42-specific antibodies from IVIG, respectively (FIG. 7I).

Figure 7J:
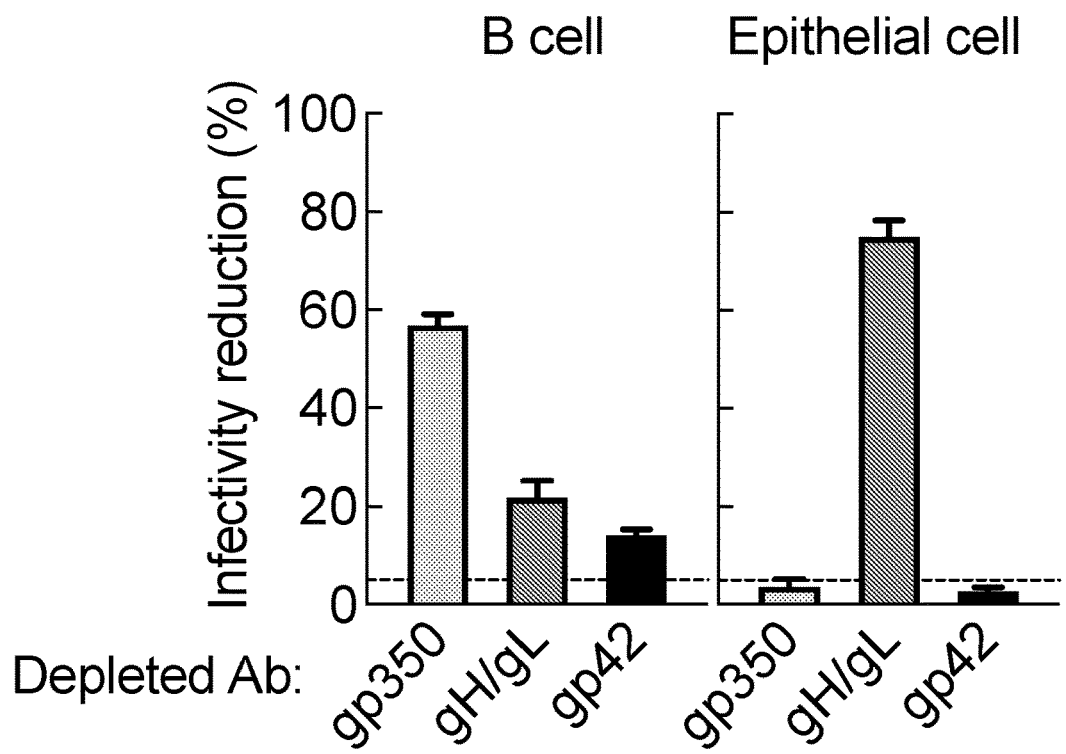
Figure 7K:
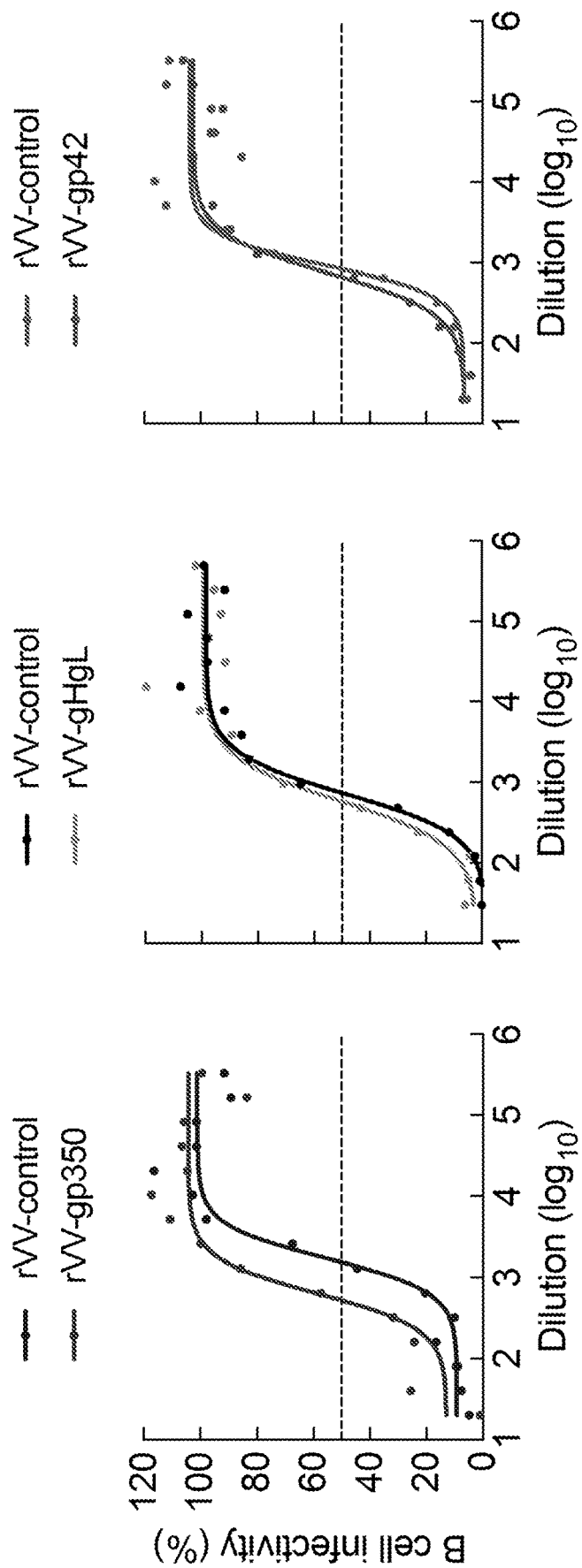
Figure 7L:
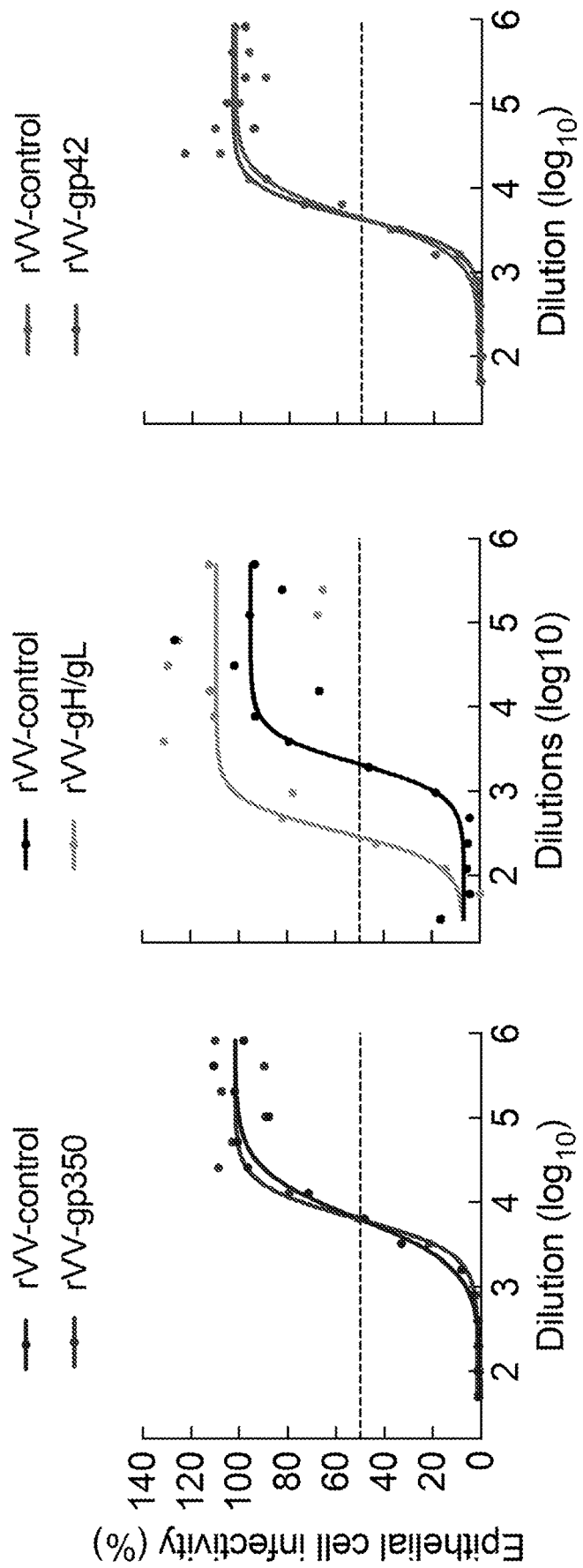

Next, the neutralizing activity of glycoprotein depleted IVIG samples was assessed. IVIG depleted with mock-infected cells had no effect on virus neutralization in B cells, while the $IC_{50}$ titer was substantially reduced when IVIG was depleted with gp350 (56.9%±2.30% [mean±SEM] reduction) (FIGS. 7J and 7K). Depletion of gH/gL and gp42 antibody had less effect on reducing virus neutralization in B cells, with 21.8%±3.39% and 14.1%±1.21% reduction, respectively (FIG. 7J). Together, these results indicate that antibodies to gp350 account for approx. 50-60% of the total neutralizing activity, while antibodies to gH/gL and gp42 each contribute approx. 15-20% of the total neutralizing activity against B cell infection. When neutralization of glycoprotein depleted IVIG was evaluated in epithelial cells, virtually no effect in virus infectivity was observed after depletion with gp350 or gp42 compared to mock-depleted control (FIG. 7L). In contrast, depletion of gH/gL antibody resulted in a marked reduction in neutralizing activity (FIG. 7L) in epithelial cells with a reduction in $IC_{50}$ of 75.0±3.46% (FIG. 7J). The contribution of gp350, gH/gL and gp42 in human plasma to B cell and epithelial cell neutralizing antibodies is shown in the following table:

|  |  | % Neutralization in | |
|---|---|---|---|
|  |  | B cells | Epithelial cells |
| Antibody | gp350 | 56.85 ± 2.30 | 3.62 ± 1.64 |
|  | gH/gL | 21.80 ± 3.39 | 74.96 ± 3.46 |
|  | gp42 | 14.11 ± 1.21 | 2.67 ± 0.86 |

Unlike their modest effect on B cell infection, antibodies to gH/gL represent the major component of epithelial cell neutralization in human plasma accounting for approx. 75% of the total neutralizing activity.

Additional neutralizing activity in B cells may be due to antibodies against gB and in epithelial cells to gB or BMRF2. Antibodies from an EBV seropositive blood donor were depleted and results similar to the depletion were observed using IVIG. In the blood donor serum, antibodies to gp350, gH/gL, and gp42 contributed 44.6%±4.37%, 46.9%±3.29%, and 10.9%±1.85% of B cell neutralization, respectively, while gH/gL antibodies contributed to 76.0%±0.89% of epithelial cell neutralization. Thus, antibodies to gp350, gH/gL, and gp42 in human plasma comprise the majority of the neutralizing activity that prevent B cell infection, while antibodies to gH/gL are the principal components that inhibit epithelial cell infection.

These data demonstrate that antibodies to EBV gH/gL in human plasma are the principal components that neutralize infection of epithelial cells and contribute to neutralization of B cell infection.

The foregoing disclosure is sufficient to enable one skilled in the art to practice the invention. The present invention is not to be limited in scope by the constructs described, because the described embodiments are intended as illustrations of certain aspects of the invention and any constructs that are functionally equivalent are within the scope of this invention.

What is claimed is:

1. A monoclonal antibody comprising:
   a) heavy chain (h) complementary determining region (CDR) 1, CDR2 and CDR3 sequences from a sequence selected from the group consisting of SEQ ID NO: 1, SEQ ID NO: 11, SEQ ID NO: 21, SEQ ID NO: 31, SEQ ID NO: 41, SEQ ID NO: 51, SEQ ID NO: 61, SEQ ID NO: 71, SEQ ID NO: 81, SEQ ID NO: 91, SEQ ID NO: 101, SEQ ID NO: 111, SEQ ID NO: 121, SEQ ID NO: 131, SEQ ID NO: 141, SEQ ID NO: 151, SEQ ID NO: 161, SEQ ID NO: 171, SEQ ID NO: 181, and SEQ ID NO: 191; and,
   b) light chain (l) CDR1, CDR2 and CDR3 sequences from a sequence selected from the group consisting of SEQ ID NO: 6, SEQ ID NO: 16, SEQ ID NO: 26, SEQ ID NO: 36, SEQ ID NO: 46, SEQ ID NO: 56, SEQ ID NO: 66, SEQ ID NO: 76, SEQ ID NO: 86, SEQ ID NO: 96, SEQ ID NO: 106, SEQ ID NO: 116, SEQ ID NO: 126, SEQ ID NO: 136, SEQ ID NO: 146, SEQ ID NO: 156, SEQ ID NO: 166, SEQ ID NO: 176, SEQ ID NO: 186, and SEQ ID NO: 196;
   wherein the monoclonal antibody binds an Epstein Barr Virus (EBV) gH protein (gH), an EBV gL protein (gL), or a gH/gL protein complex.

2. The monoclonal antibody of claim 1, comprising a complementary determining region (CDR)-heavy 1 (h1) sequence, a CDR-heavy 2 (h2) sequence, a CDR-heavy 3 (h3) sequence, a CDR-light 1 (l1) sequence, a CDR-light 2 (l2) sequence, and a CDR-light 3 (l3) sequence, wherein the CDR h1, CDR h2, CDR h3, CDR l1, CDR l2 and CDR l3 sequences respectively comprise:
   (a) SEQ ID NO: 3, SEQ ID NO: 4, SEQ ID NO: 5, SEQ ID NO: 8, SEQ ID NO: 9 and SEQ ID NO: 10;
   (b) SEQ ID NO: 13, SEQ ID NO: 14, SEQ ID NO: 15, SEQ ID NO: 18, SEQ ID NO: 19 and SEQ ID NO: 20;
   (c) SEQ ID NO: 23, SEQ ID NO: 24, SEQ ID NO: 25, SEQ ID NO: 28, SEQ ID NO: 29 and SEQ ID NO: 30;
   (d) SEQ ID NO: 33, SEQ ID NO: 34, SEQ ID NO: 35, SEQ ID NO: 38, SEQ ID NO: 39 and SEQ ID NO: 40;
   (e) SEQ ID NO: 43, SEQ ID NO: 44, SEQ ID NO: 45, SEQ ID NO: 48, SEQ ID NO: 49 and SEQ ID NO: 50;
   (f) SEQ ID NO: 53, SEQ ID NO: 54, SEQ ID NO: 55, SEQ ID NO: 58, SEQ ID NO: 59 and SEQ ID NO: 60;
   (g) SEQ ID NO: 63, SEQ ID NO: 64, SEQ ID NO: 65, SEQ ID NO: 68, SEQ ID NO: 69 and SEQ ID NO: 70;
   (h) SEQ ID NO: 73, SEQ ID NO: 74, SEQ ID NO: 75, SEQ ID NO: 78, SEQ ID NO: 79 and SEQ ID NO: 80;
   (i) SEQ ID NO: 83, SEQ ID NO: 84, SEQ ID NO: 85, SEQ ID NO: 88, SEQ ID NO: 89 and SEQ ID NO: 90;
   (j) SEQ ID NO: 93, SEQ ID NO: 94, SEQ ID NO: 95, SEQ ID NO: 98, SEQ ID NO: 99 and SEQ ID NO: 100;
   (k) SEQ ID NO: 103, SEQ ID NO: 104, SEQ ID NO: 105, SEQ ID NO: 108, SEQ ID NO: 109 and SEQ ID NO: 110;
   (l) SEQ ID NO: 113, SEQ ID NO: 114, SEQ ID NO: 115, SEQ ID NO: 118, SEQ ID NO: 119 and SEQ ID NO: 120;
   (m) SEQ ID NO: 123, SEQ ID NO: 124, SEQ ID NO: 125, SEQ ID NO: 128, SEQ ID NO: 129 and SEQ ID NO: 130;
   (n) SEQ ID NO: 133; SEQ ID NO: 134, SEQ ID NO: 135, SEQ ID NO: 138, SEQ ID NO: 139 and SEQ ID NO: 140;
   (o) SEQ ID NO: 143, SEQ ID NO: 144, SEQ ID NO: 145; SEQ ID NO: 148, SEQ ID NO: 149 and SEQ ID NO: 150;
   (p) SEQ ID NO: 153, SEQ ID NO: 154, SEQ ID NO: 155, SEQ ID NO: 158, SEQ ID NO: 159 and SEQ ID NO: 160;
   (q) SEQ ID NO: 163, SEQ ID NO: 164, SEQ ID NO: 165, SEQ ID NO: 168, SEQ ID NO: 169 and SEQ ID NO: 170;
   (r) SEQ ID NO: 173, SEQ ID NO: 174, SEQ ID NO: 175, SEQ ID NO: 178, SEQ ID NO: 179 and SEQ ID NO: 180;
   (s) SEQ ID NO: 183, SEQ ID NO: 184, SEQ ID NO: 185, SEQ ID NO: 188, SEQ ID NO: 189 and SEQ ID NO: 190; or
   (t) SEQ ID NO: 193, SEQ ID NO: 194, SEQ ID NO: 195; SEQ ID NO: 198, SEQ ID NO: 199 and SEQ ID NO: 200.

3. The monoclonal antibody of claim 1, comprising:
   the VH sequence of SEQ ID NO:1 and a VL sequence of SEQ ID NO:6;
   the VH sequence of SEQ ID NO:11 and a VL sequence of SEQ ID NO:16;
   the VH sequence of SEQ ID NO:21 and a VL sequence of SEQ ID NO:26;
   the VH sequence of SEQ ID NO:31 and a VL sequence of SEQ ID NO:36;

the VH sequence of SEQ ID NO:41 and a VL sequence of SEQ ID NO:46;
the VH sequence of SEQ ID NO:51 and a VL sequence of SEQ ID NO:56;
the VH sequence of SEQ ID NO:61 and a VL sequence of SEQ ID NO:66;
the VH sequence of SEQ ID NO:71 and a VL sequence of SEQ ID NO:76;
the VH sequence of SEQ ID NO:81 and a VL sequence of SEQ ID NO:86;
the VH sequence of SEQ ID NO:91 and a VL sequence of SEQ ID NO:96;
the VH sequence of SEQ ID NO:101 and a VL sequence of SEQ ID NO:106;
the VH sequence of SEQ ID NO: 111 and a VL sequence of SEQ ID NO:116;
the VH sequence of SEQ ID NO:121 and a VL sequence of SEQ ID NO:126;
the VH sequence of SEQ ID NO:131 and a VL sequence of SEQ ID NO:136;
the VH sequence of SEQ ID NO: 141 and a VL sequence of SEQ ID NO:146;
the VH sequence of SEQ ID NO:151 and a VL sequence of SEQ ID NO:156;
the VH sequence of SEQ ID NO:161 and a VL sequence of SEQ ID NO:166;
the VH sequence of SEQ ID NO:171 and a VL sequence of SEQ ID NO:176;
the VH sequence of SEQ ID NO: 181 and a VL sequence of SEQ ID NO:186; or
the VH sequence of SEQ ID NO: 191 and a VL sequence of SEQ ID NO:196.

4. The monoclonal antibody of claim 1, which is an antibody fragment.

5. The monoclonal antibody of claim 1, which is a chimeric antibody.

6. The monoclonal antibody of claim 1, which is a bispecific antibody.

7. The monoclonal antibody of claim 1, which is conjugated to:
a growth inhibitory agent;
a cytotoxic agent;
a label selected from a radioisotope, and a fluorescent label; or
a solid support selected from a support formed partially or entirely of glass, a polysaccharide, a polyacrylamide, a polystyrene, a polyvinyl alcohol, a silicone, an assay plate, and a purification column.

8. The monoclonal antibody of claim 1, which is produced in mammalian cells, insect cells, yeast cells, or bacterial cells.

9. The monoclonal antibody of claim 1, which induces death of a cell to which it binds.

10. A composition of matter comprising the monoclonal antibody of claim 1, in combination with a carrier.

11. The composition of matter of claim 10, wherein the carrier is a pharmaceutically acceptable carrier.

12. An article of manufacture comprising a container, and the composition of matter of claim 10 contained within the container.

13. The article of manufacture of claim 12 further comprising a label affixed to the container, or a package insert included with the container, referring to the use of the composition of matter for the therapeutic treatment of, prevention of, or the diagnostic detection of an EBV infection.

14. A method of inhibiting the growth of a cell that expresses an EBV gH protein, an EBV gL protein, or an EBV gH/gL complex, comprising contacting the cell with the monoclonal antibody of claim 1, wherein the binding of the monoclonal antibody to the EBV gH protein, the EBV gL protein or the EBV gH/gL complex causes an inhibition of growth of the cell.

15. The method of claim 14, wherein the cell is an EBV-infected cell.

16. The method of claim 14, wherein the cell is an epithelial cell, a B lymphocyte, an oropharyngeal cell, a nasopharyngeal cell or a cancer cell.

17. The method of claim 14, wherein the cell is further exposed to anti-inflammatory or interferon treatment.

18. A method of inhibiting EBV in an individual having an EBV infection, including an EBV-associated disease or disorder, comprising administering to the individual an effective amount of the monoclonal antibody of claim 1.

19. A method of determining the presence of an EBV gH protein, an EBV gL protein, or an EBV gH/gL complex in a sample suspected of containing the EBV gH protein, the EBV gL protein or the EBV gH/gL complex, comprising exposing the sample to the monoclonal antibody of claim 1 and detecting binding of the monoclonal antibody to a protein in the sample, wherein binding of the monoclonal antibody to the protein is indicative of the presence of the EBV gH protein, the EBV gL protein, or the EBV gH/gL complex in the sample.

20. The method of claim 19, wherein the monoclonal antibody is detectably labeled.

21. The method of claim 19, wherein the monoclonal antibody is conjugated to a solid support selected from a support formed partially or entirely of glass, a polysaccharide, a polyacrylamide, a polystyrene, a polyvinyl alcohol, a silicone, an assay plate, and a purification column.

22. The method of claim 19, wherein the sample comprises a cell suspected of expressing the EBV gH protein, and wherein the cell is an epithelial cell, a B lymphocyte, an oropharyngeal cell, a nasopharyngeal cell or a cancer cell.

23. A method of diagnosing the presence of an EBV infection in an individual, comprising detecting the presence of an EBV gH protein, an EBV gL protein, or a gH/gL complex, in a sample of cells obtained from the individual, comprising exposing the sample to the monoclonal antibody of claim 1 and detecting binding of the monoclonal antibody to EBV gH protein, the EBV gL protein or the EBV gH/gL complex in the sample, wherein detection of binding of the monoclonal antibody to the EBV gH protein, the EBV gL protein, or the gH/gL complex, in the sample is indicative of the presence of EBV infection in the individual.

24. The method of claim 23, wherein the monoclonal antibody is detectably labeled.

25. The method of claim 23, wherein the monoclonal antibody is conjugated to a solid support selected from a support formed partially or entirely of glass, a polysaccharide, a polyacrylamide, a polystyrene, a polyvinyl alcohol, a silicone, an assay plate, and a purification column.

26. The method of claim 23, wherein the sample of cells comprises a B lymphocyte, an epithelial cell, an oropharyngeal cell, a nasopharyngeal cell or a cancer cell.

27. A method of diagnosing the presence of an EBV infection and inhibiting EBV in an individual, comprising:
determining the level of expression of a gene encoding an EBV gH protein, or an EBV gL protein, in a test sample of tissue cells obtained from an individual; determining the level of expression of a gene encoding an EBV gH protein, or an EBV gL protein, in a control sample of known normal cells of the same tissue origin; wherein a higher level of expression of the EBV gH or gL protein in the test sample, as compared to the control sample, is indicative of the presence of an EBV infection in the individual from which the test sample was obtained, and wherein the individual determined to have the presence of the EBV infection is administered an effective amount of the monoclonal antibody of claim 1.

28. The method of claim 27, wherein the test sample of cells comprises an epithelial cell, a B lymphocyte, an oropharyngeal cell, a nasopharyngeal cell or a cancer cell.

29. The method of claim 27, wherein the individual is a human.

30. The method of claim 27, wherein the individual is a pregnant female or a cancer patient.

31. A method of inhibiting Epstein-Barr virus (EBV) infection in a subject, comprising administering to the subject an effective amount of the monoclonal antibody of claim 1.

32. A method of inhibiting an Epstein-Barr virus (EBV) in an EBV-infected subject having an EBV-associated disease or disorder, comprising administering to the subject an effective amount of the monoclonal antibody of claim 1.

\* \* \* \* \*

SEQUENCE LISTING

```
<160> NUMBER OF SEQ ID NOS: 200

<210> SEQ ID NO 1
<211> LENGTH: 116
<212> TYPE: PRT
<213> ORGANISM: Homo sapiens

<400> SEQUENCE: 1

Glu Val Gln Leu Val Glu Ala Gly Gly Gly Leu Val Arg Pro Gly Gly
1               5                   10                  15

Ser Leu Arg Leu Ser Cys Asp Ala Ser Gly Phe Thr Phe Ser Asp Ser
            20                  25                  30

Tyr Met Ser Trp Ile Arg Gln Ala Pro Gly Arg Gly Leu Glu Trp Val
        35                  40                  45

Ala Leu Ile Ser Gly Ser Gly Phe Arg Ile Phe Tyr Gly Asp Ser Val
    50                  55                  60

Lys Gly Arg Phe Thr Ile Ser Arg Asp Asn Ala Lys Lys Ser Leu Tyr
65                  70                  75                  80

Leu Gln Leu Ser Ser Leu Arg Ala Asp Asp Thr Ala Ile Tyr Tyr Cys
                85                  90                  95

Ala Arg Asp Thr Thr His Phe Asp Ser Trp Gly Gln Gly Thr Leu Val
            100                 105                 110

Thr Val Ser Ser
        115

<210> SEQ ID NO 2
<211> LENGTH: 348
<212> TYPE: PRT
<213> ORGANISM: Homo sapiens

<400> SEQUENCE: 2

Gly Ala Gly Gly Thr Gly Cys Ala Gly Cys Thr Gly Gly Thr Gly Gly
1               5                   10                  15

Ala Gly Gly Cys Ala Gly Gly Ala Gly Gly Ala Gly Gly Cys Cys Thr
            20                  25                  30

Gly Gly Thr Gly Cys Gly Gly Cys Cys Cys Gly Gly Ala Gly Gly Cys
        35                  40                  45
```

Thr Cys Thr Cys Thr Gly Ala Gly Ala Cys Thr Gly Ala Gly Cys Thr
        50                  55                  60
Gly Thr Gly Ala Cys Gly Cys Cys Thr Cys Cys Gly Gly Cys Thr Thr
65                  70                  75                  80
Cys Ala Cys Cys Thr Thr Thr Cys Cys Gly Ala Thr Thr Cys Thr Thr
                85                  90                  95
Thr Ala Cys Ala Thr Gly Thr Cys Thr Gly Gly Ala Thr Cys Ala
            100                 105                 110
Gly Ala Cys Ala Gly Gly Cys Ala Cys Cys Thr Gly Gly Ala Ala Gly
            115                 120                 125
Ala Gly Gly Cys Cys Thr Gly Gly Ala Gly Thr Gly Gly Gly Thr Gly
        130                 135                 140
Gly Cys Cys Cys Thr Gly Ala Thr Cys Ala Gly Cys Gly Gly Cys Ala
145                 150                 155                 160
Gly Cys Gly Gly Cys Thr Thr Cys Ala Gly Ala Ala Thr Cys Thr Thr
                165                 170                 175
Cys Thr Ala Cys Gly Gly Cys Gly Ala Cys Thr Cys Gly Thr Gly Gly
            180                 185                 190
Ala Ala Gly Gly Gly Cys Ala Gly Gly Thr Thr Cys Ala Cys Cys Ala
        195                 200                 205

Thr Cys Thr Cys Thr Cys Gly Cys Gly Ala Thr Ala Ala Cys Gly Cys
    210                 215                 220

Cys Ala Ala Gly Ala Ala Gly Ala Gly Cys Cys Thr Gly Thr Ala Thr
225                 230                 235                 240

Cys Thr Gly Cys Ala Gly Cys Thr Gly Ala Gly Cys Thr Cys Cys Cys
                245                 250                 255

Thr Gly Ala Gly Gly Gly Cys Cys Gly Ala Cys Gly Ala Thr Ala Cys
            260                 265                 270

Ala Gly Cys Cys Ala Thr Cys Thr Ala Cys Thr Ala Thr Thr Gly Cys
        275                 280                 285

Gly Cys Cys Cys Gly Cys Gly Ala Cys Ala Cys Cys Ala Cys Ala Cys
    290                 295                 300

Ala Cys Thr Thr Thr Gly Ala Thr Ala Gly Cys Thr Gly Gly Gly Gly
305                 310                 315                 320

Cys Cys Ala Gly Gly Gly Cys Ala Cys Cys Cys Thr Gly Gly Thr Gly
                325                 330                 335

Ala Cys Ala Gly Thr Gly Thr Cys Thr Ala Gly Cys
            340                 345

<210> SEQ ID NO 3
<211> LENGTH: 7
<212> TYPE: PRT
<213> ORGANISM: Homo sapiens

<400> SEQUENCE: 3

Gly Phe Thr Phe Ser Asp Ser
1               5

<210> SEQ ID NO 4
<211> LENGTH: 6
<212> TYPE: PRT
<213> ORGANISM: Homo sapiens

<400> SEQUENCE: 4

Ser Gly Ser Gly Phe Arg
1               5

```
<210> SEQ ID NO 5
<211> LENGTH: 7
<212> TYPE: PRT
<213> ORGANISM: Homo sapiens

<400> SEQUENCE: 5

Asp Thr Thr His Phe Asp Ser
1               5

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Asn Asn Phe Pro Phe
                85                  90                  95

Thr Phe Gly Pro Gly Thr Ser Gly His Gln
            100                 105

<210> SEQ ID NO 7
<211> LENGTH: 321
<212> TYPE: PRT
<213> ORGANISM: Homo sapiens

<400> SEQUENCE: 7

Gly Ala Cys Ala Thr Cys Cys Ala Gly Ala Thr Gly Ala Cys Cys Cys
1               5                   10                  15

Ala Gly Ala Gly Cys Cys Cys Ala Ala Gly Cys Thr Cys Cys Cys Thr
            20                  25                  30

Gly Thr Cys Cys Gly Cys Cys Thr Cys Thr Gly Thr Gly Gly Gly Cys
        35                  40                  45

Gly Ala Thr Cys Gly Gly Gly Thr Gly Ala Cys Cys Ala Thr Cys Ala
    50                  55                  60

Cys Ala Thr Gly Thr Ala Gly Ala Gly Cys Cys Ala Gly Cys Cys Ala
65                  70                  75                  80

Gly Gly Gly Cys Ala Thr Cys Ala Ala Cys Ala Ala Thr Thr Ala Cys
                85                  90                  95

Cys Thr Gly Gly Cys Cys Thr Gly Gly Thr Thr Thr Cys Ala Gly Cys
            100                 105                 110

Ala Gly Ala Ala Gly Cys Cys Cys Gly Gly Cys Ala Ala Gly Gly Cys
        115                 120                 125

Cys Cys Cys Thr Ala Ala Gly Thr Cys Cys Thr Gly Ala Thr Cys Thr
    130                 135                 140

Ala Thr Gly Cys Ala Gly Cys Cys Ala Gly Cys Ala Ala Cys Cys
145                 150                 155                 160

Thr Gly Cys Ala Gly Thr Cys Cys Gly Gly Cys Gly Thr Gly Cys Cys
```

```
                    165                 170                 175
Thr Thr Cys Thr Cys Gly Gly Thr Thr Ala Gly Cys Gly Gly Cys
                180                 185                 190
Thr Cys Cys Gly Gly Cys Thr Cys Thr Gly Gly Cys Ala Cys Ala Gly
            195                 200                 205
Ala Cys Thr Thr Cys Ala Cys Cys Thr Gly Ala Cys Ala Ala Thr
        210                 215                 220
Cys Thr Cys Thr Ala Gly Cys Cys Thr Gly Cys Ala Gly Cys Cys Ala
225                 230                 235                 240
Gly Ala Gly Gly Ala Thr Thr Cys Gly Cys Cys Ala Cys Cys Thr
            245                 250                 255
Ala Cys Thr Ala Thr Thr Gly Cys Cys Ala Gly Cys Ala Cys Thr Ala
        260                 265                 270
Cys Ala Ala Cys Ala Ala Thr Thr Thr Cys Cys Cys Thr Thr Cys
            275                 280                 285
Ala Cys Cys Thr Thr Cys Gly Gly Cys Cys Cys Gly Gly Cys Ala
        290                 295                 300
Cys Cys Ala Cys Ala Thr Cys Cys Gly Gly Cys Cys Ala Cys Cys Ala
305                 310                 315                 320
Gly

<210> SEQ ID NO 8
<211> LENGTH: 11
<212> TYPE: PRT
<213> ORGANISM: Homo sapiens

<400> SEQUENCE: 8

Arg Ala Ser Gln Gly Ile Asn Asn Tyr Leu Ala
1               5                   10

<210> SEQ ID NO 9
<211> LENGTH: 7
<212> TYPE: PRT
<213> ORGANISM: Homo sapiens

<400> SEQUENCE: 9

Ala Ala Ser Asn Leu Gln Ser
1               5

<210> SEQ ID NO 10
<211> LENGTH: 9
<212> TYPE: PRT
<213> ORGANISM: Homo sapiens

<400> SEQUENCE: 10

Gln His Tyr Asn Asn Phe Pro Phe Thr
1               5

<210> SEQ ID NO 11
<211> LENGTH: 120
<212> TYPE: PRT
<213> ORGANISM: Homo sapiens

<400> SEQUENCE: 11

Glu Val Gln Leu Val Glu Ser Gly Gly Gly Leu Val Lys Pro Gly Gly
1               5                   10                  15
Ser Leu Arg Leu Ser Cys Ser Ala Ser Gly Phe Thr Phe Ser Ser Tyr
            20                  25                  30
Ser Met Asn Trp Val Arg Gln Ala Pro Gly Lys Gly Leu Glu Phe Val
```

```
                35                  40                  45
Ser Ala Ile Thr Ser Arg Gly Thr Tyr Ile Tyr Tyr Ala Asp Ser Val
 50                  55                  60

Lys Gly Arg Phe Thr Val Ser Arg Asp Asn Ala Lys Asn Ser Leu Tyr
 65                  70                  75                  80

Leu Gln Met Ser Asn Val Arg Asp Glu Asp Thr Ala Val Tyr Tyr Cys
                 85                  90                  95

Ala Arg Glu Met Ala Gly Tyr Ser Ser Thr Phe Asp Tyr Trp Gly Gln
                100                 105                 110

Gly Ala Leu Val Thr Val Ser Phe
            115                 120

<210> SEQ ID NO 12
<211> LENGTH: 360
<212> TYPE: PRT
<213> ORGANISM: Homo sapiens

<400> SEQUENCE: 12

Gly Ala Gly Gly Thr Gly Cys Ala Gly Cys Thr Gly Thr Gly Gly
  1               5                  10                  15

Ala Gly Thr Cys Cys Gly Cys Gly Gly Ala Gly Gly Cys Cys Thr
                 20                  25                  30

Gly Gly Thr Gly Ala Ala Gly Cys Cys Ala Gly Gly Ala Gly Gly Cys
             35                  40                  45

Thr Cys Thr Cys Thr Gly Ala Gly Gly Cys Thr Gly Thr Cys Cys Thr
 50                  55                  60

Gly Thr Thr Cys Thr Gly Cys Cys Ala Gly Gly Gly Cys Thr Thr
 65                  70                  75                  80

Cys Ala Cys Cys Thr Thr Thr Ala Gly Cys Thr Cys Cys Thr Ala Cys
                 85                  90                  95

Thr Cys Cys Ala Thr Gly Ala Ala Cys Thr Gly Gly Gly Thr Gly Cys
                100                 105                 110

Gly Gly Cys Ala Gly Gly Cys Ala Cys Cys Thr Gly Gly Cys Ala Ala
            115                 120                 125

Gly Gly Gly Cys Cys Thr Gly Gly Ala Gly Thr Thr Cys Gly Thr Gly
            130                 135                 140

Thr Cys Cys Gly Cys Cys Ala Thr Cys Ala Cys Cys Thr Cys Thr Ala
145                 150                 155                 160

Gly Gly Gly Gly Cys Ala Cys Ala Thr Ala Cys Ala Thr Cys Thr Ala
                165                 170                 175

Cys Thr Ala Thr Gly Cys Cys Gly Ala Cys Thr Cys Thr Gly Thr Gly
                180                 185                 190

Ala Ala Gly Gly Gly Cys Cys Gly Thr Thr Thr Ala Cys Cys Gly
            195                 200                 205

Thr Gly Ala Gly Cys Ala Gly Ala Gly Ala Cys Ala Ala Cys Gly Cys
            210                 215                 220

Cys Ala Ala Gly Ala Ala Thr Ala Gly Cys Cys Thr Gly Thr Ala Thr
225                 230                 235                 240

Cys Thr Gly Cys Ala Gly Ala Thr Gly Thr Cys Cys Ala Ala Thr Gly
                245                 250                 255

Thr Gly Ala Gly Gly Gly Ala Cys Gly Ala Gly Gly Ala Thr Ala Cys
                260                 265                 270

Ala Gly Cys Cys Gly Thr Gly Thr Ala Cys Thr Ala Thr Thr Gly Cys
            275                 280                 285
```

```
Gly Cys Cys Gly Cys Gly Ala Gly Ala Thr Gly Gly Cys Cys Gly
    290                 295                 300
Gly Cys Thr Ala Cys Thr Cys Thr Ala Gly Cys Ala Cys Cys Thr Thr
305                 310                 315                 320
Cys Gly Ala Cys Thr Ala Thr Thr Gly Gly Gly Cys Cys Ala Gly
                325                 330                 335
Gly Gly Cys Gly Cys Cys Cys Thr Gly Thr Gly Ala Cys Ala Gly
                340                 345                 350
Thr Gly Thr Cys Thr Thr Thr Thr
                355                 360
```

<210> SEQ ID NO 13
<211> LENGTH: 7
<212> TYPE: PRT
<213> ORGANISM: Homo sapiens

<400> SEQUENCE: 13

```
Gly Phe Thr Phe Ser Ser Tyr
1               5
```

<210> SEQ ID NO 14
<211> LENGTH: 6
<212> TYPE: PRT
<213> ORGANISM: Homo sapiens

<400> SEQUENCE: 14

```
Thr Ser Arg Gly Thr Tyr
1               5
```

<210> SEQ ID NO 15
<211> LENGTH: 11
<212> TYPE: PRT
<213> ORGANISM: Homo sapiens

<400> SEQUENCE: 15

```
Glu Met Ala Gly Tyr Ser Ser Thr Phe Asp Tyr
1               5                   10
```

<210> SEQ ID NO 16
<211> LENGTH: 108
<212> TYPE: PRT
<213> ORGANISM: Homo sapiens

<400> SEQUENCE: 16

```
Glu Ile Val Leu Thr Gln Ser Pro Ala Thr Leu Ser Val Ser Pro Gly
1               5                   10                  15
Glu Gly Ala Thr Leu Ser Cys Arg Ala Ser Gln Gly Ile Asn Arg Tyr
            20                  25                  30
Ile Ala Trp Tyr Gln His Lys Pro Gly Gln Ala Pro Arg Leu Leu Ile
        35                  40                  45
Tyr Asp Ala Ser Asn Arg Ala Asn Gly Ile Pro Ala Arg Phe Ser Gly
    50                  55                  60
Arg Gly Ser Gly Thr Asp Phe Ser Leu Thr Ile Ser Ala Leu Glu Pro
65                  70                  75                  80
Glu Asp Ser Ala Val Tyr Tyr Cys Gln Gln Arg Ser Asn Trp Pro Pro
                85                  90                  95
Tyr Thr Phe Gly Gln Gly Thr Lys Leu Glu Ile Lys
            100                 105
```

<210> SEQ ID NO 17

<211> LENGTH: 324
<212> TYPE: PRT
<213> ORGANISM: Homo sapiens

<400> SEQUENCE: 17

Gly Ala Gly Ala Thr Cys Gly Thr Gly Thr Gly Ala Cys Cys Cys
1               5                   10                  15

Ala Gly Thr Cys Thr Cys Cys Thr Gly Cys Ala Cys Ala Cys Thr
                20                  25                  30

Gly Ala Gly Cys Gly Thr Gly Thr Cys Cys Cys Ala Gly Gly Ala
                35                  40                  45

Gly Ala Gly Gly Gly Ala Gly Cys Cys Ala Cys Cys Thr Gly Thr
                50                  55                  60

Cys Thr Thr Gly Thr Ala Gly Gly Cys Cys Ala Gly Cys Cys Ala
65                  70                  75                  80

Gly Gly Gly Cys Ala Thr Cys Ala Ala Cys Cys Gly Cys Thr Ala Cys
                85                  90                  95

Ala Thr Cys Gly Cys Cys Thr Gly Gly Thr Ala Thr Cys Ala Gly Cys
                100                 105                 110

Ala Cys Ala Ala Gly Cys Cys Ala Gly Gly Ala Cys Ala Gly Gly Cys
                115                 120                 125

Ala Cys Cys Ala Gly Gly Cys Thr Gly Cys Thr Gly Ala Thr Cys
                130                 135                 140

Thr Ala Cys Gly Cys Ala Gly Cys Cys Ala Gly Cys Ala Ala Cys Ala
145                 150                 155                 160

Gly Gly Gly Cys Ala Ala Ala Thr Gly Gly Cys Ala Thr Cys Cys Cys
                165                 170                 175

Cys Gly Cys Ala Cys Gly Gly Thr Thr Cys Thr Cys Cys Gly Gly Cys
                180                 185                 190

Ala Gly Ala Gly Gly Cys Thr Cys Thr Gly Gly Cys Ala Cys Cys Gly
                195                 200                 205

Ala Cys Thr Thr Thr Ala Gly Cys Cys Thr Gly Ala Cys Ala Ala Thr
                210                 215                 220

Cys Thr Cys Cys Gly Cys Cys Cys Thr Gly Gly Ala Gly Cys Cys Thr
225                 230                 235                 240

Gly Ala Gly Gly Ala Thr Thr Cys Thr Gly Cys Cys Gly Thr Gly Thr
                245                 250                 255

Ala Cys Thr Ala Thr Gly Cys Cys Ala Gly Cys Ala Gly Cys Gly
                260                 265                 270

Gly Ala Gly Cys Ala Ala Thr Thr Gly Gly Cys Cys Cys Cys Cys Thr
                275                 280                 285

Thr Ala Thr Ala Cys Cys Thr Thr Cys Gly Gly Cys Cys Ala Gly Gly
                290                 295                 300

Gly Cys Ala Cys Ala Ala Ala Gly Cys Thr Gly Gly Ala Gly Ala Thr
305                 310                 315                 320

Cys Ala Ala Gly

<210> SEQ ID NO 18
<211> LENGTH: 11
<212> TYPE: PRT
<213> ORGANISM: Homo sapiens

<400> SEQUENCE: 18

Arg Ala Ser Gln Gly Ile Asn Arg Tyr Ile Ala
1               5                   10

```
<210> SEQ ID NO 19
<211> LENGTH: 7
<212> TYPE: PRT
<213> ORGANISM: Homo sapiens

<400> SEQUENCE: 19

Asp Ala Ser Asn Arg Ala Asn
1               5

<210> SEQ ID NO 20
<211> LENGTH: 10
<212> TYPE: PRT
<213> ORGANISM: Homo sapiens

<400> SEQUENCE: 20

Gln Gln Arg Ser Asn Trp Pro Pro Tyr Thr
1               5                   10

<210> SEQ ID NO 21
<211> LENGTH: 120
<212> TYPE: PRT
<213> ORGANISM: Homo sapiens

<400> SEQUENCE: 21

Glu Val Gln Leu Val Glu Ser Gly Gly Gly Leu Val Arg Pro Gly Gly
1               5                   10                  15

Ser Leu Arg Leu Ser Cys Ser Ala Ser Gly Phe Thr Phe Ser Ser Tyr
            20                  25                  30

Ser Met Asn Trp Val Arg Gln Ala Pro Gly Lys Gly Leu Glu Phe Val
        35                  40                  45

Ser Ala Ile Thr Ser Arg Gly Thr Tyr Ile Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Thr Asn Val Arg Asp Glu Asp Thr Ala Val Tyr Tyr Cys
                85                  90                  95

Ala Arg Glu Met Ala Gly Tyr Ser Ser Thr Phe Asp Tyr Trp Gly Gln
            100                 105                 110

Gly Ala Leu Val Thr Val Ser Ser
        115                 120

<210> SEQ ID NO 22
<211> LENGTH: 360
<212> TYPE: PRT
<213> ORGANISM: Homo sapiens

<400> SEQUENCE: 22

Gly Ala Gly Gly Thr Gly Cys Ala Gly Cys Thr Gly Thr Gly Gly
1               5                   10                  15

Ala Gly Thr Cys Cys Gly Gly Cys Gly Gly Ala Gly Gly Cys Cys Thr
            20                  25                  30

Gly Gly Thr Gly Ala Gly Gly Cys Cys Gly Gly Ala Gly Gly Cys
        35                  40                  45

Thr Cys Thr Cys Thr Gly Cys Gly Cys Cys Thr Gly Ala Gly Cys Thr
    50                  55                  60

Gly Thr Thr Cys Cys Gly Cys Cys Thr Cys Gly Gly Cys Thr Thr
65                  70                  75                  80

Cys Ala Cys Cys Thr Thr Thr Ala Gly Cys Thr Cys Thr Ala Cys
                85                  90                  95
```

```
Ala Gly Cys Ala Thr Gly Ala Ala Cys Thr Gly Gly Thr Gly Ala
            100                 105                 110
Gly Gly Cys Ala Gly Gly Cys Cys Thr Gly Gly Cys Ala Ala
            115                 120                 125
Gly Gly Gly Cys Cys Thr Gly Ala Gly Thr Thr Cys Gly Thr Gly
            130                 135                 140
Ala Gly Cys Gly Cys Cys Ala Thr Cys Ala Cys Thr Cys Ala
145                 150                 155                 160
Gly Ala Gly Gly Cys Ala Cys Ala Thr Ala Cys Ala Thr Thr Ala
                    165                 170                 175
Cys Thr Ala Thr Gly Cys Cys Gly Ala Cys Thr Cys Cys Gly Thr
                    180                 185                 190
Ala Ala Gly Gly Gly Cys Cys Gly Gly Thr Thr Cys Ala Cys Cys
                    195                 200                 205
Thr Gly Ala Gly Cys Cys Gly Gly Ala Thr Ala Ala Cys Gly Cys
                    210                 215                 220
Cys Ala Ala Gly Ala Ala Thr Ala Cys Cys Thr Gly Thr Ala Thr
225                 230                 235                 240
Cys Thr Gly Cys Ala Gly Ala Thr Gly Ala Cys Cys Ala Ala Thr Gly
                    245                 250                 255
Thr Gly Cys Gly Gly Gly Ala Cys Gly Ala Gly Gly Ala Thr Ala Cys
                    260                 265                 270
Ala Gly Cys Cys Gly Thr Gly Thr Ala Cys Thr Ala Thr Thr Gly Cys
                    275                 280                 285
Gly Cys Cys Ala Gly Ala Gly Ala Thr Ala Thr Gly Gly Cys Cys Gly Gly
                    290                 295                 300
Gly Cys Thr Ala Cys Thr Cys Thr Ala Gly Cys Ala Cys Cys Thr Thr
305                 310                 315                 320
Cys Gly Ala Cys Thr Ala Thr Thr Gly Gly Gly Gly Ala Cys Ala Gly Gly
                    325                 330                 335
Gly Gly Cys Gly Cys Cys Cys Thr Gly Gly Thr Gly Ala Cys Ala Gly
                    340                 345                 350
Thr Gly Thr Cys Cys Thr Cys Thr
                    355                 360
```

<210> SEQ ID NO 23
<211> LENGTH: 7
<212> TYPE: PRT
<213> ORGANISM: Homo sapiens

<400> SEQUENCE: 23

```
Gly Phe Thr Phe Ser Ser Tyr
1               5
```

<210> SEQ ID NO 24
<211> LENGTH: 6
<212> TYPE: PRT
<213> ORGANISM: Homo sapiens

<400> SEQUENCE: 24

```
Thr Ser Arg Gly Thr Tyr
1               5
```

<210> SEQ ID NO 25
<211> LENGTH: 11
<212> TYPE: PRT
<213> ORGANISM: Homo sapiens

<400> SEQUENCE: 25

Glu Met Ala Gly Tyr Ser Ser Thr Phe Asp Tyr
1               5                   10

<210> SEQ ID NO 26
<211> LENGTH: 108
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Gln
                85                  90                  95

Val Thr Phe Gly Gly Gly Thr Lys Val Glu Ile Lys
            100                 105

<210> SEQ ID NO 27
<211> LENGTH: 324
<212> TYPE: PRT
<213> ORGANISM: Homo sapiens

<400> SEQUENCE: 27

Gly Ala Cys Ala Thr Cys Cys Ala Gly Ala Thr Gly Ala Cys Cys Cys
1               5                   10                  15

Ala Gly Thr Cys Cys Cys Cys Thr Ala Gly Cys Thr Cys Cys Cys Thr
            20                  25                  30

Gly Ala Gly Cys Gly Cys Cys Thr Cys Cys Gly Thr Gly Gly Gly Cys
        35                  40                  45

Gly Ala Cys Cys Gly Gly Gly Thr Gly Ala Cys Ala Thr Cys Ala
    50                  55                  60

Cys Ala Thr Gly Thr Ala Gly Ala Gly Cys Cys Thr Cys Thr Cys Ala
65                  70                  75                  80

Gly Gly Gly Cys Ala Thr Cys Ala Gly Ala Ala Cys Gly Ala Cys Thr
                85                  90                  95

Cys Thr Gly Gly Gly Cys Thr Gly Gly Thr Ala Cys Cys Ala Gly Cys
            100                 105                 110

Ala Gly Ala Ala Gly Cys Cys Cys Gly Gly Cys Ala Ala Gly Gly Cys
        115                 120                 125

Cys Cys Cys Thr Ala Ala Gly Cys Gly Cys Cys Thr Gly Ala Thr Cys
    130                 135                 140

Thr Ala Thr Gly Cys Ala Gly Cys Cys Thr Cys Thr Ala Gly Cys Cys
145                 150                 155                 160

Thr Gly Cys Ala Gly Thr Cys Thr Gly Gly Cys Gly Thr Gly Cys Cys
                165                 170                 175

Ala Ala Gly Cys Cys Gly Gly Thr Thr Cys Thr Cys Thr Gly Gly Cys
            180                 185                 190

Ala Gly Cys Gly Gly Cys Thr Cys Gly Cys Ala Cys Cys Gly
                195                 200                 205

Ala Gly Thr Thr Thr Ala Cys Cys Thr Gly Cys Ala Ala Thr
        210                 215                 220

Cys Thr Cys Cys Thr Cys Thr Cys Thr Gly Cys Ala Gly Cys Cys Ala
225                 230                 235                 240

Gly Ala Gly Gly Ala Thr Thr Cys Gly Cys Ala Cys Ala Thr
            245                 250                 255

Ala Cys Thr Ala Thr Thr Gly Cys Cys Thr Gly Cys Ala Gly Cys Ala
        260                 265                 270

Cys Ala Ala Thr Ala Gly Cys Thr Ala Cys Cys Cys Cys Ala Gly
            275                 280                 285

Gly Thr Gly Ala Cys Cys Thr Thr Thr Gly Gly Cys Gly Gly Cys Gly
        290                 295                 300

Gly Cys Ala Cys Ala Ala Ala Gly Gly Thr Gly Gly Ala Gly Ala Thr
305                 310                 315                 320

Cys Ala Ala Gly

<210> SEQ ID NO 28
<211> LENGTH: 11
<212> TYPE: PRT
<213> ORGANISM: Homo sapiens

<400> SEQUENCE: 28

Arg Ala Ser Gln Gly Ile Arg Asn Asp Leu Gly
1               5                   10

<210> SEQ ID NO 29
<211> LENGTH: 7
<212> TYPE: PRT
<213> ORGANISM: Homo sapiens

<400> SEQUENCE: 29

Ala Ala Ser Ser Leu Gln Ser
1               5

<210> SEQ ID NO 30
<211> LENGTH: 10
<212> TYPE: PRT
<213> ORGANISM: Homo sapiens

<400> SEQUENCE: 30

Leu Gln His Asn Ser Tyr Pro Gln Val Thr
1               5                   10

<210> SEQ ID NO 31
<211> LENGTH: 120
<212> TYPE: PRT
<213> ORGANISM: Homo sapiens

<400> SEQUENCE: 31

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Arg His
            20                  25                  30

Ala Met His Trp Val Arg Gln Ala Pro Gly Gln Gly Leu Glu Trp Leu
        35                  40                  45

Ser Met Ile Tyr Ser Asp Gly Thr Asn Lys Ile Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asp Ser Val Gly Ala Glu Asp Thr Ala Thr Tyr Phe Cys
                 85                  90                  95

Ala Thr Glu Pro Gln Thr Gly Arg Gly Pro Leu Asp Tyr Trp Gly Arg
            100                 105                 110

Gly Thr Leu Val Ile Val Ser Ser
            115                 120

<210> SEQ ID NO 32
<211> LENGTH: 360
<212> TYPE: PRT
<213> ORGANISM: Homo sapiens

<400> SEQUENCE: 32

Gly Ala Gly Gly Thr Gly Cys Ala Gly Cys Thr Gly Gly Thr Gly Gly
 1               5                   10                  15

Ala Gly Thr Cys Cys Gly Gly Cys Gly Gly Ala Gly Gly Ala Gly Thr
                20                  25                  30

Gly Gly Thr Gly Cys Ala Gly Cys Cys Ala Gly Gly Cys Cys Gly Gly
            35                  40                  45

Ala Gly Cys Cys Thr Gly Ala Gly Gly Cys Thr Gly Ala Gly Cys Thr
         50                  55                  60

Gly Thr Gly Cys Ala Gly Cys Cys Thr Cys Cys Gly Gly Cys Thr Thr
 65                  70                  75                  80

Cys Ala Cys Cys Thr Thr Thr Cys Gly Gly Ala Gly Ala Cys Ala Cys
                 85                  90                  95

Gly Cys Cys Ala Thr Gly Cys Ala Cys Thr Gly Gly Gly Thr Gly Cys
            100                 105                 110

Gly Gly Cys Ala Gly Gly Cys Ala Cys Ala Gly Gly Ala Cys Ala Ala
            115                 120                 125

Gly Gly Gly Cys Cys Thr Gly Gly Ala Gly Thr Gly Gly Cys Thr Gly
            130                 135                 140

Thr Cys Thr Ala Thr Gly Ala Thr Cys Thr Ala Cys Ala Gly Cys Gly
145                 150                 155                 160

Ala Cys Gly Gly Cys Ala Cys Ala Ala Cys Ala Ala Gly Ala Thr
            165                 170                 175

Cys Thr Ala Thr Gly Cys Cys Gly Ala Thr Thr Cys Thr Gly Thr Gly
            180                 185                 190

Ala Ala Gly Gly Gly Cys Cys Gly Gly Thr Thr Cys Ala Cys Cys Ala
            195                 200                 205

Thr Cys Thr Cys Cys Ala Gly Ala Gly Ala Cys Ala Ala Cys Thr Cys
        210                 215                 220

Thr Ala Ala Gly Ala Ala Thr Ala Cys Cys Thr Thr Thr Ala Cys
225                 230                 235                 240

Cys Thr Gly Cys Ala Gly Ala Thr Gly Gly Ala Cys Ala Gly Cys Gly
            245                 250                 255

Thr Gly Gly Gly Ala Gly Cys Ala Gly Ala Gly Ala Thr Ala Cys
            260                 265                 270

Cys Gly Cys Ala Ala Cys Ala Thr Ala Thr Thr Thr Thr Gly Cys
            275                 280                 285

Gly Cys Ala Ala Cys Cys Gly Ala Gly Cys Cys Ala Cys Ala Gly Ala
            290                 295                 300

Cys Ala Gly Gly Ala Ala Gly Gly Gly Ala Cys Cys Thr Cys Thr
305                 310                 315                 320

Gly Gly Ala Thr Thr Ala Cys Thr Gly Gly Gly Ala Ala Gly Gly
            325                 330                 335

Gly Gly Cys Ala Cys Cys Thr Gly Gly Thr Cys Ala Thr Cys Gly
            340                 345                 350

Thr Gly Ala Gly Cys Thr Cys Cys
            355                 360

<210> SEQ ID NO 33
<211> LENGTH: 7
<212> TYPE: PRT
<213> ORGANISM: Homo sapiens

<400> SEQUENCE: 33

Gly Phe Thr Phe Arg Arg His
1               5

<210> SEQ ID NO 34
<211> LENGTH: 6
<212> TYPE: PRT
<213> ORGANISM: Homo sapiens

<400> SEQUENCE: 34

Tyr Ser Asp Gly Thr Asn
1               5

<210> SEQ ID NO 35
<211> LENGTH: 11
<212> TYPE: PRT
<213> ORGANISM: Homo sapiens

<400> SEQUENCE: 35

Glu Pro Gln Thr Gly Arg Gly Pro Leu Asp Tyr
1               5                   10

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Leu Ser Gly Val Pro Ser Arg Phe Ser Gly
    50                  55                  60

Ser Gly Thr Gly Thr Asp Phe Thr Leu Thr Ile Ser Ser Leu Gln Pro
65                  70                  75                  80

Glu Asp Val Ala Thr Tyr Tyr Cys Gln Lys Tyr His Asn Ala Pro Arg
                85                  90                  95

Thr Phe Gly Gln Gly Thr Lys Val Asp Ile Lys
            100                 105

<210> SEQ ID NO 37
<211> LENGTH: 321
<212> TYPE: PRT
<213> ORGANISM: Homo sapiens

<400> SEQUENCE: 37

Gly Ala Cys Ala Thr Cys Cys Ala Gly Ala Thr Gly Ala Cys Cys
1               5                   10                  15

Ala Gly Thr Cys Thr Cys Cys Thr Ala Gly Cys Thr Cys Cys Cys Thr
            20                  25                  30

Gly Thr Cys Cys Gly Cys Cys Thr Cys Thr Gly Thr Gly Gly Gly Cys
            35                  40                  45

Gly Ala Thr Cys Gly Gly Gly Thr Gly Ala Cys Cys Ala Thr Cys Ala
            50                  55                  60

Cys Ala Thr Gly Thr Ala Gly Ala Gly Cys Cys Ala Gly Cys Cys Ala
65                  70                  75                  80

Gly Gly Gly Cys Ala Thr Cys Ala Thr Cys Ala Ala Cys Thr Ala Cys
                85                  90                  95

Cys Thr Gly Gly Cys Cys Thr Gly Gly Thr Ala Thr Cys Ala Gly Cys
                100                 105                 110

Ala Gly Ala Ala Gly Cys Cys Gly Cys Ala Ala Gly Gly Cys
                115                 120                 125

Cys Cys Cys Thr Ala Ala Gly Cys Thr Gly Cys Thr Gly Ala Thr Cys
130 135 140

Thr Ala Cys Gly Cys Ala Gly Cys Cys Thr Cys Thr Ala Cys Cys Cys
145 150 155 160

Thr Gly Cys Thr Gly Ala Gly Cys Gly Gly Cys Gly Thr Gly Cys Cys
165 170 175

Ala Thr Cys Cys Ala Gly Gly Thr Thr Cys Ala Gly Cys Gly Gly Cys
180 185 190

Thr Cys Cys Gly Gly Cys Ala Cys Cys Gly Gly Ala Ala Cys Ala Gly
195 200 205

Ala Cys Thr Thr Thr Ala Cys Cys Cys Thr Gly Ala Cys Ala Ala Thr
210 215 220

Cys Thr Cys Thr Ala Gly Cys Cys Thr Gly Cys Ala Gly Cys Cys Ala
225 230 235 240

Gly Ala Gly Gly Ala Thr Gly Thr Gly Gly Cys Cys Ala Cys Ala Thr
245 250 255

Ala Cys Thr Ala Thr Thr Gly Cys Cys Ala Gly Ala Ala Gly Thr Ala
260 265 270

Thr Cys Ala Cys Ala Ala Thr Gly Cys Ala Cys Cys Ala Cys Gly Gly
275 280 285

Ala Cys Cys Thr Thr Cys Gly Gly Cys Cys Ala Gly Gly Gly Ala Ala
290 295 300

Cys Ala Ala Ala Gly Gly Thr Gly Gly Ala Cys Ala Thr Cys Ala Ala
305 310 315 320

Gly

<210> SEQ ID NO 38
<211> LENGTH: 11
<212> TYPE: PRT
<213> ORGANISM: Homo sapiens

<400> SEQUENCE: 38

Arg Ala Ser Gln Gly Ile Ile Asn Tyr Leu Ala
1 5 10

<210> SEQ ID NO 39
<211> LENGTH: 7
<212> TYPE: PRT
<213> ORGANISM: Homo sapiens

-continued

<400> SEQUENCE: 39

Ala Ala Ser Thr Leu Leu Ser
1               5

<210> SEQ ID NO 40
<211> LENGTH: 9
<212> TYPE: PRT
<213> ORGANISM: Homo sapiens

<400> SEQUENCE: 40

Gln Lys Tyr His Asn Ala Pro Arg Thr
1               5

<210> SEQ ID NO 41
<211> LENGTH: 121
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ser Gly Ile Ser Ser Ala Ala Gly Arg His Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Ser Gly Leu Arg Ala Glu Asp Thr Ala Val Tyr Phe Cys
            85                  90                  95

Ala Lys Ala Gly Ala Arg Asn Tyr Tyr Tyr Gly Met Asp Val Trp Gly
            100                 105                 110

Gln Gly Thr Thr Val Thr Val Ser Ser
            115                 120

<210> SEQ ID NO 42
<211> LENGTH: 363
<212> TYPE: PRT
<213> ORGANISM: Homo sapiens

<400> SEQUENCE: 42

Gly Ala Gly Gly Thr Gly Cys Ala Gly Cys Thr Gly Cys Thr Gly Gly
1               5                   10                  15

Ala Gly Thr Cys Cys Gly Gly Cys Gly Gly Ala Gly Gly Cys Cys Thr
            20                  25                  30

Gly Gly Thr Gly Cys Ala Gly Cys Cys Ala Gly Gly Ala Gly Gly Cys
            35                  40                  45

Thr Cys Thr Cys Thr Gly Ala Gly Gly Cys Thr Gly Ala Gly Cys Thr
    50                  55                  60

Gly Thr Gly Cys Ala Gly Cys Cys Thr Cys Gly Gly Cys Thr Thr
65                  70                  75                  80

Cys Ala Cys Cys Thr Thr Thr Ala Ala Cys Thr Cys Thr Thr Ala Thr
            85                  90                  95

Gly Cys Cys Ala Thr Gly Ala Ala Thr Thr Gly Gly Gly Thr Gly Ala
            100                 105                 110

Gly Gly Cys Ala Gly Gly Cys Ala Cys Cys Thr Gly Gly Cys Ala Ala

```
                115                 120                 125
Gly Gly Gly Cys Cys Thr Gly Ala Gly Thr Gly Gly Thr Gly
            130                 135                 140

Thr Cys Cys Gly Gly Cys Ala Thr Cys Ala Gly Cys Thr Cys Thr
145                 150                 155                 160

Cys Thr Gly Cys Cys Gly Cys Ala Gly Gly Cys Cys Gly Gly Cys Ala
                165                 170                 175

Cys Thr Ala Cys Gly Cys Ala Gly Ala Cys Thr Cys Thr Gly Thr Gly
            180                 185                 190

Ala Ala Gly Gly Gly Cys Cys Gly Gly Thr Thr Cys Ala Cys Cys Ala
                195                 200                 205

Thr Cys Ala Gly Cys Cys Gly Gly Ala Thr Ala Ala Cys Ala Gly
            210                 215                 220

Cys Ala Ala Gly Ala Ala Thr Ala Cys Ala Cys Thr Gly Thr Ala Thr
225                 230                 235                 240

Cys Thr Gly Cys Ala Gly Ala Thr Gly Thr Cys Cys Gly Gly Cys Cys
                245                 250                 255

Thr Gly Ala Gly Gly Gly Cys Ala Gly Gly Ala Cys Ala Cys
            260                 265                 270

Cys Gly Cys Cys Gly Thr Gly Thr Ala Cys Thr Thr Thr Gly Cys
            275                 280                 285

Gly Cys Cys Ala Ala Gly Gly Cys Cys Gly Gly Cys Gly Cys Cys
290                 295                 300

Gly Cys Ala Ala Cys Thr Ala Cys Thr Ala Thr Ala Cys Gly Gly
305                 310                 315                 320

Ala Ala Thr Gly Gly Ala Cys Gly Thr Gly Thr Gly Gly Gly Ala
                325                 330                 335

Cys Ala Gly Gly Gly Ala Ala Cys Cys Ala Cys Ala Thr Gly Ala
            340                 345                 350

Cys Ala Gly Thr Gly Ala Gly Cys Thr Cys Cys
            355                 360

<210> SEQ ID NO 43
<211> LENGTH: 7
<212> TYPE: PRT
<213> ORGANISM: Homo sapiens

<400> SEQUENCE: 43

Gly Phe Thr Phe Asn Ser Tyr
1               5

<210> SEQ ID NO 44
<211> LENGTH: 6
<212> TYPE: PRT
<213> ORGANISM: Homo sapiens

<400> SEQUENCE: 44

Ser Ser Ser Ala Ala Gly
1               5

<210> SEQ ID NO 45
<211> LENGTH: 12
<212> TYPE: PRT
<213> ORGANISM: Homo sapiens

<400> SEQUENCE: 45

Ala Gly Ala Arg Asn Tyr Tyr Gly Met Asp Val
1               5                   10
```

<210> SEQ ID NO 46
<211> LENGTH: 107
<212> TYPE: PRT
<213> ORGANISM: Homo sapiens

<400> SEQUENCE: 46

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Gly Val Ser Ser Asn
            20                  25                  30

Leu Ala Trp Tyr Gln Gln Lys Phe Gly Gln Ala Pro Arg Leu Leu Ile
        35                  40                  45

Phe Ser Ala Ser Thr Arg Ala Thr Gly Thr Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Ser Phe Gly Gly Gly Thr Lys Val Glu Ile Lys
            100                 105

<210> SEQ ID NO 47
<211> LENGTH: 321
<212> TYPE: PRT
<213> ORGANISM: Homo sapiens

<400> SEQUENCE: 47

Gly Ala Gly Ala Thr Cys Gly Thr Gly Ala Thr Gly Ala Cys Cys Cys
1               5                   10                  15

Ala Gly Ala Gly Cys Cys Cys Ala Gly Cys Cys Ala Cys Ala Cys Thr
            20                  25                  30

Gly Thr Cys Cys Gly Thr Gly Thr Cys Thr Cys Cys Thr Gly Gly Ala
        35                  40                  45

Gly Ala Gly Ala Gly Gly Cys Cys Ala Cys Cys Cys Thr Gly Thr
50                  55                  60

Cys Thr Thr Gly Thr Ala Gly Ala Cys Cys Ala Gly Cys Cys Ala
65                  70                  75                  80

Gly Gly Gly Cys Gly Thr Gly Ala Gly Cys Thr Cys Ala Ala Cys
                85                  90                  95

Cys Thr Gly Gly Cys Ala Thr Gly Gly Thr Ala Cys Cys Ala Gly Cys
            100                 105                 110

Ala Gly Ala Ala Gly Thr Thr Cys Gly Gly Cys Cys Ala Gly Gly Cys
        115                 120                 125

Cys Cys Cys Ala Cys Gly Gly Cys Thr Gly Cys Thr Gly Ala Thr Cys
            130                 135                 140

Thr Thr Thr Ala Gly Cys Gly Cys Cys Thr Cys Cys Ala Cys Cys Ala
145                 150                 155                 160

Gly Gly Gly Cys Ala Ala Cys Cys Gly Gly Ala Ala Cys Ala Cys Cys
                165                 170                 175

Ala Gly Cys Cys Cys Gly Cys Thr Thr Cys Thr Cys Thr Gly Gly Cys
            180                 185                 190

Ala Gly Cys Gly Gly Cys Thr Cys Cys Gly Gly Cys Ala Cys Ala Gly
        195                 200                 205

Ala Gly Thr Thr Thr Ala Cys Cys Cys Thr Gly Ala Cys Ala Ala Thr
            210                 215                 220

-continued

Cys Thr Cys Thr Ala Gly Cys Thr Gly Cys Ala Gly Thr Cys Cys
225                 230                 235                 240

Gly Ala Gly Gly Ala Cys Thr Thr Cys Gly Cys Cys Gly Thr Gly Thr
                    245                 250                 255

Ala Cys Thr Ala Thr Thr Gly Cys Cys Ala Gly Cys Ala Gly Thr Ala
                260                 265                 270

Thr Gly Ala Thr Ala Ala Thr Thr Gly Gly Cys Cys Cys Thr Cys Gly
            275                 280                 285

Thr Cys Thr Thr Thr Thr Gly Gly Cys Gly Gly Cys Gly Gly Cys Ala
        290                 295                 300

Cys Ala Ala Ala Gly Gly Thr Gly Gly Ala Gly Ala Thr Cys Ala Ala
305                 310                 315                 320

Gly

<210> SEQ ID NO 48
<211> LENGTH: 11
<212> TYPE: PRT
<213> ORGANISM: Homo sapiens

<400> SEQUENCE: 48

Arg Ala Ser Gln Gly Val Ser Ser Asn Leu Ala
1               5                   10

<210> SEQ ID NO 49
<211> LENGTH: 7
<212> TYPE: PRT
<213> ORGANISM: Homo sapiens

<400> SEQUENCE: 49

Ser Ala Ser Thr Arg Ala Thr
1               5

<210> SEQ ID NO 50
<211> LENGTH: 9
<212> TYPE: PRT
<213> ORGANISM: Homo sapiens

<400> SEQUENCE: 50

Gln Gln Tyr Asp Asn Trp Pro Leu Ser
1               5

<210> SEQ ID NO 51
<211> LENGTH: 120
<212> TYPE: PRT
<213> ORGANISM: Homo sapiens

<400> SEQUENCE: 51

Gln Val His Leu Gln Glu Ser Gly Pro Gly Pro Val Lys Pro Ser Glu
1               5                   10                  15

Thr Leu Ser Leu Thr Cys Thr Val Ser Arg Gly Ser Met Ser Gly Tyr
                20                  25                  30

Tyr Trp Thr Trp Ile Arg Leu Pro Pro Gly Lys Gly Leu Glu Trp Ile
            35                  40                  45

Gly Asn Ile His Asp Ser Gly Thr Thr Asp Tyr Asn Pro Ser Leu Arg
        50                  55                  60

Asn Arg Val Ser Ile Ser Ala Asp Ala Ser Lys Ser Gln Phe Tyr Leu
65                  70                  75                  80

Lys Leu Ser Ser Val Thr Ala Ala Asp Thr Ala Val Tyr Tyr Cys Val
                85                  90                  95

Arg Asp Gly Arg Tyr Phe Gly Ala Thr Ala Leu Asp Pro Trp Gly Gln
                100                 105                 110

Gly Ser Leu Val Thr Val Ser Pro
        115                 120

<210> SEQ ID NO 52
<211> LENGTH: 360
<212> TYPE: PRT
<213> ORGANISM: Homo sapiens

<400> SEQUENCE: 52

Cys Ala Gly Gly Thr Gly Cys Ala Cys Thr Gly Cys Ala Gly Gly
1               5                   10                  15

Ala Gly Thr Cys Thr Gly Gly Cys Cys Ala Gly Gly Ala Cys Cys
                20                  25                  30

Ala Gly Thr Gly Ala Ala Gly Cys Ala Thr Cys Thr Gly Ala Gly
                35                  40                  45

Ala Cys Ala Cys Thr Gly Ala Gly Cys Cys Thr Gly Ala Cys Cys
                50                  55                  60

Gly Thr Ala Cys Ala Gly Thr Gly Thr Cys Cys Gly Gly Gly
65                      70                  75                  80

Cys Thr Cys Thr Ala Thr Gly Ala Gly Cys Gly Gly Cys Thr Ala Cys
                85                  90                  95

Thr Ala Thr Thr Gly Gly Ala Cys Ala Thr Gly Gly Ala Thr Cys Ala
                100                 105                 110

Gly Gly Cys Thr Gly Cys Cys Ala Cys Cys Thr Gly Gly Cys Ala Ala
                115                 120                 125

Gly Gly Gly Cys Cys Thr Gly Gly Ala Gly Thr Gly Gly Ala Thr Cys
                130                 135                 140

Gly Gly Cys Ala Ala Cys Ala Thr Cys Cys Ala Cys Gly Ala Cys Ala
145                 150                 155                 160

Gly Cys Gly Gly Cys Ala Cys Cys Ala Cys Ala Gly Ala Thr Thr Ala
                165                 170                 175

Cys Ala Ala Cys Cys Cys Thr Thr Cys Cys Cys Thr Gly Cys Gly Gly
                180                 185                 190

Ala Ala Thr Ala Gly Ala Gly Thr Gly Thr Cys Cys Ala Thr Cys Thr
                195                 200                 205

Cys Thr Gly Cys Cys Gly Ala Cys Gly Cys Cys Ala Gly Cys Ala Ala
                210                 215                 220

Gly Thr Cys Cys Cys Ala Gly Thr Thr Cys Thr Ala Thr Cys Thr Gly
225                 230                 235                 240

Ala Ala Gly Cys Thr Gly Ala Gly Cys Thr Cys Cys Gly Thr Gly Ala
                245                 250                 255

Cys Cys Gly Cys Ala Gly Cys Ala Gly Ala Cys Ala Cys Ala Gly Cys
                260                 265                 270

Cys Gly Thr Gly Thr Ala Cys Thr Ala Thr Gly Cys Gly Thr Gly
                275                 280                 285

Ala Gly Gly Gly Ala Thr Gly Gly Cys Gly Thr Ala Cys Thr
                290                 295                 300

Thr Thr Gly Gly Ala Gly Cys Ala Ala Cys Gly Cys Cys Cys Thr
305                 310                 315                 320

Gly Gly Ala Cys Cys Cys Thr Gly Gly Gly Gly Ala Cys Ala Gly
                325                 330                 335

Gly Gly Cys Thr Cys Cys Cys Thr Gly Gly Thr Gly Ala Cys Ala Gly

```
                340               345               350
Thr Gly Thr Cys Thr Cys Cys Ala
        355               360

<210> SEQ ID NO 53
<211> LENGTH: 7
<212> TYPE: PRT
<213> ORGANISM: Homo sapiens

<400> SEQUENCE: 53

Arg Gly Ser Met Ser Gly Tyr
1               5

<210> SEQ ID NO 54
<211> LENGTH: 5
<212> TYPE: PRT
<213> ORGANISM: Homo sapiens

<400> SEQUENCE: 54

His Asp Ser Gly Thr
1               5

<210> SEQ ID NO 55
<211> LENGTH: 12
<212> TYPE: PRT
<213> ORGANISM: Homo sapiens

<400> SEQUENCE: 55

Asp Gly Arg Tyr Phe Gly Ala Thr Ala Leu Asp Pro
1               5                   10

<210> SEQ ID NO 56
<211> LENGTH: 108
<212> TYPE: PRT
<213> ORGANISM: Homo sapiens

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Asn Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Arg Gly Ser Gly Thr Asp Phe Ser Leu Thr Ile Ser Ala Leu Glu Pro
65                  70                  75                  80

Glu Asp Ser Ala Val Tyr Tyr Cys Gln Gln Arg Ser Asn Trp Pro Pro
                85                  90                  95

Tyr Thr Phe Gly Gln Gly Thr Lys Leu Glu Ile Lys
            100                 105

<210> SEQ ID NO 57
<211> LENGTH: 324
<212> TYPE: PRT
<213> ORGANISM: Homo sapiens

<400> SEQUENCE: 57

Gly Ala Gly Ala Thr Cys Gly Thr Gly Cys Thr Gly Ala Cys Cys Cys
1               5                   10                  15

Ala Gly Thr Cys Thr Cys Cys Thr Gly Cys Cys Ala Cys Ala Cys Thr
```

```
                20                  25                  30
Gly Ala Gly Cys Cys Thr Gly Thr Cys Cys Cys Cys Ala Gly Gly Ala
            35                  40                  45
Gly Ala Gly Ala Gly Gly Cys Cys Ala Cys Cys Thr Gly Thr
        50                  55                  60
Cys Thr Thr Gly Thr Ala Gly Gly Cys Cys Ala Gly Cys Cys Ala
65                  70                  75                  80
Gly Gly Gly Cys Cys Thr Gly Ala Ala Cys Ala Gly Gly Thr Ala Cys
                85                  90                  95
Cys Thr Gly Gly Cys Cys Thr Gly Gly Thr Ala Thr Cys Ala Gly Cys
            100                 105                 110
Ala Gly Ala Ala Gly Cys Cys Ala Gly Gly Ala Cys Ala Gly Gly Cys
            115                 120                 125
Ala Cys Cys Ala Ala Gly Gly Cys Thr Gly Cys Thr Gly Ala Thr Cys
        130                 135                 140
Thr Ala Cys Gly Ala Cys Gly Cys Cys Ala Gly Cys Ala Ala Thr Ala
145                 150                 155                 160
Gly Ala Gly Cys Ala Ala Cys Ala Gly Gly Cys Ala Thr Cys Cys Cys
            165                 170                 175
Cys Gly Cys Ala Cys Gly Gly Thr Thr Cys Thr Cys Cys Gly Gly Cys
            180                 185                 190
Ala Gly Ala Gly Gly Cys Thr Cys Thr Gly Gly Cys Ala Cys Cys Gly
            195                 200                 205
Ala Cys Thr Thr Thr Ala Gly Cys Cys Thr Gly Ala Cys Ala Ala Thr
        210                 215                 220
Cys Thr Cys Cys Gly Cys Cys Thr Gly Gly Ala Gly Cys Cys Thr
225                 230                 235                 240
Gly Ala Gly Gly Ala Thr Thr Cys Thr Gly Cys Cys Gly Thr Gly Thr
            245                 250                 255
Ala Cys Thr Ala Thr Thr Gly Cys Cys Ala Gly Cys Ala Gly Ala Gly
            260                 265                 270
Ala Ala Gly Cys Ala Ala Cys Thr Gly Gly Cys Cys Cys Cys Cys Thr
            275                 280                 285
Thr Ala Thr Ala Cys Cys Thr Thr Cys Gly Gly Cys Cys Ala Gly Gly
        290                 295                 300
Gly Cys Ala Cys Ala Ala Ala Gly Cys Thr Gly Gly Ala Gly Ala Thr
305                 310                 315                 320
Cys Ala Ala Gly

<210> SEQ ID NO 58
<211> LENGTH: 11
<212> TYPE: PRT
<213> ORGANISM: Homo sapiens

<400> SEQUENCE: 58

Arg Ala Ser Gln Gly Leu Asn Arg Tyr Leu Ala
1               5                   10

<210> SEQ ID NO 59
<211> LENGTH: 7
<212> TYPE: PRT
<213> ORGANISM: Homo sapiens

<400> SEQUENCE: 59

Asp Ala Ser Asn Arg Ala Thr
1               5
```

<210> SEQ ID NO 60
<211> LENGTH: 10
<212> TYPE: PRT
<213> ORGANISM: Homo sapiens

<400> SEQUENCE: 60

Gln Gln Arg Ser Asn Trp Pro Pro Tyr Thr
1               5                   10

<210> SEQ ID NO 61
<211> LENGTH: 123
<212> TYPE: PRT
<213> ORGANISM: Homo sapiens

<400> SEQUENCE: 61

Glu Val Gln Leu Val Glu Ser Gly Gly Gly Val Val Gln Pro Gly Arg
1               5                   10                  15

Ser Leu Lys Ile Ser Cys Ala Val Ser Gly Phe Asp Leu Ser Ser Phe
            20                  25                  30

Gly Met His Trp Val Arg Gln Ala Pro Gly Lys Gly Leu Glu Trp Leu
        35                  40                  45

Ser Val Ile Ser His Asp Gly Asn Arg Lys Phe Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Thr Glu Asp Thr Ala Leu Tyr Tyr Cys
                85                  90                  95

Ala Arg Glu Pro Tyr Thr Ser Gly Trp Phe Phe Gly Trp Phe Asp Pro
            100                 105                 110

Trp Gly Gln Gly Thr Leu Val Thr Val Ser Ser
        115                 120

<210> SEQ ID NO 62
<211> LENGTH: 369
<212> TYPE: PRT
<213> ORGANISM: Homo sapiens

<400> SEQUENCE: 62

Gly Ala Gly Gly Thr Gly Cys Ala Gly Cys Thr Gly Gly Thr Gly Gly
1               5                   10                  15

Ala Gly Thr Cys Thr Gly Gly Cys Gly Gly Ala Gly Gly Ala Gly Thr
            20                  25                  30

Gly Gly Thr Gly Cys Ala Gly Cys Cys Ala Gly Gly Cys Cys Gly Gly
        35                  40                  45

Ala Gly Cys Cys Thr Gly Ala Ala Gly Ala Thr Cys Thr Cys Cys Thr
    50                  55                  60

Gly Thr Gly Cys Cys Gly Thr Cys Thr Gly Gly Cys Thr Thr
65                  70                  75                  80

Cys Gly Ala Cys Cys Thr Gly Ala Gly Cys Cys Thr Thr
                85                  90                  95

Gly Gly Cys Ala Thr Gly Cys Ala Cys Thr Gly Gly Gly Thr Gly Cys
            100                 105                 110

Gly Gly Cys Ala Gly Gly Cys Ala Cys Cys Ala Gly Gly Cys Ala Ala
        115                 120                 125

Gly Gly Gly Cys Cys Thr Gly Gly Ala Gly Thr Gly Gly Cys Thr Gly
    130                 135                 140

-continued

```
Thr Cys Cys Gly Thr Gly Ala Thr Cys Thr Cys Ala Cys Gly
145                 150                 155                 160

Ala Cys Gly Gly Cys Ala Ala Cys Ala Gly Ala Ala Gly Thr Thr
                165                 170                 175

Cys Thr Ala Cys Gly Cys Cys Gly Ala Thr Cys Cys Gly Thr Gly
            180                 185                 190

Ala Ala Gly Gly Gly Cys Cys Gly Gly Thr Thr Ala Cys Cys Ala
        195                 200                 205

Thr Cys Ala Gly Cys Ala Gly Ala Cys Ala Cys Thr Cys
    210                 215                 220

Cys Ala Ala Gly Ala Ala Cys Ala Cys Ala Cys Thr Gly Thr Ala Thr
225                 230                 235                 240

Cys Thr Gly Cys Ala Gly Ala Thr Gly Ala Ala Thr Cys Thr Cys
                245                 250                 255

Thr Gly Ala Gly Gly Ala Cys Cys Gly Ala Gly Gly Ala Thr Ala Cys
            260                 265                 270

Ala Gly Cys Cys Cys Thr Gly Thr Ala Cys Thr Ala Thr Gly Cys
        275                 280                 285

Gly Cys Ala Ala Gly Gly Ala Gly Cys Cys Ala Thr Ala Cys Ala
    290                 295                 300

Cys Ala Ala Gly Cys Gly Gly Cys Thr Gly Gly Thr Thr Cys Thr Thr
305                 310                 315                 320

Thr Gly Gly Cys Thr Gly Gly Thr Thr Cys Gly Ala Thr Cys Cys Thr
                325                 330                 335

Thr Gly Gly Gly Gly Cys Cys Ala Gly Gly Cys Ala Cys Cys Cys
            340                 345                 350

Thr Gly Gly Thr Gly Ala Cys Ala Gly Thr Gly Thr Cys Thr Ala Gly
        355                 360                 365

Cys

<210> SEQ ID NO 63
<211> LENGTH: 7
<212> TYPE: PRT
<213> ORGANISM: Homo sapiens

<400> SEQUENCE: 63

Gly Phe Asp Leu Ser Ser Phe
1               5

<210> SEQ ID NO 64
<211> LENGTH: 6
<212> TYPE: PRT
<213> ORGANISM: Homo sapiens

<400> SEQUENCE: 64

Ser His Asp Gly Asn Arg
1               5

<210> SEQ ID NO 65
<211> LENGTH: 14
<212> TYPE: PRT
<213> ORGANISM: Homo sapiens

<400> SEQUENCE: 65

Glu Pro Tyr Thr Ser Gly Trp Phe Phe Gly Trp Phe Asp Pro
1               5                   10

<210> SEQ ID NO 66
```

<211> LENGTH: 108
<212> TYPE: PRT
<213> ORGANISM: Homo sapiens

<400> SEQUENCE: 66

Gln Ser Ala Leu Thr Gln Pro Ala Ser Val Ser Gly Ser Pro Gly Gln
1               5                   10                  15

Ser Ile Thr Leu Ser Cys Thr Gly Thr Ser Arg Asp Val Gly Asp Tyr
            20                  25                  30

Asn Tyr Val Ser Trp Tyr Gln Gln His Pro Gly Lys Ala Pro Lys Leu
        35                  40                  45

Ile Met Tyr Glu Val His Lys Arg Pro Ser Gly Ile Ser Asn Arg Phe
50                  55                  60

Ser Gly Ser Lys Ser Gly Thr Thr Ala Ser Leu Thr Ile Ser Gly Leu
65                  70                  75                  80

Gln Ala Asp Asp Glu Gly Asp Tyr Tyr Cys Ser Ser Tyr Thr Ser Lys
                85                  90                  95

Asn Thr Tyr Val Phe Gly Ser Gly Thr Gln Val Thr
            100                 105

<210> SEQ ID NO 67
<211> LENGTH: 324
<212> TYPE: PRT
<213> ORGANISM: Homo sapiens

<400> SEQUENCE: 67

Cys Ala Gly Thr Cys Cys Gly Cys Cys Thr Gly Ala Cys Cys Cys
1               5                   10                  15

Ala Gly Cys Cys Ala Gly Cys Cys Thr Cys Thr Gly Thr Gly Ala Gly
            20                  25                  30

Cys Gly Gly Cys Thr Cys Cys Cys Cys Gly Gly Cys Cys Ala Gly
        35                  40                  45

Thr Cys Cys Ala Thr Cys Ala Cys Ala Cys Thr Gly Thr Cys Thr Thr
50                  55                  60

Gly Thr Ala Cys Cys Gly Gly Cys Ala Cys Ala Thr Cys Cys Cys Gly
65                  70                  75                  80

Gly Gly Ala Cys Gly Thr Gly Gly Gly Gly Ala Thr Thr Ala Cys
                85                  90                  95

Ala Ala Cys Thr Ala Cys Gly Thr Gly Ala Gly Cys Thr Gly Gly Thr
                100                 105                 110

Ala Cys Cys Ala Gly Cys Ala Gly Cys Ala Cys Cys Cys Ala Gly Gly
            115                 120                 125

Cys Ala Ala Gly Gly Cys Ala Cys Cys Thr Ala Ala Gly Cys Thr Gly
        130                 135                 140

Ala Thr Cys Ala Thr Gly Thr Ala Thr Gly Ala Gly Gly Thr Gly Cys
145                 150                 155                 160

Ala Cys Ala Ala Gly Cys Gly Gly Cys Cys Thr Cys Thr Gly Gly
                165                 170                 175

Cys Ala Thr Cys Ala Gly Cys Ala Ala Thr Ala Gly Ala Thr Thr Cys
                180                 185                 190

Thr Cys Thr Gly Gly Cys Ala Gly Cys Ala Ala Gly Thr Cys Cys Gly
            195                 200                 205

Gly Cys Ala Cys Ala Cys Ala Gly Cys Ala Gly Cys Cys Thr
        210                 215                 220

Gly Ala Cys Cys Ala Thr Cys Thr Cys Cys Gly Gly Cys Cys Thr Gly
225                 230                 235                 240

```
Cys Ala Gly Gly Cys Ala Gly Ala Cys Gly Ala Thr Gly Ala Gly Gly
                245                 250                 255

Gly Cys Gly Ala Cys Thr Ala Cys Thr Ala Thr Gly Cys Ala Gly
            260                 265                 270

Cys Thr Cys Cys Thr Ala Cys Ala Cys Cys Thr Cys Thr Ala Ala Gly
            275                 280                 285

Ala Ala Cys Ala Cys Ala Thr Ala Cys Gly Thr Gly Thr Thr Cys Gly
            290                 295                 300

Gly Cys Ala Gly Cys Gly Gly Cys Ala Cys Cys Cys Ala Gly Gly Thr
305                 310                 315                 320

Gly Ala Cys Ala
```

<210> SEQ ID NO 68
<211> LENGTH: 14
<212> TYPE: PRT
<213> ORGANISM: Homo sapiens

<400> SEQUENCE: 68

```
Thr Gly Thr Ser Arg Asp Val Gly Asp Tyr Asn Tyr Val Ser
1               5                   10
```

<210> SEQ ID NO 69
<211> LENGTH: 7
<212> TYPE: PRT
<213> ORGANISM: Homo sapiens

<400> SEQUENCE: 69

```
Glu Val His Lys Arg Pro Ser
1               5
```

<210> SEQ ID NO 70
<211> LENGTH: 10
<212> TYPE: PRT
<213> ORGANISM: Homo sapiens

<400> SEQUENCE: 70

```
Ser Ser Tyr Thr Ser Lys Asn Thr Tyr Val
1               5                   10
```

<210> SEQ ID NO 71
<211> LENGTH: 126
<212> TYPE: PRT
<213> ORGANISM: Homo sapiens

<400> SEQUENCE: 71

```
Gln Val His Leu Val Gln Ser Gly Ala Glu Met Lys Lys Pro Gly Ala
1               5                   10                  15

Ser Val Lys Val Ser Cys Lys Ala Ser Gly Gly Ser Phe Ser Ile Tyr
            20                  25                  30

Ala Ile Ser Trp Val Arg Gln Ala Pro Gly Gln Gly Pro Glu Trp Val
        35                  40                  45

Gly Gly Ile Val Pro Ile Ser Asp Thr Thr Thr Tyr Ala Gln Arg Phe
    50                  55                  60

Gln Gly Arg Val Thr Val Thr Ala Asp Lys Ser Thr Asp Thr Ala Tyr
65                  70                  75                  80

Met Glu Leu Arg Ser Leu Thr Ser Glu Asp Thr Ala Val Tyr Tyr Cys
                85                  90                  95

Ala Arg Asp Pro Gly Tyr Tyr Asp Ile Ser Gly Tyr Tyr His Arg Ala
            100                 105                 110
```

```
Phe Asp Ile Trp Gly Gln Gly Thr Met Val Ser Val Ser Ser
            115                 120                 125

<210> SEQ ID NO 72
<211> LENGTH: 378
<212> TYPE: PRT
<213> ORGANISM: Homo sapiens

<400> SEQUENCE: 72

Cys Ala Gly Gly Thr Gly Cys Ala Cys Cys Thr Gly Gly Thr Gly Cys
1               5                   10                  15

Ala Gly Ala Gly Cys Gly Gly Cys Gly Cys Ala Gly Ala Gly Ala Thr
            20                  25                  30

Gly Ala Ala Gly Ala Ala Gly Cys Cys Ala Gly Gly Cys Gly Cys Cys
        35                  40                  45

Ala Gly Cys Gly Thr Gly Ala Ala Gly Gly Thr Gly Thr Cys Cys Thr
    50                  55                  60

Gly Thr Ala Ala Gly Gly Cys Cys Thr Cys Thr Gly Gly Cys Gly Gly
65                  70                  75                  80

Cys Thr Cys Thr Thr Thr Cys Ala Gly Cys Ala Thr Cys Thr Ala Cys
                85                  90                  95

Gly Cys Cys Ala Thr Cys Thr Cys Thr Gly Gly Gly Thr Gly Gly Cys
            100                 105                 110

Gly Gly Cys Ala Gly Gly Cys Ala Cys Cys Ala Gly Gly Ala Cys Ala
            115                 120                 125

Gly Gly Gly Cys Cys Cys Thr Gly Ala Gly Thr Gly Gly Ala Thr Gly
        130                 135                 140

Gly Gly Cys Gly Gly Cys Ala Thr Cys Gly Thr Gly Cys Cys Cys Ala
145                 150                 155                 160

Thr Cys Thr Cys Thr Gly Ala Cys Ala Cys Ala Cys Ala Ala Cys
                165                 170                 175

Cys Thr Ala Cys Gly Cys Cys Cys Ala Gly Cys Gly Gly Thr Thr Thr
            180                 185                 190

Cys Ala Gly Gly Gly Cys Ala Gly Ala Gly Thr Gly Ala Cys Ala Gly
            195                 200                 205

Thr Gly Ala Cys Cys Gly Cys Cys Gly Ala Cys Ala Ala Gly Thr Cys
        210                 215                 220

Cys Ala Cys Ala Gly Ala Thr Ala Cys Cys Gly Cys Cys Thr Ala Thr
225                 230                 235                 240

Ala Thr Gly Gly Ala Gly Cys Thr Gly Ala Gly Gly Thr Cys Cys Cys
                245                 250                 255

Thr Gly Ala Cys Ala Thr Cys Thr Gly Ala Gly Gly Ala Cys Ala Cys
            260                 265                 270

Cys Gly Cys Cys Gly Thr Gly Thr Ala Cys Thr Ala Thr Gly Cys
            275                 280                 285

Gly Cys Cys Ala Gly Gly Ala Cys Cys Cys Gly Gly Cys Thr
        290                 295                 300

Ala Cys Thr Ala Thr Gly Ala Thr Ala Cys Ala Gly Cys Gly Gly
305                 310                 315                 320

Cys Thr Ala Cys Thr Ala Cys Ala Cys Gly Cys Gly Cys Cys
                325                 330                 335

Thr Thr Cys Gly Ala Thr Ala Thr Cys Thr Gly Gly Gly Gly Cys Cys
            340                 345                 350

Ala Gly Gly Gly Cys Ala Cys Ala Ala Thr Gly Gly Thr Gly Thr Cys
```

```
            355                 360                 365
Cys Gly Thr Gly Ala Gly Cys Thr Cys Cys
    370                 375

<210> SEQ ID NO 73
<211> LENGTH: 7
<212> TYPE: PRT
<213> ORGANISM: Homo sapiens

<400> SEQUENCE: 73

Gly Gly Ser Phe Ser Ile Tyr
1               5

<210> SEQ ID NO 74
<211> LENGTH: 6
<212> TYPE: PRT
<213> ORGANISM: Homo sapiens

<400> SEQUENCE: 74

Val Pro Ile Ser Asp Thr
1               5

<210> SEQ ID NO 75
<211> LENGTH: 17
<212> TYPE: PRT
<213> ORGANISM: Homo sapiens

<400> SEQUENCE: 75

Asp Pro Gly Tyr Tyr Asp Ile Ser Gly Tyr Tyr His Arg Ala Phe Asp
1               5                   10                  15

Ile

<210> SEQ ID NO 76
<211> LENGTH: 109
<212> TYPE: PRT
<213> ORGANISM: Homo sapiens

<400> SEQUENCE: 76

Gln Ser Ala Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

His Asp Val His Trp Tyr Gln Gln Phe Pro Lys Thr Ala Pro Gln Leu
            35                  40                  45

Leu Ile Phe Gly Asn Asn Asn Arg Pro Ser Gly Val Pro Asp Arg Phe
        50                  55                  60

Ser Gly Ser Asn Ala Gly Thr Ser Ala Ser Leu Thr Ile Thr Gly Leu
65                  70                  75                  80

Gln Thr Ala Asp Glu Ala Asp Tyr Tyr Cys Gln Ser Tyr Asp Asn Ser
                85                  90                  95

Leu Ser Gly Thr Val Phe Gly Gly Gly Thr Lys Leu Thr
            100                 105

<210> SEQ ID NO 77
<211> LENGTH: 327
<212> TYPE: PRT
<213> ORGANISM: Homo sapiens

<400> SEQUENCE: 77

Cys Ala Gly Ala Gly Cys Gly Cys Cys Thr Gly Ala Cys Cys Cys
1               5                   10                  15
```

```
Ala Gly Cys Cys Ala Cys Cys Thr Ala Gly Cys Gly Thr Cys
            20                  25                  30

Cys Gly Gly Cys Gly Cys Ala Cys Ala Cys Gly Gly Cys Ala Gly
            35                  40                  45

Cys Gly Gly Gly Thr Gly Ala Cys Cys Ala Thr Cys Thr Cys Thr
            50                  55                  60

Gly Thr Ala Cys Ala Gly Gly Cys Ala Gly Cys Thr Cys Thr Cys
65                  70                  75                  80

Thr Ala Ala Thr Ala Thr Cys Gly Gly Ala Gly Cys Ala Gly Ala
                85                  90                  95

Cys Ala Cys Gly Ala Cys Gly Thr Gly Cys Ala Cys Thr Gly Thr
            100                 105                 110

Ala Cys Cys Ala Gly Cys Ala Gly Thr Thr Cys Cys Ala Ala Ala
            115                 120                 125

Gly Ala Cys Ala Gly Cys Cys Cys Cys Ala Gly Cys Thr Gly Gly
            130                 135                 140

Cys Thr Gly Ala Thr Cys Thr Thr Gly Gly Cys Ala Ala Cys Ala
145                 150                 155                 160

Ala Thr Ala Ala Cys Cys Gly Gly Cys Cys Thr Thr Cys Gly Gly
                165                 170                 175

Cys Gly Thr Gly Cys Cys Ala Gly Ala Thr Ala Gly Ala Thr Cys
            180                 185                 190

Thr Cys Thr Gly Gly Cys Ala Gly Cys Ala Ala Thr Gly Cys Cys Gly
            195                 200                 205

Gly Cys Ala Cys Cys Thr Cys Gly Cys Cys Thr Cys Thr Cys Thr
            210                 215                 220

Gly Ala Cys Cys Ala Thr Cys Ala Cys Ala Gly Gly Cys Cys Thr Gly
225                 230                 235                 240

Cys Ala Gly Ala Cys Ala Gly Cys Cys Gly Ala Cys Gly Ala Gly Gly
                245                 250                 255

Cys Cys Gly Ala Thr Thr Ala Cys Thr Ala Thr Gly Cys Cys Ala
            260                 265                 270

Gly Thr Cys Thr Thr Ala Thr Gly Ala Cys Ala Ala Cys Ala Gly Cys
            275                 280                 285

Cys Thr Gly Thr Cys Gly Gly Cys Ala Cys Cys Gly Thr Gly Thr
            290                 295                 300

Thr Thr Gly Gly Ala Gly Gly Ala Gly Gly Ala Ala Cys Cys Ala Ala
305                 310                 315                 320

Gly Cys Thr Gly Ala Cys Ala
                325
```

<210> SEQ ID NO 78
<211> LENGTH: 14
<212> TYPE: PRT
<213> ORGANISM: Homo sapiens

<400> SEQUENCE: 78

```
Thr Gly Ser Ser Ser Asn Ile Gly Ala Gly His Asp Val His
1               5                   10
```

<210> SEQ ID NO 79
<211> LENGTH: 7
<212> TYPE: PRT
<213> ORGANISM: Homo sapiens

<400> SEQUENCE: 79

Gly Asn Asn Asn Arg Pro Ser
1               5

<210> SEQ ID NO 80
<211> LENGTH: 11
<212> TYPE: PRT
<213> ORGANISM: Homo sapiens

<400> SEQUENCE: 80

Gln Ser Tyr Asp Asn Ser Leu Ser Gly Thr Val
1               5                   10

<210> SEQ ID NO 81
<211> LENGTH: 126
<212> TYPE: PRT
<213> ORGANISM: Homo sapiens

<400> SEQUENCE: 81

Gln Val His Leu Val Gln Ser Gly Ala Glu Val Lys Lys Ser Gly Ser
1               5                   10                  15

Ser Val Thr Val Ser Cys Arg Ala Ala Gly Gly Ser Phe Ser Ile Tyr
                20                  25                  30

Ala Ile Thr Trp Val Arg Gln Ala Pro Gly His Gly Leu Glu Trp Met
            35                  40                  45

Gly Gly Ile Val Pro Met Ser Asp Thr Val Thr Tyr Ala Gln Glu Phe
        50                  55                  60

Gln Ala Arg Val Thr Ile Ser Ala Asp Lys Ser Thr Asn Thr Ala Tyr
65                  70                  75                  80

Met Glu Leu Arg Ser Leu Lys Tyr Ala Asp Ser Ala Ile Tyr Phe Cys
                85                  90                  95

Ala Arg Asp Pro Gly Tyr Tyr Asp Lys Ser Gly Tyr Tyr His Arg Ala
                100                 105                 110

Phe Asp Ile Trp Gly Gln Gly Thr Leu Val Thr Val Ser Ser
            115                 120                 125

<210> SEQ ID NO 82
<211> LENGTH: 378
<212> TYPE: PRT
<213> ORGANISM: Homo sapiens

<400> SEQUENCE: 82

Cys Ala Gly Gly Thr Gly Cys Ala Cys Cys Thr Gly Gly Thr Gly Cys
1               5                   10                  15

Ala Gly Thr Cys Cys Gly Gly Cys Gly Cys Ala Gly Ala Gly Gly Thr
                20                  25                  30

Gly Ala Ala Gly Ala Ala Gly Thr Cys Thr Gly Gly Cys Ala Gly Cys
            35                  40                  45

Thr Cys Cys Gly Thr Gly Ala Cys Cys Gly Thr Gly Ala Gly Cys Thr
        50                  55                  60

Gly Thr Ala Gly Gly Gly Cys Ala Gly Cys Gly Gly Ala Gly Gly Gly
65                  70                  75                  80

Cys Thr Cys Cys Thr Thr Cys Thr Cys Thr Ala Thr Cys Thr Ala Cys
                85                  90                  95

Gly Cys Cys Ala Thr Cys Ala Cys Ala Thr Gly Gly Gly Thr Gly Cys
                100                 105                 110

Gly Cys Cys Ala Gly Gly Cys Ala Cys Cys Ala Gly Gly Ala Cys Ala
            115                 120                 125

```
Cys Gly Gly Cys Cys Thr Gly Gly Ala Gly Thr Gly Ala Thr Gly
    130                 135                 140
Gly Gly Ala Gly Ala Ala Thr Cys Gly Thr Gly Cys Cys Thr Ala
145                 150                 155                 160
Thr Gly Thr Cys Cys Gly Ala Cys Ala Cys Gly Thr Gly Ala Cys
                165                 170                 175
Ala Thr Ala Cys Gly Cys Cys Ala Gly Ala Gly Thr Thr Thr
            180                 185                 190
Cys Ala Gly Gly Cys Cys Cys Gly Gly Thr Gly Ala Cys Cys Ala
            195                 200                 205
Thr Cys Ala Gly Cys Gly Cys Cys Gly Ala Thr Ala Gly Thr Cys
    210                 215                 220
Cys Ala Cys Cys Ala Ala Cys Ala Cys Ala Gly Cys Cys Thr Ala Thr
225                 230                 235                 240
Ala Thr Gly Gly Ala Gly Cys Thr Gly Cys Gly Gly Ala Gly Cys Cys
                245                 250                 255
Thr Gly Ala Ala Gly Thr Ala Cys Gly Cys Cys Gly Ala Cys Ala Gly
            260                 265                 270
Cys Gly Cys Cys Ala Thr Cys Thr Ala Thr Thr Thr Cys Thr Gly Cys
            275                 280                 285
Gly Cys Cys Cys Gly Gly Gly Ala Cys Cys Cys Gly Gly Cys Thr
    290                 295                 300
Ala Cys Thr Ala Thr Gly Ala Thr Ala Ala Gly Thr Cys Thr Gly Gly
305                 310                 315                 320
Cys Thr Ala Cys Thr Ala Thr Cys Ala Cys Ala Gly Ala Gly Cys Cys
                325                 330                 335
Thr Thr Thr Gly Ala Thr Ala Thr Cys Thr Gly Gly Gly Gly Cys Cys
            340                 345                 350
Ala Gly Gly Gly Cys Ala Cys Cys Cys Thr Gly Gly Thr Gly Ala Cys
            355                 360                 365
Ala Gly Thr Gly Thr Cys Thr Ala Gly Cys
    370                 375

<210> SEQ ID NO 83
<211> LENGTH: 7
<212> TYPE: PRT
<213> ORGANISM: Homo sapiens

<400> SEQUENCE: 83

Gly Gly Ser Phe Ser Ile Tyr
1               5

<210> SEQ ID NO 84
<211> LENGTH: 6
<212> TYPE: PRT
<213> ORGANISM: Homo sapiens

<400> SEQUENCE: 84

Val Pro Met Ser Asp Thr
1               5

<210> SEQ ID NO 85
<211> LENGTH: 17
<212> TYPE: PRT
<213> ORGANISM: Homo sapiens

<400> SEQUENCE: 85

Asp Pro Gly Tyr Tyr Asp Lys Ser Gly Tyr Tyr His Arg Ala Phe Asp
```

1   5   10   15

Ile

<210> SEQ ID NO 86
<211> LENGTH: 109
<212> TYPE: PRT
<213> ORGANISM: Homo sapiens

<400> SEQUENCE: 86

Gln Ser Val Leu Thr Gln Pro Pro Ser Val Ser Gly Ala Pro Gly Gln
1               5                   10                  15

Arg Val Thr Ile Ser Cys Thr Gly Gly Ser Asn Ile Gly Ala Asp
            20                  25                  30

His Asp Val His Trp Tyr Gln Gln Tyr Pro Gly Ala Ala Pro Lys Leu
        35                  40                  45

Leu Ile Phe Gly Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65              70                  75                  80

Gln Ala Glu Asp Glu Ala Asp Tyr Tyr Cys Gln Ser Tyr Asp Asn Ser
                85                  90                  95

Leu Ser Arg Ala Val Phe Gly Gly Gly Thr Lys Leu Thr
            100                 105

<210> SEQ ID NO 87
<211> LENGTH: 327
<212> TYPE: PRT
<213> ORGANISM: Homo sapiens

<400> SEQUENCE: 87

Cys Ala Gly Ala Gly Cys Gly Thr Gly Cys Thr Gly Ala Cys Cys Cys
1               5                   10                  15

Ala Gly Cys Cys Ala Cys Cys Thr Ala Gly Cys Gly Thr Gly Thr Cys
            20                  25                  30

Cys Gly Gly Cys Gly Cys Ala Cys Cys Ala Gly Gly Cys Cys Ala Gly
        35                  40                  45

Ala Gly Gly Gly Thr Gly Ala Cys Cys Ala Thr Cys Ala Gly Cys Thr
    50                  55                  60

Gly Thr Ala Cys Ala Gly Gly Ala Gly Gly Ala Gly Cys Thr Cys
65              70                  75                  80

Cys Ala Ala Cys Ala Thr Cys Gly Gly Ala Gly Cys Ala Gly Ala Cys
                85                  90                  95

Cys Ala Cys Gly Ala Thr Gly Thr Gly Cys Ala Cys Thr Gly Gly Thr
            100                 105                 110

Ala Cys Cys Ala Gly Cys Ala Gly Thr Ala Cys Cys Ala Gly Gly
        115                 120                 125

Ala Gly Cys Ala Gly Cys Ala Cys Cys Ala Ala Gly Cys Thr Gly
    130                 135                 140

Cys Thr Gly Ala Thr Cys Thr Thr Cys Gly Gly Cys Gly Ala Cys Ala
145                 150                 155                 160

Ala Cys Ala Ala Thr Cys Gly Gly Cys Cys Thr Thr Cys Cys Gly Gly
            165                 170                 175

Cys Gly Thr Gly Cys Cys Ala Gly Ala Thr Ala Gly Ala Thr Thr Thr
        180                 185                 190

Thr Cys Thr Gly Gly Cys Ala Gly Cys Ala Ala Gly Thr Cys Cys Gly
            195                 200                 205

```
Gly Cys Ala Cys Cys Thr Cys Thr Gly Cys Cys Ala Gly Cys Cys Thr
    210                 215                 220
Gly Gly Cys Cys Ala Thr Cys Ala Cys Ala Gly Gly Cys Cys Thr Gly
225                 230                 235                 240
Cys Ala Gly Gly Cys Ala Gly Ala Gly Gly Ala Cys Gly Ala Gly Gly
                245                 250                 255
Cys Ala Gly Ala Thr Thr Ala Cys Thr Ala Thr Thr Gly Cys Cys Ala
                260                 265                 270
Gly Thr Cys Thr Thr Ala Cys Gly Ala Cys Ala Ala Thr Thr Cys Cys
            275                 280                 285
Cys Thr Gly Thr Cys Thr Cys Gly Gly Gly Cys Cys Gly Thr Gly Thr
        290                 295                 300
Thr Cys Gly Gly Ala Gly Gly Ala Gly Gly Ala Ala Cys Cys Ala Ala
305                 310                 315                 320
Gly Cys Thr Gly Ala Cys Ala
                325

<210> SEQ ID NO 88
<211> LENGTH: 14
<212> TYPE: PRT
<213> ORGANISM: Homo sapiens

<400> SEQUENCE: 88

Thr Gly Gly Gly Ser Asn Ile Gly Ala Asp His Asp Val His
1               5                   10

<210> SEQ ID NO 89
<211> LENGTH: 7
<212> TYPE: PRT
<213> ORGANISM: Homo sapiens

<400> SEQUENCE: 89

Gly Asp Asn Asn Arg Pro Ser
1               5

<210> SEQ ID NO 90
<211> LENGTH: 11
<212> TYPE: PRT
<213> ORGANISM: Homo sapiens

<400> SEQUENCE: 90

Gln Ser Tyr Asp Asn Ser Leu Ser Arg Ala Val
1               5                   10

<210> SEQ ID NO 91
<211> LENGTH: 125
<212> TYPE: PRT
<213> ORGANISM: Homo sapiens

<400> SEQUENCE: 91

Gln Val Gln Leu Gln Glu Ser Gly Pro Gly Leu Val Arg Pro Ser Glu
1               5                   10                  15
Thr Leu Ser Leu Thr Cys Ser Val Ser Gly Gly Ser Ile Ile Gly Tyr
            20                  25                  30
Tyr Trp Ser Trp Ile Arg Gln Pro Pro Gly Lys Gly Leu Glu Trp Ile
        35                  40                  45
Gly Tyr Ile Phe Tyr Ser Asp Asn Ile Arg Tyr Ser Pro Ser Leu Lys
    50                  55                  60
Ser Arg Val Ala Ile Ser Ala Asp Ser Ser Arg Asn Glu Val Ser Leu
```

```
                65                  70                  75                  80
Arg Leu Asn Ser Val Thr Ala Ala Asp Thr Ala Val Tyr Tyr Cys Ala
                    85                  90                  95

Arg Asp Gly Asn Tyr Tyr Asp Ser Ser Gly Pro Thr Arg Leu Trp Phe
                    100                 105                 110

Asp Pro Trp Gly Gln Gly Thr Leu Val Thr Val Ser Ser
                    115                 120                 125

<210> SEQ ID NO 92
<211> LENGTH: 375
<212> TYPE: PRT
<213> ORGANISM: Homo sapiens

<400> SEQUENCE: 92

Cys Ala Gly Gly Thr Gly Cys Ala Gly Cys Thr Gly Cys Ala Gly Gly
1               5                   10                  15

Ala Gly Thr Cys Cys Gly Gly Cys Cys Cys Ala Gly Gly Cys Cys Thr
                20                  25                  30

Gly Gly Thr Gly Ala Gly Gly Cys Cys Thr Cys Cys Gly Cys Ala Gly
                35                  40                  45

Ala Cys Ala Cys Thr Gly Thr Cys Thr Cys Thr Gly Ala Cys Ala Thr
                50                  55                  60

Gly Thr Ala Gly Cys Gly Thr Cys Thr Cys Gly Gly Cys Gly Gly Gly
65                  70                  75                  80

Cys Thr Cys Cys Ala Thr Cys Ala Thr Cys Gly Gly Cys Thr Ala Cys
                85                  90                  95

Thr Ala Thr Thr Gly Gly Thr Cys Thr Thr Gly Gly Ala Thr Cys Ala
                100                 105                 110

Gly Ala Cys Ala Gly Cys Cys Ala Cys Cys Thr Gly Gly Cys Ala Ala
                115                 120                 125

Gly Gly Gly Cys Cys Thr Gly Gly Ala Gly Thr Gly Gly Ala Thr Cys
                130                 135                 140

Gly Gly Cys Thr Ala Cys Ala Thr Cys Thr Ala Thr Ala Thr Ala
145                 150                 155                 160

Gly Cys Gly Ala Cys Ala Ala Cys Ala Thr Cys Ala Gly Gly Thr Ala
                165                 170                 175

Cys Thr Cys Thr Cys Cys Ala Gly Cys Cys Thr Gly Ala Ala Gly
                180                 185                 190

Ala Gly Cys Cys Gly Cys Gly Thr Gly Cys Ala Ala Thr Cys Thr
                195                 200                 205

Cys Cys Gly Cys Cys Gly Ala Thr Ala Cys Thr Cys Cys Cys Gly
                210                 215                 220

Gly Ala Ala Cys Gly Ala Gly Thr Gly Thr Cys Thr Cys Thr Gly
225                 230                 235                 240

Ala Gly Ala Cys Thr Gly Ala Ala Thr Ala Gly Cys Gly Thr Gly
                245                 250                 255

Cys Cys Gly Cys Cys Gly Cys Cys Gly Ala Cys Ala Cys Gly Cys
                260                 265                 270

Cys Gly Thr Gly Thr Ala Cys Thr Ala Thr Gly Cys Gly Cys Cys
                275                 280                 285

Cys Gly Gly Gly Ala Cys Gly Gly Cys Ala Ala Thr Thr Ala Cys Thr
                290                 295                 300

Ala Thr Gly Ala Thr Thr Cys Thr Ala Gly Cys Gly Gly Cys Cys Cys
305                 310                 315                 320
```

```
Thr Ala Cys Cys Ala Gly Ala Cys Thr Gly Thr Gly Thr Thr Thr
                325                 330                 335
Gly Ala Thr Cys Cys Ala Thr Gly Gly Gly Cys Cys Ala Gly Gly
                340                 345                 350
Gly Cys Ala Cys Cys Thr Gly Gly Thr Gly Ala Cys Ala Gly Thr
                355                 360                 365
Gly Thr Cys Cys Thr Cys Thr
                370                 375

<210> SEQ ID NO 93
<211> LENGTH: 7
<212> TYPE: PRT
<213> ORGANISM: Homo sapiens

<400> SEQUENCE: 93

Gly Gly Ser Ile Ile Gly Tyr
1               5

<210> SEQ ID NO 94
<211> LENGTH: 5
<212> TYPE: PRT
<213> ORGANISM: Homo sapiens

<400> SEQUENCE: 94

Phe Tyr Ser Asp Asn
1               5

<210> SEQ ID NO 95
<211> LENGTH: 17
<212> TYPE: PRT
<213> ORGANISM: Homo sapiens

<400> SEQUENCE: 95

Asp Gly Asn Tyr Tyr Asp Ser Ser Gly Pro Thr Arg Leu Trp Phe Asp
1               5                   10                  15
Pro

<210> SEQ ID NO 96
<211> LENGTH: 109
<212> TYPE: PRT
<213> ORGANISM: Homo sapiens

<400> SEQUENCE: 96

Gln Ser Val Leu Thr Gln Pro Pro Ser Val Ser Gly Ala Pro Gly Gln
1               5                   10                  15
Arg Val Ser Ile Ser Cys Thr Gly Ser Thr Ser Asn Ile Gly Ala Asp
                20                  25                  30
Tyr Asp Val His Trp Tyr Gln His Ser Pro Gly Thr Gly Pro Arg Leu
            35                  40                  45
Leu Ile Phe Gly Ser Thr Asn Arg Pro Ser Gly Val Pro Asp Arg Phe
        50                  55                  60
Ser Gly Ser Lys Ser Gly Thr Ser Ala Ser Leu Ala Ile Thr Gly Leu
65                  70                  75                  80
Gln Ala Asp Asp Glu Ala Glu Tyr Tyr Cys Gln Ser Tyr Asp Arg Thr
                85                  90                  95
Leu Gly Gly Tyr Val Phe Gly Thr Gly Thr Gln Val Thr
            100                 105

<210> SEQ ID NO 97
<211> LENGTH: 327
```

```
<212> TYPE: PRT
<213> ORGANISM: Homo sapiens

<400> SEQUENCE: 97

Cys Ala Gly Thr Cys Thr Gly Thr Gly Cys Thr Gly Ala Cys Cys Cys
1               5                   10                  15

Ala Gly Cys Cys Ala Cys Cys Thr Ala Gly Cys Gly Thr Gly Thr Cys
                20                  25                  30

Cys Gly Gly Cys Gly Cys Ala Cys Cys Ala Gly Gly Cys Cys Ala Gly
            35                  40                  45

Ala Gly Gly Gly Thr Gly Thr Cys Thr Ala Thr Cys Ala Gly Cys Thr
        50                  55                  60

Gly Thr Ala Cys Cys Gly Gly Cys Thr Cys Cys Ala Cys Ala Thr Cys
65                  70                  75                  80

Thr Ala Ala Cys Ala Thr Cys Gly Gly Cys Gly Cys Cys Gly Ala Cys
                85                  90                  95

Thr Ala Cys Gly Ala Thr Gly Thr Gly Cys Ala Cys Thr Gly Gly Thr
            100                 105                 110

Ala Thr Cys Ala Gly Cys Ala Cys Thr Cys Cys Cys Ala Gly Gly Gly
        115                 120                 125

Ala Ala Cys Cys Gly Gly Ala Cys Cys Cys Ala Gly Ala Cys Thr Gly
        130                 135                 140

Cys Thr Gly Ala Thr Cys Thr Cys Gly Gly Cys Thr Cys Thr Ala
145                 150                 155                 160

Cys Ala Ala Ala Thr Ala Gly Gly Cys Cys Thr Ala Gly Cys Gly Gly
            165                 170                 175

Cys Gly Thr Gly Cys Cys Ala Gly Ala Cys Cys Gly Gly Thr Thr Cys
            180                 185                 190

Ala Gly Cys Gly Gly Cys Ala Gly Cys Ala Ala Gly Cys Thr Gly
        195                 200                 205

Gly Cys Ala Cys Ala Gly Cys Gly Cys Thr Cys Cys Thr
210                 215                 220

Gly Gly Cys Cys Ala Thr Cys Ala Cys Gly Gly Cys Cys Thr Gly
225                 230                 235                 240

Cys Ala Gly Gly Cys Ala Gly Ala Cys Gly Ala Thr Ala Gly Gly
            245                 250                 255

Cys Cys Gly Ala Gly Thr Ala Cys Thr Ala Thr Thr Gly Cys Cys Ala
            260                 265                 270

Gly Ala Gly Cys Thr Ala Cys Gly Ala Thr Cys Gly Gly Ala Cys Cys
            275                 280                 285

Cys Thr Gly Gly Gly Cys Gly Gly Ala Thr Ala Cys Gly Thr Gly Thr
            290                 295                 300

Thr Cys Gly Gly Ala Ala Cys Cys Gly Gly Cys Ala Cys Ala Cys Ala
305                 310                 315                 320

Gly Gly Thr Gly Ala Cys Ala
                325

<210> SEQ ID NO 98
<211> LENGTH: 14
<212> TYPE: PRT
<213> ORGANISM: Homo sapiens

<400> SEQUENCE: 98

Thr Gly Ser Thr Ser Asn Ile Gly Ala Asp Tyr Asp Val His
1               5                   10
```

```
<210> SEQ ID NO 99
<211> LENGTH: 7
<212> TYPE: PRT
<213> ORGANISM: Homo sapiens

<400> SEQUENCE: 99

Gly Ser Thr Asn Arg Pro Ser
1               5

<210> SEQ ID NO 100
<211> LENGTH: 11
<212> TYPE: PRT
<213> ORGANISM: Homo sapiens

<400> SEQUENCE: 100

Gln Ser Tyr Asp Arg Thr Leu Gly Gly Tyr Val
1               5                   10

<210> SEQ ID NO 101
<211> LENGTH: 127
<212> TYPE: PRT
<213> ORGANISM: Homo sapiens

<400> SEQUENCE: 101

Gln Val Gln Leu Met Gln Ser Gly Ala Glu Val Arg Lys Pro Gly Ser
1               5                   10                  15

Ser Val Arg Val Ser Cys Thr Ala Ser Gly Gly Thr Phe Thr Asn Phe
                20                  25                  30

Ala Phe Thr Trp Val Arg Arg Ala Pro Gly Gln Gly Leu Glu Trp Met
            35                  40                  45

Gly Gly Phe Leu Pro Phe Phe Gly Thr Ser Asn Tyr Ala Gln His Leu
        50                  55                  60

Gln Gly Arg Val Ala Ile Thr Ala Asp Lys Ser Thr Ser Thr Val Tyr
65                  70                  75                  80

Met Glu Leu Arg Ser Leu Arg Pro Glu Asp Thr Gly Val Tyr Tyr Cys
                85                  90                  95

Ala Arg Ala Ser Gly Asp Thr Gly Gly Tyr Tyr Leu Ser Tyr Tyr Tyr
            100                 105                 110

Gly Met Asp Val Trp Gly Gln Gly Thr Thr Val Thr Val Ser Ser
        115                 120                 125

<210> SEQ ID NO 102
<211> LENGTH: 381
<212> TYPE: PRT
<213> ORGANISM: Homo sapiens

<400> SEQUENCE: 102

Cys Ala Gly Gly Thr Gly Cys Ala Gly Cys Thr Gly Ala Thr Gly Cys
1               5                   10                  15

Ala Gly Thr Cys Thr Gly Gly Cys Gly Cys Ala Gly Ala Gly Gly Thr
                20                  25                  30

Gly Cys Gly Gly Ala Ala Gly Cys Cys Ala Gly Gly Cys Ala Gly Cys
            35                  40                  45

Thr Cys Cys Gly Thr Gly Ala Gly Ala Gly Thr Gly Ala Gly Cys Thr
        50                  55                  60

Gly Thr Ala Cys Cys Gly Cys Cys Thr Cys Cys Gly Gly Cys Gly Gly
65                  70                  75                  80

Cys Ala Cys Cys Thr Thr Cys Ala Cys Ala Ala Cys Thr Thr Cys
                85                  90                  95
```

Gly Cys Cys Thr Thr Ala Cys Ala Thr Gly Gly Thr Gly Cys
            100                 105                 110

Gly Gly Ala Gly Ala Gly Cys Ala Cys Cys Ala Gly Gly Ala Cys Ala
            115                 120                 125

Gly Gly Gly Cys Cys Thr Gly Ala Gly Thr Gly Ala Thr Gly
            130                 135                 140

Gly Gly Cys Gly Gly Cys Thr Thr Thr Cys Thr Gly Cys Cys Thr Thr
145                 150                 155                 160

Thr Cys Thr Thr Thr Gly Gly Cys Ala Cys Ala Gly Cys Ala Ala
                165                 170                 175

Thr Thr Ala Thr Gly Cys Ala Cys Ala Gly Cys Ala Cys Thr Gly
                180                 185                 190

Cys Ala Gly Gly Gly Ala Ala Gly Gly Gly Thr Gly Gly Cys Ala Ala
                195                 200                 205

Thr Cys Ala Cys Ala Gly Cys Cys Gly Ala Cys Ala Ala Gly Thr Cys
            210                 215                 220

Cys Ala Cys Cys Thr Cys Thr Ala Cys Ala Gly Thr Gly Thr Ala Cys
225                 230                 235                 240

Ala Thr Gly Gly Ala Gly Cys Thr Gly Ala Gly Gly Thr Cys Cys Cys
                245                 250                 255

Thr Gly Cys Gly Cys Cys Cys Gly Ala Gly Ala Cys Ala Cys
            260                 265                 270

Cys Gly Gly Cys Gly Thr Gly Thr Ala Cys Thr Ala Thr Thr Gly Cys
            275                 280                 285

Gly Cys Cys Ala Gly Ala Gly Cys Cys Thr Cys Thr Gly Gly Cys Gly
            290                 295                 300

Ala Thr Ala Cys Ala Gly Gly Cys Gly Gly Cys Thr Ala Cys Thr Ala
305                 310                 315                 320

Thr Cys Thr Gly Ala Gly Cys Thr Ala Cys Thr Ala Thr Ala Cys
                325                 330                 335

Gly Gly Ala Ala Thr Gly Gly Ala Cys Gly Thr Gly Thr Gly Gly Gly
                340                 345                 350

Gly Ala Cys Ala Gly Gly Ala Ala Cys Cys Ala Cys Ala Gly Thr
            355                 360                 365

Gly Ala Cys Cys Gly Thr Gly Thr Cys Thr Ala Gly Cys
        370                 375                 380

<210> SEQ ID NO 103
<211> LENGTH: 7
<212> TYPE: PRT
<213> ORGANISM: Homo sapiens

<400> SEQUENCE: 103

Gly Gly Thr Phe Thr Asn Phe
1               5

<210> SEQ ID NO 104
<211> LENGTH: 6
<212> TYPE: PRT
<213> ORGANISM: Homo sapiens

<400> SEQUENCE: 104

Leu Pro Phe Phe Gly Thr
1               5

<210> SEQ ID NO 105

```
<211> LENGTH: 18
<212> TYPE: PRT
<213> ORGANISM: Homo sapiens

<400> SEQUENCE: 105

Ala Ser Gly Asp Thr Gly Gly Tyr Tyr Leu Ser Tyr Tyr Tyr Gly Met
1               5                   10                  15

Asp Val

<210> SEQ ID NO 106
<211> LENGTH: 110
<212> TYPE: PRT
<213> ORGANISM: Homo sapiens

<400> SEQUENCE: 106

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Gly
65                  70                  75                  80

Gly Val Glu Ala Glu Asp Val Gly Val Tyr Tyr Cys Val Arg Ala Leu
                85                  90                  95

Arg Gly Leu Ser Phe Gly Gly Gly Thr Glu Val Glu Ile Glu
            100                 105                 110

<210> SEQ ID NO 107
<211> LENGTH: 330
<212> TYPE: PRT
<213> ORGANISM: Homo sapiens

<400> SEQUENCE: 107

Gly Ala Cys Ala Thr Cys Gly Thr Gly Ala Thr Gly Ala Cys Cys Cys
1               5                   10                  15

Ala Gly Thr Cys Cys Cys Cys Ala Cys Thr Gly Thr Cys Thr Cys Thr
            20                  25                  30

Gly Cys Cys Cys Gly Thr Gly Ala Cys Ala Cys Cys Thr Gly Gly Cys
        35                  40                  45

Gly Ala Gly Cys Cys Ala Gly Cys Cys Thr Cys Thr Ala Thr Cys Ala
    50                  55                  60

Gly Cys Thr Gly Thr Cys Gly Gly Ala Gly Thr Cys Ala Gly Cys Ala
65                  70                  75                  80

Gly Thr Cys Thr Cys Thr Gly Cys Thr Gly Cys Ala Cys Ala Cys Cys
                85                  90                  95

Ala Ala Cys Gly Gly Cys Thr Ala Cys Ala Ala Thr Ala Thr Cys Thr
            100                 105                 110

Thr Gly Gly Ala Thr Thr Gly Gly Thr Ala Cys Thr Gly Cys Ala Gly
        115                 120                 125

Gly Ala Ala Gly Cys Cys Cys Gly Gly Cys Cys Ala Gly Ala Gly Cys
    130                 135                 140

Cys Cys Thr Cys Ala Gly Cys Thr Gly Cys Thr Gly Ala Thr Cys Thr
145                 150                 155                 160

Ala Thr Cys Thr Gly Gly Gly Cys Ala Gly Cys Ala Ala Cys Ala Gly
```

```
                165                 170                 175
Gly Gly Cys Cys Thr Cys Cys Gly Cys Gly Thr Gly Cys Cys Cys
            180                 185                 190

Gly Ala Cys Cys Gly Cys Thr Thr Cys Thr Cys Cys Gly Gly Cys Thr
            195                 200                 205

Cys Thr Gly Gly Cys Ala Gly Cys Gly Gly Cys Ala Cys Cys Gly Ala
        210                 215                 220

Cys Thr Thr Cys Ala Cys Cys Thr Gly Ala Ala Gly Gly Gly Ala
225                 230                 235                 240

Gly Gly Ala Gly Thr Gly Gly Ala Gly Gly Cys Ala Gly Ala Gly Gly
            245                 250                 255

Ala Cys Gly Thr Gly Gly Cys Gly Thr Gly Thr Ala Cys Thr Ala
        260                 265                 270

Thr Thr Gly Cys Gly Thr Gly Cys Gly Gly Cys Cys Cys Thr Gly
            275                 280                 285

Ala Gly Ala Gly Cys Cys Thr Gly Thr Cys Thr Thr Thr Cys Gly
        290                 295                 300

Gly Cys Gly Gly Cys Gly Gly Cys Ala Cys Ala Gly Ala Gly Thr
305                 310                 315                 320

Gly Gly Ala Gly Ala Thr Cys Gly Ala Gly
            325                 330

<210> SEQ ID NO 108
<211> LENGTH: 16
<212> TYPE: PRT
<213> ORGANISM: Homo sapiens

<400> SEQUENCE: 108

Arg Ser Ser Gln Ser Leu Leu His Thr Asn Gly Tyr Asn Tyr Leu Asp
1               5                   10                  15

<210> SEQ ID NO 109
<211> LENGTH: 7
<212> TYPE: PRT
<213> ORGANISM: Homo sapiens

<400> SEQUENCE: 109

Leu Gly Ser Asn Arg Ala Ser
1               5

<210> SEQ ID NO 110
<211> LENGTH: 8
<212> TYPE: PRT
<213> ORGANISM: Homo sapiens

<400> SEQUENCE: 110

Val Arg Ala Leu Arg Gly Leu Ser
1               5

<210> SEQ ID NO 111
<211> LENGTH: 129
<212> TYPE: PRT
<213> ORGANISM: Homo sapiens

<400> SEQUENCE: 111

Glu Val Gln Leu Val Glu Ser Gly Gly Gly Ile Val Gln Pro Gly Gly
1               5                   10                  15

Ser Leu Arg Val Ser Cys Ala Ala Ser Gly Phe Ser Leu Ser Asp His
            20                  25                  30
```

Tyr Met Asp Trp Val Arg Gln Ala Pro Gly Arg Gly Leu Glu Trp Val
             35                  40                  45

Gly Arg Ser Arg Asn Lys Glu Asn Ser Phe Thr Thr Glu Phe Ala Ala
 50                  55                  60

Ser Val Arg Arg Phe Thr Ile Ser Arg Asp Asp Ser Asn Ser Leu
 65                  70                  75                  80

Leu His Leu Gln Met Asn Asn Leu Lys Ser Glu Asp Thr Ala Val Tyr
                 85                  90                  95

Phe Cys Ala Arg Val Gly Tyr Tyr Asp Leu Trp Ser Gly Tyr Ser Gly
                100                 105                 110

Asn Trp Tyr Ile Asp Val Trp Gly Arg Gly Thr Leu Val Ile Val Ser
             115                 120                 125

Ser

<210> SEQ ID NO 112
<211> LENGTH: 387
<212> TYPE: PRT
<213> ORGANISM: Homo sapiens

<400> SEQUENCE: 112

Gly Ala Gly Gly Thr Gly Cys Ala Gly Cys Thr Gly Gly Thr Gly Gly
 1               5                  10                  15

Ala Gly Thr Cys Cys Gly Gly Cys Gly Gly Ala Gly Gly Ala Ala Thr
                20                  25                  30

Cys Gly Thr Gly Cys Ala Gly Cys Cys Ala Gly Gly Ala Gly Gly Cys
             35                  40                  45

Thr Cys Thr Cys Thr Gly Cys Gly Gly Gly Thr Gly Ala Gly Cys Thr
         50                  55                  60

Gly Thr Gly Cys Ala Gly Cys Thr Cys Cys Gly Gly Cys Thr Thr
 65                  70                  75                  80

Cys Thr Cys Thr Cys Thr Gly Ala Gly Cys Gly Ala Cys Cys Ala Cys
                 85                  90                  95

Thr Ala Cys Ala Thr Gly Gly Ala Thr Thr Gly Gly Gly Thr Gly Ala
                100                 105                 110

Gly Ala Cys Ala Gly Gly Cys Ala Cys Cys Thr Gly Gly Ala Ala Gly
             115                 120                 125

Gly Gly Gly Cys Cys Thr Gly Gly Ala Gly Thr Gly Gly Gly Thr Gly
 130                 135                 140

Gly Gly Cys Cys Gly Cys Thr Cys Thr Cys Gly Gly Ala Ala Cys Ala
 145                 150                 155                 160

Ala Gly Gly Ala Gly Ala Ala Thr Ala Gly Cys Thr Thr Cys Ala Cys
                 165                 170                 175

Cys Ala Cys Ala Gly Ala Gly Thr Thr Thr Gly Cys Cys Gly Cys Cys
                 180                 185                 190

Thr Cys Cys Gly Thr Gly Cys Gly Gly Ala Gly Ala Gly Gly Thr
                 195                 200                 205

Thr Cys Ala Cys Cys Ala Thr Cys Ala Gly Cys Cys Gly Gly Gly Ala
             210                 215                 220

Cys Gly Ala Thr Thr Cys Cys Ala Ala Cys Thr Cys Thr Cys Thr Gly
 225                 230                 235                 240

Cys Thr Gly Cys Ala Cys Cys Thr Gly Cys Ala Gly Ala Thr Gly Ala
                 245                 250                 255

Ala Cys Ala Ala Thr Cys Thr Gly Ala Ala Gly Thr Cys Thr Gly Ala
                 260                 265                 270

Gly Gly Ala Cys Ala Cys Ala Gly Cys Cys Thr Gly Thr Ala Thr
            275                 280                 285

Thr Thr Thr Thr Gly Cys Gly Cys Cys Gly Cys Gly Thr Gly Gly
    290                 295                 300

Gly Cys Thr Ala Cys Thr Ala Thr Gly Ala Cys Cys Thr Gly Thr
305                 310                 315                 320

Gly Ala Gly Cys Gly Gly Cys Thr Ala Cys Thr Cys Cys Gly Cys
                325                 330                 335

Ala Ala Thr Thr Gly Gly Thr Ala Thr Ala Thr Cys Gly Ala Cys Gly
                340                 345                 350

Thr Gly Thr Gly Gly Gly Ala Ala Gly Gly Gly Cys Ala Cys
    355                 360                 365

Cys Cys Thr Gly Gly Thr Cys Ala Thr Cys Gly Thr Gly Ala Gly Cys
    370                 375                 380

Thr Cys Cys
385

<210> SEQ ID NO 113
<211> LENGTH: 7
<212> TYPE: PRT
<213> ORGANISM: Homo sapiens

<400> SEQUENCE: 113

Gly Phe Ser Leu Ser Asp His
1               5

<210> SEQ ID NO 114
<211> LENGTH: 8
<212> TYPE: PRT
<213> ORGANISM: Homo sapiens

<400> SEQUENCE: 114

Arg Asn Lys Glu Asn Ser Phe Thr
1               5

<210> SEQ ID NO 115
<211> LENGTH: 18
<212> TYPE: PRT
<213> ORGANISM: Homo sapiens

<400> SEQUENCE: 115

Val Gly Tyr Tyr Asp Leu Trp Ser Gly Tyr Ser Gly Asn Trp Tyr Ile
1               5                   10                  15

Asp Val

<210> SEQ ID NO 116
<211> LENGTH: 107
<212> TYPE: PRT
<213> ORGANISM: Homo sapiens

<400> SEQUENCE: 116

Asp Ile Gln Met Thr Gln Ser Pro Ser Ser Leu Ser Ala Ser Leu Gly
1               5                   10                  15

Asp Ser Val Thr Ile Thr Cys Arg Ala Ser Gln Thr Met Ser Asn Phe
            20                  25                  30

Leu Asn Trp Tyr Gln Gln Lys Pro Gly Lys Ala Pro Lys Phe Leu Ile
        35                  40                  45

Tyr Ala Ala Ser Arg Leu Gln Ser Gly Val Pro Ser Arg Phe Ser Gly
    50                  55                  60

```
Ser Gly Ser Gly Thr Gln Phe Thr Leu Thr Ile Ser Asn Leu Gln Pro
 65                  70                  75                  80

Glu Asp Phe Ala Thr Tyr Tyr Cys Gln Gln Ser Phe Ile Phe Pro Tyr
                 85                  90                  95

Thr Phe Gly Gly Gly Thr Lys Val Glu Val Glu
                100                 105

<210> SEQ ID NO 117
<211> LENGTH: 321
<212> TYPE: PRT
<213> ORGANISM: Homo sapiens

<400> SEQUENCE: 117

Gly Ala Cys Ala Thr Cys Cys Ala Gly Ala Thr Gly Ala Cys Cys Cys
  1               5                  10                  15

Ala Gly Ala Gly Cys Cys Cys Thr Ala Gly Cys Thr Cys Cys Cys Thr
                 20                  25                  30

Gly Thr Cys Thr Gly Cys Cys Ala Gly Cys Cys Thr Gly Gly Gly Cys
             35                  40                  45

Gly Ala Thr Thr Cys Cys Gly Thr Gly Ala Cys Cys Ala Thr Cys Ala
 50                  55                  60

Cys Ala Thr Gly Thr Cys Gly Gly Cys Cys Thr Cys Cys Cys Cys Ala
 65                  70                  75                  80

Gly Ala Cys Ala Ala Thr Gly Cys Thr Ala Ala Cys Thr Thr Cys Cys
                 85                  90                  95

Cys Thr Gly Ala Ala Thr Gly Gly Thr Ala Cys Cys Ala Gly Gly Cys
                100                 105                 110

Ala Gly Ala Ala Gly Cys Cys Cys Gly Gly Cys Ala Ala Gly Gly Cys
                115                 120                 125

Cys Cys Cys Thr Ala Ala Gly Thr Thr Thr Cys Thr Gly Ala Thr Cys
             130                 135                 140

Thr Ala Thr Gly Cys Ala Gly Cys Cys Ala Gly Cys Cys Gly Gly Cys
145                 150                 155                 160

Thr Gly Cys Ala Gly Thr Cys Cys Gly Gly Cys Gly Thr Gly Cys Cys
                165                 170                 175

Ala Ala Gly Cys Cys Gly Gly Thr Thr Cys Ala Gly Cys Gly Gly Cys
                180                 185                 190

Ala Gly Cys Gly Gly Cys Ala Gly Cys Gly Gly Cys Ala Cys Cys Cys
                195                 200                 205

Ala Gly Thr Thr Thr Ala Cys Cys Cys Thr Gly Ala Cys Ala Ala Thr
             210                 215                 220

Cys Thr Cys Thr Ala Ala Cys Cys Thr Gly Cys Ala Gly Cys Cys Ala
225                 230                 235                 240

Gly Ala Gly Gly Ala Cys Thr Thr Cys Gly Cys Cys Ala Cys Ala Thr
                245                 250                 255

Ala Cys Thr Ala Thr Thr Gly Cys Cys Ala Gly Cys Ala Gly Thr Cys
                260                 265                 270

Cys Thr Thr Cys Ala Thr Cys Thr Thr Cys Cys Cys Thr Ala Cys Ala
             275                 280                 285

Cys Cys Thr Thr Cys Gly Gly Cys Gly Gly Cys Gly Gly Cys Ala
             290                 295                 300

Cys Ala Ala Ala Gly Gly Thr Gly Gly Ala Gly Gly Thr Gly Gly Ala
305                 310                 315                 320

Gly
```

```
<210> SEQ ID NO 118
<211> LENGTH: 11
<212> TYPE: PRT
<213> ORGANISM: Homo sapiens

<400> SEQUENCE: 118

Arg Ala Ser Gln Thr Met Ser Asn Phe Leu Asn
1               5                   10

<210> SEQ ID NO 119
<211> LENGTH: 7
<212> TYPE: PRT
<213> ORGANISM: Homo sapiens

<400> SEQUENCE: 119

Ala Ala Ser Arg Leu Gln Ser
1               5

<210> SEQ ID NO 120
<211> LENGTH: 9
<212> TYPE: PRT
<213> ORGANISM: Homo sapiens

<400> SEQUENCE: 120

Gln Gln Ser Phe Ile Phe Pro Tyr Thr
1               5

<210> SEQ ID NO 121
<211> LENGTH: 119
<212> TYPE: PRT
<213> ORGANISM: Homo sapiens

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ser Arg Tyr
            20                  25                  30

Ala Ile Ser Trp Val Arg Gln Ala Pro Gly Gln Gly Leu Glu Trp Val
        35                  40                  45

Gly Trp Ile Asn Pro Tyr Thr Gly Thr Ala Asn Tyr Ala Gln Ile Leu
    50                  55                  60

Gln Gly Arg Val Thr Val Thr Thr Asp Thr Ser Thr Thr Thr Ala Tyr
65                  70                  75                  80

Met Glu Leu Arg Ser Leu Thr Ser Asp Asp Thr Ala Met Tyr Tyr Cys
                85                  90                  95

Ala Arg His Leu Pro Gly Thr Ala Val Ala Ser Tyr Phe Gly Gln Gly
            100                 105                 110

Ser Leu Val Thr Val Ser Phe
        115

<210> SEQ ID NO 122
<211> LENGTH: 357
<212> TYPE: PRT
<213> ORGANISM: Homo sapiens

<400> SEQUENCE: 122

Cys Ala Gly Gly Thr Gly Cys Ala Gly Cys Thr Gly Thr Gly Cys
1               5                   10                  15

Ala Gly Thr Cys Cys Gly Gly Cys Gly Cys Ala Gly Ala Gly Gly Thr
            20                  25                  30
```

```
Gly Ala Ala Gly Ala Gly Cys Ala Gly Gly Ala Gly Cys Cys
        35                  40                  45
Thr Cys Thr Gly Thr Gly Ala Ala Gly Gly Thr Gly Ala Gly Cys Thr
50                  55                  60
Gly Thr Ala Ala Gly Ala Cys Ala Thr Cys Cys Gly Gly Cys Thr Ala
65                  70                  75                  80
Cys Ala Cys Cys Thr Thr Cys Thr Cys Thr Cys Gly Gly Thr Ala Thr
                85                  90                  95
Gly Cys Ala Ala Thr Cys Ala Gly Cys Thr Gly Gly Gly Thr Gly Ala
            100                 105                 110
Gly Ala Cys Ala Gly Gly Cys Ala Cys Cys Ala Gly Gly Ala Cys Ala
            115                 120                 125
Gly Gly Gly Cys Cys Thr Gly Gly Ala Gly Thr Gly Gly Thr Gly Gly
            130                 135                 140
Gly Gly Cys Thr Gly Gly Ala Thr Cys Ala Ala Cys Cys Cys Thr Thr
145                 150                 155                 160
Ala Cys Ala Cys Ala Gly Gly Cys Ala Cys Cys Gly Cys Cys Ala Ala
                165                 170                 175
Thr Thr Ala Thr Gly Cys Cys Cys Ala Gly Ala Ala Thr Thr Thr Cys
                180                 185                 190
Cys Ala Gly Gly Gly Cys Cys Gly Gly Gly Thr Cys Ala Cys Ala Gly
                195                 200                 205
Thr Gly Ala Cys Cys Ala Cys Ala Gly Ala Cys Ala Cys Cys Thr Cys
            210                 215                 220
Thr Ala Cys Cys Ala Cys Ala Cys Cys Gly Cys Cys Thr Ala Cys Ala
225                 230                 235                 240
Ala Thr Gly Gly Ala Gly Cys Thr Gly Ala Gly Gly Ala Gly Cys Cys
                245                 250                 255
Thr Gly Ala Cys Ala Thr Cys Cys Gly Ala Cys Gly Ala Thr Ala Cys
            260                 265                 270
Cys Gly Cys Cys Ala Thr Gly Thr Ala Cys Thr Ala Thr Thr Gly Cys
            275                 280                 285
Gly Cys Ala Ala Gly Gly Cys Ala Cys Cys Thr Gly Cys Cys Ala Gly
            290                 295                 300
Gly Ala Ala Cys Ala Gly Cys Ala Gly Thr Gly Gly Cys Cys Ala Gly
305                 310                 315                 320
Cys Thr Ala Thr Thr Thr Cys Gly Gly Cys Cys Ala Gly Gly Gly Cys
                325                 330                 335
Thr Cys Cys Cys Thr Gly Gly Thr Gly Ala Cys Cys Gly Thr Gly Thr
            340                 345                 350
Cys Thr Thr Thr Thr
        355

<210> SEQ ID NO 123
<211> LENGTH: 7
<212> TYPE: PRT
<213> ORGANISM: Homo sapiens

<400> SEQUENCE: 123

Gly Tyr Thr Phe Ser Arg Tyr
1               5

<210> SEQ ID NO 124
<211> LENGTH: 6
<212> TYPE: PRT
<213> ORGANISM: Homo sapiens
```

-continued

<400> SEQUENCE: 124

Asn Pro Tyr Thr Gly Thr
1               5

<210> SEQ ID NO 125
<211> LENGTH: 10
<212> TYPE: PRT
<213> ORGANISM: Homo sapiens

<400> SEQUENCE: 125

His Leu Pro Gly Thr Ala Val Ala Ser Tyr
1               5                   10

<210> SEQ ID NO 126
<211> LENGTH: 106
<212> TYPE: PRT
<213> ORGANISM: Homo sapiens

<400> SEQUENCE: 126

Glu Ile Val Met Thr Gln Ser Pro Ser Ser Val Ser Pro Gly Glu
1               5                   10                  15

Arg Ala Thr Leu Ser Cys Arg Ala Ser Gln Gly Val Ser Asn Leu
                20                  25                  30

Ala Trp Tyr Gln Gln Lys Phe Gly Gln Ala Pro Arg Leu Leu Ile Phe
            35                  40                  45

Ser Ala Ser Thr Arg Ala Thr Gly Thr Pro Ala Arg Phe Ser Gly Ser
        50                  55                  60

Gly Ser Gly Thr Glu Phe Thr Leu Thr Ile Ser Ser Leu Gln Ser Glu
65                  70                  75                  80

Asp Phe Ala Val Tyr Tyr Cys Gln Gln Tyr Asp Asn Trp Pro Leu Ser
                85                  90                  95

Phe Gly Gly Gly Thr Lys Val Glu Ile Lys
            100                 105

<210> SEQ ID NO 127
<211> LENGTH: 318
<212> TYPE: PRT
<213> ORGANISM: Homo sapiens

<400> SEQUENCE: 127

Gly Ala Gly Ala Thr Cys Gly Thr Gly Ala Thr Gly Ala Cys Cys Cys
1               5                   10                  15

Ala Gly Thr Cys Thr Cys Cys Ala Gly Cys Thr Cys Cys Thr Cys Thr
                20                  25                  30

Thr Gly Thr Gly Ala Gly Cys Cys Cys Thr Gly Gly Ala Gly Ala Gly
            35                  40                  45

Ala Gly Gly Gly Cys Cys Ala Cys Ala Cys Thr Gly Ala Gly Cys Thr
        50                  55                  60

Gly Thr Ala Gly Ala Gly Cys Cys Thr Cys Cys Ala Gly Gly Gly
65                  70                  75                  80

Cys Gly Thr Gly Ala Gly Cys Thr Cys Cys Ala Ala Cys Thr Gly
                85                  90                  95

Gly Cys Ala Thr Gly Gly Thr Ala Cys Cys Ala Gly Cys Ala Gly Ala
            100                 105                 110

Ala Gly Thr Thr Cys Gly Gly Cys Cys Ala Gly Gly Cys Cys Cys Cys
        115                 120                 125

Ala Cys Gly Gly Cys Thr Gly Cys Thr Gly Ala Thr Cys Thr Thr Thr

```
                130             135             140
Thr Cys Cys Gly Cys Cys Thr Cys Thr Ala Cys Cys Ala Gly Gly
145                 150                 155                 160

Cys Ala Ala Cys Cys Gly Gly Ala Ala Cys Ala Cys Cys Ala Gly Cys
                165                 170                 175

Ala Cys Gly Cys Thr Thr Cys Ala Gly Cys Gly Gly Cys Thr Cys Cys
                180                 185                 190

Gly Gly Cys Thr Cys Thr Gly Gly Cys Ala Cys Ala Gly Ala Gly Thr
                195                 200                 205

Thr Thr Ala Cys Cys Cys Thr Gly Ala Cys Ala Ala Thr Cys Thr Cys
210                 215                 220

Thr Ala Gly Cys Cys Thr Gly Cys Ala Gly Thr Cys Cys Gly Ala Gly
225                 230                 235                 240

Gly Ala Cys Thr Thr Cys Gly Cys Cys Gly Thr Gly Thr Ala Cys Thr
                245                 250                 255

Ala Thr Thr Gly Cys Cys Ala Gly Cys Ala Gly Thr Ala Thr Gly Ala
                260                 265                 270

Thr Ala Ala Thr Thr Gly Gly Cys Cys Cys Thr Gly Thr Cys Thr
275                 280                 285

Thr Thr Thr Gly Gly Cys Gly Gly Ala Gly Gly Cys Ala Cys Cys Ala
                290                 295                 300

Ala Gly Gly Thr Gly Gly Ala Gly Ala Thr Cys Ala Ala Gly
305                 310                 315

<210> SEQ ID NO 128
<211> LENGTH: 11
<212> TYPE: PRT
<213> ORGANISM: Homo sapiens

<400> SEQUENCE: 128

Arg Ala Ser Gln Gly Val Ser Ser Asn Leu Ala
1               5                   10

<210> SEQ ID NO 129
<211> LENGTH: 7
<212> TYPE: PRT
<213> ORGANISM: Homo sapiens

<400> SEQUENCE: 129

Ser Ala Ser Thr Arg Ala Thr
1               5

<210> SEQ ID NO 130
<211> LENGTH: 9
<212> TYPE: PRT
<213> ORGANISM: Homo sapiens

<400> SEQUENCE: 130

Gln Gln Tyr Asp Asn Trp Pro Leu Ser
1               5

<210> SEQ ID NO 131
<211> LENGTH: 120
<212> TYPE: PRT
<213> ORGANISM: Homo sapiens

<400> SEQUENCE: 131

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Thr Tyr
            20                  25                  30

Ala Met Asp Trp Val Arg Gln Ala Pro Gly Lys Gly Leu Glu Trp Val
        35                  40                  45

Ser Leu Ile Ser Ser Arg Ser Ser Asn Ile Tyr Tyr Ser Asp Ser Val
50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ala Gly Gly Phe His Ser His Phe Asp Met Trp Gly Gln
            100                 105                 110

Gly Thr Leu Val Thr Val Ser Ser
            115                 120

<210> SEQ ID NO 132
<211> LENGTH: 360
<212> TYPE: PRT
<213> ORGANISM: Homo sapiens

<400> SEQUENCE: 132

Gly Ala Gly Gly Thr Gly Cys Ala Gly Cys Thr Gly Gly Thr Gly Gly
1               5                   10                  15

Ala Gly Thr Cys Thr Gly Gly Cys Gly Gly Ala Gly Gly Cys Cys Thr
            20                  25                  30

Gly Gly Thr Gly Ala Ala Gly Cys Cys Ala Gly Gly Ala Gly Gly Cys
            35                  40                  45

Thr Cys Thr Cys Thr Gly Ala Gly Cys Thr Gly Ala Gly Cys Thr
        50                  55                  60

Gly Thr Gly Cys Ala Gly Cys Cys Thr Cys Gly Gly Cys Thr Thr
65                  70                  75                  80

Cys Ala Cys Cys Thr Thr Thr Cys Thr Ala Cys Ala Thr Ala Cys
                85                  90                  95

Gly Cys Ala Ala Thr Gly Gly Ala Cys Thr Gly Gly Gly Thr Gly Cys
            100                 105                 110

Gly Gly Cys Ala Gly Gly Cys Ala Cys Cys Thr Gly Gly Cys Ala Ala
            115                 120                 125

Gly Gly Gly Cys Cys Thr Gly Gly Ala Gly Thr Gly Gly Gly Thr Gly
            130                 135                 140

Ala Gly Cys Cys Thr Gly Ala Thr Cys Ala Gly Cys Thr Cys Cys Ala
145                 150                 155                 160

Gly Gly Thr Cys Thr Ala Gly Cys Ala Ala Cys Ala Thr Cys Thr Ala
                165                 170                 175

Cys Thr Ala Thr Ala Gly Cys Gly Ala Cys Thr Cys Cys Gly Thr Gly
                180                 185                 190

Ala Ala Gly Gly Gly Cys Cys Gly Gly Thr Thr Cys Ala Cys Cys Ala
            195                 200                 205

Thr Cys Ala Gly Cys Cys Gly Gly Gly Ala Thr Ala Ala Cys Gly Cys
        210                 215                 220

Cys Ala Ala Gly Ala Ala Thr Ala Gly Cys Thr Thr Gly Thr Thr Thr
225                 230                 235                 240

Cys Thr Gly Cys Ala Gly Ala Thr Gly Ala Ala Thr Thr Cys Cys
            245                 250                 255

Thr Gly Ala Gly Gly Gly Cys Cys Gly Ala Gly Gly Ala Cys Ala Cys
            260                 265                 270
```

Ala Gly Cys Cys Gly Thr Gly Thr Ala Cys Thr Ala Thr Gly Cys
            275                 280                 285

Gly Cys Ala Ala Gly Gly Ala Gly Gly Cys Ala Gly Gly Ala Gly
            290                 295                 300

Gly Ala Thr Thr Cys Cys Ala Cys Ala Gly Cys Ala Cys Thr Thr
305                 310                 315                 320

Thr Gly Ala Thr Ala Thr Gly Thr Gly Gly Gly Cys Cys Ala Gly
            325                 330                 335

Gly Gly Cys Ala Cys Cys Thr Gly Gly Thr Gly Ala Cys Ala Gly
            340                 345                 350

Thr Gly Thr Cys Cys Thr Cys Thr
            355                 360

<210> SEQ ID NO 133
<211> LENGTH: 7
<212> TYPE: PRT
<213> ORGANISM: Homo sapiens

<400> SEQUENCE: 133

Gly Phe Thr Phe Ser Thr Tyr
1               5

<210> SEQ ID NO 134
<211> LENGTH: 6
<212> TYPE: PRT
<213> ORGANISM: Homo sapiens

<400> SEQUENCE: 134

Ser Ser Arg Ser Ser Asn
1               5

<210> SEQ ID NO 135
<211> LENGTH: 11
<212> TYPE: PRT
<213> ORGANISM: Homo sapiens

<400> SEQUENCE: 135

Glu Ala Gly Gly Phe His Ser His Phe Asp Met
1               5                   10

<210> SEQ ID NO 136
<211> LENGTH: 108
<212> TYPE: PRT
<213> ORGANISM: Homo sapiens

<400> SEQUENCE: 136

Gln Ser Val Leu Thr Gln Pro Ala Ser Val Ser Gly Ser Leu Gly Gln
1               5                   10                  15

Ser Val Thr Ile Ser Cys Thr Gly Thr Ser Ser Asp Val Gly Gly Tyr
            20                  25                  30

Asp Tyr Val Ser Trp Tyr Gln Gln His Pro Gly Lys Ala Pro Lys Leu
        35                  40                  45

Met Ile Phe Glu Val Asn Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Ser Thr Thr
                85                  90                  95

Thr Thr Trp Val Phe Gly Gly Gly Thr Ser Leu Thr

<210> SEQ ID NO 137
<211> LENGTH: 324
<212> TYPE: PRT
<213> ORGANISM: Homo sapiens

<400> SEQUENCE: 137

Cys Ala Gly Thr Cys Thr Gly Thr Gly Cys Thr Gly Ala Cys Cys Cys
1               5                   10                  15

Ala Gly Cys Cys Ala Gly Cys Cys Thr Cys Thr Gly Thr Gly Ala Gly
            20                  25                  30

Cys Gly Gly Cys Thr Cys Cys Thr Gly Gly Cys Cys Ala Gly
            35                  40                  45

Ala Gly Cys Gly Thr Gly Ala Cys Ala Ala Thr Cys Thr Cys Thr
        50                  55                  60

Gly Thr Ala Cys Cys Gly Gly Cys Ala Cys Ala Ala Gly Cys Thr Cys
65                  70                  75                  80

Cys Gly Ala Cys Gly Thr Gly Gly Ala Gly Gly Ala Thr Ala Cys
                85                  90                  95

Gly Ala Thr Thr Ala Thr Gly Thr Gly Ala Gly Cys Thr Gly Gly Thr
                100                 105                 110

Ala Cys Cys Ala Gly Cys Ala Gly Cys Ala Cys Cys Ala Gly Gly
            115                 120                 125

Cys Ala Ala Gly Gly Cys Ala Cys Cys Thr Ala Ala Gly Cys Thr Gly
        130                 135                 140

Ala Thr Gly Ala Thr Cys Thr Thr Cys Gly Ala Gly Gly Thr Gly Ala
145                 150                 155                 160

Ala Cys Ala Ala Thr Cys Gly Gly Cys Cys Thr Cys Cys Gly Gly
                165                 170                 175

Cys Gly Thr Gly Thr Cys Thr Ala Cys Cys Ala Gly Ala Thr Thr Thr
            180                 185                 190

Thr Cys Thr Gly Gly Cys Ala Gly Cys Ala Ala Gly Thr Cys Cys Gly
        195                 200                 205

Gly Cys Ala Ala Cys Ala Cys Cys Gly Cys Cys Thr Cys Thr Cys Thr
        210                 215                 220

Gly Ala Cys Ala Ala Thr Cys Ala Gly Cys Gly Gly Cys Cys Thr Gly
225                 230                 235                 240

Cys Ala Gly Gly Cys Ala Gly Ala Gly Gly Ala Cys Gly Ala Gly Gly
                245                 250                 255

Cys Ala Gly Ala Thr Thr Ala Cys Thr Ala Thr Gly Cys Ala Ala
            260                 265                 270

Thr Thr Cys Thr Thr Ala Thr Ala Gly Cys Ala Cys Ala Cys Ala
        275                 280                 285

Ala Cys Cys Ala Cys Ala Thr Gly Gly Thr Gly Thr Thr Cys Gly
        290                 295                 300

Gly Ala Gly Gly Ala Gly Gly Cys Ala Cys Cys Thr Cys Cys Cys Thr
305                 310                 315                 320

Gly Ala Cys Ala

<210> SEQ ID NO 138
<211> LENGTH: 14
<212> TYPE: PRT
<213> ORGANISM: Homo sapiens

<400> SEQUENCE: 138

```
Thr Gly Thr Ser Ser Asp Val Gly Gly Tyr Asp Tyr Val Ser
1               5                   10
```

<210> SEQ ID NO 139
<211> LENGTH: 7
<212> TYPE: PRT
<213> ORGANISM: Homo sapiens

<400> SEQUENCE: 139

```
Glu Val Asn Asn Arg Pro Ser
1               5
```

<210> SEQ ID NO 140
<211> LENGTH: 10
<212> TYPE: PRT
<213> ORGANISM: Homo sapiens

<400> SEQUENCE: 140

```
Asn Ser Tyr Ser Thr Thr Thr Trp Val
1               5                   10
```

<210> SEQ ID NO 141
<211> LENGTH: 120
<212> TYPE: PRT
<213> ORGANISM: Homo sapiens

<400> SEQUENCE: 141

```
Glu Val Gln Leu Val Glu Ser Gly Gly Gly Leu Val Arg Pro Gly Gly
1               5                   10                  15

Ser Leu Arg Leu Ser Cys Ser Ala Ser Gly Phe Thr Phe Ser Ser Tyr
                20                  25                  30

Ser Met Asn Trp Val Arg Gln Ala Pro Gly Lys Gly Leu Glu Phe Val
            35                  40                  45

Ser Ala Ile Thr Ser Arg Gly Thr Tyr Ile Tyr Tyr Ala Asp Ser Val
        50                  55                  60

Lys Gly Arg Phe Thr Val Ser Arg Asp Asn Ala Lys Asn Ser Leu Tyr
65                  70                  75                  80

Leu Gln Met Thr Asn Val Arg Asp Glu Asp Thr Ala Val Tyr Tyr Cys
                85                  90                  95

Ala Arg Glu Met Ala Gly Tyr Ser Ser Thr Phe Asp Tyr Trp Gly Gln
            100                 105                 110

Gly Ala Leu Val Thr Val Ser Ser
        115                 120
```

<210> SEQ ID NO 142
<211> LENGTH: 360
<212> TYPE: PRT
<213> ORGANISM: Homo sapiens

<400> SEQUENCE: 142

```
Gly Ala Gly Gly Thr Gly Cys Ala Gly Cys Thr Gly Gly Thr Gly Gly
1               5                   10                  15

Ala Gly Thr Cys Cys Gly Gly Cys Gly Gly Ala Gly Gly Cys Cys Thr
                20                  25                  30

Gly Gly Thr Gly Ala Gly Gly Cys Cys Cys Gly Gly Ala Gly Gly Cys
            35                  40                  45

Thr Cys Thr Cys Thr Gly Cys Gly Cys Thr Gly Ala Gly Cys Thr
        50                  55                  60

Gly Thr Thr Cys Cys Gly Cys Cys Thr Cys Thr Gly Gly Cys Thr Thr
```

```
            65                  70                  75                  80
Cys Ala Cys Cys Thr Thr Thr Ala Gly Cys Thr Cys Cys Thr Ala Cys
                85                  90                  95
Ala Gly Cys Ala Thr Gly Ala Ala Cys Thr Gly Gly Thr Gly Ala
            100                 105                 110
Gly Gly Cys Ala Gly Gly Cys Ala Cys Cys Thr Gly Gly Cys Ala Ala
            115                 120                 125
Gly Gly Gly Cys Cys Thr Gly Gly Ala Gly Thr Thr Cys Gly Thr Gly
            130                 135                 140
Ala Gly Cys Gly Cys Cys Ala Thr Cys Ala Cys Cys Thr Cys Cys Ala
145                 150                 155                 160
Gly Ala Gly Gly Cys Ala Cys Ala Thr Ala Cys Ala Thr Cys Thr Ala
                165                 170                 175
Cys Thr Ala Thr Gly Cys Cys Gly Ala Cys Thr Cys Cys Gly Thr Gly
            180                 185                 190
Ala Ala Gly Gly Gly Cys Cys Gly Gly Thr Thr Cys Ala Cys Cys Gly
                195                 200                 205
Thr Gly Ala Gly Cys Cys Gly Gly Ala Thr Ala Ala Cys Gly Cys
            210                 215                 220
Cys Ala Ala Gly Ala Ala Thr Ala Gly Cys Cys Thr Gly Thr Ala Thr
225                 230                 235                 240
Cys Thr Gly Cys Ala Gly Ala Thr Gly Ala Cys Cys Ala Ala Thr Gly
                245                 250                 255
Thr Gly Cys Gly Gly Gly Ala Cys Gly Ala Gly Gly Ala Thr Ala Cys
            260                 265                 270
Ala Gly Cys Cys Gly Thr Gly Thr Ala Cys Thr Ala Thr Thr Gly Cys
            275                 280                 285
Gly Cys Cys Ala Gly Ala Gly Ala Thr Gly Gly Cys Cys Gly
            290                 295                 300
Gly Cys Thr Ala Cys Thr Cys Thr Ala Gly Cys Ala Cys Cys Thr Thr
305                 310                 315                 320
Cys Gly Ala Cys Thr Ala Thr Thr Gly Gly Gly Gly Ala Cys Ala Gly
                325                 330                 335
Gly Gly Cys Gly Cys Cys Thr Gly Gly Thr Gly Ala Cys Ala Gly
            340                 345                 350
Thr Gly Thr Cys Cys Thr Cys Thr
            355                 360

<210> SEQ ID NO 143
<211> LENGTH: 7
<212> TYPE: PRT
<213> ORGANISM: Homo sapiens

<400> SEQUENCE: 143

Gly Phe Thr Phe Ser Ser Tyr
1               5

<210> SEQ ID NO 144
<211> LENGTH: 6
<212> TYPE: PRT
<213> ORGANISM: Homo sapiens

<400> SEQUENCE: 144

Thr Ser Arg Gly Thr Tyr
1               5
```

```
<210> SEQ ID NO 145
<211> LENGTH: 11
<212> TYPE: PRT
<213> ORGANISM: Homo sapiens

<400> SEQUENCE: 145

Glu Met Ala Gly Tyr Ser Ser Thr Phe Asp Tyr
1               5                   10

<210> SEQ ID NO 146
<211> LENGTH: 109
<212> TYPE: PRT
<213> ORGANISM: Homo sapiens

<400> SEQUENCE: 146

Gln Ser Val Leu Ser Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asp Tyr Val Ser Trp Tyr Gln Gln Tyr Ser Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ile Ser Tyr Thr Thr Ile
                85                  90                  95

Thr Thr Leu Trp Val Phe Gly Gly Gly Thr Lys Leu Thr
            100                 105

<210> SEQ ID NO 147
<211> LENGTH: 327
<212> TYPE: PRT
<213> ORGANISM: Homo sapiens

<400> SEQUENCE: 147

Cys Ala Gly Thr Cys Thr Gly Thr Gly Cys Thr Gly Ala Gly Cys Cys
1               5                   10                  15

Ala Gly Cys Cys Ala Gly Cys Cys Thr Cys Thr Gly Thr Gly Ala Gly
            20                  25                  30

Cys Gly Gly Cys Thr Cys Cys Cys Thr Gly Gly Cys Cys Ala Gly Cys
            35                  40                  45

Ala Gly Cys Ala Thr Cys Ala Cys Cys Ala Thr Cys Thr Cys Cys Thr
    50                  55                  60

Gly Thr Ala Cys Cys Gly Gly Cys Ala Cys Ala Ala Gly Cys Thr Cys
65                  70                  75                  80

Cys Gly Ala Cys Ala Thr Cys Gly Gly Cys Gly Gly Cys Thr Ala Cys
                85                  90                  95

Gly Ala Thr Thr Ala Cys Gly Thr Gly Ala Gly Cys Thr Gly Gly Thr
            100                 105                 110

Ala Cys Cys Ala Gly Cys Ala Gly Thr Ala Thr Thr Cys Thr Gly Gly
            115                 120                 125

Cys Ala Ala Gly Gly Cys Cys Cys Ala Ala Ala Gly Cys Thr Gly
            130                 135                 140

Ala Thr Gly Ala Thr Cys Thr Ala Cys Gly Ala Gly Gly Thr Gly Ala
145                 150                 155                 160

Gly Cys Ala Ala Cys Ala Gly Gly Cys Cys Ala Thr Cys Cys Gly Gly
                165                 170                 175
```

Cys Gly Thr Gly Thr Cys Thr Ala Ala Thr Ala Gly Ala Thr Thr Cys
            180                 185                 190

Thr Cys Thr Gly Gly Cys Ala Gly Cys Ala Ala Gly Thr Cys Cys Gly
            195                 200                 205

Gly Cys Ala Ala Cys Ala Cys Cys Gly Cys Thr Cys Thr Cys Thr
210                 215                 220

Gly Ala Cys Ala Ala Thr Cys Ala Gly Cys Gly Cys Cys Thr Gly
225                 230                 235                 240

Cys Ala Gly Gly Cys Ala Gly Ala Gly Ala Cys Gly Ala Gly Gly
            245                 250                 255

Cys Ala Gly Ala Thr Thr Ala Cys Thr Ala Thr Gly Cys Ala Thr
            260                 265                 270

Cys Thr Cys Cys Thr Ala Thr Ala Cys Cys Ala Cys Ala Ala Thr Cys
            275                 280                 285

Ala Cys Cys Ala Cys Ala Cys Thr Gly Thr Gly Gly Thr Gly Thr
290                 295                 300

Thr Thr Gly Gly Cys Gly Gly Cys Gly Gly Cys Ala Cys Cys Ala Ala
305                 310                 315                 320

Gly Cys Thr Gly Ala Cys Ala
            325

<210> SEQ ID NO 148
<211> LENGTH: 14
<212> TYPE: PRT
<213> ORGANISM: Homo sapiens

<400> SEQUENCE: 148

Thr Gly Thr Ser Ser Asp Ile Gly Gly Tyr Asp Tyr Val Ser
1               5                   10

<210> SEQ ID NO 149
<211> LENGTH: 7
<212> TYPE: PRT
<213> ORGANISM: Homo sapiens

<400> SEQUENCE: 149

Glu Val Ser Asn Arg Pro Ser
1               5

<210> SEQ ID NO 150
<211> LENGTH: 11
<212> TYPE: PRT
<213> ORGANISM: Homo sapiens

<400> SEQUENCE: 150

Ile Ser Tyr Thr Thr Ile Thr Thr Leu Trp Val
1               5                   10

<210> SEQ ID NO 151
<211> LENGTH: 121
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Ile Asn Trp Val Arg Gln Ala Pro Gly Lys Gly Leu Glu Trp Val

```
                35                  40                  45
Ser Ala Ile Ser Ser Gly Gly Arg His Tyr Ala Asp Ser Val
         50                  55                  60

Arg Gly Arg Phe Thr Ile Ser Arg Asp Asn Ser Lys Asn Thr Leu Tyr
 65                  70                  75                  80

Leu His Met Ser Gly Leu Arg Ala Glu Asp Thr Ala Val Tyr Phe Cys
                 85                  90                  95

Ala Lys Ala Gly Ala Arg Asn Tyr Tyr Tyr Gly Met Asp Val Trp Gly
            100                 105                 110

Gln Gly Thr Thr Val Thr Val Ser Ser
            115                 120

<210> SEQ ID NO 152
<211> LENGTH: 363
<212> TYPE: PRT
<213> ORGANISM: Homo sapiens

<400> SEQUENCE: 152

Gly Ala Gly Gly Thr Gly Cys Ala Gly Cys Thr Gly Cys Thr Gly Gly
 1               5                  10                  15

Ala Gly Thr Cys Cys Gly Gly Cys Gly Gly Ala Gly Gly Cys Cys Thr
                20                  25                  30

Gly Gly Thr Gly Cys Ala Gly Cys Cys Ala Gly Gly Ala Gly Gly Cys
            35                  40                  45

Thr Cys Thr Cys Thr Gly Ala Gly Gly Cys Thr Gly Ala Gly Cys Thr
         50                  55                  60

Gly Thr Gly Cys Cys Gly Cys Cys Thr Cys Cys Gly Gly Cys Thr Thr
 65                  70                  75                  80

Cys Ala Cys Cys Thr Thr Thr Gly Ala Cys Thr Cys Thr Thr Ala Thr
                 85                  90                  95

Gly Cys Cys Ala Thr Cys Ala Cys Thr Gly Gly Gly Thr Gly Gly Ala
            100                 105                 110

Gly Ala Cys Ala Gly Gly Cys Ala Cys Cys Thr Gly Gly Cys Ala Ala
            115                 120                 125

Gly Gly Gly Cys Cys Thr Gly Gly Ala Gly Thr Gly Gly Gly Thr Gly
        130                 135                 140

Thr Cys Cys Gly Cys Cys Ala Thr Cys Ala Gly Cys Thr Cys Cys Thr
145                 150                 155                 160

Cys Thr Gly Gly Cys Gly Gly Ala Gly Gly Cys Ala Gly Gly Cys Ala
                165                 170                 175

Cys Thr Ala Cys Gly Cys Ala Gly Ala Cys Thr Cys Thr Gly Thr Gly
            180                 185                 190

Cys Gly Gly Gly Gly Cys Ala Gly Ala Thr Thr Cys Ala Cys Cys Ala
            195                 200                 205

Thr Cys Thr Cys Thr Cys Gly Cys Gly Ala Cys Ala Ala Cys Ala Gly
        210                 215                 220

Cys Ala Ala Gly Ala Ala Thr Ala Cys Ala Cys Thr Gly Thr Ala Thr
225                 230                 235                 240

Cys Thr Gly Cys Ala Cys Ala Thr Gly Thr Cys Cys Gly Gly Cys Cys
                245                 250                 255

Thr Gly Ala Gly Gly Gly Cys Ala Gly Ala Gly Gly Ala Cys Ala Cys
            260                 265                 270

Cys Gly Cys Cys Gly Thr Gly Thr Ala Cys Thr Thr Thr Gly Cys
            275                 280                 285
```

Gly Cys Cys Ala Ala Gly Cys Cys Gly Gly Cys Cys Ala
    290                 295                 300

Gly Ala Ala Ala Thr Thr Ala Cys Thr Ala Thr Ala Cys Gly Gly
305                     310                 315                 320

Ala Ala Thr Gly Gly Ala Cys Gly Thr Gly Thr Gly Gly Gly Ala
                325                 330                 335

Cys Ala Gly Gly Gly Ala Ala Cys Cys Ala Cys Ala Gly Thr Gly Ala
            340                 345                 350

Cys Ala Gly Thr Gly Ala Gly Cys Thr Cys Cys
            355                 360

<210> SEQ ID NO 153
<211> LENGTH: 7
<212> TYPE: PRT
<213> ORGANISM: Homo sapiens

<400> SEQUENCE: 153

Gly Phe Thr Phe Asp Ser Tyr
1               5

<210> SEQ ID NO 154
<211> LENGTH: 6
<212> TYPE: PRT
<213> ORGANISM: Homo sapiens

<400> SEQUENCE: 154

Ser Ser Ser Gly Gly Gly
1               5

<210> SEQ ID NO 155
<211> LENGTH: 12
<212> TYPE: PRT
<213> ORGANISM: Homo sapiens

<400> SEQUENCE: 155

Ala Gly Ala Arg Asn Tyr Tyr Tyr Gly Met Asp Val
1               5                   10

<210> SEQ ID NO 156
<211> LENGTH: 107
<212> TYPE: PRT
<213> ORGANISM: Homo sapiens

<400> SEQUENCE: 156

Gln Ser Val Leu Ser Gln Pro Pro Ser Ala Ser Gly Thr Pro Gly Gln
1               5                   10                  15

Thr Val Thr Ile Ser Cys Ser Gly Gly Asn Ser Asn Ile Gly Lys Asn
            20                  25                  30

Phe Val Tyr Trp Tyr Arg Gln Leu Pro Gly Thr Ala Pro Lys Leu Leu
        35                  40                  45

Ile His Ser Asn Asp Arg Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Thr Gly Leu Phe Gly Thr Gly Thr Arg Val Thr
            100                 105

<210> SEQ ID NO 157

```
<211> LENGTH: 321
<212> TYPE: PRT
<213> ORGANISM: Homo sapiens

<400> SEQUENCE: 157

Cys Ala Gly Ala Gly Cys Gly Thr Gly Cys Thr Gly Cys Cys Cys
1               5                   10                  15

Ala Gly Cys Cys Ala Cys Cys Thr Ala Gly Cys Gly Cys Thr Cys
            20                  25                  30

Cys Gly Gly Cys Ala Cys Cys Cys Ala Gly Gly Cys Cys Ala Gly
            35                  40                  45

Ala Cys Cys Gly Thr Gly Ala Cys Ala Ala Thr Cys Thr Cys Thr Thr
50                  55                      60

Gly Thr Ala Gly Cys Gly Gly Cys Gly Gly Cys Ala Ala Cys Thr Cys
65                      70                  75              80

Cys Ala Ala Thr Ala Thr Cys Gly Gly Cys Ala Ala Gly Ala Ala Cys
                85                  90                  95

Thr Thr Cys Gly Thr Gly Thr Ala Cys Thr Gly Gly Thr Ala Thr Ala
            100                 105                 110

Gly Gly Cys Ala Gly Cys Thr Gly Cys Cys Ala Gly Ala Ala Cys
            115                 120                 125

Cys Gly Cys Ala Cys Cys Ala Ala Gly Cys Thr Gly Cys Thr Gly
130                 135                 140

Ala Thr Cys Cys Ala Cys Thr Cys Cys Ala Ala Thr Gly Ala Cys Ala
145                 150                 155                 160

Gly Ala Cys Gly Gly Cys Cys Thr Cys Thr Gly Gly Cys Gly Thr
            165                 170                 175

Gly Cys Cys Ala Gly Ala Thr Ala Gly Gly Thr Thr Thr Cys Cys
            180                 185                 190

Gly Gly Cys Thr Cys Thr Ala Ala Gly Ala Cys Gly Gly Cys Ala
            195                 200                 205

Cys Ala Thr Cys Thr Gly Cys Cys Thr Cys Thr Gly Gly Cys
210                 215                 220

Cys Ala Thr Cys Thr Cys Thr Gly Gly Cys Cys Thr Gly Cys Gly Cys
225                 230                 235                 240

Ala Gly Cys Gly Ala Gly Gly Ala Cys Gly Ala Gly Cys Ala Gly
            245                 250                 255

Ala Thr Thr Ala Cys Thr Ala Thr Thr Gly Cys Gly Cys Ala Gly Cys
            260                 265                 270

Ala Thr Gly Gly Gly Ala Cys Gly Ala Thr Thr Cys Thr Cys Thr Gly
            275                 280                 285

Ala Cys Cys Gly Gly Cys Cys Thr Gly Thr Cys Gly Gly Cys Ala
            290                 295                 300

Cys Cys Gly Gly Cys Ala Cys Ala Ala Gly Gly Thr Gly Ala Cys
305                 310                 315                 320

Ala

<210> SEQ ID NO 158
<211> LENGTH: 13
<212> TYPE: PRT
<213> ORGANISM: Homo sapiens

<400> SEQUENCE: 158

Ser Gly Gly Asn Ser Asn Ile Gly Lys Asn Phe Val Tyr
1               5                   10
```

```
<210> SEQ ID NO 159
<211> LENGTH: 7
<212> TYPE: PRT
<213> ORGANISM: Homo sapiens

<400> SEQUENCE: 159

Ser Asn Asp Arg Arg Pro Ser
1               5

<210> SEQ ID NO 160
<211> LENGTH: 10
<212> TYPE: PRT
<213> ORGANISM: Homo sapiens

<400> SEQUENCE: 160

Ala Ala Trp Asp Asp Ser Leu Thr Gly Leu
1               5                   10

<210> SEQ ID NO 161
<211> LENGTH: 122
<212> TYPE: PRT
<213> ORGANISM: Homo sapiens

<400> SEQUENCE: 161

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Ile His Trp Val Arg Gln Ala Pro Gly Lys Gly Leu Glu Trp Val
        35                  40                  45

Ala Val Val Ser Arg Asp Gly Gly Phe Lys Tyr Tyr Ala Asp Ser Val
    50                  55                  60

Lys Gly Arg Phe Thr Ile Ser Arg Asp Asn Ser Glu Asn Thr Met Phe
65                  70                  75                  80

Leu Gln Met Asn Ser Leu Arg Ala Glu Asp Thr Ala Val Tyr Tyr Cys
                85                  90                  95

Ala Lys Glu Gly Tyr Ser Gly Gly Tyr Gly Ala Tyr Phe Glu Ser Trp
            100                 105                 110

Gly Gln Gly Thr Leu Val Ala Val Ser Ser
        115                 120

<210> SEQ ID NO 162
<211> LENGTH: 366
<212> TYPE: PRT
<213> ORGANISM: Homo sapiens

<400> SEQUENCE: 162

Gly Ala Gly Gly Thr Gly Cys Ala Gly Cys Thr Gly Thr Gly Gly
1               5                   10                  15

Ala Gly Ala Gly Cys Gly Gly Cys Gly Gly Ala Gly Gly Ala Gly Thr
            20                  25                  30

Gly Gly Thr Gly Cys Ala Gly Cys Cys Ala Gly Gly Cys Cys Gly Gly
        35                  40                  45

Ala Gly Cys Cys Thr Gly Ala Gly Ala Cys Thr Gly Ala Gly Cys Thr
    50                  55                  60

Gly Thr Gly Cys Cys Gly Cys Cys Thr Cys Gly Gly Cys Thr Thr
65                  70                  75                  80

Cys Ala Cys Cys Thr Thr Thr Thr Cys Cys Ala Cys Ala Thr Ala Cys
                85                  90                  95
```

-continued

Gly Gly Cys Ala Thr Cys Cys Ala Thr Gly Gly Thr Gly Cys
            100                 105                 110
Gly Gly Cys Ala Gly Gly Cys Ala Cys Thr Gly Gly Cys Ala Ala
            115                 120                 125
Gly Gly Gly Cys Cys Thr Gly Ala Gly Thr Gly Gly Thr Gly
            130                 135                 140
Gly Cys Ala Gly Thr Gly Thr Gly Ala Gly Cys Ala Gly Gly
145                 150                 155                 160
Ala Cys Gly Gly Ala Gly Gly Cys Thr Thr Cys Ala Ala Thr Ala
                165                 170                 175
Cys Thr Ala Thr Gly Cys Cys Gly Ala Thr Thr Cys Cys Gly Thr Gly
                180                 185                 190
Ala Ala Gly Gly Gly Cys Ala Gly Gly Thr Thr Thr Ala Cys Cys Ala
                195                 200                 205
Thr Cys Thr Cys Thr Cys Gly Cys Gly Ala Cys Ala Ala Cys Ala Gly
                210                 215                 220
Cys Gly Ala Gly Ala Ala Thr Ala Cys Ala Ala Thr Gly Thr Thr Cys
225                 230                 235                 240
Cys Thr Gly Cys Ala Gly Ala Thr Gly Ala Ala Cys Thr Cys Thr Cys
                245                 250                 255
Thr Gly Cys Gly Gly Cys Cys Gly Ala Gly Gly Ala Thr Ala Cys
                260                 265                 270
Cys Gly Cys Cys Gly Thr Gly Thr Ala Cys Thr Ala Thr Gly Cys
                275                 280                 285
Gly Cys Cys Ala Ala Gly Gly Ala Gly Gly Gly Cys Thr Ala Thr Thr
                290                 295                 300
Cys Cys Gly Gly Cys Gly Gly Cys Thr Ala Cys Gly Gly Cys Gly Cys
305                 310                 315                 320
Cys Thr Ala Thr Thr Thr Thr Gly Ala Gly Thr Cys Thr Thr Gly Gly
                325                 330                 335
Gly Gly Cys Cys Ala Gly Gly Cys Ala Cys Ala Cys Thr Gly Gly
                340                 345                 350
Thr Gly Gly Cys Cys Gly Thr Gly Ala Gly Cys Thr Cys Cys
                355                 360                 365

<210> SEQ ID NO 163
<211> LENGTH: 7
<212> TYPE: PRT
<213> ORGANISM: Homo sapiens

<400> SEQUENCE: 163

Gly Phe Thr Phe Ser Thr Tyr
1               5

<210> SEQ ID NO 164
<211> LENGTH: 6
<212> TYPE: PRT
<213> ORGANISM: Homo sapiens

<400> SEQUENCE: 164

Ser Arg Asp Gly Gly Phe
1               5

<210> SEQ ID NO 165
<211> LENGTH: 14
<212> TYPE: PRT
<213> ORGANISM: Homo sapiens

<400> SEQUENCE: 165

Glu Gly Tyr Ser Ser Phe Phe Tyr Gly Ala Tyr Phe Glu Ser
1               5                   10

<210> SEQ ID NO 166
<211> LENGTH: 107
<212> TYPE: PRT
<213> ORGANISM: Homo sapiens

<400> SEQUENCE: 166

Glu Ile Val Met Thr Gln Ser Pro Phe Ser Leu Ser Val Ser Pro Gly
1               5                   10                  15

Glu Arg Ala Thr Leu Ser Cys Arg Ala Ser Gln Ser Ile Ser Ser His
            20                  25                  30

Leu Ala Trp Tyr Gln Gln Lys Pro Gly Gln Ala Pro Arg Leu Val Met
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Ile Ile Ser Ser Leu Gln Ser
65                  70                  75                  80

Glu Asp Phe Ala Val Tyr Tyr Cys His Gln Tyr Asp Asn Trp Pro Val
                85                  90                  95

Thr Ile Gly Gln Gly Thr Lys Val Glu Ile Lys
            100                 105

<210> SEQ ID NO 167
<211> LENGTH: 321
<212> TYPE: PRT
<213> ORGANISM: Homo sapiens

<400> SEQUENCE: 167

Gly Ala Gly Ala Thr Cys Gly Thr Gly Ala Thr Gly Ala Cys Cys Cys
1               5                   10                  15

Ala Gly Ala Gly Cys Cys Cys Ala Thr Thr Cys Thr Cys Cys Cys Thr
            20                  25                  30

Gly Thr Cys Thr Gly Thr Gly Ala Gly Cys Cys Cys Ala Gly Gly Ala
        35                  40                  45

Gly Ala Gly Ala Gly Gly Cys Cys Ala Cys Ala Cys Thr Gly Thr Thr
    50                  55                  60

Cys Cys Thr Gly Thr Ala Gly Ala Gly Cys Thr Cys Cys Cys Ala Gly
65                  70                  75                  80

Gly Thr Cys Thr Ala Thr Cys Ala Gly Thr Cys Cys Cys Ala Cys Cys
                85                  90                  95

Cys Thr Gly Gly Cys Ala Thr Gly Gly Thr Ala Cys Cys Ala Gly Cys
            100                 105                 110

Ala Gly Ala Ala Gly Cys Cys Ala Gly Gly Ala Cys Ala Gly Gly Cys
        115                 120                 125

Ala Cys Cys Thr Ala Gly Gly Cys Thr Gly Gly Cys Ala Thr Gly Gly
    130                 135                 140

Thr Ala Thr Gly Gly Cys Gly Cys Cys Thr Cys Thr Ala Cys Cys Ala
145                 150                 155                 160

Gly Gly Gly Cys Ala Ala Cys Ala Gly Cys Ala Thr Cys Cys Cys
                165                 170                 175

Thr Gly Cys Ala Cys Gly Cys Thr Thr Cys Ala Gly Cys Gly Gly Cys
            180                 185                 190

-continued

```
Thr Cys Cys Gly Gly Cys Thr Cys Thr Gly Gly Cys Ala Cys Cys Gly
            195                 200                 205
Ala Gly Thr Thr Thr Ala Cys Ala Cys Thr Gly Ala Thr Cys Ala Thr
210                 215                 220
Cys Thr Cys Thr Ala Gly Cys Cys Thr Gly Cys Ala Gly Thr Cys Cys
225                 230                 235                 240
Gly Ala Gly Gly Ala Cys Thr Thr Gly Cys Cys Gly Thr Gly Gly Thr
                245                 250                 255
Ala Cys Thr Ala Thr Thr Gly Cys Cys Ala Cys Cys Ala Gly Thr Ala
                260                 265                 270
Cys Gly Ala Thr Ala Ala Cys Thr Gly Gly Cys Cys Cys Gly Thr Gly
            275                 280                 285
Ala Cys Cys Ala Thr Cys Gly Gly Cys Ala Gly Gly Gly Cys Ala
            290                 295                 300
Cys Ala Ala Ala Gly Gly Thr Gly Gly Ala Gly Ala Thr Cys Ala Ala
305                 310                 315                 320
Gly
```

<210> SEQ ID NO 168
<211> LENGTH: 11
<212> TYPE: PRT
<213> ORGANISM: Homo sapiens

<400> SEQUENCE: 168

```
Arg Ala Ser Gln Ser Ile Ser Ser His Leu Ala
1               5                   10
```

<210> SEQ ID NO 169
<211> LENGTH: 7
<212> TYPE: PRT
<213> ORGANISM: Homo sapiens

<400> SEQUENCE: 169

```
Gly Ala Ser Thr Arg Ala Thr
1               5
```

<210> SEQ ID NO 170
<211> LENGTH: 9
<212> TYPE: PRT
<213> ORGANISM: Homo sapiens

<400> SEQUENCE: 170

```
His Gln Tyr Asp Asn Trp Pro Val Thr
1               5
```

<210> SEQ ID NO 171
<211> LENGTH: 124
<212> TYPE: PRT
<213> ORGANISM: Homo sapiens

<400> SEQUENCE: 171

```
Glu Val Gln Leu Val Glu Ser Gly Gly Phe Ala Gln Pro Gly Arg
1               5                   10                  15
Ser Leu Arg Ile Ser Cys Ser Ala Ser Gly Phe Thr Phe Asp Asp Tyr
                20                  25                  30
Ala Ile His Trp Val Arg Gln Ala Pro Gly Lys Gly Leu Glu Trp Val
            35                  40                  45
Ser Gly Ile Ile Trp Asn Ser Asp Leu Lys Asp Tyr Ala Asp Ser Val
        50                  55                  60
```

Lys Gly Arg Phe Thr Ile Ser Arg Asp Thr Ala Lys Asn Ser Leu Tyr
65                  70                  75                  80

Leu Gln Met Asn Ser Leu Arg Ala Asp Asp Thr Ala Leu Tyr Tyr Cys
            85                  90                  95

Ala Arg Val Thr Gly Tyr Asn Tyr Gly Ser Ala Leu Asp Ala Phe Gly
            100                 105                 110

Ile Trp Gly Thr Gly Thr Met Val Ile Val Ser Ser
            115                 120

<210> SEQ ID NO 172
<211> LENGTH: 372
<212> TYPE: PRT
<213> ORGANISM: Homo sapiens

<400> SEQUENCE: 172

Gly Ala Gly Gly Thr Gly Cys Ala Gly Cys Thr Gly Gly Thr Gly Gly
1               5                   10                  15

Ala Gly Thr Cys Cys Gly Gly Cys Gly Gly Ala Gly Gly Ala Thr Thr
            20                  25                  30

Cys Gly Cys Ala Cys Ala Gly Cys Cys Ala Gly Gly Cys Cys Gly Gly
            35                  40                  45

Ala Gly Cys Cys Thr Gly Cys Gly Gly Ala Thr Cys Thr Cys Thr Thr
            50                  55                  60

Gly Thr Ala Gly Cys Gly Cys Thr Cys Gly Gly Cys Thr Thr Cys Thr
65                  70                  75                  80

Cys Ala Cys Cys Thr Thr Thr Gly Ala Cys Gly Ala Thr Thr Ala Cys
            85                  90                  95

Gly Cys Ala Ala Thr Cys Cys Ala Cys Thr Gly Gly Gly Thr Gly Cys
            100                 105                 110

Gly Gly Cys Ala Gly Gly Cys Ala Cys Thr Gly Gly Cys Ala Ala
            115                 120                 125

Gly Gly Gly Cys Cys Thr Gly Gly Ala Gly Thr Gly Gly Gly Thr Gly
            130                 135                 140

Thr Cys Thr Gly Gly Cys Ala Thr Cys Ala Cys Thr Gly Gly Ala
145                 150                 155                 160

Ala Cys Ala Gly Cys Gly Ala Cys Cys Thr Gly Ala Cys Gly Gly Ala
            165                 170                 175

Thr Thr Ala Cys Gly Cys Gly Ala Cys Ala Gly Cys Gly Thr Gly
            180                 185                 190

Ala Ala Gly Gly Gly Cys Ala Gly Gly Thr Thr Cys Ala Cys Cys Ala
            195                 200                 205

Thr Cys Thr Cys Cys Cys Gly Cys Gly Ala Thr Ala Cys Ala Gly Cys
            210                 215                 220

Cys Ala Ala Gly Ala Ala Cys Thr Cys Thr Cys Thr Gly Thr Ala Thr
225                 230                 235                 240

Cys Thr Gly Cys Ala Gly Ala Thr Gly Ala Ala Thr Ala Gly Cys Cys
            245                 250                 255

Thr Gly Cys Gly Gly Gly Cys Cys Gly Ala Cys Gly Ala Thr Ala Cys
            260                 265                 270

Cys Gly Cys Cys Thr Gly Thr Ala Cys Thr Ala Thr Thr Gly Cys
            275                 280                 285

Gly Cys Cys Ala Gly Gly Gly Thr Gly Ala Cys Ala Gly Gly Cys Thr
            290                 295                 300

Ala Cys Ala Ala Thr Thr Ala Thr Gly Gly Cys Thr Cys Cys Gly Cys
305                 310                 315                 320

```
Cys Cys Thr Gly Gly Ala Cys Gly Cys Thr Thr Gly Gly Cys
            325                 330                 335

Ala Thr Cys Thr Gly Gly Gly Cys Ala Cys Gly Gly Cys Ala
            340                 345                 350

Cys Ala Ala Thr Gly Gly Thr Cys Ala Thr Cys Gly Thr Gly Ala Gly
            355                 360                 365

Cys Thr Cys Cys
    370

<210> SEQ ID NO 173
<211> LENGTH: 7
<212> TYPE: PRT
<213> ORGANISM: Homo sapiens

<400> SEQUENCE: 173

Gly Phe Thr Phe Asp Asp Tyr
1               5

<210> SEQ ID NO 174
<211> LENGTH: 6
<212> TYPE: PRT
<213> ORGANISM: Homo sapiens

<400> SEQUENCE: 174

Ile Trp Asn Ser Asp Leu
1               5

<210> SEQ ID NO 175
<211> LENGTH: 15
<212> TYPE: PRT
<213> ORGANISM: Homo sapiens

<400> SEQUENCE: 175

Val Thr Gly Tyr Asn Tyr Gly Ser Ala Leu Asp Ala Phe Gly Ile
1               5                   10                  15

<210> SEQ ID NO 176
<211> LENGTH: 106
<212> TYPE: PRT
<213> ORGANISM: Homo sapiens

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Gly Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Phe Gln Ala Ser Thr Leu Glu Ser Gly Val Ser Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Ser
                85                  90                  95

Phe Gly Gln Gly Thr Lys Leu Glu Ile Lys
            100                 105

<210> SEQ ID NO 177
<211> LENGTH: 318
<212> TYPE: PRT
```

<213> ORGANISM: Homo sapiens

<400> SEQUENCE: 177

Gly Ala Cys Ala Thr Cys Cys Ala Gly Ala Thr Gly Ala Cys Cys Cys
1               5                   10                  15
Ala Gly Thr Cys Cys Cys Ala Ala Gly Cys Thr Cys Cys Thr
            20                  25                  30
Gly Ala Gly Cys Gly Cys Cys Thr Cys Cys Gly Thr Gly Gly Gly Cys
            35                  40                  45
Gly Ala Thr Cys Gly Gly Thr Gly Ala Cys Cys Ala Thr Cys Ala
            50                  55                  60
Cys Ala Gly Gly Cys Ala Gly Ala Cys Cys Thr Cys Thr Cys Ala
65                  70                  75                  80
Gly Ala Gly Cys Ala Thr Cys Thr Cys Cys Ala Gly Gly Thr Gly Gly
                    85                  90                  95
Cys Thr Gly Gly Cys Cys Thr Gly Gly Thr Ala Cys Cys Ala Gly Cys
                100                 105                 110
Ala Gly Ala Ala Gly Cys Cys Cys Gly Gly Cys Ala Ala Gly Gly Cys
                115                 120                 125
Cys Cys Cys Thr Ala Ala Gly Cys Thr Gly Cys Thr Gly Ala Thr Cys
            130                 135                 140
Thr Thr Cys Cys Ala Gly Gly Cys Cys Thr Cys Cys Ala Cys Cys Cys
145                 150                 155                 160
Thr Gly Gly Ala Gly Thr Cys Thr Gly Gly Cys Gly Thr Gly Thr Cys
                165                 170                 175
Thr Ala Gly Cys Cys Gly Gly Thr Thr Cys Thr Cys Thr Gly Gly Cys
                180                 185                 190
Ala Gly Cys Gly Gly Cys Thr Cys Cys Gly Gly Cys Ala Cys Ala Gly
                195                 200                 205
Ala Gly Thr Thr Thr Ala Cys Cys Thr Gly Ala Cys Ala Ala Thr
                210                 215                 220
Cys Thr Cys Cys Thr Cys Thr Cys Thr Gly Cys Ala Gly Cys Cys Cys
225                 230                 235                 240
Gly Ala Cys Gly Ala Thr Thr Thr Cys Gly Cys Cys Ala Cys Cys Thr
                245                 250                 255
Ala Cys Thr Ala Thr Thr Gly Thr Cys Ala Gly Cys Ala Gly Thr Ala
                260                 265                 270
Thr Ala Ala Cys Thr Cys Thr Thr Ala Cys Thr Ala Thr Ala Gly Cys
                275                 280                 285
Thr Thr Thr Gly Gly Cys Cys Ala Gly Gly Gly Cys Ala Cys Ala Ala
                290                 295                 300
Ala Gly Cys Thr Gly Gly Ala Gly Ala Thr Cys Ala Ala Gly
305                 310                 315

<210> SEQ ID NO 178
<211> LENGTH: 11
<212> TYPE: PRT
<213> ORGANISM: Homo sapiens

<400> SEQUENCE: 178

Arg Ala Ser Gln Ser Ile Ser Arg Trp Leu Ala
1               5                   10

<210> SEQ ID NO 179
<211> LENGTH: 7
<212> TYPE: PRT

<213> ORGANISM: Homo sapiens

<400> SEQUENCE: 179

Gln Ala Ser Thr Leu Glu Ser
1               5

<210> SEQ ID NO 180
<211> LENGTH: 8
<212> TYPE: PRT
<213> ORGANISM: Homo sapiens

<400> SEQUENCE: 180

Gln Gln Tyr Asn Ser Tyr Tyr Ser
1               5

<210> SEQ ID NO 181
<211> LENGTH: 126
<212> TYPE: PRT
<213> ORGANISM: Homo sapiens

<400> SEQUENCE: 181

His Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Lys Gly Asp Thr His Tyr Ala Gln Lys Phe
        50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Gly Thr Ala Val Tyr Tyr Cys
                85                  90                  95

Ala Arg Ser Tyr Asp Tyr Val Trp Ile Ser Tyr Arg Tyr Arg Thr Asn
            100                 105                 110

Phe Asp Tyr Trp Gly Gln Gly Thr Leu Val Thr Val Ser Ser
        115                 120                 125

<210> SEQ ID NO 182
<211> LENGTH: 378
<212> TYPE: PRT
<213> ORGANISM: Homo sapiens

<400> SEQUENCE: 182

Cys Ala Cys Gly Thr Gly Cys Ala Gly Cys Thr Gly Gly Thr Gly Cys
1               5                   10                  15

Ala Gly Thr Cys Thr Gly Gly Cys Gly Gly Ala Gly Ala Gly Gly Thr
                20                  25                  30

Gly Ala Ala Gly Ala Ala Gly Cys Cys Ala Gly Gly Ala Gly Cys Cys
            35                  40                  45

Ala Gly Cys Gly Thr Gly Ala Ala Gly Gly Thr Gly Thr Cys Cys Thr
        50                  55                  60

Gly Thr Ala Ala Gly Gly Cys Cys Thr Cys Thr Gly Gly Cys Thr Ala
65                  70                  75                  80

Cys Ala Cys Cys Thr Thr Cys Ala Cys Ala Gly Ala Cys Thr Ala Thr
                85                  90                  95

Gly Gly Ala Ala Thr Cys Thr Cys Thr Thr Gly Gly Thr Gly Cys
            100                 105                 110

Gly Gly Cys Ala Gly Gly Cys Ala Cys Cys Thr Gly Ala Cys Ala
            115                 120                 125

Gly Gly Gly Cys Cys Thr Gly Ala Gly Thr Gly Ala Thr Gly
            130                 135                 140

Gly Gly Cys Thr Gly Gly Ala Thr Cys Ala Gly Cys Ala Cys Ala Thr
145                 150                 155                 160

Ala Cys Ala Ala Gly Gly Cys Gly Ala Cys Ala Cys Cys Ala
                165                 170                 175

Cys Thr Ala Thr Gly Cys Cys Cys Ala Gly Ala Ala Gly Thr Thr Thr
            180                 185                 190

Cys Ala Gly Gly Gly Cys Ala Gly Gly Gly Thr Gly Ala Cys Cys Ala
            195                 200                 205

Thr Gly Ala Cys Ala Gly Cys Cys Gly Ala Thr Ala Cys Cys Thr Cys
210                 215                 220

Thr Ala Cys Ala Ala Gly Cys Ala Cys Cys Gly Cys Thr Ala Cys
225                 230                 235                 240

Ala Thr Gly Gly Ala Gly Cys Thr Gly Ala Gly Gly Thr Cys Cys Cys
                245                 250                 255

Thr Gly Cys Gly Cys Thr Cys Thr Gly Ala Cys Gly Gly Cys Ala Cys
            260                 265                 270

Ala Gly Cys Cys Gly Thr Gly Thr Ala Cys Thr Ala Thr Gly Cys
            275                 280                 285

Gly Cys Cys Gly Gly Ala Gly Cys Thr Ala Cys Gly Ala Thr Thr
            290                 295                 300

Ala Cys Gly Thr Gly Thr Gly Ala Thr Cys Thr Cys Cys Thr Ala
305                 310                 315                 320

Cys Cys Gly Gly Thr Ala Thr Ala Gly Ala Cys Cys Ala Ala Cys
                325                 330                 335

Thr Thr Cys Gly Ala Thr Thr Ala Thr Gly Gly Gly Cys Cys
            340                 345                 350

Ala Gly Gly Gly Cys Ala Cys Ala Cys Thr Gly Gly Thr Gly Ala Cys
            355                 360                 365

Cys Gly Thr Gly Ala Gly Cys Thr Cys Cys
    370                 375

<210> SEQ ID NO 183
<211> LENGTH: 7
<212> TYPE: PRT
<213> ORGANISM: Homo sapiens

<400> SEQUENCE: 183

Gly Tyr Thr Phe Thr Asp Tyr
1               5

<210> SEQ ID NO 184
<211> LENGTH: 6
<212> TYPE: PRT
<213> ORGANISM: Homo sapiens

<400> SEQUENCE: 184

Ser Thr Tyr Lys Gly Asp
1               5

<210> SEQ ID NO 185
<211> LENGTH: 17
<212> TYPE: PRT
<213> ORGANISM: Homo sapiens

<400> SEQUENCE: 185

Ser Tyr Asp Tyr Val Trp Ile Ser Tyr Arg Tyr Arg Thr Asn Phe Asp
1               5                   10                  15

Tyr

<210> SEQ ID NO 186
<211> LENGTH: 107
<212> TYPE: PRT
<213> ORGANISM: Homo sapiens

<400> SEQUENCE: 186

Ala Ile Gln Met Thr Gln Ser Pro Phe Ser Leu Ser Ala Ser Val Gly
1               5                   10                  15

Asp Arg Val Thr Ile Thr Cys Arg Ala Ser Gln Gly Ile Gly Asn Asp
            20                  25                  30

Leu Gly Trp Tyr Gln Gln Ile Pro Gly Arg Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Leu Gln Asp Tyr Thr Tyr Pro Tyr
                85                  90                  95

Ser Phe Gly Gln Gly Thr Lys Leu Glu Ile Lys
            100                 105

<210> SEQ ID NO 187
<211> LENGTH: 321
<212> TYPE: PRT
<213> ORGANISM: Homo sapiens

<400> SEQUENCE: 187

Gly Cys Cys Ala Thr Cys Cys Ala Gly Ala Thr Gly Ala Cys Ala Cys
1               5                   10                  15

Ala Gly Ala Gly Cys Cys Cys Thr Thr Thr Cys Ala Gly Cys Cys Thr
            20                  25                  30

Gly Thr Cys Cys Gly Cys Cys Thr Cys Thr Gly Thr Gly Gly Gly Cys
        35                  40                  45

Gly Ala Cys Cys Gly Gly Gly Thr Gly Ala Cys Cys Ala Thr Cys Ala
    50                  55                  60

Cys Ala Thr Gly Thr Ala Gly Ala Gly Cys Cys Thr Cys Cys Cys Ala
65                  70                  75                  80

Gly Gly Gly Cys Ala Thr Cys Gly Gly Cys Ala Ala Cys Gly Ala Thr
                85                  90                  95

Cys Thr Gly Gly Gly Cys Thr Gly Gly Thr Ala Thr Cys Ala Gly Cys
            100                 105                 110

Ala Gly Ala Thr Cys Cys Cys Gly Gly Cys Ala Gly Gly Gly Cys Cys
        115                 120                 125

Cys Cys Cys Thr Ala Ala Gly Cys Thr Gly Cys Thr Gly Ala Thr Cys
    130                 135                 140

Thr Ala Cys Gly Cys Ala Gly Cys Cys Ala Gly Cys Ala Ala Thr Cys
145                 150                 155                 160

Thr Gly Cys Ala Gly Thr Cys Cys Gly Gly Cys Gly Thr Gly Cys Cys
                165                 170                 175

Ala Thr Cys Thr Cys Gly Gly Thr Thr Cys Ala Gly Cys Gly Gly Cys
            180                 185                 190

```
Thr Cys Cys Gly Gly Cys Thr Cys Thr Gly Gly Cys Ala Cys Ala Gly
        195                 200                 205
Ala Cys Thr Thr Thr Ala Cys Cys Cys Thr Gly Ala Cys Ala Ala Thr
        210                 215                 220
Cys Ala Cys Cys Thr Cys Thr Cys Thr Gly Cys Ala Gly Cys Cys Ala
225                 230                 235                 240
Gly Ala Gly Gly Ala Cys Thr Thr Cys Gly Cys Cys Ala Cys Ala Thr
                245                 250                 255
Ala Cys Thr Ala Thr Thr Gly Cys Cys Thr Gly Cys Ala Gly Gly Ala
        260                 265                 270
Thr Thr Ala Cys Ala Cys Cys Thr Ala Thr Cys Cys Cys Thr Ala Cys
        275                 280                 285
Ala Gly Cys Thr Thr Thr Gly Gly Cys Cys Ala Gly Gly Gly Cys Ala
        290                 295                 300
Cys Cys Ala Ala Gly Cys Thr Gly Gly Ala Gly Ala Thr Cys Ala Ala
305                 310                 315                 320
Gly

<210> SEQ ID NO 188
<211> LENGTH: 11
<212> TYPE: PRT
<213> ORGANISM: Homo sapiens

<400> SEQUENCE: 188

Arg Ala Ser Gln Gly Ile Gly Asn Asp Leu Gly
1               5                   10

<210> SEQ ID NO 189
<211> LENGTH: 7
<212> TYPE: PRT
<213> ORGANISM: Homo sapiens

<400> SEQUENCE: 189

Ala Ala Ser Asn Leu Gln Ser
1               5

<210> SEQ ID NO 190
<211> LENGTH: 9
<212> TYPE: PRT
<213> ORGANISM: Homo sapiens

<400> SEQUENCE: 190

Leu Gln Asp Tyr Thr Tyr Pro Tyr Ser
1               5

<210> SEQ ID NO 191
<211> LENGTH: 125
<212> TYPE: PRT
<213> ORGANISM: Homo sapiens

<400> SEQUENCE: 191

Gln Val Gln Phe Gln Gln Trp Gly Ala Gly Leu Leu Lys Pro Ser Glu
1               5                   10                  15
Thr Leu Ser Leu Thr Cys Gly Val Tyr Gly Gly Ser Leu Ser Gly Tyr
            20                  25                  30
Tyr Trp Ser Trp Ile Arg Gln Thr Pro Gly Lys Gly Leu Glu Trp Ile
        35                  40                  45
Gly Glu Ile Asn His Thr Gly Thr Thr Asn Tyr Asn Pro Ser Leu Lys
    50                  55                  60
```

Ser Arg Val Thr Met Ser Val Asp Thr Ser Lys Asn Gln Phe Ser Leu
65                  70                  75                  80

Lys Met Ser Ser Leu Thr Ala Ala Asp Thr Ala Leu Tyr Tyr Cys Ala
            85                  90                  95

Arg Glu Gly Ala Pro Arg Trp Ala Leu Lys Arg Pro Ser Asn Trp Phe
        100                 105                 110

Asp Pro Trp Gly Gln Gly Thr Leu Val Thr Val Ser Ser
        115                 120                 125

<210> SEQ ID NO 192
<211> LENGTH: 375
<212> TYPE: PRT
<213> ORGANISM: Homo sapiens

<400> SEQUENCE: 192

Cys Ala Gly Gly Thr Gly Cys Ala Gly Thr Thr Cys Ala Gly Cys
1               5                   10                  15

Ala Gly Thr Gly Gly Gly Ala Gly Cys Ala Gly Gly Cys Cys Thr
            20                  25                  30

Gly Cys Thr Gly Ala Ala Gly Cys Cys Thr Thr Cys Thr Gly Ala Gly
        35                  40                  45

Ala Cys Ala Cys Thr Gly Ala Gly Cys Cys Thr Gly Ala Cys Ala Thr
    50                  55                  60

Gly Thr Gly Gly Cys Gly Thr Gly Thr Ala Cys Gly Gly Cys
65                  70                  75                  80

Cys Thr Cys Cys Cys Thr Gly Thr Cys Thr Gly Gly Cys Thr Ala Cys
            85                  90                  95

Thr Ala Thr Thr Gly Gly Thr Cys Cys Thr Gly Gly Ala Thr Cys Ala
        100                 105                 110

Gly Ala Cys Ala Gly Ala Cys Cys Cys Ala Gly Gly Cys Ala Ala
    115                 120                 125

Gly Gly Gly Cys Cys Thr Gly Ala Gly Thr Gly Gly Ala Thr Cys
        130                 135                 140

Gly Gly Ala Gly Ala Gly Ala Thr Cys Ala Ala Cys Cys Ala Cys Ala
145                 150                 155                 160

Cys Ala Gly Gly Cys Ala Cys Cys Ala Cys Ala Ala Cys Thr Ala
            165                 170                 175

Thr Ala Ala Thr Cys Cys Cys Ala Gly Cys Cys Thr Gly Ala Ala Gly
        180                 185                 190

Thr Cys Cys Cys Gly Gly Gly Thr Gly Ala Cys Ala Thr Gly Thr
    195                 200                 205

Cys Cys Gly Thr Gly Gly Ala Cys Ala Cys Ala Thr Cys Ala Ala
        210                 215                 220

Gly Ala Ala Thr Cys Ala Gly Thr Thr Cys Ala Gly Cys Cys Thr Gly
225                 230                 235                 240

Ala Ala Gly Ala Thr Gly Ala Gly Cys Thr Cys Cys Thr Gly Ala
            245                 250                 255

Cys Cys Gly Cys Cys Gly Cys Cys Gly Ala Thr Ala Cys Ala Gly Cys
        260                 265                 270

Cys Cys Thr Gly Thr Ala Cys Thr Ala Thr Thr Gly Thr Gly Cys Ala
    275                 280                 285

Ala Gly Gly Gly Ala Gly Gly Ala Gly Cys Ala Cys Cys Ala Ala
        290                 295                 300

Gly Ala Thr Gly Gly Gly Cys Cys Cys Thr Gly Ala Ala Gly Ala Gly

```
                305                 310                 315                 320
Gly Cys Cys Cys Thr Cys Cys Ala Ala Cys Thr Gly Gly Thr Thr Thr
                    325                 330                 335
Gly Ala Cys Cys Thr Thr Gly Gly Gly Cys Cys Ala Gly Gly
                340                 345                 350
Gly Cys Ala Cys Cys Thr Gly Thr Gly Ala Cys Ala Gly Thr
                355                 360                 365
Gly Thr Cys Thr Ala Gly Cys
            370                 375
```

<210> SEQ ID NO 193
<211> LENGTH: 7
<212> TYPE: PRT
<213> ORGANISM: Homo sapiens

<400> SEQUENCE: 193

```
Gly Gly Ser Leu Ser Gly Tyr
1               5
```

<210> SEQ ID NO 194
<211> LENGTH: 5
<212> TYPE: PRT
<213> ORGANISM: Homo sapiens

<400> SEQUENCE: 194

```
Asn His Thr Gly Thr
1               5
```

<210> SEQ ID NO 195
<211> LENGTH: 17
<212> TYPE: PRT
<213> ORGANISM: Homo sapiens

<400> SEQUENCE: 195

```
Glu Gly Ala Pro Arg Trp Ala Leu Lys Arg Pro Ser Asn Trp Phe Asp
1               5                   10                  15
Pro
```

<210> SEQ ID NO 196
<211> LENGTH: 108
<212> TYPE: PRT
<213> ORGANISM: Homo sapiens

<400> SEQUENCE: 196

```
Glu Ile Val Leu Thr Gln Ser Pro Val Ser Leu Ser Leu Ser Pro Gly
1               5                   10                  15
Glu Arg Ala Thr Leu Ser Cys Arg Ala Ser Gln Ser Ile Ser Ser Thr
                20                  25                  30
Tyr Leu Ala Trp Tyr Gln Gln Ile Pro Gly Gln Ala Pro Arg Leu Leu
            35                  40                  45
Ile Tyr Gly Ala Ser Ser Arg Ala Ala Gly Ile Pro Asp Arg Phe Ser
        50                  55                  60
Gly Gly Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Arg Ser Phe Gly Gln Gly Thr Lys Leu Glu Ile Lys
                100                 105
```

```
<210> SEQ ID NO 197
<211> LENGTH: 324
<212> TYPE: PRT
<213> ORGANISM: Homo sapiens

<400> SEQUENCE: 197

Gly Ala Gly Ala Thr Cys Gly Thr Gly Thr Gly Ala Cys Cys Cys
1               5                   10                  15

Ala Gly Thr Cys Cys Cys Ala Gly Thr Gly Ala Gly Cys Cys Thr
                20                  25                  30

Gly Thr Cys Cys Cys Thr Gly Thr Cys Thr Cys Ala Gly Gly Ala
                35                  40                  45

Gly Ala Gly Ala Gly Gly Gly Cys Cys Ala Cys Cys Thr Gly Thr
        50                  55                  60

Cys Thr Thr Gly Thr Ala Gly Ala Gly Cys Cys Ala Gly Cys Ala
65                  70                  75                  80

Gly Thr Cys Cys Ala Thr Cys Ala Gly Thr Cys Cys Ala Cys Ala
                    85                  90                  95

Thr Ala Cys Cys Thr Gly Gly Cys Cys Thr Gly Gly Thr Ala Thr Cys
                    100                 105                 110

Ala Gly Cys Ala Gly Ala Thr Cys Cys Ala Gly Gly Ala Cys Ala
                    115                 120                 125

Gly Gly Cys Ala Cys Cys Thr Ala Gly Cys Thr Gly Cys Thr Gly
        130                 135                 140

Ala Thr Cys Thr Ala Cys Gly Gly Ala Gly Cys Cys Thr Cys Ala
145                 150                 155                 160

Gly Cys Ala Gly Gly Cys Ala Gly Cys Ala Gly Gly Cys Ala Thr
                    165                 170                 175

Cys Cys Cys Cys Gly Ala Cys Cys Gly Cys Thr Thr Cys Thr Cys Thr
                180                 185                 190

Gly Gly Cys Gly Gly Ala Gly Gly Cys Ala Gly Cys Gly Gly Cys Ala
                    195                 200                 205

Cys Cys Gly Ala Cys Thr Thr Cys Ala Cys Cys Thr Gly Ala Cys
                210                 215                 220

Ala Ala Thr Cys Ala Gly Cys Cys Gly Gly Cys Thr Gly Gly Ala Gly
225                 230                 235                 240

Cys Cys Thr Gly Ala Gly Gly Ala Cys Thr Thr Cys Gly Cys Cys Gly
                    245                 250                 255

Thr Gly Thr Ala Cys Thr Ala Thr Thr Gly Cys Cys Ala Gly Cys Ala
                    260                 265                 270

Gly Thr Ala Thr Gly Gly Cys Thr Cys Cys Thr Cys Cys Cys Ala
                275                 280                 285

Ala Gly Gly Thr Cys Cys Thr Thr Thr Gly Gly Cys Cys Ala Gly Gly
                    290                 295                 300

Gly Cys Ala Cys Ala Ala Ala Gly Cys Thr Gly Gly Ala Gly Ala Thr
305                 310                 315                 320

Cys Ala Ala Gly

<210> SEQ ID NO 198
<211> LENGTH: 12
<212> TYPE: PRT
<213> ORGANISM: Homo sapiens

<400> SEQUENCE: 198

Arg Ala Ser Gln Ser Ile Ser Ser Thr Tyr Leu Ala
1               5                   10
```

```
<210> SEQ ID NO 199
<211> LENGTH: 7
<212> TYPE: PRT
<213> ORGANISM: Homo sapiens

<400> SEQUENCE: 199

Gly Ala Ser Ser Arg Ala Ala
1               5

<210> SEQ ID NO 200
<211> LENGTH: 9
<212> TYPE: PRT
<213> ORGANISM: Homo sapiens

<400> SEQUENCE: 200

Gln Gln Tyr Gly Ser Ser Pro Arg Ser
1               5
```